(12) United States Patent
Yanase et al.

(10) Patent No.: US 7,569,377 B2
(45) Date of Patent: Aug. 4, 2009

(54) METHOD OF HEAT-STABILIZING α-GLUCAN PHOSPHORYLASE(GP)

(75) Inventors: Michiyo Yanase, Kobe (JP); Hiroki Takata, Kobe (JP); Kazutoshi Fujii, Suita (JP); Takeshi Takaha, Kobe (JP); Takashi Kuriki, Suita (JP)

(73) Assignee: Ezaki Glico Co., Ltd., Osaka (JP)

( * ) Notice: Subject to any disclaimer, the term of this patent is extended or adjusted under 35 U.S.C. 154(b) by 236 days.

(21) Appl. No.: 10/560,491

(22) PCT Filed: Jun. 15, 2004

(86) PCT No.: PCT/JP2004/008362

§ 371 (c)(1),
(2), (4) Date: Jun. 9, 2006

(87) PCT Pub. No.: WO2004/113525

PCT Pub. Date: Dec. 29, 2004

(65) Prior Publication Data

US 2006/0275875 A1    Dec. 7, 2006

(30) Foreign Application Priority Data

Jun. 18, 2003   (JP) .............................. 2003-173972

(51) Int. Cl.
*C12N 9/12*    (2006.01)
*C07H 21/04*    (2006.01)
(52) U.S. Cl. ...................... 435/194; 536/23.2
(58) Field of Classification Search .............. 435/194; 536/23.2
See application file for complete search history.

(56) References Cited

FOREIGN PATENT DOCUMENTS

JP    10-14580 A    1/1998

OTHER PUBLICATIONS

Sequence search alignment between Accession No. Q9LKJ3 (2000) and Applicants' SEQ ID No. 2.*
International Search Report for corresponding Application No. PCT/JP2004/008362 mailed Aug. 17, 2004.
Shin, H.J. et al.; Formation of a αD-glucose-1-phosphate by thermophilic α-1, 4-D-glucan phosphorylase., Journal of Industrial Microbiology, vol. 24, pp. 89 to 93, 2000.
Takaha, T. et al., Structure and Properties of *Thermus aquaticus* α-Glucan Phosphorylase Express in *Escherichia coli*.J.Appl. Glycosci., vol. 48, No. 1, pp. 71 to 78, 2000.
Nakano, K. et al., The complete amino acid sequence of potato alpha-glucan phosphorylase., J.Biol.Chem., vol. 261, pp. 8230 to 8236, 1986.
Mori, H. et al., Potato tuber type H phosphorylase isozyme., Molecular cloning, nucleotide sequence, and expression of a full-length cDNA in *Escherichia coli*.J.Biol.Chem., vol. 266, pp. 18446 to 18453, 1991.

* cited by examiner

*Primary Examiner*—Tekchand Saidha
(74) *Attorney, Agent, or Firm*—Renner, Otto, Boisselle & Sklar, LLP

(57) ABSTRACT

An α-glucan phosphorylase having improved thermostability, which obtained by modifying natural α-glucan phosphorylase, and a method for producing this α-glucan phosphorylase having improved thermostability are provided. The natural α-glucan phosphorylase is derived from a plant, this α-glucan phosphorylase having improved thermostability has an amino acid residue which is different from that of the natural α-glucan phosphorylase in at least one position selected from the group consisting of a position corresponding to position 4 in a motif sequence 1L or 1H, a position corresponding to position 4 in a motif sequence 2, and a position corresponding to position 7 in a motif sequence 3L or 3H, and wherein the enzyme activity of α-glucan phosphorylase having improved thermostability at 37° C., after heating in a 20 mM citrate buffer (pH 6.7) at 60° C. for 10 minutes, is 20% or more of the enzyme activity of the α-glucan phosphorylase having improved thermostability at 37° C., before heating.

10 Claims, 18 Drawing Sheets

| | | |
|---|---|---|
| Potato type L | -50: | ————————————MATANGAH-LFNHYS-SNS-RFIHFTSR-NTSSKLFLT -17 |
| Potato type L2 | -81: | ——————————MA—TFAVSGLNSISSISSFNNNFRSKNSNIL-LSRRRILLFS -42 |
| Sweet potato type L | -43: | ———————————M————SR-LSGITP-RA—RDDRSQFQ-NPRLEIAVP -16 |
| Fava bean type L | -64: | MASMT-MRFHPNSTAVTESVPRRGSVYGFI-GYRSSS-LFV—RTNVIKY—RSVKRNLE -12 |
| Arabidopsis thaliana type L | 1: | ——MDTMRISGVSTGAEVLIQCN-SLSSLV-SRRCD——DGKWRTRMFPARNRDLRPSPT 52 |
| Spinach | 1: | ——MATLPLSSTTPSTGRTENCFSSYYSSSISRVMEFGLKNGCNSK—LLFSSVNYKPMI 55 |
| Rice type L | 1: | ————————————————————————————— 1 |
| Rice type L2 | 1: | ——————————MATASAPLQLATASRPLPVG-VGCGGGGGGGLHVGGAR 37 |
| Corn type L | 1: | ——————————GDDHLAAAAARHRLPPARLLLRRW-RGSPPRAVPE—VGSRR 39 |
| Potato type H | 1: | ————————————————————————————— 1 |
| Fava bean type H | 1: | ————————————————————————————— 1 |
| Arabidopsis thaliana type H | 1: | ————————————————————————————— 1 |
| Rice type H | 1: | ————————————————————————————— 1 |
| Wheat | 1: | ————————————————————————————— 1 |
| Citrus type H | 1: | ————————————————————————————— 1 |
| E.coli MalQ | 1: | ————————————————————————————— 1 |

| | | |
|---|---|---|
| Potato type L | -16: | K-TSHFR-RP-KRCFHVNNTLSEK——IHHPITEQGGESDLSSF-APDA-ASIT-SSIKY 35 |
| Potato type L2 | -41: | FRRRRRSFSVSSVASDQKQKTKDSSSDEGFT—LDVFQ——PDSTSVLS——S-IKY 7 |
| Sweet potato type L | -15: | DRTAGLQ-RT-KRTLLVKCVLDETKQTIQHVVTEKNEGTLLDA——A-S-IA-SSIKY 35 |
| Fava bean type L | -11: | FRRRSAF-S-VKCGSGNEAKQKVK-DQEVQQEAK—TSPS-SFA—PDT-TSIV-SSIKY 39 |
| Arabidopsis thaliana type L | 53: | R—R-SF-LSVKSISSEP-KAKVT-DAVLDSEQEVFISSMNPFA—PDA-ASVA-SSIKY 102 |
| Spinach | 56: | MRGSRRCIVIRNVFSESKPKSEEPIIEQETPSILNPLSN—LSPDSASRQS——S-IKY 108 |
| Rice type L | 1: | ——————RS—VAS-DRGVQGSVSP-EEEISSVLN-SIDS-STIA-SNIKH 37 |
| Rice type L2 | 38: | -GGGAAPARR—RLAVRS—VAS-DRGVQGSVSP-EEEISSVLN-SIDS-STIA-SNIKH 87 |
| Corn type L | 40: | -VGVGVEGRLQRRVSARS—VAS-DRDVQGPVSP-AEGLPNVLN-SIGS-SAIA-SNIKH 91 |
| Potato type H | 1: | ——————————MEGGAKSND-VSAA-P-IAQPLSEDPTD-IASN-IKY 32 |
| Fava bean type H | 1: | ——————————MGFKVE-TNGGDG—SLVSAKVPPLANPLAEKPDE-IASN-ISY 39 |
| Arabidopsis thaliana type H | 1: | ——————————MANA————N—GKAATS-LPEKISAKANPEADDATE-IAGN-IVY 36 |
| Rice type H | 1: | ——————————MPESN——GAACGAAEKVKPAA—SPASEEPAA-IAGN-ISF 35 |
| Wheat | 1: | ——————————————M-SA-ADKVKPAA—SPASEDPSA-IAGN-ISY 27 |
| Citrus type H | 1: | ——————————MADAKA——N—GKNEAAKLA-KIPAAANPLANEPSA-IASN-ISY 38 |
| E.coli MalQ | 1: | ————————————————————————MSQPIFND 8 |

Fig. 1A

Positions of motif sequences 1L and 1H

F39

| | |
|---|---|
| Potato type L | 36:HAEFTPVFSPE—RFE-LPKAFFATAQS-V—RDSLLINWNA-TYDIYEKLNMKQ-AYYL 87 |
| Potato type L2 | 8:HAEFTPSFSPE—KFELP-KAYYATAES-V—RDTLIINWNA-TYEFYEKMNVKQ-AYYL 59 |
| Sweet potato type L | 36:HAEFSPAFSPE—RFE-LPKAYFATAQS-V—RDALIVNWNA-TYDYYEKLNMKQ-AYYL 87 |
| Fava bean type L | 40:HAEFTPLFSPE—KFE-LPQAFIATAQS-V—RDALIINWNA-TYDYYEKLNVKQ-AYYL 91 |
| Arabidopsis thaliana type L | 103:HAEFTPLFSPE—KFE-LPKAFFATAQS-V—RDALIMNWNA-TYEYYNRVNVKQ-AYYL 154 |
| Spinach | 109:HAEFTPLFAPN—DFSLP-KAFFAAAQS-V—RDSLIINWNA-TYAHYEKMNMKQ-AYYL 160 |
| Rice type L | 38:HAEFTPVFSPE—HFSPL-KAYHATAKS-V—LDTLIMNWNA-TYDYYDRTNVKQ-AYYL 89 |
| Rice type L2 | 88:HAEFTPVFSPE—HFSPL-KAYHATAKS-V—LDTLIMNWNA-TYDYYDRTNVKQ-AYYL 139 |
| Corn type L | 92:HAEFAPLFSPD—HFSPL-KAYHATAKS-V—LDALLINWNA-TYDYYNKMNVKQ-AYYL 143 |
| Potato type H | 33:HAQYTPHFSPF—KFEPLQ-AYYAAT-A-DSVRDRLIKQWND-TYLHYDKVNPKQ-TYYL 85 |
| Fava bean type H | 40:HAQYTPHFSPF—KFQ-LQQAYYATA-E-S-VRDRLIQQWNE-TYLHFHKVDPKQ-TYYL 91 |
| Arabidopsis thaliana type H | 37:HAKYSPHFSPL—KFGPEQALYATAE-S-L—RDRLIQLWNE-TYVHFNKVDPKQ-TYYL 88 |
| Rice type H | 36:HAQYSPHFSPL—AFGPEQAFYSTAE-S-V—RDHLVQRWNE-TYLHFHKTDPKQ-TYYL 87 |
| Wheat | 28:HAQYSPHFSPL—AFGPEQAFYATAE-S-V—RDHLLQRWND-TYLHFHKTDPKQ-TYYL 79 |
| Citrus type H | 39:HVQYSPHFSPT—KFEPEQAFFATAE-V-V—RDRLIQQWNE-TYHHFNKVDPKQ-TYYL 90 |
| E.coli MalQ | 9:KQFQEA-LSRQWQRYGLNSAAEMTPRQWWLAVSEALAEMLRAQPFAKPVANQR-HVN-YI 65 |

Position of motif sequence 2

N135

| | |
|---|---|
| Potato type L | 88:SMEFLQGRALLNAIGNLELTGAFAEALKNLGHNLENVASQEPDAALGNGGLGRLASCFLD 147 |
| Potato type L2 | 60:SMEFLQGRALLNAIGNLGLTGPYADALTKLGYSLEDVARQEPDAALGNGGLGRLASCFLD 119 |
| Sweet potato type L | 88:SMEFLQGRALLNAIGNLELTGEYAEALNKLGHNLENVASKEPDAALGNGGLGRLASCFLD 147 |
| Fava bean type L | 92:SMEFLQGRALLNAIGNLELTGPYAEALSQLSYKLEDVAHQEPDAALGNGGLGRLASCFLD 151 |
| Arabidopsis thaliana type L | 155:SMEFLQGRALSNAVGNLGLNSAYGDALKRLGFDLESVASQEPDPALGNGGLGRLASCFLD 214 |
| Spinach | 161:SMEFLQGRALLNAIGNLELTDAYGDALKKLGHNLEAVACQERDAALGNGGLGRLASCFLD 220 |
| Rice type L | 90:SMEFLQGRALTNAVGNLELTGQYAEALQQLGHSLEDVATQEPDAALGNGGLGRLASCFLD 149 |
| Rice type L2 | 140:SMEFLQGRALTNAVGNLELTGQYAEALQQLGHSLEDVATQEPDAALGNGGLGRLASCFLD 199 |
| Corn type L | 144:SMEFLQGRALTNAIGNLEITGEYAEALKQLGQNLEDVASQEPDAALGNGGLGRLASCFLD 203 |
| Potato type H | 86:SMEYLQGRALTNAVGNLDIHNAYADALNKLGQQLEEVVEQEKDAALGNGGLGRLASCFLD 145 |
| Fava bean type H | 92:SMEFLQGRALTNAIGNLNIQDAYADALRKFGLELEEITEQEKDAALGNGGLGRLASCFLD 151 |
| Arabidopsis thaliana type H | 89:SMEYLQGRALTNAIGNLNLQGPYADALRTLGYELEEIAEQEKDAALGNGGLGRLASCFLD 148 |
| Rice type H | 88:SMEYLQGRALTNAVGNLGITGAYAEAVKKFGYELEALVGQEKDAALGNGGLGRLASCFLD 147 |
| Wheat | 80:SMEYLQGRALTNAVGNLAITGAYADALKKFGYELEAIAGQERDAALGNGGLGRLASCFLD 139 |
| Citrus type H | 91:SMEFLQGRTLTNAIGSLDIQNAYADALNNLGHVLEEIAEQEKDAALGNGGLGRLASCFLD 150 |
| E.coli MalQ | 66:SMEFLIGRLTGNNLLNLGWYQDVQDSLKAYDINLTDLLEEEIDPALGNGGLGRLAACFLD 125 |

Fig. 1B

| | |
|---|---|
| Potato type L | 148: SLATLNYPAWGYGLRYKYGLFKQRITKDGQEEVAEDWLEIGSPWEVVRN-DV-SYPIKFY 205 |
| Potato type L2 | 120: SMATLNYPAWGYGLRYQYGLFKQLITKDGQEEVAENWLEMGNPWEIVRN-DI-SYPVKFY 177 |
| Sweet potato type L | 148: SLATLNYPAWGYGLRYKYGLFKQRITKDGQEEVAEDWLELGNPWEIIRM-DV-SYPVKFF 205 |
| Fava bean type L | 152: SLATLNYPAWGYGLRYKYGLFKQRITKDGQEEVAEDWLEMGNPWEIVRN-DV-SYPVRFY 209 |
| Arabidopsis thaliana type L | 215: SMATLNYPAWGYGLRYKYGLFKQRITKDGQEEAAEDWLELSNPWEIVRN-DV-SYPIKFY 272 |
| Spinach | 221: SLATLNYPAWGYGLRYKYGLFKQMITKDGQEEVAENWLEIANPWELVRN-DV-SYSIKFY 278 |
| Rice type L | 150: SLATLNYPAWGYGLRYKHGLFKQIITKDGQEEVAENWLEMGNPWEIVRT-DV-SYPVKFY 207 |
| Rice type L2 | 200: SLATLNYPAWGYGLRYKHGLFKANHTKDGQEEVAENWLEMGNPWEIVRT-DV-SYPVKFY 257 |
| Corn type L | 204: SLATLNYPALGYGLRYEYGLFKQIITKDGQEEIAENWLEMGYPWEVVRN-DV-SYPVKFY 261 |
| Potato type H | 146: SMATLNLPAWGYGLRYRYGLFKQLITKAGQEEVPEDWLEKFSPWEIVRH-DV-VFPIRFF 203 |
| Fava bean type H | 152: SMATLNLPAWGYGLRYRYGLFKQIITKEGQEEVAEDWLEKFSPWEIVRH-DV-LYPIRFF 209 |
| Arabidopsis thaliana type H | 149: SMATLNLPAWGYGLRYRHGLFKQIITKKGQEEIPEDWLEKFSPWEIVRH-DV-VFPVRFF 206 |
| Rice type H | 148: SMATLNLPAWGYGLRYRYGLFKQCITKEGQEEIAEDWLEKFSPWEIVRH-DI-VYPIRFF 205 |
| Wheat | 140: SMATLNLPSWGYGLRYRYGLFKQRIAKEGQEEIAEDWLDKFSPWEIVRH-DV-VYPIRFF 197 |
| Citrus type H | 151: SMATLNLPAWGYGLRYRYGLFKQKITKQGQEEVAEDWLEKFSPWEVVRH-DV-VFPVRFF 208 |
| E.coli MalQ | 126: SMATVGQSATGYGLNYQYGLFRQSFVDGKQVEAPDDWHRSNYPWF---RHNEALDVQVGIG 183 |

| | |
|---|---|
| Potato type L | 206: GKVSTGSDGKRYWIGGEDIKAVAYDVPIPGYKTRTTISLRLWSTQVPSADFDLSAFNAGE 265 |
| Potato type L2 | 178: GKVIEGADGRKEWAGGEDITAVAYDVPIPGYKTKTTINLRLWTTKLAAEAFDLYAFNNGD 237 |
| Sweet potato type L | 206: GKVITGSDGKKHWIGGEDILAVAYDVPIPGYKTRTTISLRLWSTKVPSEDFDLYSFNAGE 265 |
| Fava bean type L | 210: GKVVSGSDGKKHWVGGEDIKAVAHDVPIPGYKTRSTINLRLWSTKAASEEFDLNAFNSGR 269 |
| Arabidopsis thaliana type L | 273: GKVVFGSDGKKRWIGGEDIVAVAYDVPIPGYKTKTTINLRLWSTKAPSEDFDLSSYNSGK 332 |
| Spinach | 279: GKVVSGSDGRSHWTGGEDIRAVAYDVPIPGYQTKTTINLRLWCTTVSSEDFDLSAFNAGE 338 |
| Rice type L | 208: GKVVEGTDGRMHWIGGENIKVVAHDIPIPGYKTKTTNNLRLWSTTVPSQDFDLEAFNAGD 267 |
| Rice type L2 | 258: GKVVEGTDGRMHWIGGENIKVVAHDIPIPGYKTKTTNNLRLWSTTVPSQDFDLEAFNAGD 317 |
| Corn type L | 262: GKVVEGTDGRKHWIGGENIKAVAHDVPIPGYKTRTTNNLRLWSTTVPAQDFDLAAFNSGD 321 |
| Potato type H | 204: GHVEVLPSGSRKWVGGEVLQALAYDVPIPGYRTKNTNSLRLWEAKASSEDFNLFLFNDGQ 263 |
| Fava bean type H | 210: GQVEVNPDGSRQWIGGEVIQALAYDVPIPGYQTKNTISLRLWEAKACADDFDLFLFNDGQ 269 |
| Arabidopsis thaliana type H | 207: GKVQVNPDGSRKWVDGDVVQALAYDVPIPGYGTKNTISLRLWEAKARAEDLDLFQFNEGE 266 |
| Rice type H | 206: GHVEILPDGSRKWVGGEVLNALAYDVPIPGYKTKNAISLRLWDAKASAEDFNLFQFNDGQ 265 |
| Wheat | 198: GHVEISPDGKRKWAGGEVLNALAYDVPIPGYKTKNAISLRLWDATATAEDFNLFQFNDGQ 257 |
| Citrus type H | 209: GSVMVNPNGTRKWVGGEVVQAVAYDIPIPGYKTKNTISLRLWDAKASAEDFNLFQFNDGQ 268 |
| E.coli MalQ | 184: GKVTK---DGR---WEPEFTITGQAWDLPVVGYRNGVAQPLRLWQATHAHP-FDLTKFNDGD 238 |

Fig. 1C

| | |
|---|---|
| Potato type L | 266:HTKACEAQANAEKICYILYPGDESEEGKILRLKQQYTLCSASLQDIISRFERRSGDRIK- 324 |
| Potato type L2 | 238:HAKAYEAQKKAEKICYVLYPGDESLEGKTLRLKQQYTLCSASLQDIIARFEKRSGNAVN- 296 |
| Sweet potato type L | 266:HTKACEAQANAEKICYILYPGDESIEGKILRLKQQYTLCSASLQDIIARFERRSGEYVK- 324 |
| Fava bean type L | 270:HTEASEALANAEKICYILYPGDESIEGKTLRLKQQYTLCSASLQDIIARFERRSGASVN- 328 |
| Arabidopsis thaliana type L | 333:HTEAAEALFNAEKICFVLYPGDESTEGKALRLKQQYTLCSASLQDIVARFETRSGGNVN- 391 |
| Spinach | 339:HAKANEARANAEKICSVLYPGDESMEGKILRLKQQYTLCSASLQDIISQFERRSGEHVN- 397 |
| Rice type L | 268:HASAYEAHLNAEKICHVLYPGDESPEGKVLRLKQQYTLCSASLQDIIARFERRAGDSLS- 326 |
| Rice type L2 | 318:HASAYEAHLNAEK----------P--------HY-----R-DIIARFERRAGDSLS- 349 |
| Corn type L | 322:HTKAYEAHLNAKKICHILYPGDESLEGKVLRLKQQYTLCSASLQDIIARFESRAGESLN- 380 |
| Potato type H | 264:YDAAAQLHSRAQQICAVLYPGDATENGKLLRLKQQFFLCSASLQDIIARFKEREDGKGSH 323 |
| Fava bean type H | 270:LESASVLHSRAQQICSVLYPGDATEGGKLLRLKQQYFLCSASLQDIISRFKERROG--- 325 |
| Arabidopsis thaliana type H | 267:YELAAQLHSRAQQICTVLYPGDATENGKLLRLKQQFFLCSASLQDIISRFHERSTTEGSR 326 |
| Rice type H | 266:YESAAQLHARAQQICAVLYPGDATEEGKLLRLKQQYFLCSASLQDIFFRFKERKADRVSG 325 |
| Wheat | 258:YESAAQLHSRAQQICAVLYPGDATEEGKLLRLKQQYFLCSASLQDIIFRFKERKADRVSG 317 |
| Citrus type H | 269:YESAAQLHSRAQQICAVLYPGDSTEEGKLLRLKQQFFLCSASLQDMILRFKERKS---GR- 325 |
| E.coli MalQ | 239:FLRAEQQGINAEKLTKVLYPNDNHTAGKKLRLMQQYFQCACSVADILRRH---HLAG---R 293 |

| | |
|---|---|
| Potato type L | 325:-WEE---FPEKVAVQMNDTHPTLCIPELMRILIDLKGLNWNEAWNITQRTVAYTNHTVLP 380 |
| Potato type L2 | 297:-WDQ---FPEKVAVQMNDTHPTLCIPELLRILMDVKGLSWKQAWEITQRTVAYTNHTVLP 352 |
| Sweet potato type L | 325:-WEE---FPEKVAVQMNDTHPTLCIPELIRILIDLKGLSWKEAWNITQRTVAYTNHTVLP 380 |
| Fava bean type L | 329:-WED---FPEKVAVQMNDTHPTLCIPELMRILIDIKGLSWKDAWNITQRTVAYTNHTVLP 384 |
| Arabidopsis thaliana type L | 392:-WEE---FPEKVAVQMNDTHPTLCIPELMRILMDLKGLSWEDAWKITQRTVAYTNHTVLP 447 |
| Spinach | 398:-WEE---FPEKVAVQMNDTHPTLCIPELMRILIDVKGLAWKEAWNITQRTVAYTNHTVLP 453 |
| Rice type L | 327:-WED---FPSKVAVQMNDTHPTLCIPELMRILIDVKGLSWNEAWSITERTVAYTNHTVLP 382 |
| Rice type L2 | 350:-WED---FPSKVAVQMNDTHPTLCIPELMRILIDVKGLSWNEAWSITERTVAYTNHTVLP 405 |
| Corn type L | 381:-WED---FPSKVAVQMNDTHPTLCIPELMRILMDVKGLSWSEAWSITERTVAYTNHTVLP 436 |
| Potato type H | 324:Q--WS-EFPKKVAIQLNDTHPTLTIPELMRLLMDDEGLGWDESWNITTRTIAYTNHTVLP 380 |
| Fava bean type H | 326:PWNWS-EFPTKVAVQLNDTHPTLSIPELMRLLMDDEGLGWDEAWAVTSKTVAYTNHTVLP 384 |
| Arabidopsis thaliana type H | 327:KWS---EFPSKVAVQMNDTHPTLAIPELMRLLMDDNGLGWDEAWDVTSKTVAYTNHTVLP 383 |
| Rice type H | 326:KWS---EFPAKVAVQLNDTHPTLAIPELMRLLMDVEGLGWDEAWDITNKTIAYTNHTVLP 382 |
| Wheat | 318:KWS---EFPSKVAVQMNDTHPTLAIPELMRLLMDVEGLGWDEAWAVTNKTVAYTNHTVLP 374 |
| Citrus type H | 326:QWS---EFPSKVAVQLNDTHPTLAIPELMRLLMDEEGLGWDEAWDITTRTVAYTNHTVLP 382 |
| E.coli MalQ | 294:ELHELADYEV--IQLNDTHPTIAIPELLRVLIDEHQMSWDDAWAITSKTFAYTNHTLMP 350 |

Fig. 1D

```
Potato type L            381:EALEKWSYELMQKLLPRHVEIIEAIDEELVHEIVLKYGSMDLNKLEEKLTTMRILENFDL 440
Potato type L2           353:EALEKWSFTLLGELLPRHVEIIAMIDEELLHTILAEYGTEDLDLLQEKLNQMRILDNVEI 412
Sweet potato type L      381:EALEKWSYELMEKLLPRHIEIIEMIDEQLINEIVSEYGTSDLDMLEKKLNDMRILENFDI 440
Fava bean type L         385:EALEKWSMDLMEKLLPRHVEIIEMIDEELIRTIIAEYGTADSDLLDKKLKEMRILENVEL 444
Arabidopsis thaliana type L  448:EALEKWSLELMEKLLPRHVEIIEKIDEELVRTIVSEYGTADPDLLEEKLKAMRILENVEL 507
Spinach                  454:EALEKWSFELMQSLLPRHVEIIEKIDEELVDTIVSEYGTDDPKLLMGKLNELRILENFHL 513
Rice type L              383:EALEKWSLDIMQKLLPRHVEIIEKIDGELMNIIISKYGTEDTSLLKKKIKEMRILDNIDL 442
Rice type L2             406:EALEKWSLDIMQKLLPRHVEIIEKIDGELMNIIISKYGTEDTSLLKKKIKEMRILDNIDL 465
Corn type L              437:EALEKWSLDIMQKLLPRHVEIIETIDEELINNIVSKYGTTDTELLKKKLKEMRILDNVDL 496
Potato type H            381:EALEKWSQAVMWKLLPRHMEIIEEIDKRFVATIMS----ERP-DLENKMPS-MRIL---- 430
Fava bean type H         385:EALEKWSQPVMWKLLPRHMEIIEEIDRRFVALISK--TRL-DLEDEVSN-MRIL---- 434
Arabidopsis thaliana type H  384:EALEKWSQSLMWKLLPRHMEIIEEIDKRFVQTIRD--TRV-DLEDKISS-LSIL---- 433
Rice type H              383:EALEKWSQIVMRKLLPRHMEIIEEIDKRFKEMVIS--TRK-EMEGKIDS-MRIL---- 432
Wheat                    375:EALEKWSQAVMKKLLPRHMEIIEEIDKRFREMVIS--TRK-DMEGKIES-MRVL---- 424
Citrus type H            383:EALEKWSQAVMWKLLPRHMEIIEEIDKRFIAMVRS--TRS-DLESKIPS-MCIL---- 432
E.coli MalQ              351:EALERWDVKLVKGLLPRHMQIINEINTR-----------F--KT------L----- 382

Potato type L            441:PSSVAELFIKPEISVDDDTETVEVHD-KVEASDKVVTNDEDDTGKKTSVKIEAAAE---- 495
Potato type L2           413:PSSVLELLIKAEE-SAADV-----E--KAADEEQEEEGKDD-SKDEETEA-VKAETTNEE 462
Sweet potato type L      441:PSSIANLFTKPK--ET--SIVDPSE-EVEVSGKVVTESVEVSDKVVTESEKDELEE--- 491
Fava bean type L         445:PAEFADILVKTKEATDISSEEVQIS--KEGGEEEE-TSKEGGEEEEEKEVGGGREEGDDG 502
Arabidopsis thaliana type L  508:PSAFADVIVKPVNKPVTAKDA-QNGV-KTEQEE-EKTA----GEEEED--------- 548
Spinach                  514:PSSVASII-KDKITCQVDE-----D--KKI--------EIS-DEVD-GLVVVEESE-- 551
Rice type L              443:PDSIAKLFVKPKEKKESPAKLKEKLLVK-SL-EPSVVVEEKTVSKV--EINEDSEEVEYD 498
Rice type L2             466:PDSIAKLFVKPKEKKESPAKLKEKLLVK-SL-EPSVVVEEKTVSKV--EINEDSEEVEVD 521
Corn type L              497:PASISQLFVKPKDKKESPAKSKQKLLVK-SL-ETIVEVEEKTELEEEAEVLSEIEEEKLE 554
Potato type H            431:----------------------------DH-------N-------- 433
Fava bean type H         435:----------------------------DN-------N-------- 437
Arabidopsis thaliana type H  434:----------------------------DN-------N-------- 436
Rice type H              433:----------------------------DN-------S-------- 435
Wheat                    425:----------------------------DN-------N-------- 427
Citrus type H            433:----------------------------DN-------N-------- 435
E.coli MalQ              383:--------V-----EKTWPGDEKVWAK--LAV------------- 399
```

Fig. 1E

| | | |
|---|---|---|
| Potato type L | 496: | K-----------DIDKKTPVS-----PEPAVIPPKKVRMANLCVVGGHAVNGVAEIHSE 538 |
| Potato type L2 | 463: | EETEVKKVEVEDSQAKIK----RIFG-PHPNKPQV--VHMANLCVVSGHAVNGVAEIHSE 515 |
| Sweet potato type L | 492: | K-----------DTELEKDED-----PVPAPIPPKMVRMANLCVVGGHAVNGVAEIHSD 534 |
| Fava bean type L | 503: | KEDEVEKAIAEKDGTVKSSIGDKKKKLPEPVPVPPKLVRMANLCVVGGHAVNGVAEIHSE 562 |
| Arabidopsis thaliana type L | 549: | ---EV-----------------IPEPTVEPPKMVRMANLAVVGGHAVNGVAEIHSE 584 |
| Spinach | 552: | -EGDIEKQAVEEPVPK-----------PAKL----VRMANLCIVGGHAVNGVAEIHSQ 593 |
| Rice type L | 499: | SEEVVEAENEDSEDELDPFV--KSD----PKL-PRV-VRMANLCVVGGHSVNGVAAIHSE 550 |
| Rice type L2 | 522: | SEEVVEAENEDSEDELDPFV--KSD----PKL-PRV-VRMANLCVVGGHSVNGVAAIHSE 573 |
| Corn type L | 555: | SEEVEAEEAS-SEDELDPFV--KSD----PKL-PRV-VRMANLCVVGGHSVNGVAEIHSE 605 |
| Potato type H | 434: | -----------------------ATK-PVV--HMANLCVVSSHTVNGVAQLHSD 461 |
| Fava bean type H | 438: | -----------------------LQK-PVV--RMANLCVVSSHTVNGVAQLHSD 465 |
| Arabidopsis thaliana type H | 437: | -----------------------PQK-PVV--RMANLCVVSSHTVNGVAQLHSD 464 |
| Rice type H | 436: | ----------------------NPQKPVV--RMANLCVVSAHTVNGVAELHSN 464 |
| Wheat | 428: | -----------------------P-EKPVV--RMANLCVVAGHTVNGVAELHSN 455 |
| Citrus type H | 436: | -----------------------PKK-PVV--RMANLCVVSAHTVNGVAQLHSD 463 |
| E.coli MalQ | 400: | ---------VHD-------KQV-----------HMANLCVVGGFAVNGVAALHSD 427 |

| | | |
|---|---|---|
| Potato type L | 559: | IVKEEVFNDFYELWPEKFQNKTNGVTPRRWIRFCNPPLSAIITKWTGTEDWVLKTEKLAE 598 |
| Potato type L2 | 516: | IVKDEVFNEFYKLWPEKFQNKTNGVTPRRWLSFCNPELSEIITKWTGSDDWLVNTEKLAE 575 |
| Sweet potato type L | 535: | IVKEDVFNDFYQLWPEKFQNKTNGVTPRRWIRFCNPALSNIITKWIGTEDWVLNTEKLAE 594 |
| Fava bean type L | 563: | IVKDDVFNAFYKLWPEKFQNKTNGVTPRRWIRFCNPDLSKIITQWIGTEDWILNTEKLAE 621 |
| Arabidopsis thaliana type L | 585: | IVKQDVFNDFVQLWPEKFQNKTNGVTPRRWIRFCNPYLSDIITNWIGTEDWVLNTEKVAE 644 |
| Spinach | 594: | IVKEQVFRDFFELWPEKFQNKTNGVTPRRWIRFCNPELSSILTKWIGSDDWVLNTEKLAE 653 |
| Rice type L | 551: | IVKEDVFNSFYEMWPAKFQNKTNGVTPRRWIRFCNPELSAIISKWIGSDDWVLNTDKLAE 610 |
| Rice type L2 | 574: | IVKEDVFNSFYEMWPAKFQNKTNGVTPRRWIRFCNPELSAIISKWIGSDDWVLNTDKLAE 633 |
| Corn type L | 606: | IVKQDVFNSFYEMWPTKFQNKTNGVTPRRWIRFCNPALSALISKWIGSDDWVLNTDKLAE 665 |
| Potato type H | 462: | ILKAELFADYVSVWPTKFQNKTNGITPRRWIRFCSPELSHIITKWLKTDQWVTNLELLAN 521 |
| Fava bean type H | 466: | ILKSELFASYVSIWPTKFQNKTNGITPRRWINFCSPELSRIITKWLKTDKWVTNLDLLTG 525 |
| Arabidopsis thaliana type H | 465: | ILKAELFADYVSIWPNKFQNKTNGITPRRWLRFCSPELSDIITKWLKTDKWITDLDLLTG 524 |
| Rice type H | 465: | ILKEEFLADYLSIWPNKFQNKTNGITPRRWLRFCNPELSEIVTKWLKTDQWTSNLDLLTG 524 |
| Wheat | 456: | ILKQELFADYVSIWPNKFQNKTNGITPRRWLRFCNPELSEIVTKWLKTDQWTSNLDLLTG 515 |
| Citrus type H | 464: | ILKADLFADYVSLWPNKLQNKTNGITPRRWLRFCNPELSKIITKWLKTDQWVTNLDLLVG 523 |
| E.coli MalQ | 428: | LVVKDLFPEYHQLWPNKFHNVTNGITPRRWIKQCNPALAALLDKSLQKE-WANDLDQLIN 486 |

Fig. 1F

| | |
|---|---|
| Potato type L | 599:LQKFADNEDLQNEWREAKRSNKIKVVSFLKEKTGYSVVPDAMFDIQVKRIHEYKRQLLNI 658 |
| Potato type L2 | 576:LRKFADNEELQSEWRKAKGNNKMKIVSLIKEKTGYVVSPDAMFDVQIKRIHEYKRQLLNI 635 |
| Sweet potato type L | 595:LRKFADNEDLQIEWRAAKRSNKVKVASFLKERTGYSVSPNAMFDIQVKRIHEYKRQLLNI 654 |
| Fava bean type L | 622:LRKFADNEDLQTQWREAKRNNKVKVAAFLRERTGYSVSPDSMFDIQVKRIHEYKRQLLNI 681 |
| Arabidopsis thaliana type L | 645:LRKFADNEDLQSEWRAAKKKNKLKVVSLIKERTGYTVSPDAMFDIQIKRIHEYKRQLLNI 704 |
| Spinach | 654:LRKFADNKDLHTEWMEAKRNNKQKVVSLIKERTGYTVSPDAMFDIQIKRIHEYKRQLMNI 713 |
| Rice type L | 611:LKKFADDEDLQSEWRAAKKANKVKVVSLIREKTGYIVSPDAMFDVQVKRIHEYKRQLLNI 670 |
| Rice type L2 | 634:LKKFADDEDLQSEWRAAKKANKVKVVSLIREKTGYIVSPDAMFDVQVKRIHEYKRQLLNI 693 |
| Corn type L | 666:LKKFADNEDLHSEWRAAKKANKMKVISLIREKTGYIVSPDAMFDVQVKRIHEYKRQLLNI 725 |
| Potato type H | 522:LREFADNSELHAEWESAKMANKQRLAQYILHVTGVSIDPNSLFDIQVKRIHEYKRQLLNI 581 |
| Fava bean type H | 526:LREFADNEDLQAEWLSAKRANKQRLAQYVLQVTGENIDPDSLFDIQVKRIHEYKRQLLNI 585 |
| Arabidopsis thaliana type H | 525:LRQFADNEELQSEWASAKTANKKRLAQYIERVTGVSIDPTSLFDIQVKRIHEYKRQLMNI 584 |
| Rice type H | 525:LRKFADDEKLHAEWASAKLASKKRLAKHVLDVTGVTIDPNSLFDIQIKRIHEYKRQLLNI 584 |
| Wheat | 516:LRKFADDEKLHAEWAAAKLASKKRLAKHVLDVTGVTIDPDSLFDIQIKRIHEYKRQLMNI 575 |
| Citrus type H | 524:LRQFADNTELQAEWESAKMASKKHLADYIWRVTGVTIDPNSLFDIQVKRIHEYKRQLLNI 583 |
| E.coli MalQ | 487:LVKLADDAKFRDLYRVIKQANKVRLAEFVKVRTGIDINPQAIFDIQIKRLHEYKRQHLNL 546 |

Positions of motif sequences 3L and 3H

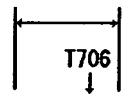
T706

| | |
|---|---|
| Potato type L | 659:FGIVYRYKKMKEMTAAERKTNFVPRVCIFGGKAFATYVQAKRIVKFITDVGATINHDPEI 718 |
| Potato type L2 | 636:FGIVYRYKKMKEMSPEERKEKFVPRVCIFGGKAFATYVQAKRIVKFITDVGETVNHDPEI 695 |
| Sweet potato type L | 655:LGIVYRYKQMKEMSAREREAKFVPRVCIFGGKAFATYVQAKRIAKFITDVGATINHDPEI 714 |
| Fava bean type L | 682:FGIVYRYKKMKEMNAAERKENFVPRVCIFGGKAFATYVQAKRIVKFITDVGATVNHDPEI 741 |
| Arabidopsis thaliana type L | 705:LGIVYRYKKMKEMSASEREKAFVPRVCIFGGKAFATYVQAKRIVKFITDVASTINHDPEI 764 |
| Spinach | 714:LGIVYRYKKMKEMSAAERKEKYVPRVCIFGGKAFATYVQAKRIVKFITDVGATINHDPEI 773 |
| Rice type L | 671:LGIVYRYKKMKEMSAKDRINSFVPRVCIFGGKAFATYVQAKRIVKFITDVAATVNHDPEI 730 |
| Rice type L2 | 694:LGIVYRYKKMKEMSAKDRINSFVPRVCIFGGKAFATYVQAKRIVKFITDVAATVNHDPEI 753 |
| Corn type L | 726:LGIVYRYKKMKEMSTEERAKSFVPRVCIFGGKAFATYIQAKRIVKFITDVAATVNHDSDI 785 |
| Potato type H | 582:LGVIYRYKKLKGMSPEERKNTT-PRTVMIGGKAFATYTNAKRIVKLVTDVGDVVNSDPDV 640 |
| Fava bean type H | 586:LGVIYRYKKLKEMSPEERKSTT-ARTVMIGGKAFATYTNAKRIVKLVDDVGSVVNSDPEV 644 |
| Arabidopsis thaliana type H | 585:LGVVYRFKKLKEMKPEERKKTV-PRTVMIGGKAFATYTNAKRIVKLVNDVGDVVNSDPEV 643 |
| Rice type H | 585:LGAVYRYKKLKGMSAEERQKVT-PRTVMIGGKAFATYTNAKRIVKLVNDVGAVVNNDPDV 643 |
| Wheat | 576:LGAVYRYKKLKEMSAADRQKVT-PRTVMVGGKAFATYTNAKRIVKLVNDVGAVVNNDADV 634 |
| Citrus type H | 584:LGAIYRYKKLKEMSPQERKKTT-PRTIMFGGKAFATYTNAKRIVKLVNDVGEVVNTDPEV 642 |
| E.coli MalQ | 547:LHILALYKEIRENPQADRV----PRVFLFGAKAAPGYYLAKNIIFAINKVADVINNDPLV 602 |

Fig. 1G

| | |
|---|---|
| Potato type L | 719:GDLLKVVFVPDYNVSVAELLIPASDLSEHISTAGMEASGTSNMKFAMNGCIQIGTLDGAN 778 |
| Potato type L2 | 696:GDLLKVVFVPDYNVSVAEVLIPGSELSQHISTAGMEASGTSNMKFSMNGCLLIGTLDGAN 755 |
| Sweet potato type L | 715:GDLLKVIFVPDYNVSAAELLIPASGLSQHISTAGMEASGQSNMKFAMNGCILIGTLDGAN 774 |
| Fava bean type L | 742:GDLLKVIFVPDYNVSVAEMLIPASELSQHISTAGMEASGTSNMKFAMNGCLQIGTLDGAN 801 |
| Arabidopsis thaliana type L | 765:GDLLKVIFVPDYNVSVAELLIPASELSQHISTAGMEASGTSNMKFSMNGCVLIGTLDGAN 824 |
| Spinach | 774:GDLLKVVFIPDYNVSVAELLIPASELSQHISTAGMEASGTSNMKFSMNGCILIGTLDGAN 833 |
| Rice type L | 731:GDLLKVVFIPDYNVSVAEALIPASELSQHISTAGMEASGTSNMKFAMNGCILIGTLDGAN 790 |
| Rice type L2 | 754:GDLLKVVFIPDYNVSVAEALIPASELSQHISTAGMEASGTSNMKFAMNGCILIGTLDGAN 813 |
| Corn type L | 786:GDLLKVVFVPDYNVSVAEALIPASELSQHISTAGMEASGTSNMKFAMNGCILIGTLDGAN 845 |
| Potato type H | 641:NDYLKVVFVPNYNVSVAEMLIPGSELSQHISTAGMEASGTSNMKFALNGCLIIGTLDGAN 700 |
| Fava bean type H | 645:NSYLKVVFVPNYNVSVAEVLIPGSELSQHISTAGMEASGTSNMKFALNRVLIIGTLDGAN 704 |
| Arabidopsis thaliana type H | 644:NEYLKVVFVPNYNVTVAEMLIPGSELSQHISTAGMEASGTSNMKFALNGCLIIGTLDGAN 703 |
| Rice type H | 644:NKYLKVVFIPNYNVSVAEVLIPGSELSQHISTAGMEASGTSNMKFSLNGCVIIGTLDGAN 703 |
| Wheat | 635:NKYLKVVFIPNYNVSVAEVLIPGSELSQHISTAGMEASGTSNMKFSLNGCVIIGTLDGAN 694 |
| Citrus type H | 643:NSYLKVVFVPNYNVSVAELLIPGSELSQHISTAGMEASGTSNMKFSLNGCLIIGTLDGAN 702 |
| E.coli MalQ | 603:GDKLKVVFLPDYCVSAAEKLIPAADISEQISTAGKEASGTGNMKLALHNGALTVGTLDGAN 662 |

| | |
|---|---|
| Potato type L | 779:VEIREEVGEENFFLFGAQAHEIAGLR-KERADGKFVPDERFEEVK--EFVRSGAFGSYN- 834 |
| Potato type L2 | 756:VEIREEVGEDNFFLFGAQAHEIAGLR-KERAEGKFVPDPRFEEVK--AFIRTGVFGTYN- 811 |
| Sweet potato type L | 775:VEIRQEVGEENFFLFGAEAHEIAGLR-KERAEGKFVPDERFEEVK--EFIKRGVFGSNT- 830 |
| Fava bean type L | 802:VEIREEVGADNFFLFGAKAREIVGLR-KERARGKFVPDPRFEEVK--KFVRSGVFGSYN- 857 |
| Arabidopsis thaliana type L | 825:VEIREEVGEENFFLFGAKADQIVNLR-KERAEGKFVPDPTFEEVK--KFVGSGVFGSNS- 880 |
| Spinach | 834:VEIREEVGEDNFFLFGARAHDIAGLR-KERAEGKYVPDPCFEEVK--EYVRSGVFGSNS- 889 |
| Rice type L | 791:VEIREEVGEENFFLFGAEAHEIAGLR-KERAQGKFVPDPRFEEVK--RFVRSGVFGTYN- 846 |
| Rice type L2 | 814:VEIREEVGEENFFLFGAEAHEIAGLR-KERAQGKFVPDPRFEEVK--RFVRSGVFGTYN- 869 |
| Corn type L | 846:VEIREEVGEENFFLFGAEAHEIAGLR-KERAEGKFVPDPRFEEVK--EFVRSGVFGTYS- 901 |
| Potato type H | 701:VEIREEIGEDNFFLFGATADEVPQLR-KDRENGLFKPDPRFEEAK--QFIRSGAFGTYD- 756 |
| Fava bean type H | 705:VEIREEIGEENFFLFGATADEVPRLR-KERENGLFKPDPRFEEAK--KFIRSGVFGSYD- 760 |
| Arabidopsis thaliana type H | 704:VEIREEVGEENFFLFGATADQVPRLR-KEREDGLFKPDPRFEEAK--QFVKSGVFGSYD- 759 |
| Rice type H | 704:VEIREEVGQENFFLFGAKADQVAGLR-KDRENGLFKPDPRFEEAK--QLIRSGAFGTYD- 759 |
| Wheat | 695:VEIREEVGQDNFFLFGAKADQVAGLR-KDRENGLFKPDPRFEEAK--QFIRSGAFGTYD- 750 |
| Citrus type H | 703:VEIRQEIGEENFFLFGAGADQVPKLR-KEREDGLFKPDPRFEEAK--QFIRSGAFGSYD- 758 |
| E.coli MalQ | 663:VEIAEKVGEENIFIFGHTVKQVKAILAKGYDPVKWRKKDKVLDAVLKELES-GKYSDGDK 721 |

Fig. 1H

| | | | |
|---|---|---|---|
| Potato type L | 835:---YDDLIGSLEGNEGFGRADYFLVGKDFPSYIECQEKVDEAYRDQKRWTTMSILNTAGSY | 892 | |
| Potato type L2 | 812:---YEELMGSLEGNEGYGRADYFLVGKDFPDYIECQDKVDEAYRDQKKWTKMSILNTAGSF | 869 | |
| Sweet potato type L | 831:---YDELLGSLEGNEGFGRGDYFLVGKDFPSYIECQEKVDEAYRDQKIWTRMSILNTAGSY | 888 | |
| Fava bean type L | 858:---YDELIGSLEGNEGFGRADYFLVGQDFPSYLECQEEVDKAYRDQKKWTRMSILNTAGSS | 915 | |
| Arabidopsis thaliana type L | 881:---YDELIGSLEGNEGFGRADYFLVGKDFPSYIECQEKVDEAYRDQKRWTRMSIMNTAGSF | 938 | |
| Spinach | 890:---YDELLGSLEGNEGFGRADYFLVGKDFPSYVECQEQVDQAYRDQQKWTRMSILNTAGSF | 947 | |
| Rice type L | 847:---YDDLMGSLEGNEGYGRADYFLVGKDFPSYIECQEKVDKAYRDQKLWTRMSILNTASSS | 904 | |
| Rice type L2 | 870:---YDDLMGSLEGNEGYGRADYFLVGKDFPSYIECQEKVDKAYRDQKLWTRMSILNTASSS | 927 | |
| Corn type L | 902:---YDELMGSLEGNEGYGRADYFLVGKDFPSYIECQEKVDEAYRDQKLWTRMSILNTAGSS | 959 | |
| Potato type H | 757:---YNPLLESLEGNSGYGRGDYFLVGHDFPSYMDAQARVDEAYKDRKRWIKMSILSTSGSG | 814 | |
| Fava bean type H | 761:---YNPLLDSLEGNSGYGRGDYFLVGYDFPSYMDAQEKVDEAYRDKKRWLKMSILSTAGSG | 818 | |
| Arabidopsis thaliana type H | 760:---YGPLLDSLEGNTGFGRGDYFLVGYDFPSYMDAQAKVDEAYKDRKGWLKMSILSTAGSG | 817 | |
| Rice type H | 760:---YAPLLDSLEGNSGFGRGDYFLVGYDFPSYIDAQAQVDEAYKDKKKWIKMSILNTAGSG | 817 | |
| Wheat | 751:---YTPLLDSLEGNTGFGRGDYFLVGYDFPSYIDAQARVDEAYKDKKKWVKMSILNTAGSG | 808 | |
| Citrus type H | 759:---YNPLLDSLEGNTGYGRGDYFLVGYDFPSYLEAQDRVDQAYKDRKKWLKMSILSTAGSG | 816 | |
| E.coli MalQ | 722:HAFDQMLHSIGKQGG-DP---YLVMA-DFAAYVEAQKQVDVLYRDQEAWTRAAILNTARCG | 777 | |

| | | | |
|---|---|---|---|
| Potato type L | 893:KFSSDRTIHEYAKDIW--NIEAVEIA | 916 | (SEQ ID NO:2) |
| Potato type L2 | 870:KFSSDRTIHQYARDIW--RIEPVELP | 893 | (SEQ ID NO:6) |
| Sweet potato type L | 889:KFSSDRTIHEYAKDIW--NIQPVVFP | 912 | (SEQ ID NO:4) |
| Fava bean type L | 916:KFSSDRTIHEYAREIW--NIEPVKLE | 939 | (SEQ ID NO:8) |
| Arabidopsis thaliana type L | 939:KFSSDRTIHEYAKDIW--NIKQVELP | 962 | (SEQ ID NO:10) |
| Spinach | 948:KFSSDRTIHQYAKDIW--NIHPVNLP | 971 | (SEQ ID NO:12) |
| Rice type L | 905:KFNSDRTIHEYAKDIW--DIKPVILP | 928 | (SEQ ID NO:16) |
| Rice type L2 | 928:KFNSDRTIHEYAKDIW--DIKPVILP | 951 | (SEQ ID NO:18) |
| Corn type L | 960:KFSSDRTIHEYAKDIW--DISPAILP | 983 | (SEQ ID NO:14) |
| Potato type H | 815:KFSSDRTISQYAKEIW--NIAECRVP | 838 | (SEQ ID NO:30) |
| Fava bean type H | 819:KFSSDRTIAQYAKEIW--NIEECRVP | 842 | (SEQ ID NO:26) |
| Arabidopsis thaliana type H | 818:KFSSDRTIAQYAKEIW--NIEACPVP | 841 | (SEQ ID NO:28) |
| Rice type H | 818:KFSSDRTIAQYAKEIW--GITASPVS | 841 | (SEQ ID NO:24) |
| Wheat | 809:KFSSDRTIDQYAKEIW--GISACPVP | 832 | (SEQ ID NO:20) |
| Citrus type H | 817:KFSSDRTIAQYAKEIW--NITECRTS | 840 | (SEQ ID NO:22) |
| E.coli MalQ | 778:MFSSDRSIRDYQARIWQAKR------ | 797 | (SEQ ID NO:35) |

Fig. 1I

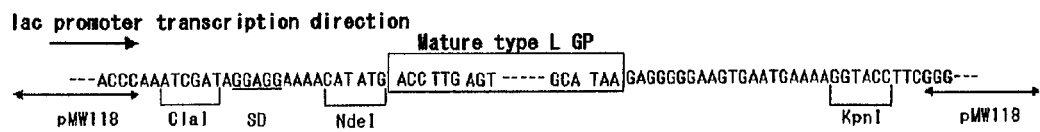

Fig. 2

Remaining activity of Potato type H GP (%)

<Immediately after purification>
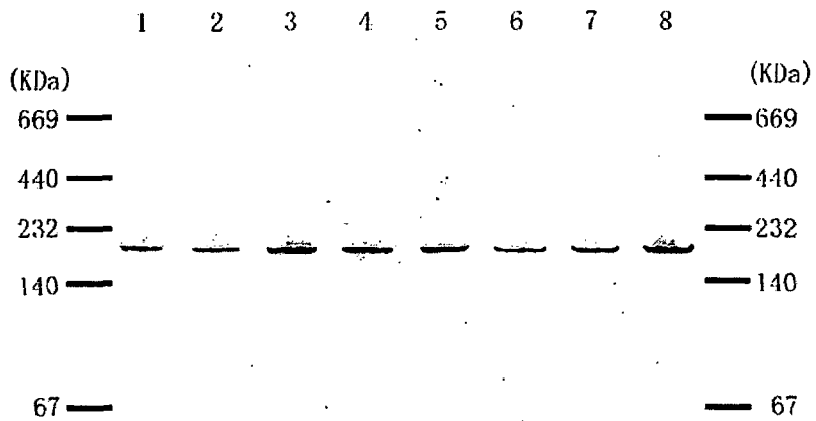
<4°C 5 months>
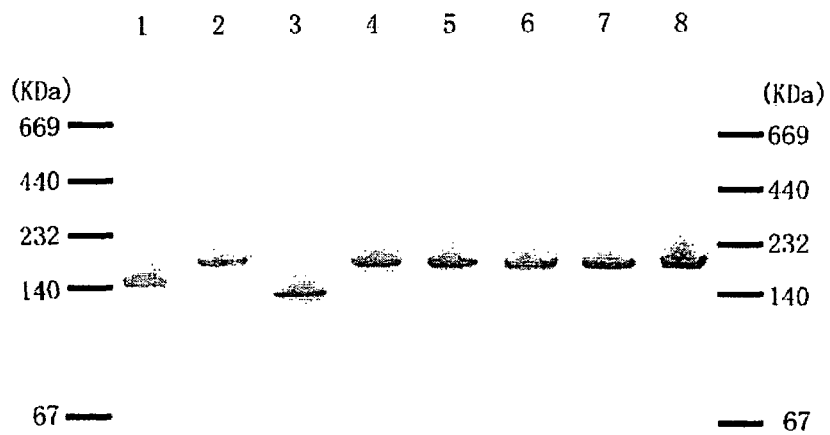
1 : Wild type　2 : F39L　3 : N135S　4 : T706I　5 : F39L+N135S
6 : F39L+T706I　7 : N135S+T706I　8 : F39L+N135S+T706I
Fig. 13

SEQUENCE LISTING

```
<160> NUMBER OF SEQ ID NOS: 48

<210> SEQ ID NO 1
<211> LENGTH: 3101
<212> TYPE: DNA
<213> ORGANISM: Solanum tuberosum
<220> FEATURE:
<221> NAME/KEY: CDS
<222> LOCATION: (44)..(2941)
<220> FEATURE:
<221> NAME/KEY: mat_peptide
<222> LOCATION: (194)..(2941)
```

<400> SEQUENCE: 1

```
atcactctca ttcgaaaagc tagatttgca tagagagcac aaa atg gcg act gca        55
                                              Met Ala Thr Ala
                                              -50 aat gga gca cac ttg ttc aac cat tac agc tcc aat tcc aga ttc atc       103
Asn Gly Ala His Leu Phe Asn His Tyr Ser Ser Asn Ser Arg Phe Ile
    -45                 -40                 -35 cat ttc act tct aga aac aca agc tcc aaa ttg ttc ctt acc aaa acc       151
His Phe Thr Ser Arg Asn Thr Ser Ser Lys Leu Phe Leu Thr Lys Thr
-30                 -25                 -20                 -15 tcc cat ttt cgg aga ccc aaa cgc tgt ttc cat gtc aac aat acc ttg       199
Ser His Phe Arg Arg Pro Lys Arg Cys Phe His Val Asn Asn Thr Leu
                -10                 -5                  -1   1 agt gag aaa att cac cat ccc att act gaa caa ggt ggt gag agc gac       247
Ser Glu Lys Ile His His Pro Ile Thr Glu Gln Gly Gly Glu Ser Asp
        5                   10                  15 ctg agt tct ttt gct cct gat gcc gca tct att acc tca agt atc aaa       295
Leu Ser Ser Phe Ala Pro Asp Ala Ala Ser Ile Thr Ser Ser Ile Lys
    20                  25                  30 tac cat gca gaa ttc aca cct gta ttc tct cct gaa agg ttt gag ctc       343
Tyr His Ala Glu Phe Thr Pro Val Phe Ser Pro Glu Arg Phe Glu Leu
35                  40                  45                  50 cct aag gca ttc ttt gca aca gct caa agt gtt cgt gat tcg ctc ctt       391
Pro Lys Ala Phe Phe Ala Thr Ala Gln Ser Val Arg Asp Ser Leu Leu
                55                  60                  65 att aat tgg aat gct acg tat gat att tat gaa aag ctg aac atg aag       439
Ile Asn Trp Asn Ala Thr Tyr Asp Ile Tyr Glu Lys Leu Asn Met Lys
            70                  75                  80 caa gcg tac tat cta tcc atg gaa ttt ctg cag ggt aga gca ttg tta       487
Gln Ala Tyr Tyr Leu Ser Met Glu Phe Leu Gln Gly Arg Ala Leu Leu
        85                  90                  95 aat gca att ggt aat ctg gag ctt act ggt gca ttt gcg gaa gct ttg       535
Asn Ala Ile Gly Asn Leu Glu Leu Thr Gly Ala Phe Ala Glu Ala Leu
    100                 105                 110 aaa aac ctt ggc cac aat cta gaa aat gtg gct tct cag gaa cca gat       583
Lys Asn Leu Gly His Asn Leu Glu Asn Val Ala Ser Gln Glu Pro Asp
115                 120                 125                 130 gct gct ctt gga aat ggg ggt ttg gga cgg ctt gct tcc tgt ttt ctg       631
Ala Ala Leu Gly Asn Gly Gly Leu Gly Arg Leu Ala Ser Cys Phe Leu
                135                 140                 145 gac tct ttg gca aca cta aac tac cca gca tgg ggc tat gga ctt agg       679
Asp Ser Leu Ala Thr Leu Asn Tyr Pro Ala Trp Gly Tyr Gly Leu Arg
            150                 155                 160 tac aag tat ggt tta ttt aag caa cgg att aca aaa gat ggt cag gag       727
Tyr Lys Tyr Gly Leu Phe Lys Gln Arg Ile Thr Lys Asp Gly Gln Glu
        165                 170                 175 gag gtg gct gaa gat tgg ctt gaa att ggc agt cca tgg gaa gtt gtg       775
Glu Val Ala Glu Asp Trp Leu Glu Ile Gly Ser Pro Trp Glu Val Val
    180                 185                 190 agg aat gat gtt tca tat cct atc aaa ttc tat gga aaa gtc tct aca       823
Arg Asn Asp Val Ser Tyr Pro Ile Lys Phe Tyr Gly Lys Val Ser Thr
195                 200                 205                 210 gga tca gat gga aag agg tat tgg att ggt gga gag gat ata aag gca       871
Gly Ser Asp Gly Lys Arg Tyr Trp Ile Gly Gly Glu Asp Ile Lys Ala
                215                 220                 225 gtt gcg tat gat gtt ccc ata cca ggg tat aag acc aga acc aca atc       919
Val Ala Tyr Asp Val Pro Ile Pro Gly Tyr Lys Thr Arg Thr Thr Ile
            230                 235                 240 agc ctt cga ctg tgg tct aca cag gtt cca tca gcg gat ttt gat tta       967
```

-continued

```
Ser Leu Arg Leu Trp Ser Thr Gln Val Pro Ser Ala Asp Phe Asp Leu
        245                 250                 255 tct gct ttc aat gct gga gag cac acc aaa gca tgt gaa gcc caa gca    1015
Ser Ala Phe Asn Ala Gly Glu His Thr Lys Ala Cys Glu Ala Gln Ala
260                 265                 270 aac gct gag aag ata tgt tac ata ctc tac cct ggg gat gaa tca gag    1063
Asn Ala Glu Lys Ile Cys Tyr Ile Leu Tyr Pro Gly Asp Glu Ser Glu
275                 280                 285                 290 gag gga aag atc ctt cgg ttg aag caa caa tat acc tta tgc tcg gct    1111
Glu Gly Lys Ile Leu Arg Leu Lys Gln Gln Tyr Thr Leu Cys Ser Ala
                295                 300                 305 tct ctc caa gat att att tct cga ttt gag agg aga tca ggt gat cgt    1159
Ser Leu Gln Asp Ile Ile Ser Arg Phe Glu Arg Arg Ser Gly Asp Arg
            310                 315                 320 att aag tgg gaa gag ttt cct gaa aaa gtt gct gtg cag atg aat gac    1207
Ile Lys Trp Glu Glu Phe Pro Glu Lys Val Ala Val Gln Met Asn Asp
        325                 330                 335 act cac cct aca ctt tgt atc cct gag ctg atg aga ata ttg ata gat    1255
Thr His Pro Thr Leu Cys Ile Pro Glu Leu Met Arg Ile Leu Ile Asp
340                 345                 350 ctg aag ggc ttg aat tgg aat gaa gct tgg aat att act caa aga act    1303
Leu Lys Gly Leu Asn Trp Asn Glu Ala Trp Asn Ile Thr Gln Arg Thr
355                 360                 365                 370 gtg gcc tac aca aac cat act gtt ttg cct gag gca ctg gag aaa tgg    1351
Val Ala Tyr Thr Asn His Thr Val Leu Pro Glu Ala Leu Glu Lys Trp
                375                 380                 385 agt tat gaa ttg atg cag aaa ctc ctt ccc aga cat gtc gaa atc att    1399
Ser Tyr Glu Leu Met Gln Lys Leu Leu Pro Arg His Val Glu Ile Ile
            390                 395                 400 gag gcg att gac gag gag ctg gta cat gaa att gta tta aaa tat ggt    1447
Glu Ala Ile Asp Glu Glu Leu Val His Glu Ile Val Leu Lys Tyr Gly
        405                 410                 415 tca atg gat ctg aac aaa ttg gag gaa aag ttg act aca atg aga atc    1495
Ser Met Asp Leu Asn Lys Leu Glu Glu Lys Leu Thr Thr Met Arg Ile
420                 425                 430 tta gaa aat ttt gat ctt ccc agt tct gtt gct gaa tta ttt att aag    1543
Leu Glu Asn Phe Asp Leu Pro Ser Ser Val Ala Glu Leu Phe Ile Lys
435                 440                 445                 450 cct gaa atc tca gtt gat gat gat act gaa aca gta gaa gtc cat gac    1591
Pro Glu Ile Ser Val Asp Asp Asp Thr Glu Thr Val Glu Val His Asp
                455                 460                 465 aaa gtt gaa gct tcc gat aaa gtt gtg act aat gat gaa gat gac act    1639
Lys Val Glu Ala Ser Asp Lys Val Val Thr Asn Asp Glu Asp Asp Thr
            470                 475                 480 ggt aag aaa act agt gtg aag ata gaa gca gct gca gaa aaa gac att    1687
Gly Lys Lys Thr Ser Val Lys Ile Glu Ala Ala Ala Glu Lys Asp Ile
        485                 490                 495 gac aag aaa act ccc gtg agt ccg gaa cca gct gtt ata cca cct aag    1735
Asp Lys Lys Thr Pro Val Ser Pro Glu Pro Ala Val Ile Pro Pro Lys
500                 505                 510 aag gta cgc atg gcc aac ttg tgt gtt gtg ggc ggc cat gct gtt aat    1783
Lys Val Arg Met Ala Asn Leu Cys Val Val Gly Gly His Ala Val Asn
515                 520                 525                 530 gga gtt gct gag atc cat agt gaa att gtg aag gag gag gtt ttc aat    1831
Gly Val Ala Glu Ile His Ser Glu Ile Val Lys Glu Glu Val Phe Asn
                535                 540                 545 gac ttc tat gag ctc tgg ccg gaa aag ttc caa aac aaa aca aat gga    1879
Asp Phe Tyr Glu Leu Trp Pro Glu Lys Phe Gln Asn Lys Thr Asn Gly
            550                 555                 560
```

```
gtg act cca aga aga tgg att cgt ttc tgc aat cct cct ctt agt gcc    1927
Val Thr Pro Arg Arg Trp Ile Arg Phe Cys Asn Pro Pro Leu Ser Ala
        565                 570                 575 atc ata act aag tgg act ggt aca gag gat tgg gtc ctg aaa act gaa    1975
Ile Ile Thr Lys Trp Thr Gly Thr Glu Asp Trp Val Leu Lys Thr Glu
580                 585                 590 aag ttg gca gaa ttg cag aag ttt gct gat aat gaa gat ctt caa aat    2023
Lys Leu Ala Glu Leu Gln Lys Phe Ala Asp Asn Glu Asp Leu Gln Asn
595                 600                 605                 610 gag tgg agg gaa gca aaa agg agc aac aag att aaa gtt gtc tcc ttt    2071
Glu Trp Arg Glu Ala Lys Arg Ser Asn Lys Ile Lys Val Val Ser Phe
            615                 620                 625 ctc aaa gaa aag aca ggg tat tct gtt gtc cca gat gca atg ttt gat    2119
Leu Lys Glu Lys Thr Gly Tyr Ser Val Val Pro Asp Ala Met Phe Asp
        630                 635                 640 att cag gta aaa cgc att cat gag tac aag cga caa ctg tta aat atc    2167
Ile Gln Val Lys Arg Ile His Glu Tyr Lys Arg Gln Leu Leu Asn Ile
        645                 650                 655 ttc ggc atc gtt tat cgg tat aag aag atg aaa gaa atg aca gct gca    2215
Phe Gly Ile Val Tyr Arg Tyr Lys Lys Met Lys Glu Met Thr Ala Ala
660                 665                 670 gaa aga aag act aac ttc gtt cct cga gta tgc ata ttt ggg gga aaa    2263
Glu Arg Lys Thr Asn Phe Val Pro Arg Val Cys Ile Phe Gly Gly Lys
675                 680                 685                 690 gct ttt gcc aca tat gtg caa gcc aag agg att gta aaa ttt atc aca    2311
Ala Phe Ala Thr Tyr Val Gln Ala Lys Arg Ile Val Lys Phe Ile Thr
            695                 700                 705 gat gtt ggt gct act ata aat cat gat cca gaa atc ggt gat ctg ttg    2359
Asp Val Gly Ala Thr Ile Asn His Asp Pro Glu Ile Gly Asp Leu Leu
        710                 715                 720 aag gta gtc ttt gtg cca gat tac aat gtc agt gtt gct gaa ttg cta    2407
Lys Val Val Phe Val Pro Asp Tyr Asn Val Ser Val Ala Glu Leu Leu
        725                 730                 735 att cct gct agc gat cta tca gaa cat atc agt acg gct gga atg gag    2455
Ile Pro Ala Ser Asp Leu Ser Glu His Ile Ser Thr Ala Gly Met Glu
        740                 745                 750 gcc agt gga acc agt aat atg aag ttt gca atg aat ggt tgt atc caa    2503
Ala Ser Gly Thr Ser Asn Met Lys Phe Ala Met Asn Gly Cys Ile Gln
755                 760                 765                 770 att ggt aca ttg gat ggc gct aat gtt gaa ata agg gaa gag gtt gga    2551
Ile Gly Thr Leu Asp Gly Ala Asn Val Glu Ile Arg Glu Glu Val Gly
            775                 780                 785 gaa gaa aac ttc ttt ctc ttt ggt gct caa gct cat gaa att gca ggg    2599
Glu Glu Asn Phe Phe Leu Phe Gly Ala Gln Ala His Glu Ile Ala Gly
        790                 795                 800 ctt aga aaa gaa aga gct gac gga aag ttt gta cct gat gaa cgt ttt    2647
Leu Arg Lys Glu Arg Ala Asp Gly Lys Phe Val Pro Asp Glu Arg Phe
        805                 810                 815 gaa gag gtg aag gaa ttt gtt aga agc ggt gct ttt ggc tct tat aac    2695
Glu Glu Val Lys Glu Phe Val Arg Ser Gly Ala Phe Gly Ser Tyr Asn
        820                 825                 830 tat gat gac cta att gga tcg ttg gaa gga aat gaa ggt ttt ggc cgt    2743
Tyr Asp Asp Leu Ile Gly Ser Leu Glu Gly Asn Glu Gly Phe Gly Arg
835                 840                 845                 850 gct gac tat ttc ctt gtg ggc aag gac ttc ccc agt tac ata gaa tgc    2791
Ala Asp Tyr Phe Leu Val Gly Lys Asp Phe Pro Ser Tyr Ile Glu Cys
            855                 860                 865 caa gag aaa gtt gat gag gca tat cgc gac cag aaa agg tgg aca acg    2839
Gln Glu Lys Val Asp Glu Ala Tyr Arg Asp Gln Lys Arg Trp Thr Thr
        870                 875                 880
```

```
atg tca atc ttg aat aca gcg gga tcg tac aag ttc agc agt gac aga    2887
Met Ser Ile Leu Asn Thr Ala Gly Ser Tyr Lys Phe Ser Ser Asp Arg
        885                 890                 895 aca atc cat gaa tat gcc aaa gac att tgg aac att gaa gct gtg gaa    2935
Thr Ile His Glu Tyr Ala Lys Asp Ile Trp Asn Ile Glu Ala Val Glu
    900                 905                 910 ata gca taagaggggg aagtgaatga aaataacaa aggcacagta agtagtttct      2991
Ile Ala
915 cttttttatca tgtgatgaag gtatataatg tatgtgtaag aggatgatgt tattaccaca  3051
taataagaga tgaagagtct cattttgctt caaaaaaaaa aaaaaaaaa              3101

<210> SEQ ID NO 2
<211> LENGTH: 966
<212> TYPE: PRT
<213> ORGANISM: Solanum tuberosum

<400> SEQUENCE: 2

Met Ala Thr Ala Asn Gly Ala His Leu Phe Asn His Tyr Ser Ser Asn
-50                 -45                 -40                 -35

Ser Arg Phe Ile His Phe Thr Ser Arg Asn Thr Ser Ser Lys Leu Phe
                -30                 -25                 -20

Leu Thr Lys Thr Ser His Phe Arg Arg Pro Lys Arg Cys Phe His Val
            -15                 -10                  -5

Asn Asn Thr Leu Ser Glu Lys Ile His His Pro Ile Thr Glu Gln Gly
     -1  1                  5                  10

Gly Glu Ser Asp Leu Ser Ser Phe Ala Pro Asp Ala Ala Ser Ile Thr
15                  20                  25                  30

Ser Ser Ile Lys Tyr His Ala Glu Phe Thr Pro Val Phe Ser Pro Glu
                35                  40                  45

Arg Phe Glu Leu Pro Lys Ala Phe Ala Thr Ala Gln Ser Val Arg
            50                  55                  60

Asp Ser Leu Leu Ile Asn Trp Asn Ala Thr Tyr Asp Ile Tyr Glu Lys
65                  70                  75

Leu Asn Met Lys Gln Ala Tyr Tyr Leu Ser Met Glu Phe Leu Gln Gly
            80                  85                  90

Arg Ala Leu Leu Asn Ala Ile Gly Asn Leu Glu Leu Thr Gly Ala Phe
95                  100                 105                 110

Ala Glu Ala Leu Lys Asn Leu Gly His Asn Leu Glu Asn Val Ala Ser
                115                 120                 125

Gln Glu Pro Asp Ala Ala Leu Gly Asn Gly Gly Leu Gly Arg Leu Ala
            130                 135                 140

Ser Cys Phe Leu Asp Ser Leu Ala Thr Leu Asn Tyr Pro Ala Trp Gly
            145                 150                 155

Tyr Gly Leu Arg Tyr Lys Tyr Gly Leu Phe Lys Gln Arg Ile Thr Lys
            160                 165                 170

Asp Gly Gln Glu Glu Val Ala Glu Asp Trp Leu Glu Ile Gly Ser Pro
175                 180                 185                 190

Trp Glu Val Val Arg Asn Asp Val Ser Tyr Pro Ile Lys Phe Tyr Gly
                195                 200                 205

Lys Val Ser Thr Gly Ser Asp Gly Lys Arg Tyr Trp Ile Gly Gly Glu
            210                 215                 220

Asp Ile Lys Ala Val Ala Tyr Asp Val Pro Ile Pro Gly Tyr Lys Thr
            225                 230                 235
```

-continued

```
Arg Thr Thr Ile Ser Leu Arg Leu Trp Ser Thr Gln Val Pro Ser Ala
240                 245                 250
Asp Phe Asp Leu Ser Ala Phe Asn Ala Gly Glu His Thr Lys Ala Cys
255                 260                 265                 270
Glu Ala Gln Ala Asn Ala Glu Lys Ile Cys Tyr Ile Leu Tyr Pro Gly
                275                 280                 285
Asp Glu Ser Glu Glu Gly Lys Ile Leu Arg Leu Lys Gln Gln Tyr Thr
            290                 295                 300
Leu Cys Ser Ala Ser Leu Gln Asp Ile Ile Ser Arg Phe Glu Arg Arg
        305                 310                 315
Ser Gly Asp Arg Ile Lys Trp Glu Glu Phe Pro Glu Lys Val Ala Val
    320                 325                 330
Gln Met Asn Asp Thr His Pro Thr Leu Cys Ile Pro Glu Leu Met Arg
335                 340                 345                 350
Ile Leu Ile Asp Leu Lys Gly Leu Asn Trp Asn Glu Ala Trp Asn Ile
                355                 360                 365
Thr Gln Arg Thr Val Ala Tyr Thr Asn His Thr Val Leu Pro Glu Ala
            370                 375                 380
Leu Glu Lys Trp Ser Tyr Glu Leu Met Gln Lys Leu Leu Pro Arg His
        385                 390                 395
Val Glu Ile Ile Glu Ala Ile Asp Glu Glu Leu Val His Glu Ile Val
    400                 405                 410
Leu Lys Tyr Gly Ser Met Asp Leu Asn Lys Leu Glu Glu Lys Leu Thr
415                 420                 425                 430
Thr Met Arg Ile Leu Glu Asn Phe Asp Leu Pro Ser Ser Val Ala Glu
                435                 440                 445
Leu Phe Ile Lys Pro Glu Ile Ser Val Asp Asp Thr Glu Thr Val
            450                 455                 460
Glu Val His Asp Lys Val Glu Ala Ser Asp Lys Val Val Thr Asn Asp
        465                 470                 475
Glu Asp Asp Thr Gly Lys Lys Thr Ser Val Lys Ile Glu Ala Ala Ala
    480                 485                 490
Glu Lys Asp Ile Asp Lys Lys Thr Pro Val Ser Pro Glu Pro Ala Val
495                 500                 505                 510
Ile Pro Pro Lys Lys Val Arg Met Ala Asn Leu Cys Val Val Gly Gly
                515                 520                 525
His Ala Val Asn Gly Val Ala Glu Ile His Ser Glu Ile Val Lys Glu
            530                 535                 540
Glu Val Phe Asn Asp Phe Tyr Glu Leu Trp Pro Glu Lys Phe Gln Asn
        545                 550                 555
Lys Thr Asn Gly Val Thr Pro Arg Arg Trp Ile Arg Phe Cys Asn Pro
    560                 565                 570
Pro Leu Ser Ala Ile Ile Thr Lys Trp Thr Gly Thr Glu Asp Trp Val
575                 580                 585                 590
Leu Lys Thr Glu Lys Leu Ala Glu Leu Gln Lys Phe Ala Asp Asn Glu
                595                 600                 605
Asp Leu Gln Asn Glu Trp Arg Glu Ala Lys Arg Ser Asn Lys Ile Lys
            610                 615                 620
Val Val Ser Phe Leu Lys Glu Lys Thr Gly Tyr Ser Val Val Pro Asp
        625                 630                 635
Ala Met Phe Asp Ile Gln Val Lys Arg Ile His Glu Tyr Lys Arg Gln
    640                 645                 650
Leu Leu Asn Ile Phe Gly Ile Val Tyr Arg Tyr Lys Lys Met Lys Glu
```

```
                    655              660              665              670

Met Thr Ala Ala Glu Arg Lys Thr Asn Phe Val Pro Arg Val Cys Ile
                675              680              685

Phe Gly Gly Lys Ala Phe Ala Thr Tyr Val Gln Ala Lys Arg Ile Val
            690              695              700

Lys Phe Ile Thr Asp Val Gly Ala Thr Ile Asn His Asp Pro Glu Ile
        705              710              715

Gly Asp Leu Leu Lys Val Val Phe Val Pro Asp Tyr Asn Val Ser Val
    720              725              730

Ala Glu Leu Leu Ile Pro Ala Ser Asp Leu Ser Glu His Ile Ser Thr
735              740              745              750

Ala Gly Met Glu Ala Ser Gly Thr Ser Asn Met Lys Phe Ala Met Asn
                755              760              765

Gly Cys Ile Gln Ile Gly Thr Leu Asp Gly Ala Asn Val Glu Ile Arg
            770              775              780

Glu Glu Val Gly Glu Asn Phe Phe Leu Phe Gly Ala Gln Ala His
        785              790              795

Glu Ile Ala Gly Leu Arg Lys Glu Arg Ala Asp Gly Lys Phe Val Pro
    800              805              810

Asp Glu Arg Phe Glu Glu Val Lys Glu Phe Val Arg Ser Gly Ala Phe
815              820              825              830

Gly Ser Tyr Asn Tyr Asp Asp Leu Ile Gly Ser Leu Glu Gly Asn Glu
                835              840              845

Gly Phe Gly Arg Ala Asp Tyr Phe Leu Val Gly Lys Asp Phe Pro Ser
            850              855              860

Tyr Ile Glu Cys Gln Glu Lys Val Asp Glu Ala Tyr Arg Asp Gln Lys
        865              870              875

Arg Trp Thr Thr Met Ser Ile Leu Asn Thr Ala Gly Ser Tyr Lys Phe
    880              885              890

Ser Ser Asp Arg Thr Ile His Glu Tyr Ala Lys Asp Ile Trp Asn Ile
895              900              905              910

Glu Ala Val Glu Ile Ala
                915

<210> SEQ ID NO 3
<211> LENGTH: 3292
<212> TYPE: DNA
<213> ORGANISM: Ipomoea batatas
<220> FEATURE:
<221> NAME/KEY: CDS
<222> LOCATION: (86)..(2950)
<220> FEATURE:
<221> NAME/KEY: mat_peptide
<222> LOCATION: (215)..(2950)

<400> SEQUENCE: 3
gaattccgct tagctaatat cgcaccgata gagagagacc gacagagagc aatggcagct      60
tcaccgtact ccgtttctcg gagca atg tcg agg ctt tcc ggc att acg cct     112
                             Met Ser Arg Leu Ser Gly Ile Thr Pro
                                             -40              -35 cga gct cga gat gat cga tct caa ttc cag aat ccg agg ctc gaa att     160
Arg Ala Arg Asp Asp Arg Ser Gln Phe Gln Asn Pro Arg Leu Glu Ile
                -30              -25              -20 gcg gtt cct gac cga acg gcc ggc tta cag aga acg aaa cgg act ctc     208
Ala Val Pro Asp Arg Thr Ala Gly Leu Gln Arg Thr Lys Arg Thr Leu
        -15              -10               -5 ctt gtc aag tgc gtg ttg gat gag acg aaa caa acg att cag cat gtg     256
```

```
                Leu Val Lys Cys Val Leu Asp Glu Thr Lys Gln Thr Ile Gln His Val
                 -1  1           5                  10 gtt act gaa aaa aat gaa ggt acc tta ctt gat gct gca tct att gct                304
Val Thr Glu Lys Asn Glu Gly Thr Leu Leu Asp Ala Ala Ser Ile Ala
 15          20                  25                  30 tca agc atc aaa tac cat gca gaa ttc tca cca gca ttt tct ccc gag                352
Ser Ser Ile Lys Tyr His Ala Glu Phe Ser Pro Ala Phe Ser Pro Glu
                 35                  40                  45 agg ttt gag ctt cca aag gct tac ttt gca aca gca caa agt gtt cgt                400
Arg Phe Glu Leu Pro Lys Ala Tyr Phe Ala Thr Ala Gln Ser Val Arg
             50                  55                  60 gat gca ctg att gtc aat tgg aat gca aca tac gat tac tat gag aag                448
Asp Ala Leu Ile Val Asn Trp Asn Ala Thr Tyr Asp Tyr Tyr Glu Lys
             65                  70                  75 ttg aat atg aag cag gca tac tat ctc tct atg gag ttt cta cag ggt                496
Leu Asn Met Lys Gln Ala Tyr Tyr Leu Ser Met Glu Phe Leu Gln Gly
     80                  85                  90 aga gca ttg tta aat gca att ggt aat ctg gag ctt act ggt gaa tat                544
Arg Ala Leu Leu Asn Ala Ile Gly Asn Leu Glu Leu Thr Gly Glu Tyr
 95              100                 105                 110 gct gaa gca ctg aac aag ctt ggc cac aat cta gaa aat gtt gct tct                592
Ala Glu Ala Leu Asn Lys Leu Gly His Asn Leu Glu Asn Val Ala Ser
                 115                 120                 125 aag gag cca gat gct gct ctt gga aat gga ggt ttg ggg cgg ctt gct                640
Lys Glu Pro Asp Ala Ala Leu Gly Asn Gly Gly Leu Gly Arg Leu Ala
             130                 135                 140 tcc tgt ttt ctt gac tct ttg gca aca ttg aat tat cca gca tgg ggg                688
Ser Cys Phe Leu Asp Ser Leu Ala Thr Leu Asn Tyr Pro Ala Trp Gly
             145                 150                 155 tat gga ctc agg tac aag tat gga tta ttt aag caa cgc att aca aaa                736
Tyr Gly Leu Arg Tyr Lys Tyr Gly Leu Phe Lys Gln Arg Ile Thr Lys
     160                 165                 170 gat gga cag gag gag gtg gct gaa gat tgg ctt gaa ctt ggc aat cct                784
Asp Gly Gln Glu Glu Val Ala Glu Asp Trp Leu Glu Leu Gly Asn Pro
175                 180                 185                 190 tgg gag ata atc aga atg gat gtt tca tac cct gtg aag ttc ttt ggc                832
Trp Glu Ile Ile Arg Met Asp Val Ser Tyr Pro Val Lys Phe Phe Gly
                 195                 200                 205 aaa gtg atc aca ggg tca gat gga aag aag cac tgg att ggt ggg gag                880
Lys Val Ile Thr Gly Ser Asp Gly Lys Lys His Trp Ile Gly Gly Glu
             210                 215                 220 gac att ctg gca gtt gca tac gat gtt cca att cca gga tat aag act                928
Asp Ile Leu Ala Val Ala Tyr Asp Val Pro Ile Pro Gly Tyr Lys Thr
             225                 230                 235 aga acc aca att agc ctt cgc cta tgg tct act aag gtt cca tcc gag                976
Arg Thr Thr Ile Ser Leu Arg Leu Trp Ser Thr Lys Val Pro Ser Glu
 240                 245                 250 gat ttt gat cta tat tct ttc aat gca gga gag cac acc aaa gcg tgt                1024
Asp Phe Asp Leu Tyr Ser Phe Asn Ala Gly Glu His Thr Lys Ala Cys
255                 260                 265                 270 gag gcc caa gca aat gct gaa aaa ata tgt tac ata ctc tac cct ggg                1072
Glu Ala Gln Ala Asn Ala Glu Lys Ile Cys Tyr Ile Leu Tyr Pro Gly
                 275                 280                 285 gat gaa tca att gaa gga aaa att tta cga ctg aag caa caa tac acc                1120
Asp Glu Ser Ile Glu Gly Lys Ile Leu Arg Leu Lys Gln Gln Tyr Thr
             290                 295                 300 ttg tgc tct gct tct cta caa gat ata att gcc cga ttt gag agg aga                1168
Leu Cys Ser Ala Ser Leu Gln Asp Ile Ile Ala Arg Phe Glu Arg Arg
             305                 310                 315
```

```
tct ggt gaa tat gtt aaa tgg gag gag ttt cct gaa aaa gtt gct gtc       1216
Ser Gly Glu Tyr Val Lys Trp Glu Glu Phe Pro Glu Lys Val Ala Val
320                 325                 330 cag atg aat gac acc cac cca act cta tgt atc cct gaa ctg att aga       1264
Gln Met Asn Asp Thr His Pro Thr Leu Cys Ile Pro Glu Leu Ile Arg
335                 340                 345                 350 ata ttg ata gat ttg aag ggc ttg agt tgg aag gaa gct tgg aat atc       1312
Ile Leu Ile Asp Leu Lys Gly Leu Ser Trp Lys Glu Ala Trp Asn Ile
            355                 360                 365 act caa agg act gtg gct tac aca aat cat act gtt ctg cct gag gca       1360
Thr Gln Arg Thr Val Ala Tyr Thr Asn His Thr Val Leu Pro Glu Ala
        370                 375                 380 ctg gag aaa tgg agt tat gag ctg atg gag aag ctg ctc cct aga cat       1408
Leu Glu Lys Trp Ser Tyr Glu Leu Met Glu Lys Leu Leu Pro Arg His
    385                 390                 395 ata gag att ata gag atg ata gac gag cag ctg ata aat gaa ata gta       1456
Ile Glu Ile Ile Glu Met Ile Asp Glu Gln Leu Ile Asn Glu Ile Val
400                 405                 410 tca gaa tat ggc acg tca gat ctt gac atg tta gaa aaa aag ttg aat       1504
Ser Glu Tyr Gly Thr Ser Asp Leu Asp Met Leu Glu Lys Lys Leu Asn
415                 420                 425                 430 gat atg aga att ttg gag aat ttt gat att ccc agc tct att gcc aac       1552
Asp Met Arg Ile Leu Glu Asn Phe Asp Ile Pro Ser Ser Ile Ala Asn
            435                 440                 445 ttg ttt acc aaa cca aag gaa act tct att gtt gat cct agt gaa gaa       1600
Leu Phe Thr Lys Pro Lys Glu Thr Ser Ile Val Asp Pro Ser Glu Glu
        450                 455                 460 gtt gaa gtt tct ggt aaa gtg gtg act gag agt gtt gaa gtt tct gat       1648
Val Glu Val Ser Gly Lys Val Val Thr Glu Ser Val Glu Val Ser Asp
    465                 470                 475 aaa gtg gtg act gag agt gaa aaa gat gaa ctt gaa gaa aaa gac aca       1696
Lys Val Val Thr Glu Ser Glu Lys Asp Glu Leu Glu Glu Lys Asp Thr
480                 485                 490 gaa ctg gag aaa gat gag gac cca gta cca gct cct ata cca ccc aag       1744
Glu Leu Glu Lys Asp Glu Asp Pro Val Pro Ala Pro Ile Pro Pro Lys
495                 500                 505                 510 atg gtc cgc atg gct aat ctc tgc gtt gtt ggt ggt cat gct gta aat       1792
Met Val Arg Met Ala Asn Leu Cys Val Val Gly Gly His Ala Val Asn
            515                 520                 525 gga gtt gcc gag att cat agt gat ata gtg aag gaa gat gtt ttt aat       1840
Gly Val Ala Glu Ile His Ser Asp Ile Val Lys Glu Asp Val Phe Asn
        530                 535                 540 gac ttt tac cag ctt tgg cct gag aaa ttt caa aac aaa aca aat ggt       1888
Asp Phe Tyr Gln Leu Trp Pro Glu Lys Phe Gln Asn Lys Thr Asn Gly
    545                 550                 555 gtg aca cca aga aga tgg atc cga ttt tgt aat cct gct cta agt aat       1936
Val Thr Pro Arg Arg Trp Ile Arg Phe Cys Asn Pro Ala Leu Ser Asn
560                 565                 570 atc att act aag tgg att ggt aca gag gac tgg gtc cta aac aca gaa       1984
Ile Ile Thr Lys Trp Ile Gly Thr Glu Asp Trp Val Leu Asn Thr Glu
575                 580                 585                 590 aag ttg gca gaa ctg cgc aag ttt gca gat aat gaa gat ctt caa ata       2032
Lys Leu Ala Glu Leu Arg Lys Phe Ala Asp Asn Glu Asp Leu Gln Ile
            595                 600                 605 gag tgg agg gct gca aaa aga agc aac aaa gtt aag gtt gcc tca ttc       2080
Glu Trp Arg Ala Ala Lys Arg Ser Asn Lys Val Lys Val Ala Ser Phe
        610                 615                 620 cta aaa gaa agg aca ggg tat tcg gtc agc ccc aat gca atg ttt gat       2128
Leu Lys Glu Arg Thr Gly Tyr Ser Val Ser Pro Asn Ala Met Phe Asp
    625                 630                 635
```

| | |
|---|---|
| atc cag gta aaa cga att cat gaa tac aag cgc caa ctc ttg aat atc<br>Ile Gln Val Lys Arg Ile His Glu Tyr Lys Arg Gln Leu Leu Asn Ile<br>640                      645                      650 | 2176 |
| ttg gga att gtt tat cgc tac aag cag atg aaa gaa atg agc gca cga<br>Leu Gly Ile Val Tyr Arg Tyr Lys Gln Met Lys Glu Met Ser Ala Arg<br>655                      660                      665                      670 | 2224 |
| gaa aga gaa gct aag ttt gtt cct cga gta tgc ata ttt gga gga aaa<br>Glu Arg Glu Ala Lys Phe Val Pro Arg Val Cys Ile Phe Gly Gly Lys<br>                675                      680                      685 | 2272 |
| gct ttt gct aca tat gtt caa gct aaa agg atc gca aaa ttc ata aca<br>Ala Phe Ala Thr Tyr Val Gln Ala Lys Arg Ile Ala Lys Phe Ile Thr<br>            690                      695                      700 | 2320 |
| gat gtt gga gcc acc ata aac cat gat cct gag ata ggt gat ttg ttg<br>Asp Val Gly Ala Thr Ile Asn His Asp Pro Glu Ile Gly Asp Leu Leu<br>705                      710                      715 | 2368 |
| aag gtt att ttt gtc cca gat tac aat gtc agt gct gca gaa ctg ctg<br>Lys Val Ile Phe Val Pro Asp Tyr Asn Val Ser Ala Ala Glu Leu Leu<br>720                      725                      730 | 2416 |
| att cca gct agt gga ctt tca caa cat atc agt act gcc gga atg gag<br>Ile Pro Ala Ser Gly Leu Ser Gln His Ile Ser Thr Ala Gly Met Glu<br>735                      740                      745                      750 | 2464 |
| gcc agt gga caa agc aat atg aaa ttt gcc atg aat ggt tgc atc tta<br>Ala Ser Gly Gln Ser Asn Met Lys Phe Ala Met Asn Gly Cys Ile Leu<br>                755                      760                      765 | 2512 |
| att ggg acc ttg gat gga gcc aat gtt gag ata agg caa gag gtt gga<br>Ile Gly Thr Leu Asp Gly Ala Asn Val Glu Ile Arg Gln Glu Val Gly<br>            770                      775                      780 | 2560 |
| gag gaa aac ttc ttt ctc ttt ggg gct gaa gct cat gag att gca ggg<br>Glu Glu Asn Phe Phe Leu Phe Gly Ala Glu Ala His Glu Ile Ala Gly<br>                785                      790                      795 | 2608 |
| ctt cgg aaa gaa aga gct gag gga aag ttt gta cca gat gaa cgt ttt<br>Leu Arg Lys Glu Arg Ala Glu Gly Lys Phe Val Pro Asp Glu Arg Phe<br>800                      805                      810 | 2656 |
| gag gaa gtc aag gaa ttc ata aag cgt ggt gtt ttt ggc tcc aat acc<br>Glu Glu Val Lys Glu Phe Ile Lys Arg Gly Val Phe Gly Ser Asn Thr<br>815                      820                      825                      830 | 2704 |
| tat gat gag ctt ctt gga tct ttg gag gga aat gaa ggc ttt ggt cgt<br>Tyr Asp Glu Leu Leu Gly Ser Leu Glu Gly Asn Glu Gly Phe Gly Arg<br>                835                      840                      845 | 2752 |
| gga gac tat ttc ctt gtg ggc aag gac ttc cct agt tac ata gaa tgc<br>Gly Asp Tyr Phe Leu Val Gly Lys Asp Phe Pro Ser Tyr Ile Glu Cys<br>            850                      855                      860 | 2800 |
| caa gag aag gtt gat gag gca tat cga gac caa aag ata tgg act aga<br>Gln Glu Lys Val Asp Glu Ala Tyr Arg Asp Gln Lys Ile Trp Thr Arg<br>865                      870                      875 | 2848 |
| atg tca atc ttg aac aca gcc gga agt tac aaa ttc agc agt gat aga<br>Met Ser Ile Leu Asn Thr Ala Gly Ser Tyr Lys Phe Ser Ser Asp Arg<br>880                      885                      890 | 2896 |
| aca att cat gaa tat gcc aag gac ata tgg aac atc cag cca gtt gtg<br>Thr Ile His Glu Tyr Ala Lys Asp Ile Trp Asn Ile Gln Pro Val Val<br>895                      900                      905                      910 | 2944 |
| ttt ccc tagaaattaa agaatgaacc aattttctga gcagcagtaa taaaatgtcg<br>Phe Pro | 3000 |
| tcttaggtcc tatgttcttg tttatgtaca tgtaggtgca agatcctgtg atgatctaat | 3060 |
| aaatcttgct tccttctatt atgcagatcc ttttataagg gtcatgtact tctgatcatc | 3120 |
| cttaataatc aatattttag tttcacatcg gacataagaa gttgattgca gtaagaaatc | 3180 |
| atgagttttt actactgtaa attctacaac ttggaataca aggatgacta ttccagaggc | 3240 | aaaaaaaaaa aaaaaaaaaa aaaaaaaaaa aaaaaaaaaa aaaaaaaaaa aa        3292

<210> SEQ ID NO 4
<211> LENGTH: 955
<212> TYPE: PRT
<213> ORGANISM: Ipomoea batatas

<400> SEQUENCE: 4

```
Met Ser Arg Leu Ser Gly Ile Thr Pro Arg Ala Arg Asp Asp Arg Ser
            -40                 -35                 -30

Gln Phe Gln Asn Pro Arg Leu Glu Ile Ala Val Pro Asp Arg Thr Ala
            -25                 -20                 -15

Gly Leu Gln Arg Thr Lys Arg Thr Leu Leu Val Lys Cys Val Leu Asp
            -10                  -5          -1   1                5

Glu Thr Lys Gln Thr Ile Gln His Val Val Thr Glu Lys Asn Glu Gly
                     10                  15                  20

Thr Leu Leu Asp Ala Ala Ser Ile Ala Ser Ser Ile Lys Tyr His Ala
                 25                  30                  35

Glu Phe Ser Pro Ala Phe Ser Pro Glu Arg Phe Glu Leu Pro Lys Ala
             40                  45                  50

Tyr Phe Ala Thr Ala Gln Ser Val Arg Asp Ala Leu Ile Val Asn Trp
         55                  60                  65

Asn Ala Thr Tyr Asp Tyr Glu Lys Leu Asn Met Lys Gln Ala Tyr
 70              75                  80                  85

Tyr Leu Ser Met Glu Phe Leu Gln Gly Arg Ala Leu Leu Asn Ala Ile
                 90                  95                 100

Gly Asn Leu Glu Leu Thr Gly Glu Tyr Ala Glu Ala Leu Asn Lys Leu
                105                 110                 115

Gly His Asn Leu Glu Asn Val Ala Ser Lys Glu Pro Asp Ala Ala Leu
            120                 125                 130

Gly Asn Gly Gly Leu Gly Arg Leu Ala Ser Cys Phe Leu Asp Ser Leu
            135                 140                 145

Ala Thr Leu Asn Tyr Pro Ala Trp Gly Tyr Gly Leu Arg Tyr Lys Tyr
150                 155                 160                 165

Gly Leu Phe Lys Gln Arg Ile Thr Lys Asp Gly Gln Glu Glu Val Ala
                170                 175                 180

Glu Asp Trp Leu Glu Leu Gly Asn Pro Trp Glu Ile Ile Arg Met Asp
            185                 190                 195

Val Ser Tyr Pro Val Lys Phe Phe Gly Lys Val Ile Thr Gly Ser Asp
            200                 205                 210

Gly Lys Lys His Trp Ile Gly Gly Glu Asp Ile Leu Ala Val Ala Tyr
215                 220                 225

Asp Val Pro Ile Pro Gly Tyr Lys Thr Arg Thr Thr Ile Ser Leu Arg
230                 235                 240                 245

Leu Trp Ser Thr Lys Val Pro Ser Glu Asp Phe Asp Leu Tyr Ser Phe
                250                 255                 260

Asn Ala Gly Glu His Thr Lys Ala Cys Glu Ala Gln Ala Asn Ala Glu
                265                 270                 275

Lys Ile Cys Tyr Ile Leu Tyr Pro Gly Asp Glu Ser Ile Glu Gly Lys
            280                 285                 290

Ile Leu Arg Leu Lys Gln Gln Tyr Thr Leu Cys Ser Ala Ser Leu Gln
            295                 300                 305

Asp Ile Ile Ala Arg Phe Glu Arg Arg Ser Gly Glu Tyr Val Lys Trp
310                 315                 320                 325
```

```
Glu Glu Phe Pro Glu Lys Val Ala Val Gln Met Asn Asp Thr His Pro
                330                 335                 340
Thr Leu Cys Ile Pro Glu Leu Ile Arg Ile Leu Ile Asp Leu Lys Gly
                345                 350                 355
Leu Ser Trp Lys Glu Ala Trp Asn Ile Thr Gln Arg Thr Val Ala Tyr
            360                 365                 370
Thr Asn His Thr Val Leu Pro Glu Ala Leu Glu Lys Trp Ser Tyr Glu
            375                 380                 385
Leu Met Glu Lys Leu Leu Pro Arg His Ile Glu Ile Ile Glu Met Ile
390                 395                 400                 405
Asp Glu Gln Leu Ile Asn Glu Ile Val Ser Glu Tyr Gly Thr Ser Asp
                410                 415                 420
Leu Asp Met Leu Glu Lys Lys Leu Asn Asp Met Arg Ile Leu Glu Asn
            425                 430                 435
Phe Asp Ile Pro Ser Ser Ile Ala Asn Leu Phe Thr Lys Pro Lys Glu
            440                 445                 450
Thr Ser Ile Val Asp Pro Ser Glu Glu Val Glu Val Ser Gly Lys Val
            455                 460                 465
Val Thr Glu Ser Val Glu Val Ser Asp Lys Val Val Thr Glu Ser Glu
470                 475                 480                 485
Lys Asp Glu Leu Glu Glu Lys Asp Thr Glu Leu Glu Lys Asp Glu Asp
                490                 495                 500
Pro Val Pro Ala Pro Ile Pro Pro Lys Met Val Arg Met Ala Asn Leu
            505                 510                 515
Cys Val Val Gly Gly His Ala Val Asn Gly Val Ala Glu Ile His Ser
            520                 525                 530
Asp Ile Val Lys Glu Asp Val Phe Asn Asp Phe Tyr Gln Leu Trp Pro
            535                 540                 545
Glu Lys Phe Gln Asn Lys Thr Asn Gly Val Thr Pro Arg Arg Trp Ile
550                 555                 560                 565
Arg Phe Cys Asn Pro Ala Leu Ser Asn Ile Ile Thr Lys Trp Ile Gly
            570                 575                 580
Thr Glu Asp Trp Val Leu Asn Thr Glu Lys Leu Ala Glu Leu Arg Lys
            585                 590                 595
Phe Ala Asp Asn Glu Asp Leu Gln Ile Glu Trp Arg Ala Ala Lys Arg
            600                 605                 610
Ser Asn Lys Val Lys Val Ala Ser Phe Leu Lys Glu Arg Thr Gly Tyr
            615                 620                 625
Ser Val Ser Pro Asn Ala Met Phe Asp Ile Gln Val Lys Arg Ile His
630                 635                 640                 645
Glu Tyr Lys Arg Gln Leu Leu Asn Ile Leu Gly Ile Val Tyr Arg Tyr
                650                 655                 660
Lys Gln Met Lys Glu Met Ser Ala Arg Glu Arg Glu Ala Lys Phe Val
            665                 670                 675
Pro Arg Val Cys Ile Phe Gly Gly Lys Ala Phe Ala Thr Tyr Val Gln
            680                 685                 690
Ala Lys Arg Ile Ala Lys Phe Ile Thr Asp Val Gly Ala Thr Ile Asn
            695                 700                 705
His Asp Pro Glu Ile Gly Asp Leu Leu Lys Val Ile Phe Val Pro Asp
710                 715                 720                 725
Tyr Asn Val Ser Ala Ala Glu Leu Leu Ile Pro Ala Ser Gly Leu Ser
                730                 735                 740
```

-continued

```
Gln His Ile Ser Thr Ala Gly Met Glu Ala Ser Gly Gln Ser Asn Met
            745                 750                 755
Lys Phe Ala Met Asn Gly Cys Ile Leu Ile Gly Thr Leu Asp Gly Ala
        760                 765                 770
Asn Val Glu Ile Arg Gln Glu Val Gly Glu Asn Phe Phe Leu Phe
    775                 780                 785
Gly Ala Glu Ala His Glu Ile Ala Gly Leu Arg Lys Glu Arg Ala Glu
790                 795                 800                 805
Gly Lys Phe Val Pro Asp Glu Arg Phe Glu Glu Val Lys Glu Phe Ile
                810                 815                 820
Lys Arg Gly Val Phe Gly Ser Asn Thr Tyr Asp Glu Leu Leu Gly Ser
            825                 830                 835
Leu Glu Gly Asn Glu Gly Phe Gly Arg Gly Asp Tyr Phe Leu Val Gly
        840                 845                 850
Lys Asp Phe Pro Ser Tyr Ile Glu Cys Gln Glu Lys Val Asp Glu Ala
    855                 860                 865
Tyr Arg Asp Gln Lys Ile Trp Thr Arg Met Ser Ile Leu Asn Thr Ala
870                 875                 880                 885
Gly Ser Tyr Lys Phe Ser Ser Asp Arg Thr Ile His Glu Tyr Ala Lys
                890                 895                 900
Asp Ile Trp Asn Ile Gln Pro Val Val Phe Pro
            905                 910

<210> SEQ ID NO 5
<211> LENGTH: 3171
<212> TYPE: DNA
<213> ORGANISM: Solanum tuberosum
<220> FEATURE:
<221> NAME/KEY: CDS
<222> LOCATION: (87)..(3008)
<220> FEATURE:
<221> NAME/KEY: mat_peptide
<222> LOCATION: (330)..(3008)

<400> SEQUENCE: 5
tttttttttt caacatgcac aacaattatt ttgattaaat tttgtatcta aaaatttagc      60
attttgaaat tcagttcaga gacatc atg gca act ttt gct gtc tct gga ttg     113
                              Met Ala Thr Phe Ala Val Ser Gly Leu
                                  -80                 -75 aac tca att tca agt att tct agt ttt aat aac aat ttc aga agc aaa     161
Asn Ser Ile Ser Ser Ile Ser Ser Phe Asn Asn Asn Phe Arg Ser Lys
        -70                 -65                 -60 aac tca aac att ttg ttg agt aga agg agg att tta ttg ttc agt ttt     209
Asn Ser Asn Ile Leu Leu Ser Arg Arg Arg Ile Leu Leu Phe Ser Phe
    -55                 -50                 -45 aga aga aga aga aga agt ttc tct gtt agc agt gtt gct agt gat caa     257
Arg Arg Arg Arg Arg Ser Phe Ser Val Ser Ser Val Ala Ser Asp Gln
-40                 -35                 -30                 -25 aag cag aag aca aag gat tct tcc tct gat gaa gga ttt aca tta gat     305
Lys Gln Lys Thr Lys Asp Ser Ser Ser Asp Glu Gly Phe Thr Leu Asp
                -20                 -15                 -10 gtt ttt cag ccg gac tcc acg tct gtt tta tca agt ata aag tat cac     353
Val Phe Gln Pro Asp Ser Thr Ser Val Leu Ser Ser Ile Lys Tyr His
        -5                  -1   1                5 gct gag ttc aca cca tca ttt tct cct gag aag ttt gaa ctt ccc aag     401
Ala Glu Phe Thr Pro Ser Phe Ser Pro Glu Lys Phe Glu Leu Pro Lys
    10                  15                  20 gca tac tat gca act gca gag agt gtt cga gat acg ctc att ata aat     449
Ala Tyr Tyr Ala Thr Ala Glu Ser Val Arg Asp Thr Leu Ile Ile Asn
```

```
           25                  30                  35                  40 tgg aat gcc aca tac gaa ttc tat gaa aag atg aat gta aag cag gca         497
Trp Asn Ala Thr Tyr Glu Phe Tyr Glu Lys Met Asn Val Lys Gln Ala
                45                  50                  55 tat tac ttg tct atg gaa ttt ctt cag gga aga gct ttg ctc aat gct         545
Tyr Tyr Leu Ser Met Glu Phe Leu Gln Gly Arg Ala Leu Leu Asn Ala
                60                  65                  70 att ggt aac ttg ggg cta acc gga cct tat gca gat gct tta act aag         593
Ile Gly Asn Leu Gly Leu Thr Gly Pro Tyr Ala Asp Ala Leu Thr Lys
                75                  80                  85 ctc gga tac agt tta gag gat gta gcc agg cag gaa ccg gat gca gct         641
Leu Gly Tyr Ser Leu Glu Asp Val Ala Arg Gln Glu Pro Asp Ala Ala
                90                  95                 100 tta ggt aat gga ggt tta gga aga ctt gct tct tgc ttt ctg gac tca         689
Leu Gly Asn Gly Gly Leu Gly Arg Leu Ala Ser Cys Phe Leu Asp Ser
            105                 110                 115                 120 atg gcg aca cta aac tac cct gca tgg ggc tat gga ctt aga tac caa         737
Met Ala Thr Leu Asn Tyr Pro Ala Trp Gly Tyr Gly Leu Arg Tyr Gln
                125                 130                 135 tat ggc ctt ttc aaa cag ctt att aca aaa gat gga cag gag gaa gtt         785
Tyr Gly Leu Phe Lys Gln Leu Ile Thr Lys Asp Gly Gln Glu Glu Val
            140                 145                 150 gct gaa aat tgg ctc gag atg gga aat cca tgg gaa att gtg agg aat         833
Ala Glu Asn Trp Leu Glu Met Gly Asn Pro Trp Glu Ile Val Arg Asn
            155                 160                 165 gat att tcg tat ccc gta aaa ttc tat ggg aag gtc att gaa gga gct         881
Asp Ile Ser Tyr Pro Val Lys Phe Tyr Gly Lys Val Ile Glu Gly Ala
        170                 175                 180 gat ggg agg aag gaa tgg gct ggc gga gaa gat ata act gct gtt gcc         929
Asp Gly Arg Lys Glu Trp Ala Gly Gly Glu Asp Ile Thr Ala Val Ala
185                 190                 195                 200 tat gat gtc cca ata cca gga tat aaa aca aaa aca acg att aac ctt         977
Tyr Asp Val Pro Ile Pro Gly Tyr Lys Thr Lys Thr Thr Ile Asn Leu
                205                 210                 215 cga ttg tgg aca aca aag cta gct gca gaa gct ttt gat tta tat gct        1025
Arg Leu Trp Thr Thr Lys Leu Ala Ala Glu Ala Phe Asp Leu Tyr Ala
            220                 225                 230 ttt aac aat gga gac cat gcc aaa gca tat gag gcc cag aaa aag gct        1073
Phe Asn Asn Gly Asp His Ala Lys Ala Tyr Glu Ala Gln Lys Lys Ala
            235                 240                 245 gaa aag att tgc tat gtc tta tat cca ggt gac gaa tcg ctt gaa gga        1121
Glu Lys Ile Cys Tyr Val Leu Tyr Pro Gly Asp Glu Ser Leu Glu Gly
            250                 255                 260 aag acg ctt agg tta aag cag caa tac aca cta tgt tct gct tct ctt        1169
Lys Thr Leu Arg Leu Lys Gln Gln Tyr Thr Leu Cys Ser Ala Ser Leu
265                 270                 275                 280 cag gac att att gca cgg ttc gag aag aga tca ggg aat gca gta aac        1217
Gln Asp Ile Ile Ala Arg Phe Glu Lys Arg Ser Gly Asn Ala Val Asn
                285                 290                 295 tgg gat cag ttc ccc gaa aag gtt gca gta cag atg aat gac act cat        1265
Trp Asp Gln Phe Pro Glu Lys Val Ala Val Gln Met Asn Asp Thr His
            300                 305                 310 cca aca ctt tgt ata cca gaa ctt tta agg ata ttg atg gat gtt aaa        1313
Pro Thr Leu Cys Ile Pro Glu Leu Leu Arg Ile Leu Met Asp Val Lys
            315                 320                 325 ggt ttg agc tgg aag cag gca tgg gaa att act caa aga acg gtc gca        1361
Gly Leu Ser Trp Lys Gln Ala Trp Glu Ile Thr Gln Arg Thr Val Ala
            330                 335                 340 tac act aac cac act gtt cta cct gag gct ctt gag aaa tgg agc ttc        1409
```

-continued

```
Tyr Thr Asn His Thr Val Leu Pro Glu Ala Leu Glu Lys Trp Ser Phe
345                 350                 355                 360 aca ctt ctt ggt gaa ctg ctt cct cgg cac gtg gag atc ata gca atg    1457
Thr Leu Leu Gly Glu Leu Leu Pro Arg His Val Glu Ile Ile Ala Met
            365                 370                 375 ata gat gag gag ctc ttg cat act ata ctt gct gaa tat ggt act gaa    1505
Ile Asp Glu Glu Leu Leu His Thr Ile Leu Ala Glu Tyr Gly Thr Glu
        380                 385                 390 gat ctt gac ttg ttg caa gaa aag cta aac caa atg agg att ctg gat    1553
Asp Leu Asp Leu Leu Gln Glu Lys Leu Asn Gln Met Arg Ile Leu Asp
        395                 400                 405 aat gtt gaa ata cca agt tct gtt ttg gag ttg ctt ata aaa gcc gaa    1601
Asn Val Glu Ile Pro Ser Ser Val Leu Glu Leu Leu Ile Lys Ala Glu
    410                 415                 420 gaa agt gct gct gat gtc gaa aag gca gca gat gaa gaa caa gaa gaa    1649
Glu Ser Ala Ala Asp Val Glu Lys Ala Ala Asp Glu Glu Gln Glu Glu
425                 430                 435                 440 gaa ggt aag gat gac agt aaa gat gag gaa act gag gct gta aag gca    1697
Glu Gly Lys Asp Asp Ser Lys Asp Glu Glu Thr Glu Ala Val Lys Ala
                445                 450                 455 gaa act acg aac gaa gag gag gaa act gag gtt aag aag gtt gag gtg    1745
Glu Thr Thr Asn Glu Glu Glu Glu Thr Glu Val Lys Lys Val Glu Val
            460                 465                 470 gag gat agt caa gca aaa ata aaa cgt ata ttc ggg cca cat cca aat    1793
Glu Asp Ser Gln Ala Lys Ile Lys Arg Ile Phe Gly Pro His Pro Asn
        475                 480                 485 aaa cca cag gtg gtt cac atg gca aat cta tgt gta gtt agc ggg cat    1841
Lys Pro Gln Val Val His Met Ala Asn Leu Cys Val Val Ser Gly His
    490                 495                 500 gca gtt aac ggt gtt gct gag att cat agt gaa ata gtt aag gat gaa    1889
Ala Val Asn Gly Val Ala Glu Ile His Ser Glu Ile Val Lys Asp Glu
505                 510                 515                 520 gtt ttc aat gaa ttt tac aag tta tgg cca gag aaa ttc caa aac aag    1937
Val Phe Asn Glu Phe Tyr Lys Leu Trp Pro Glu Lys Phe Gln Asn Lys
                525                 530                 535 aca aat ggt gtg aca cca aga aga tgg cta agt ttc tgt aat cca gag    1985
Thr Asn Gly Val Thr Pro Arg Arg Trp Leu Ser Phe Cys Asn Pro Glu
            540                 545                 550 ttg agt gaa att ata acc aag tgg aca gga tct gat gat tgg tta gta    2033
Leu Ser Glu Ile Ile Thr Lys Trp Thr Gly Ser Asp Asp Trp Leu Val
        555                 560                 565 aac act gaa aaa ttg gca gag ctt cga aag ttt gct gat aac gaa gaa    2081
Asn Thr Glu Lys Leu Ala Glu Leu Arg Lys Phe Ala Asp Asn Glu Glu
        570                 575                 580 ctc cag tct gag tgg agg aag gca aaa gga aat aac aaa atg aag att    2129
Leu Gln Ser Glu Trp Arg Lys Ala Lys Gly Asn Asn Lys Met Lys Ile
585                 590                 595                 600 gtc tct ctc att aaa gaa aaa aca gga tac gtg gtc agt ccc gat gca    2177
Val Ser Leu Ile Lys Glu Lys Thr Gly Tyr Val Val Ser Pro Asp Ala
                605                 610                 615 atg ttt gat gtt cag atc aag cgc atc cat gag tat aaa agg cag cta    2225
Met Phe Asp Val Gln Ile Lys Arg Ile His Glu Tyr Lys Arg Gln Leu
            620                 625                 630 tta aat ata ttt gga atc gtt tat cgc tat aag aag atg aaa gaa atg    2273
Leu Asn Ile Phe Gly Ile Val Tyr Arg Tyr Lys Lys Met Lys Glu Met
        635                 640                 645 agc cct gaa gaa cga aaa gaa aag ttt gtc cct cga gtt tgc ata ttt    2321
Ser Pro Glu Glu Arg Lys Glu Lys Phe Val Pro Arg Val Cys Ile Phe
650                 655                 660
```

-continued

| | | |
|---|---|---|
| gga gga aaa gca ttt gct aca tat gtt cag gcc aag aga att gta aaa<br>Gly Gly Lys Ala Phe Ala Thr Tyr Val Gln Ala Lys Arg Ile Val Lys<br>665                            670                            675                        680 | 2369 | |
| ttt atc act gat gta ggg gaa aca gtc aac cat gat ccc gag att ggt<br>Phe Ile Thr Asp Val Gly Glu Thr Val Asn His Asp Pro Glu Ile Gly<br>685                            690                            695 | 2417 | |
| gat ctt ttg aag gtt gta ttt gtt cct gat tac aat gtc agt gta gca<br>Asp Leu Leu Lys Val Val Phe Val Pro Asp Tyr Asn Val Ser Val Ala<br>700                            705                            710 | 2465 | |
| gaa gtg cta att cct ggt agt gag ttg tcc cag cat att agt act gct<br>Glu Val Leu Ile Pro Gly Ser Glu Leu Ser Gln His Ile Ser Thr Ala<br>715                            720                            725 | 2513 | |
| ggt atg gag gct agt gga acc agc aac atg aaa ttt tca atg aat ggc<br>Gly Met Glu Ala Ser Gly Thr Ser Asn Met Lys Phe Ser Met Asn Gly<br>730                            735                            740 | 2561 | |
| tgc ctc ctc atc ggg aca tta gat ggt gcc aat gtt gag ata aga gag<br>Cys Leu Leu Ile Gly Thr Leu Asp Gly Ala Asn Val Glu Ile Arg Glu<br>745                            750                            755                        760 | 2609 | |
| gaa gtt gga gag gac aat ttc ttt ctt ttc gga gct cag gct cat gaa<br>Glu Val Gly Glu Asp Asn Phe Phe Leu Phe Gly Ala Gln Ala His Glu<br>                          765                            770                            775 | 2657 | |
| att gct ggc cta cga aag gaa aga gcc gag gga aag ttt gtc ccg gac<br>Ile Ala Gly Leu Arg Lys Glu Arg Ala Glu Gly Lys Phe Val Pro Asp<br>780                            785                            790 | 2705 | |
| cca aga ttt gaa gaa gta aag gcg ttc att agg aca ggc gtc ttt ggc<br>Pro Arg Phe Glu Glu Val Lys Ala Phe Ile Arg Thr Gly Val Phe Gly<br>                          795                            800                            805 | 2753 | |
| acc tac aac tat gaa gaa ctc atg gga tcc ttg gaa gga aac gaa ggc<br>Thr Tyr Asn Tyr Glu Glu Leu Met Gly Ser Leu Glu Gly Asn Glu Gly<br>810                            815                            820 | 2801 | |
| tat ggt cgt gct gac tat ttt ctt gta gga aag gat ttc ccc gat tat<br>Tyr Gly Arg Ala Asp Tyr Phe Leu Val Gly Lys Asp Phe Pro Asp Tyr<br>825                            830                            835                        840 | 2849 | |
| ata gag tgc caa gat aaa gtt gat gaa gca tat cga gac cag aag aaa<br>Ile Glu Cys Gln Asp Lys Val Asp Glu Ala Tyr Arg Asp Gln Lys Lys<br>                          845                            850                            855 | 2897 | |
| tgg acc aaa atg tcg atc tta aac aca gct gga tcg ttc aaa ttt agc<br>Trp Thr Lys Met Ser Ile Leu Asn Thr Ala Gly Ser Phe Lys Phe Ser<br>860                            865                            870 | 2945 | |
| agt gat cga aca att cat caa tat gca aga gat ata tgg aga att gaa<br>Ser Asp Arg Thr Ile His Gln Tyr Ala Arg Asp Ile Trp Arg Ile Glu<br>875                            880                            885 | 2993 | |
| cct gtt gaa tta cct taaaagttag ccagttaaag gatgaaagcc aattttttcc<br>Pro Val Glu Leu Pro<br>890 | 3048 | |
| ccctgaggtt ctcccatact gtttattagt acatatattg tcaattgttg ctactgaaat | 3108 | |
| gatagaagtt ttgaatattt actgtcaata aaatacagtt gattccattt gaaaaaaaaa | 3168 | |
| aaa | 3171 | |

<210> SEQ ID NO 6
<211> LENGTH: 974
<212> TYPE: PRT
<213> ORGANISM: Solanum tuberosum

<400> SEQUENCE: 6

Met Ala Thr Phe Ala Val Ser Gly Leu Asn Ser Ile Ser Ser Ile Ser
        -80                  -75                  -70

Ser Phe Asn Asn Asn Phe Arg Ser Lys Asn Ser Asn Ile Leu Leu Ser
-65                  -60                  -55                  -50

-continued

```
Arg Arg Arg Ile Leu Leu Phe Ser Phe Arg Arg Arg Arg Ser Phe
            -45                 -40                 -35

Ser Val Ser Val Ala Ser Asp Gln Lys Gln Lys Thr Lys Asp Ser
            -30                 -25                 -20

Ser Ser Asp Glu Gly Phe Thr Leu Asp Val Phe Gln Pro Asp Ser Thr
            -15                 -10                  -5

Ser Val Leu Ser Ser Ile Lys Tyr His Ala Glu Phe Thr Pro Ser Phe
 -1   1              5                  10                  15

Ser Pro Glu Lys Phe Glu Leu Pro Lys Ala Tyr Tyr Ala Thr Ala Glu
                 20                  25                  30

Ser Val Arg Asp Thr Leu Ile Ile Asn Trp Asn Ala Thr Tyr Glu Phe
                 35                  40                  45

Tyr Glu Lys Met Asn Val Lys Gln Ala Tyr Tyr Leu Ser Met Glu Phe
                 50                  55                  60

Leu Gln Gly Arg Ala Leu Leu Asn Ala Ile Gly Asn Leu Gly Leu Thr
                 65                  70                  75

Gly Pro Tyr Ala Asp Ala Leu Thr Lys Leu Gly Tyr Ser Leu Glu Asp
 80                  85                  90                  95

Val Ala Arg Gln Glu Pro Asp Ala Ala Leu Gly Asn Gly Gly Leu Gly
                100                 105                 110

Arg Leu Ala Ser Cys Phe Leu Asp Ser Met Ala Thr Leu Asn Tyr Pro
                115                 120                 125

Ala Trp Gly Tyr Gly Leu Arg Tyr Gln Tyr Gly Leu Phe Lys Gln Leu
                130                 135                 140

Ile Thr Lys Asp Gly Gln Glu Val Ala Glu Asn Trp Leu Glu Met
                145                 150                 155

Gly Asn Pro Trp Glu Ile Val Arg Asn Asp Ile Ser Tyr Pro Val Lys
160                 165                 170                 175

Phe Tyr Gly Lys Val Ile Glu Gly Ala Asp Gly Arg Lys Glu Trp Ala
                180                 185                 190

Gly Gly Glu Asp Ile Thr Ala Val Ala Tyr Asp Val Pro Ile Pro Gly
                195                 200                 205

Tyr Lys Thr Lys Thr Thr Ile Asn Leu Arg Leu Trp Thr Thr Lys Leu
                210                 215                 220

Ala Ala Glu Ala Phe Asp Leu Tyr Ala Phe Asn Asn Gly Asp His Ala
                225                 230                 235

Lys Ala Tyr Glu Ala Gln Lys Lys Ala Glu Lys Ile Cys Tyr Val Leu
240                 245                 250                 255

Tyr Pro Gly Asp Glu Ser Leu Glu Gly Lys Thr Leu Arg Leu Lys Gln
                260                 265                 270

Gln Tyr Thr Leu Cys Ser Ala Ser Leu Gln Asp Ile Ile Ala Arg Phe
                275                 280                 285

Glu Lys Arg Ser Gly Asn Ala Val Asn Trp Asp Gln Phe Pro Glu Lys
                290                 295                 300

Val Ala Val Gln Met Asn Asp Thr His Pro Thr Leu Cys Ile Pro Glu
305                 310                 315

Leu Leu Arg Ile Leu Met Asp Val Lys Gly Leu Ser Trp Lys Gln Ala
320                 325                 330                 335

Trp Glu Ile Thr Gln Arg Thr Val Ala Tyr Thr Asn His Thr Val Leu
                340                 345                 350

Pro Glu Ala Leu Glu Lys Trp Ser Phe Thr Leu Leu Gly Glu Leu Leu
                355                 360                 365
```

-continued

```
Pro Arg His Val Glu Ile Ile Ala Met Ile Asp Glu Glu Leu Leu His
        370                 375                 380
Thr Ile Leu Ala Glu Tyr Gly Thr Glu Asp Leu Asp Leu Leu Gln Glu
    385                 390                 395
Lys Leu Asn Gln Met Arg Ile Leu Asp Asn Val Glu Ile Pro Ser Ser
400                 405                 410                 415
Val Leu Glu Leu Leu Ile Lys Ala Glu Ser Ala Ala Asp Val Glu
                420                 425                 430
Lys Ala Ala Asp Glu Glu Gln Glu Glu Gly Lys Asp Asp Ser Lys
                435                 440                 445
Asp Glu Glu Thr Glu Ala Val Lys Ala Glu Thr Asn Glu Glu Glu
        450                 455                 460
Glu Thr Glu Val Lys Lys Val Glu Val Glu Asp Ser Gln Ala Lys Ile
    465                 470                 475
Lys Arg Ile Phe Gly Pro His Pro Asn Lys Pro Gln Val Val His Met
480                 485                 490                 495
Ala Asn Leu Cys Val Val Ser Gly His Ala Val Asn Gly Val Ala Glu
                500                 505                 510
Ile His Ser Glu Ile Val Lys Asp Glu Val Phe Asn Glu Phe Tyr Lys
        515                 520                 525
Leu Trp Pro Glu Lys Phe Gln Asn Lys Thr Asn Gly Val Thr Pro Arg
        530                 535                 540
Arg Trp Leu Ser Phe Cys Asn Pro Glu Leu Ser Glu Ile Ile Thr Lys
        545                 550                 555
Trp Thr Gly Ser Asp Asp Trp Leu Val Asn Thr Glu Lys Leu Ala Glu
560                 565                 570                 575
Leu Arg Lys Phe Ala Asp Asn Glu Glu Leu Gln Ser Glu Trp Arg Lys
                580                 585                 590
Ala Lys Gly Asn Asn Lys Met Lys Ile Val Ser Leu Ile Lys Glu Lys
                595                 600                 605
Thr Gly Tyr Val Val Ser Pro Asp Ala Met Phe Asp Val Gln Ile Lys
        610                 615                 620
Arg Ile His Glu Tyr Lys Arg Gln Leu Leu Asn Ile Phe Gly Ile Val
        625                 630                 635
Tyr Arg Tyr Lys Lys Met Lys Glu Met Ser Pro Glu Glu Arg Lys Glu
640                 645                 650                 655
Lys Phe Val Pro Arg Val Cys Ile Phe Gly Gly Lys Ala Phe Ala Thr
                660                 665                 670
Tyr Val Gln Ala Lys Arg Ile Val Lys Phe Ile Thr Asp Val Gly Glu
        675                 680                 685
Thr Val Asn His Asp Pro Glu Ile Gly Asp Leu Leu Lys Val Val Phe
        690                 695                 700
Val Pro Asp Tyr Asn Val Ser Val Ala Glu Val Leu Ile Pro Gly Ser
705                 710                 715
Glu Leu Ser Gln His Ile Ser Thr Ala Gly Met Glu Ala Ser Gly Thr
720                 725                 730                 735
Ser Asn Met Lys Phe Ser Met Asn Gly Cys Leu Leu Ile Gly Thr Leu
                740                 745                 750
Asp Gly Ala Asn Val Glu Ile Arg Glu Glu Val Gly Glu Asp Asn Phe
                755                 760                 765
Phe Leu Phe Gly Ala Gln Ala His Glu Ile Ala Gly Leu Arg Lys Glu
        770                 775                 780
Arg Ala Glu Gly Lys Phe Val Pro Asp Pro Arg Phe Glu Glu Val Lys
```

```
                785               790               795
Ala Phe Ile Arg Thr Gly Val Phe Gly Thr Tyr Asn Tyr Glu Glu Leu
800               805               810               815

Met Gly Ser Leu Glu Gly Asn Glu Gly Tyr Gly Arg Ala Asp Tyr Phe
              820               825               830

Leu Val Gly Lys Asp Phe Pro Asp Tyr Ile Glu Cys Gln Asp Lys Val
              835               840               845

Asp Glu Ala Tyr Arg Asp Gln Lys Lys Trp Thr Lys Met Ser Ile Leu
              850               855               860

Asn Thr Ala Gly Ser Phe Lys Phe Ser Ser Asp Arg Thr Ile His Gln
865               870               875

Tyr Ala Arg Asp Ile Trp Arg Ile Glu Pro Val Glu Leu Pro
880               885               890

<210> SEQ ID NO 7
<211> LENGTH: 3283
<212> TYPE: DNA
<213> ORGANISM: Vicia faba
<220> FEATURE:
<221> NAME/KEY: CDS
<222> LOCATION: (58)..(3066)
<220> FEATURE:
<221> NAME/KEY: mat_peptide
<222> LOCATION: (250)..(3066)

<400> SEQUENCE: 7
acaatacaaa caatcaaagc tctgtgagtg tgtgagtgag tgagagaaat tccaatt        57 atg gct tcc atg aca atg cgg ttt cat cca aat tcc acc gcc gta acc     105
Met Ala Ser Met Thr Met Arg Phe His Pro Asn Ser Thr Ala Val Thr
             -60               -55               -50 gaa tcc gtt cct cgc cgt ggc tcc gtt tac gga ttc atc ggt tac aga     153
Glu Ser Val Pro Arg Arg Gly Ser Val Tyr Gly Phe Ile Gly Tyr Arg
         -45               -40               -35 tcc tcg tcg ttg ttc gtc cga acg aac gtt atc aag tat cgt tct gtt     201
Ser Ser Ser Leu Phe Val Arg Thr Asn Val Ile Lys Tyr Arg Ser Val
     -30               -25               -20 aag cgt aat ctg gaa ttt agg agg aga agc gct ttc tct gtg aag tgt     249
Lys Arg Asn Leu Glu Phe Arg Arg Arg Ser Ala Phe Ser Val Lys Cys
 -15               -10                -5                -1 ggt tct ggt aat gaa gcg aaa cag aaa gtc aag gat cag gaa gtt caa     297
Gly Ser Gly Asn Glu Ala Lys Gln Lys Val Lys Asp Gln Glu Val Gln
 1               5                10                15 caa gaa gct aaa act tct ccg agc tca ttt gca cca gat act act tcc     345
Gln Glu Ala Lys Thr Ser Pro Ser Ser Phe Ala Pro Asp Thr Thr Ser
             20                25                30 att gtg tca agt att aag tac cat gca gag ttc aca cca ctg ttt tct     393
Ile Val Ser Ser Ile Lys Tyr His Ala Glu Phe Thr Pro Leu Phe Ser
         35                40                45 ccg gaa aaa ttt gag ctt cca caa gct ttc att gca act gca cag agt     441
Pro Glu Lys Phe Glu Leu Pro Gln Ala Phe Ile Ala Thr Ala Gln Ser
 50                55                60 gtt cgt gat gct ctc ata ata aac tgg aat gct act tat gat tac tat     489
Val Arg Asp Ala Leu Ile Ile Asn Trp Asn Ala Thr Tyr Asp Tyr Tyr
 65                70                75                80 gag aag ctg aat gtt aag cag gca tat tac ctt tca atg gaa ttt tta     537
Glu Lys Leu Asn Val Lys Gln Ala Tyr Tyr Leu Ser Met Glu Phe Leu
                 85                90                95 cag gga aga gca tta ttg aat gca att ggc aat tta gag cta act ggt     585
Gln Gly Arg Ala Leu Leu Asn Ala Ile Gly Asn Leu Glu Leu Thr Gly
             100               105               110
```

```
ccc tat gca gag gct ttg agc cag ctt agt tat aaa tta gaa gac gtg      633
Pro Tyr Ala Glu Ala Leu Ser Gln Leu Ser Tyr Lys Leu Glu Asp Val
        115                 120                 125 gca cac cag gag ccg gat gct gca ctt gga aat ggg ggt ctt gga cga      681
Ala His Gln Glu Pro Asp Ala Ala Leu Gly Asn Gly Gly Leu Gly Arg
    130                 135                 140 ctt gct tca tgt ttc ttg gac tct ttg gct acc ttg aat tat ccg gca      729
Leu Ala Ser Cys Phe Leu Asp Ser Leu Ala Thr Leu Asn Tyr Pro Ala
145                 150                 155                 160 tgg ggt tat gga ctg aga tac aag tat ggc tta ttc aaa caa cga atc      777
Trp Gly Tyr Gly Leu Arg Tyr Lys Tyr Gly Leu Phe Lys Gln Arg Ile
                165                 170                 175 acc aaa gat ggg caa gag gaa gtt gct gaa gat tgg ctc gag atg ggc      825
Thr Lys Asp Gly Gln Glu Glu Val Ala Glu Asp Trp Leu Glu Met Gly
            180                 185                 190 aat cct tgg gag atc gtt aga aat gac gtc tca tac cct gta agg ttc      873
Asn Pro Trp Glu Ile Val Arg Asn Asp Val Ser Tyr Pro Val Arg Phe
        195                 200                 205 tat ggc aaa gtt gtt tca ggc tca gat ggt aaa aaa cat tgg gtt gga      921
Tyr Gly Lys Val Val Ser Gly Ser Asp Gly Lys Lys His Trp Val Gly
    210                 215                 220 gga gaa gat atc aaa gct gtt gca cac gat gtc ccc ata ccc gga tat      969
Gly Glu Asp Ile Lys Ala Val Ala His Asp Val Pro Ile Pro Gly Tyr
225                 230                 235                 240 aag acc aga agc aca att aac ctg aga ctt tgg tct aca aaa gct gca     1017
Lys Thr Arg Ser Thr Ile Asn Leu Arg Leu Trp Ser Thr Lys Ala Ala
                245                 250                 255 tcc gaa gaa ttt gat tta aat gct ttt aat tct gga agg cac acc gaa     1065
Ser Glu Glu Phe Asp Leu Asn Ala Phe Asn Ser Gly Arg His Thr Glu
            260                 265                 270 gca tct gag gct cta gca aat gct gaa aag att tgc tat ata ctt tac     1113
Ala Ser Glu Ala Leu Ala Asn Ala Glu Lys Ile Cys Tyr Ile Leu Tyr
        275                 280                 285 ccc ggg gat gaa tct ata gag gga aaa acc ctt cgc ctc aag caa caa     1161
Pro Gly Asp Glu Ser Ile Glu Gly Lys Thr Leu Arg Leu Lys Gln Gln
    290                 295                 300 tat act tta tgt tcg gct tct ctt caa gat atc att gct cgt ttt gag     1209
Tyr Thr Leu Cys Ser Ala Ser Leu Gln Asp Ile Ile Ala Arg Phe Glu
305                 310                 315                 320 aga aga tca ggg gca agt gtg aat tgg gaa gac ttt cct gaa aag gtt     1257
Arg Arg Ser Gly Ala Ser Val Asn Trp Glu Asp Phe Pro Glu Lys Val
                325                 330                 335 gca gtg cag atg aat gat act cac cca act ttg tgc atc cca gag ctg     1305
Ala Val Gln Met Asn Asp Thr His Pro Thr Leu Cys Ile Pro Glu Leu
            340                 345                 350 atg aga atc ctg ata gat ata aag ggt tta agc tgg aag gat gct tgg     1353
Met Arg Ile Leu Ile Asp Ile Lys Gly Leu Ser Trp Lys Asp Ala Trp
        355                 360                 365 aat atc acc caa cgg act gta gca tac aca aac cat act gtt ctt ccg     1401
Asn Ile Thr Gln Arg Thr Val Ala Tyr Thr Asn His Thr Val Leu Pro
    370                 375                 380 gag gca tta gag aaa tgg agc atg gac ctt atg gag aaa ttg ctt cca     1449
Glu Ala Leu Glu Lys Trp Ser Met Asp Leu Met Glu Lys Leu Leu Pro
385                 390                 395                 400 cgc cat gtt gag att ata gaa atg att gat gag gag ctg att cgg acc     1497
Arg His Val Glu Ile Ile Glu Met Ile Asp Glu Glu Leu Ile Arg Thr
                405                 410                 415 ata atc gca gaa tat ggc aca gca gat tca gac tta ctt gat aag aaa     1545
Ile Ile Ala Glu Tyr Gly Thr Ala Asp Ser Asp Leu Leu Asp Lys Lys
```

-continued

```
                 420                 425                 430
ttg aag gaa atg aga ata cta gaa aat gtt gaa ttg cct gca gaa ttt      1593
Leu Lys Glu Met Arg Ile Leu Glu Asn Val Glu Leu Pro Ala Glu Phe
            435                 440                 445 gca gat ata cta gtt aaa acc aag gag gcc act gat att tct agt gag      1641
Ala Asp Ile Leu Val Lys Thr Lys Glu Ala Thr Asp Ile Ser Ser Glu
        450                 455                 460 gaa gtg caa att tct aaa gaa ggg gga gaa gaa gaa act tct aaa          1689
Glu Val Gln Ile Ser Lys Glu Gly Gly Glu Glu Glu Thr Ser Lys
465                 470                 475                 480 gaa ggg gga gaa gaa gaa gaa aaa gaa gta gga gga aga gaa              1737
Glu Gly Gly Glu Glu Glu Glu Lys Glu Val Gly Gly Arg Glu
                485                 490                 495 gaa ggc gat gat ggt aag gaa gat gaa gtg gaa aaa gca att gct gaa      1785
Glu Gly Asp Asp Gly Lys Glu Asp Glu Val Glu Lys Ala Ile Ala Glu
            500                 505                 510 aag gat gga acg gtt aaa agc tcc att ggg gat aag aaa aag aag ttg      1833
Lys Asp Gly Thr Val Lys Ser Ser Ile Gly Asp Lys Lys Lys Lys Leu
        515                 520                 525 cct gag cca gta cca gta ccg cca aaa ttg gtt cgt atg gcc aat ctt      1881
Pro Glu Pro Val Pro Val Pro Pro Lys Leu Val Arg Met Ala Asn Leu
    530                 535                 540 tgt gtt gtg ggt ggt cat gca gtg aat ggg gtt gca gag ata cat agt      1929
Cys Val Val Gly Gly His Ala Val Asn Gly Val Ala Glu Ile His Ser
545                 550                 555                 560 gaa att gtc aag gat gac gtg ttc aat gca ttt tat aag ttg tgg cct      1977
Glu Ile Val Lys Asp Asp Val Phe Asn Ala Phe Tyr Lys Leu Trp Pro
                565                 570                 575 gag aaa ttc cag aac aaa aca aat ggc gtg acg cct agg aga tgg att      2025
Glu Lys Phe Gln Asn Lys Thr Asn Gly Val Thr Pro Arg Arg Trp Ile
            580                 585                 590 agg ttc tgc aat cca gat ttg agt aaa ata ata act cag tgg ata ggc      2073
Arg Phe Cys Asn Pro Asp Leu Ser Lys Ile Ile Thr Gln Trp Ile Gly
        595                 600                 605 aca gaa gac tgg atc cta aat act gag aaa ctg gct gaa ctg cgg aag      2121
Thr Glu Asp Trp Ile Leu Asn Thr Glu Lys Leu Ala Glu Leu Arg Lys
    610                 615                 620 ttt gca gat aat gag gat ctg caa aca caa tgg agg gaa gca aaa agg      2169
Phe Ala Asp Asn Glu Asp Leu Gln Thr Gln Trp Arg Glu Ala Lys Arg
625                 630                 635                 640 aat aac aag gtg aaa gtt gca gca ttc ctc aga gaa aga aca gga tat      2217
Asn Asn Lys Val Lys Val Ala Ala Phe Leu Arg Glu Arg Thr Gly Tyr
                645                 650                 655 tct gtc agt cct gat tca atg ttt gac atc cag gtg aaa aga atc cat      2265
Ser Val Ser Pro Asp Ser Met Phe Asp Ile Gln Val Lys Arg Ile His
            660                 665                 670 gaa tat aaa cga caa tta tta aat ata ttt gga att gtt tat cgc tac      2313
Glu Tyr Lys Arg Gln Leu Leu Asn Ile Phe Gly Ile Val Tyr Arg Tyr
        675                 680                 685 aag aag atg aaa gaa atg aat gct gct gaa aga aaa gaa aat ttt gtt      2361
Lys Lys Met Lys Glu Met Asn Ala Ala Glu Arg Lys Glu Asn Phe Val
    690                 695                 700 cca aga gtt tgt ata ttt ggg gga aaa gca ttt gct act tat gtg caa      2409
Pro Arg Val Cys Ile Phe Gly Gly Lys Ala Phe Ala Thr Tyr Val Gln
705                 710                 715                 720 gcc aaa aga att gtg aaa ttt att aca gat gtt gga gct act gta aat      2457
Ala Lys Arg Ile Val Lys Phe Ile Thr Asp Val Gly Ala Thr Val Asn
                725                 730                 735 cat gat cca gaa ata gga gat ctt ctt aag gtt att ttt gtc cct gac      2505
```

```
His Asp Pro Glu Ile Gly Asp Leu Leu Lys Val Ile Phe Val Pro Asp
            740                 745                 750 tac aat gtt agt gtt gcg gag atg ctt att cct gct agt gaa ttg tca      2553
Tyr Asn Val Ser Val Ala Glu Met Leu Ile Pro Ala Ser Glu Leu Ser
        755                 760                 765 caa cat atc agt act gct gga atg gag gca agt gga act agc aac atg      2601
Gln His Ile Ser Thr Ala Gly Met Glu Ala Ser Gly Thr Ser Asn Met
770                 775                 780 aaa ttt gca atg aat gga tgc tta cag att gga act ttg gat ggg gcc      2649
Lys Phe Ala Met Asn Gly Cys Leu Gln Ile Gly Thr Leu Asp Gly Ala
785                 790                 795                 800 aat gtt gaa ata agg gaa gag gtt ggt gct gac aac ttc ttc ctt ttt      2697
Asn Val Glu Ile Arg Glu Glu Val Gly Ala Asp Asn Phe Phe Leu Phe
                805                 810                 815 ggt gct aag gct cgt gaa att gtt ggg ctc agg aaa gaa aga gca aga      2745
Gly Ala Lys Ala Arg Glu Ile Val Gly Leu Arg Lys Glu Arg Ala Arg
            820                 825                 830 ggg aag ttt gtc cct gat cca cga ttc gaa gaa gtt aaa aaa ttt gtc      2793
Gly Lys Phe Val Pro Asp Pro Arg Phe Glu Glu Val Lys Lys Phe Val
        835                 840                 845 aga agt ggt gtc ttt ggg tct tac aac tat gat gaa ctg att gga tcc      2841
Arg Ser Gly Val Phe Gly Ser Tyr Asn Tyr Asp Glu Leu Ile Gly Ser
850                 855                 860 tta gaa gga aat gaa ggt ttt ggt cga gca gat tat ttt ctt gtg ggc      2889
Leu Glu Gly Asn Glu Gly Phe Gly Arg Ala Asp Tyr Phe Leu Val Gly
865                 870                 875                 880 cag gac ttc cct agc tat tta gaa tgc cag gag gag gtc gac aaa gct      2937
Gln Asp Phe Pro Ser Tyr Leu Glu Cys Gln Glu Glu Val Asp Lys Ala
                885                 890                 895 tat cgc gac caa aaa aaa tgg aca aga atg tca ata ttg aac aca gca      2985
Tyr Arg Asp Gln Lys Lys Trp Thr Arg Met Ser Ile Leu Asn Thr Ala
            900                 905                 910 ggc tca tcc aaa ttc agc agt gac cgt acc att cat gaa tat gca cga      3033
Gly Ser Ser Lys Phe Ser Ser Asp Arg Thr Ile His Glu Tyr Ala Arg
        915                 920                 925 gaa ata tgg aac att gag cca gtc aaa ttg gag tagagggta atctatacta    3086
Glu Ile Trp Asn Ile Glu Pro Val Lys Leu Glu
        930                 935 taccctttggt aatagcagag aatcggtgcc acgtcgtaat atgatcacta ctttaccaag   3146
tacccattag tgaaaataa actaagtttt gtaaaattaa aataagggtc tggttttaca    3206
tactgaaata aacagaagtt ttgtaaaatt aaaataaggg tctggctgtt gtcctccaaa   3266
acaagcctac attcctg                                                   3283

<210> SEQ ID NO 8
<211> LENGTH: 1003
<212> TYPE: PRT
<213> ORGANISM: Vicia faba

<400> SEQUENCE: 8

Met Ala Ser Met Thr Met Arg Phe His Pro Asn Ser Thr Ala Val Thr
                -60                 -55                 -50

Glu Ser Val Pro Arg Arg Gly Ser Val Tyr Gly Phe Ile Gly Tyr Arg
            -45                 -40                 -35

Ser Ser Ser Leu Phe Val Arg Thr Asn Val Ile Lys Tyr Arg Ser Val
        -30                 -25                 -20

Lys Arg Asn Leu Glu Phe Arg Arg Arg Ser Ala Phe Ser Val Lys Cys
    -15                 -10                 -5                  -1
```

-continued

```
Gly Ser Gly Asn Glu Ala Lys Gln Lys Val Lys Asp Gln Glu Val Gln
1               5                   10                  15

Gln Glu Ala Lys Thr Ser Pro Ser Phe Ala Pro Asp Thr Thr Ser
            20              25                  30

Ile Val Ser Ser Ile Lys Tyr His Ala Glu Phe Thr Pro Leu Phe Ser
        35                  40                  45

Pro Glu Lys Phe Glu Leu Pro Gln Ala Phe Ile Ala Thr Ala Gln Ser
    50                  55                  60

Val Arg Asp Ala Leu Ile Ile Asn Trp Asn Ala Thr Tyr Asp Tyr Tyr
65                  70                  75                  80

Glu Lys Leu Asn Val Lys Gln Ala Tyr Tyr Leu Ser Met Glu Phe Leu
                85                  90                  95

Gln Gly Arg Ala Leu Leu Asn Ala Ile Gly Asn Leu Glu Leu Thr Gly
            100                 105                 110

Pro Tyr Ala Glu Ala Leu Ser Gln Leu Ser Tyr Lys Leu Glu Asp Val
        115                 120                 125

Ala His Gln Glu Pro Asp Ala Leu Gly Asn Gly Gly Leu Gly Arg
        130                 135                 140

Leu Ala Ser Cys Phe Leu Asp Ser Leu Ala Thr Leu Asn Tyr Pro Ala
145                 150                 155                 160

Trp Gly Tyr Gly Leu Arg Tyr Lys Tyr Gly Leu Phe Lys Gln Arg Ile
                165                 170                 175

Thr Lys Asp Gly Gln Glu Glu Val Ala Glu Asp Trp Leu Glu Met Gly
            180                 185                 190

Asn Pro Trp Glu Ile Val Arg Asn Asp Val Ser Tyr Pro Val Arg Phe
        195                 200                 205

Tyr Gly Lys Val Val Ser Gly Ser Asp Gly Lys Lys His Trp Val Gly
210                 215                 220

Gly Glu Asp Ile Lys Ala Val Ala His Asp Val Pro Ile Pro Gly Tyr
225                 230                 235                 240

Lys Thr Arg Ser Thr Ile Asn Leu Arg Leu Trp Ser Thr Lys Ala Ala
                245                 250                 255

Ser Glu Glu Phe Asp Leu Asn Ala Phe Asn Ser Gly Arg His Thr Glu
            260                 265                 270

Ala Ser Glu Ala Leu Ala Asn Ala Glu Lys Ile Cys Tyr Ile Leu Tyr
        275                 280                 285

Pro Gly Asp Glu Ser Ile Glu Gly Lys Thr Leu Arg Leu Lys Gln Gln
    290                 295                 300

Tyr Thr Leu Cys Ser Ala Ser Leu Gln Asp Ile Ile Ala Arg Phe Glu
305                 310                 315                 320

Arg Arg Ser Gly Ala Ser Val Asn Trp Glu Asp Phe Pro Glu Lys Val
                325                 330                 335

Ala Val Gln Met Asn Asp Thr His Pro Thr Leu Cys Ile Pro Glu Leu
            340                 345                 350

Met Arg Ile Leu Ile Asp Ile Lys Gly Leu Ser Trp Lys Asp Ala Trp
        355                 360                 365

Asn Ile Thr Gln Arg Thr Val Ala Tyr Thr Asn His Thr Val Leu Pro
    370                 375                 380

Glu Ala Leu Glu Lys Trp Ser Met Asp Leu Met Glu Lys Leu Leu Pro
385                 390                 395                 400

Arg His Val Glu Ile Ile Glu Met Ile Asp Glu Glu Leu Ile Arg Thr
                405                 410                 415

Ile Ile Ala Glu Tyr Gly Thr Ala Asp Ser Asp Leu Leu Asp Lys Lys
```

-continued

```
            420                 425                 430
Leu Lys Glu Met Arg Ile Leu Glu Asn Val Glu Leu Pro Ala Glu Phe
            435                 440                 445

Ala Asp Ile Leu Val Lys Thr Lys Glu Ala Thr Asp Ile Ser Ser Glu
450                 455                 460

Glu Val Gln Ile Ser Lys Glu Gly Glu Glu Glu Thr Ser Lys
465                 470                 475                 480

Glu Gly Gly Glu Glu Glu Glu Lys Glu Val Gly Gly Arg Glu
                485                 490                 495

Glu Gly Asp Asp Gly Lys Glu Asp Glu Val Lys Ala Ile Ala Glu
            500                 505                 510

Lys Asp Gly Thr Val Lys Ser Ser Ile Gly Asp Lys Lys Lys Leu
            515                 520                 525

Pro Glu Pro Val Pro Val Pro Pro Lys Leu Val Arg Met Ala Asn Leu
530                 535                 540

Cys Val Val Gly Gly His Ala Val Asn Gly Val Ala Glu Ile His Ser
545                 550                 555                 560

Glu Ile Val Lys Asp Asp Val Phe Asn Ala Phe Tyr Lys Leu Trp Pro
                565                 570                 575

Glu Lys Phe Gln Asn Lys Thr Asn Gly Val Thr Pro Arg Arg Trp Ile
            580                 585                 590

Arg Phe Cys Asn Pro Asp Leu Ser Lys Ile Ile Thr Gln Trp Ile Gly
        595                 600                 605

Thr Glu Asp Trp Ile Leu Asn Thr Glu Lys Leu Ala Glu Leu Arg Lys
    610                 615                 620

Phe Ala Asp Asn Glu Asp Leu Gln Thr Gln Trp Arg Glu Ala Lys Arg
625                 630                 635                 640

Asn Asn Lys Val Lys Val Ala Ala Phe Leu Arg Glu Arg Thr Gly Tyr
                645                 650                 655

Ser Val Ser Pro Asp Ser Met Phe Asp Ile Gln Val Lys Arg Ile His
            660                 665                 670

Glu Tyr Lys Arg Gln Leu Leu Asn Ile Phe Gly Ile Val Tyr Arg Tyr
        675                 680                 685

Lys Lys Met Lys Glu Met Asn Ala Ala Glu Arg Lys Glu Asn Phe Val
    690                 695                 700

Pro Arg Val Cys Ile Phe Gly Gly Lys Ala Phe Ala Thr Tyr Val Gln
705                 710                 715                 720

Ala Lys Arg Ile Val Lys Phe Ile Thr Asp Val Gly Ala Thr Val Asn
                725                 730                 735

His Asp Pro Glu Ile Gly Asp Leu Leu Lys Val Ile Phe Val Pro Asp
            740                 745                 750

Tyr Asn Val Ser Val Ala Glu Met Leu Ile Pro Ala Ser Glu Leu Ser
        755                 760                 765

Gln His Ile Ser Thr Ala Gly Met Glu Ala Ser Gly Thr Ser Asn Met
    770                 775                 780

Lys Phe Ala Met Asn Gly Cys Leu Gln Ile Gly Thr Leu Asp Gly Ala
785                 790                 795                 800

Asn Val Glu Ile Arg Glu Glu Val Gly Ala Asp Asn Phe Phe Leu Phe
                805                 810                 815

Gly Ala Lys Ala Arg Glu Ile Val Gly Leu Arg Lys Glu Arg Ala Arg
            820                 825                 830

Gly Lys Phe Val Pro Asp Pro Arg Phe Glu Glu Val Lys Lys Phe Val
        835                 840                 845
```

```
Arg Ser Gly Val Phe Gly Ser Tyr Asn Tyr Asp Glu Leu Ile Gly Ser
    850                 855                 860

Leu Glu Gly Asn Glu Gly Phe Gly Arg Ala Asp Tyr Phe Leu Val Gly
865                 870                 875                 880

Gln Asp Phe Pro Ser Tyr Leu Glu Cys Gln Glu Val Asp Lys Ala
                885                 890                 895

Tyr Arg Asp Gln Lys Lys Trp Thr Arg Met Ser Ile Leu Asn Thr Ala
            900                 905                 910

Gly Ser Ser Lys Phe Ser Ser Asp Arg Thr Ile His Glu Tyr Ala Arg
                915                 920                 925

Glu Ile Trp Asn Ile Glu Pro Val Lys Leu Glu
    930                 935

<210> SEQ ID NO 9
<211> LENGTH: 2889
<212> TYPE: DNA
<213> ORGANISM: Arabidopsis thaliana
<220> FEATURE:
<221> NAME/KEY: CDS
<222> LOCATION: (1)..(2889)

<400> SEQUENCE: 9 atg gat acg atg cga atc tcc ggt gta tca acc gga gct gag gtt tta      48
Met Asp Thr Met Arg Ile Ser Gly Val Ser Thr Gly Ala Glu Val Leu
1               5                   10                  15 ata caa tgc aat tcc tta tca agc ctc gtt tct cgt cgt tgc gac gac      96
Ile Gln Cys Asn Ser Leu Ser Ser Leu Val Ser Arg Arg Cys Asp Asp
                20                  25                  30 gga aaa tgg cga acg aga atg ttt ccg gcg aga aac aga gac ttg cgt     144
Gly Lys Trp Arg Thr Arg Met Phe Pro Ala Arg Asn Arg Asp Leu Arg
            35                  40                  45 cca tcg ccg acg aga aga tcc ttt ttg tcg gtg aaa tct atc tct agc     192
Pro Ser Pro Thr Arg Arg Ser Phe Leu Ser Val Lys Ser Ile Ser Ser
        50                  55                  60 gaa ccg aaa gcc aaa gta acc gac gca gtt ctc gat tcc gaa caa gaa     240
Glu Pro Lys Ala Lys Val Thr Asp Ala Val Leu Asp Ser Glu Gln Glu
65                  70                  75                  80 gtg ttt att agc tcg atg aat ccg ttt gcg cca gat gct gct tcg gta     288
Val Phe Ile Ser Ser Met Asn Pro Phe Ala Pro Asp Ala Ala Ser Val
                85                  90                  95 gct tcg agt atc aag tac cac gcg gag ttt acg cca ttg ttt tca ccg     336
Ala Ser Ser Ile Lys Tyr His Ala Glu Phe Thr Pro Leu Phe Ser Pro
                100                 105                 110 gag aag ttt gag ttg cca aag gcg ttc ttt gcg act gcg caa agt gtt     384
Glu Lys Phe Glu Leu Pro Lys Ala Phe Phe Ala Thr Ala Gln Ser Val
            115                 120                 125 aga gat gct ttg atc atg aat tgg aat gca act tat gag tat tac aac     432
Arg Asp Ala Leu Ile Met Asn Trp Asn Ala Thr Tyr Glu Tyr Tyr Asn
        130                 135                 140 aga gtg aat gtg aaa caa gcg tat tat ttg tca atg gag ttt ttg cag     480
Arg Val Asn Val Lys Gln Ala Tyr Tyr Leu Ser Met Glu Phe Leu Gln
145                 150                 155                 160 ggt aga gcc tta tcg aat gcc gtg ggt aac ctt ggg ctt aat agc gct     528
Gly Arg Ala Leu Ser Asn Ala Val Gly Asn Leu Gly Leu Asn Ser Ala
                165                 170                 175 tat ggt gat gct ttg aag agg ctt ggt ttt gat ttg gaa agc gtg gct     576
Tyr Gly Asp Ala Leu Lys Arg Leu Gly Phe Asp Leu Glu Ser Val Ala
                180                 185                 190 agt cag gag cca gat cct gca ctt ggg aat ggt gga ctc ggg aga ctt     624
```

```
                Ser Gln Glu Pro Asp Pro Ala Leu Gly Asn Gly Gly Leu Gly Arg Leu
                            195                 200                 205 gcc tcg tgt ttt ttg gat tcc atg gca act ttg aat tat ccg gct tgg      672
Ala Ser Cys Phe Leu Asp Ser Met Ala Thr Leu Asn Tyr Pro Ala Trp
210                 215                 220 ggt tat gga ctt aga tac aag tat ggc ttg ttc aaa cag aga att aca      720
Gly Tyr Gly Leu Arg Tyr Lys Tyr Gly Leu Phe Lys Gln Arg Ile Thr
225                 230                 235                 240 aaa gat gga cag gag gaa gct gca gaa gat tgg ctt gag cta agc aat      768
Lys Asp Gly Gln Glu Glu Ala Ala Glu Asp Trp Leu Glu Leu Ser Asn
                245                 250                 255 cct tgg gaa ata gtc aga aat gat gtc tca tat cct att aag ttc tat      816
Pro Trp Glu Ile Val Arg Asn Asp Val Ser Tyr Pro Ile Lys Phe Tyr
            260                 265                 270 ggg aaa gtg gtt ttt gga tca gat ggt aag aaa cgg tgg att ggt gga      864
Gly Lys Val Val Phe Gly Ser Asp Gly Lys Lys Arg Trp Ile Gly Gly
        275                 280                 285 gaa gac att gtt gct gtt gct tat gat gtt cct ata cct ggt tat aaa      912
Glu Asp Ile Val Ala Val Ala Tyr Asp Val Pro Ile Pro Gly Tyr Lys
    290                 295                 300 act aag aca act atc aat ctg cgg ctc tgg tca aca aaa gct cct tcc      960
Thr Lys Thr Thr Ile Asn Leu Arg Leu Trp Ser Thr Lys Ala Pro Ser
305                 310                 315                 320 gaa gat ttt gat tta tct tca tat aac tct ggg aag cat act gag gca     1008
Glu Asp Phe Asp Leu Ser Ser Tyr Asn Ser Gly Lys His Thr Glu Ala
                325                 330                 335 gca gaa gct cta ttc aac gct gaa aag att tgc ttc gtg ctt tac ccc     1056
Ala Glu Ala Leu Phe Asn Ala Glu Lys Ile Cys Phe Val Leu Tyr Pro
            340                 345                 350 gga gat gag tca act gaa gga aag gct ctt cgt ctg aag caa caa tac     1104
Gly Asp Glu Ser Thr Glu Gly Lys Ala Leu Arg Leu Lys Gln Gln Tyr
        355                 360                 365 act ctg tgc tca gcc tcg cta caa gat atc gta gca cgt ttt gag aca     1152
Thr Leu Cys Ser Ala Ser Leu Gln Asp Ile Val Ala Arg Phe Glu Thr
    370                 375                 380 agg tct gga gga aac gtc aac tgg gaa gaa ttt cca gag aag gtt gca     1200
Arg Ser Gly Gly Asn Val Asn Trp Glu Glu Phe Pro Glu Lys Val Ala
385                 390                 395                 400 gtg cag atg aat gac act cac cct acc cta tgc att cct gag cta atg     1248
Val Gln Met Asn Asp Thr His Pro Thr Leu Cys Ile Pro Glu Leu Met
                405                 410                 415 agg att cta atg gat tta aaa gga cta agc tgg gaa gac gct tgg aaa     1296
Arg Ile Leu Met Asp Leu Lys Gly Leu Ser Trp Glu Asp Ala Trp Lys
            420                 425                 430 atc aca caa agg act gtg gca tac aca aac cat aca gtc ttg cct gag     1344
Ile Thr Gln Arg Thr Val Ala Tyr Thr Asn His Thr Val Leu Pro Glu
        435                 440                 445 gca ctg gag aag tgg agt tta gaa ctc atg gag aaa ttg ctt cct cgt     1392
Ala Leu Glu Lys Trp Ser Leu Glu Leu Met Glu Lys Leu Leu Pro Arg
    450                 455                 460 cat gtg gag att atc gaa aag att gat gag gag cta gtt cgc aca att     1440
His Val Glu Ile Ile Glu Lys Ile Asp Glu Glu Leu Val Arg Thr Ile
465                 470                 475                 480 gtt tca gag tat ggc acc gcg gat cct gac tta ctt gaa gaa aaa ctg     1488
Val Ser Glu Tyr Gly Thr Ala Asp Pro Asp Leu Leu Glu Glu Lys Leu
                485                 490                 495 aag gca atg agg atc ttg gaa aat gtc gag ttg cct tct gcc ttt gca     1536
Lys Ala Met Arg Ile Leu Glu Asn Val Glu Leu Pro Ser Ala Phe Ala
            500                 505                 510
```

```
                                                            -continued gat gtg atc gtg aag ccg gtg aac aaa cca gtt act gca aaa gat gct     1584
Asp Val Ile Val Lys Pro Val Asn Lys Pro Val Thr Ala Lys Asp Ala
            515                 520                 525 caa aat ggc gtg aaa acg gaa caa gaa gag gaa aaa act gct gga gag     1632
Gln Asn Gly Val Lys Thr Glu Gln Glu Glu Glu Lys Thr Ala Gly Glu
530                 535                 540 gaa gag gaa gac gaa gtt atc cca gaa cca aca gta gaa ccc ccc aag     1680
Glu Glu Glu Asp Glu Val Ile Pro Glu Pro Thr Val Glu Pro Pro Lys
545                 550                 555                 560 atg gtc cgt atg gcc aac ctt gct gtt gtg ggt ggt cat gct gta aat     1728
Met Val Arg Met Ala Asn Leu Ala Val Val Gly Gly His Ala Val Asn
                565                 570                 575 ggc gtt gca gag ata cac agt gaa ata gtg aag cag gac gtg ttt aat     1776
Gly Val Ala Glu Ile His Ser Glu Ile Val Lys Gln Asp Val Phe Asn
            580                 585                 590 gat ttc gta cag ttg tgg cca gaa aaa ttt cag aac aaa aca aat gga     1824
Asp Phe Val Gln Leu Trp Pro Glu Lys Phe Gln Asn Lys Thr Asn Gly
        595                 600                 605 gta aca cca agg cga tgg att cgt ttt tgc aac cca tat tta agt gat     1872
Val Thr Pro Arg Arg Trp Ile Arg Phe Cys Asn Pro Tyr Leu Ser Asp
610                 615                 620 att ata act aac tgg ata ggc aca gaa gac tgg gtc tta aat acc gaa     1920
Ile Ile Thr Asn Trp Ile Gly Thr Glu Asp Trp Val Leu Asn Thr Glu
625                 630                 635                 640 aag gtt gcg gaa cta aga aag ttt gca gat aat gaa gat ctc caa tct     1968
Lys Val Ala Glu Leu Arg Lys Phe Ala Asp Asn Glu Asp Leu Gln Ser
                645                 650                 655 gag tgg agg gca gca aag aag aag aac aag ttg aag gtt gta tca ctt     2016
Glu Trp Arg Ala Ala Lys Lys Lys Asn Lys Leu Lys Val Val Ser Leu
            660                 665                 670 atc aag gaa aga act gga tat act gtc agc ccc gat gca atg ttc gac     2064
Ile Lys Glu Arg Thr Gly Tyr Thr Val Ser Pro Asp Ala Met Phe Asp
        675                 680                 685 att cag atc aag cgt ata cat gag tac aag cga caa ctg cta aat atc     2112
Ile Gln Ile Lys Arg Ile His Glu Tyr Lys Arg Gln Leu Leu Asn Ile
690                 695                 700 ttg gga att gtt tac cgc tac aaa aag atg aag gaa atg agt gct agt     2160
Leu Gly Ile Val Tyr Arg Tyr Lys Lys Met Lys Glu Met Ser Ala Ser
705                 710                 715                 720 gag aga gag aaa gca ttt gtt cca aga gtt tgc ata ttt ggg gga aaa     2208
Glu Arg Glu Lys Ala Phe Val Pro Arg Val Cys Ile Phe Gly Gly Lys
                725                 730                 735 gca ttt gcc aca tat gtg caa gct aag aga att gtt aaa ttt atc aca     2256
Ala Phe Ala Thr Tyr Val Gln Ala Lys Arg Ile Val Lys Phe Ile Thr
            740                 745                 750 gat gtt gcg tct aca att aac cat gat cca gaa ata ggt gac ctc ctt     2304
Asp Val Ala Ser Thr Ile Asn His Asp Pro Glu Ile Gly Asp Leu Leu
        755                 760                 765 aag gtt atc ttt gtt cct gat tac aat gtc agt gtt gct gaa ttg ctc     2352
Lys Val Ile Phe Val Pro Asp Tyr Asn Val Ser Val Ala Glu Leu Leu
770                 775                 780 att cca gca agt gag ctt tct cag cac atc agt act gct ggg atg gaa     2400
Ile Pro Ala Ser Glu Leu Ser Gln His Ile Ser Thr Ala Gly Met Glu
785                 790                 795                 800 gct agt ggg aca agc aac atg aaa ttt tcg atg aac ggt tgc gtt ttg     2448
Ala Ser Gly Thr Ser Asn Met Lys Phe Ser Met Asn Gly Cys Val Leu
                805                 810                 815 att gga acc ttg gat ggg gcg aat gtc gag att aga gaa gaa gtt gga     2496
Ile Gly Thr Leu Asp Gly Ala Asn Val Glu Ile Arg Glu Glu Val Gly
            820                 825                 830
```

```
gaa gaa aat ttc ttc ctc ttt ggt gcc aaa gct gat cag att gtg aac      2544
Glu Glu Asn Phe Phe Leu Phe Gly Ala Lys Ala Asp Gln Ile Val Asn
        835                 840                 845 ctc agg aag gag aga gca gag gga aag ttt gtt ccc gat cct act ttt      2592
Leu Arg Lys Glu Arg Ala Glu Gly Lys Phe Val Pro Asp Pro Thr Phe
850                 855                 860 gaa gaa gtc aag aag ttc gtt gga agc ggc gtc ttt ggc tca aat agc      2640
Glu Glu Val Lys Lys Phe Val Gly Ser Gly Val Phe Gly Ser Asn Ser
865                 870                 875                 880 tat gat gaa cta atc ggc tct ttg gaa gga aac gaa ggc ttt gga cga      2688
Tyr Asp Glu Leu Ile Gly Ser Leu Glu Gly Asn Glu Gly Phe Gly Arg
            885                 890                 895 gcg gat tac ttc cta gtt ggc aaa gac ttt cct agt tac atc gaa tgc      2736
Ala Asp Tyr Phe Leu Val Gly Lys Asp Phe Pro Ser Tyr Ile Glu Cys
        900                 905                 910 caa gaa aaa gtc gac gag gca tac cga gac cag aaa aga tgg acg aga      2784
Gln Glu Lys Val Asp Glu Ala Tyr Arg Asp Gln Lys Arg Trp Thr Arg
    915                 920                 925 atg tca ata atg aac aca gca ggt tca ttc aag ttt agc agt gac cgg      2832
Met Ser Ile Met Asn Thr Ala Gly Ser Phe Lys Phe Ser Ser Asp Arg
930                 935                 940 acg atc cac gaa tac gcc aaa gac ata tgg aat att aag caa gtg gaa      2880
Thr Ile His Glu Tyr Ala Lys Asp Ile Trp Asn Ile Lys Gln Val Glu
945                 950                 955                 960 ctt cca tga                                                           2889
Leu Pro <210> SEQ ID NO 10
<211> LENGTH: 962
<212> TYPE: PRT
<213> ORGANISM: Arabidopsis thaliana

<400> SEQUENCE: 10

Met Asp Thr Met Arg Ile Ser Gly Val Ser Thr Gly Ala Glu Val Leu
1               5                   10                  15

Ile Gln Cys Asn Ser Leu Ser Ser Leu Val Ser Arg Arg Cys Asp Asp
            20                  25                  30

Gly Lys Trp Arg Thr Arg Met Phe Pro Ala Arg Asn Arg Asp Leu Arg
        35                  40                  45

Pro Ser Pro Thr Arg Arg Ser Phe Leu Ser Val Lys Ser Ile Ser Ser
    50                  55                  60

Glu Pro Lys Ala Lys Val Thr Asp Ala Val Leu Asp Ser Glu Gln Glu
65                  70                  75                  80

Val Phe Ile Ser Ser Met Asn Pro Phe Ala Pro Asp Ala Ala Ser Val
                85                  90                  95

Ala Ser Ser Ile Lys Tyr His Ala Glu Phe Thr Pro Leu Phe Ser Pro
            100                 105                 110

Glu Lys Phe Glu Leu Pro Lys Ala Phe Phe Ala Thr Ala Gln Ser Val
        115                 120                 125

Arg Asp Ala Leu Ile Met Asn Trp Asn Ala Thr Tyr Glu Tyr Tyr Asn
    130                 135                 140

Arg Val Asn Val Lys Gln Ala Tyr Tyr Leu Ser Met Glu Phe Leu Gln
145                 150                 155                 160

Gly Arg Ala Leu Ser Asn Ala Val Gly Asn Leu Gly Leu Asn Ser Ala
                165                 170                 175

Tyr Gly Asp Ala Leu Lys Arg Leu Gly Phe Asp Leu Glu Ser Val Ala
            180                 185                 190
```

-continued

```
Ser Gln Glu Pro Asp Pro Ala Leu Gly Asn Gly Gly Leu Gly Arg Leu
        195                 200                 205

Ala Ser Cys Phe Leu Asp Ser Met Ala Thr Leu Asn Tyr Pro Ala Trp
210                 215                 220

Gly Tyr Gly Leu Arg Tyr Lys Tyr Gly Leu Phe Lys Gln Arg Ile Thr
225                 230                 235                 240

Lys Asp Gly Gln Glu Ala Ala Glu Asp Trp Leu Glu Leu Ser Asn
                245                 250                 255

Pro Trp Glu Ile Val Arg Asn Asp Val Ser Tyr Pro Ile Lys Phe Tyr
            260                 265                 270

Gly Lys Val Val Phe Gly Ser Asp Gly Lys Lys Arg Trp Ile Gly Gly
                275                 280                 285

Glu Asp Ile Val Ala Val Ala Tyr Asp Val Pro Ile Pro Gly Tyr Lys
        290                 295                 300

Thr Lys Thr Thr Ile Asn Leu Arg Leu Trp Ser Thr Lys Ala Pro Ser
305                 310                 315                 320

Glu Asp Phe Asp Leu Ser Ser Tyr Asn Ser Gly Lys His Thr Glu Ala
                325                 330                 335

Ala Glu Ala Leu Phe Asn Ala Glu Lys Ile Cys Phe Val Leu Tyr Pro
            340                 345                 350

Gly Asp Glu Ser Thr Glu Gly Lys Ala Leu Arg Leu Lys Gln Gln Tyr
        355                 360                 365

Thr Leu Cys Ser Ala Ser Leu Gln Asp Ile Val Ala Arg Phe Glu Thr
    370                 375                 380

Arg Ser Gly Gly Asn Val Asn Trp Glu Glu Phe Pro Glu Lys Val Ala
385                 390                 395                 400

Val Gln Met Asn Asp Thr His Pro Thr Leu Cys Ile Pro Glu Leu Met
                405                 410                 415

Arg Ile Leu Met Asp Leu Lys Gly Leu Ser Trp Glu Asp Ala Trp Lys
            420                 425                 430

Ile Thr Gln Arg Thr Val Ala Tyr Thr Asn His Thr Val Leu Pro Glu
        435                 440                 445

Ala Leu Glu Lys Trp Ser Leu Glu Leu Met Glu Lys Leu Leu Pro Arg
450                 455                 460

His Val Glu Ile Ile Glu Lys Ile Asp Glu Glu Leu Val Arg Thr Ile
465                 470                 475                 480

Val Ser Glu Tyr Gly Thr Ala Asp Pro Asp Leu Leu Glu Glu Lys Leu
                485                 490                 495

Lys Ala Met Arg Ile Leu Glu Asn Val Glu Leu Pro Ser Ala Phe Ala
            500                 505                 510

Asp Val Ile Val Lys Pro Val Asn Lys Pro Val Thr Ala Lys Asp Ala
        515                 520                 525

Gln Asn Gly Val Lys Thr Glu Gln Glu Glu Lys Thr Ala Gly Glu
    530                 535                 540

Glu Glu Glu Asp Glu Val Ile Pro Glu Pro Thr Val Glu Pro Pro Lys
545                 550                 555                 560

Met Val Arg Met Ala Asn Leu Ala Val Val Gly Gly His Ala Val Asn
                565                 570                 575

Gly Val Ala Glu Ile His Ser Glu Ile Val Lys Gln Asp Val Phe Asn
            580                 585                 590

Asp Phe Val Gln Leu Trp Pro Glu Lys Phe Gln Asn Lys Thr Asn Gly
        595                 600                 605
```

```
Val Thr Pro Arg Arg Trp Ile Arg Phe Cys Asn Pro Tyr Leu Ser Asp
    610                 615                 620

Ile Ile Thr Asn Trp Ile Gly Thr Glu Asp Trp Val Leu Asn Thr Glu
625                 630                 635                 640

Lys Val Ala Glu Leu Arg Lys Phe Ala Asp Asn Glu Asp Leu Gln Ser
            645                 650                 655

Glu Trp Arg Ala Ala Lys Lys Asn Lys Leu Lys Val Val Ser Leu
        660                 665                 670

Ile Lys Glu Arg Thr Gly Tyr Thr Val Ser Pro Asp Ala Met Phe Asp
    675                 680                 685

Ile Gln Ile Lys Arg Ile His Glu Tyr Lys Arg Gln Leu Leu Asn Ile
690                 695                 700

Leu Gly Ile Val Tyr Arg Tyr Lys Lys Met Lys Glu Met Ser Ala Ser
705                 710                 715                 720

Glu Arg Glu Lys Ala Phe Val Pro Arg Val Cys Ile Phe Gly Gly Lys
            725                 730                 735

Ala Phe Ala Thr Tyr Val Gln Ala Lys Arg Ile Val Lys Phe Ile Thr
            740                 745                 750

Asp Val Ala Ser Thr Ile Asn His Asp Pro Glu Ile Gly Asp Leu Leu
            755                 760                 765

Lys Val Ile Phe Val Pro Asp Tyr Asn Val Ser Val Ala Glu Leu Leu
770                 775                 780

Ile Pro Ala Ser Glu Leu Ser Gln His Ile Ser Thr Ala Gly Met Glu
785                 790                 795                 800

Ala Ser Gly Thr Ser Asn Met Lys Phe Ser Met Asn Gly Cys Val Leu
            805                 810                 815

Ile Gly Thr Leu Asp Gly Ala Asn Val Glu Ile Arg Glu Glu Val Gly
            820                 825                 830

Glu Glu Asn Phe Phe Leu Phe Gly Ala Lys Ala Asp Gln Ile Val Asn
            835                 840                 845

Leu Arg Lys Glu Arg Ala Glu Gly Lys Phe Val Pro Asp Pro Thr Phe
850                 855                 860

Glu Glu Val Lys Lys Phe Val Gly Ser Gly Val Phe Gly Ser Asn Ser
865                 870                 875                 880

Tyr Asp Glu Leu Ile Gly Ser Leu Glu Gly Asn Glu Gly Phe Gly Arg
            885                 890                 895

Ala Asp Tyr Phe Leu Val Gly Lys Asp Phe Pro Ser Tyr Ile Glu Cys
            900                 905                 910

Gln Glu Lys Val Asp Glu Ala Tyr Arg Asp Gln Lys Arg Trp Thr Arg
        915                 920                 925

Met Ser Ile Met Asn Thr Ala Gly Ser Phe Lys Phe Ser Ser Asp Arg
    930                 935                 940

Thr Ile His Glu Tyr Ala Lys Asp Ile Trp Asn Ile Lys Gln Val Glu
945                 950                 955                 960

Leu Pro

<210> SEQ ID NO 11
<211> LENGTH: 3088
<212> TYPE: DNA
<213> ORGANISM: Spinacia oleracea
<220> FEATURE:
<221> NAME/KEY: CDS
<222> LOCATION: (57)..(2972)

<400> SEQUENCE: 11
```

-continued

```
ggcacgaggt gtatcggagt cactcagagt cagagagatt attcaagaga tcaaca atg         59
                                                                 Met
                                                                 1 gcg aca ttg cca tta tca tca aca aca cct tca acc gga aga aca gag          107
Ala Thr Leu Pro Leu Ser Ser Thr Thr Pro Ser Thr Gly Arg Thr Glu
        5               10              15 aat tgt ttc tct tcg tac tat tca tcg tca att tca cga gtt atg gaa          155
Asn Cys Phe Ser Ser Tyr Tyr Ser Ser Ser Ile Ser Arg Val Met Glu
            20              25              30 ttt ggg tta aaa aac ggc tgt aat tcc aag ctg ttg ttt tct tct gtc          203
Phe Gly Leu Lys Asn Gly Cys Asn Ser Lys Leu Leu Phe Ser Ser Val
    35              40              45 aat tat aaa cct atg att atg aga ggt tca aga agg tgt atc gta att          251
Asn Tyr Lys Pro Met Ile Met Arg Gly Ser Arg Arg Cys Ile Val Ile
50              55              60              65 aga aat gtg ttc agt gaa tcg aag ccg aaa tcg gag gaa ccg atc att          299
Arg Asn Val Phe Ser Glu Ser Lys Pro Lys Ser Glu Glu Pro Ile Ile
                70              75              80 gaa caa gaa act cca agc att ttg aac ccg ttg agt aac ttg agt cca          347
Glu Gln Glu Thr Pro Ser Ile Leu Asn Pro Leu Ser Asn Leu Ser Pro
            85              90              95 gat tct gct tca agg caa tca agt att aaa tac cat gcg gag ttc act          395
Asp Ser Ala Ser Arg Gln Ser Ser Ile Lys Tyr His Ala Glu Phe Thr
    100             105             110 ccg ttg ttt gct cca aat gac ttt tct ctt ccc aag gct ttc ttc gcc          443
Pro Leu Phe Ala Pro Asn Asp Phe Ser Leu Pro Lys Ala Phe Phe Ala
115             120             125 gct gca cag agt gtt aga gat tca ctt att att aac tgg aat gct act          491
Ala Ala Gln Ser Val Arg Asp Ser Leu Ile Ile Asn Trp Asn Ala Thr
130             135             140             145 tat gcc cat tat gag aag atg aac atg aag caa gct tat tat ttg tcc         539
Tyr Ala His Tyr Glu Lys Met Asn Met Lys Gln Ala Tyr Tyr Leu Ser
            150             155             160 atg gaa ttt ctc cag ggt aga gca ctg ttg aat gcg att ggg aat ttg         587
Met Glu Phe Leu Gln Gly Arg Ala Leu Leu Asn Ala Ile Gly Asn Leu
    165             170             175 gaa cta acc gat gct tat gga gat gct ttg aaa aag ctt gga cac aat         635
Glu Leu Thr Asp Ala Tyr Gly Asp Ala Leu Lys Lys Leu Gly His Asn
180             185             190 ctg gaa gct gta gct tgt cag gaa cga gat gct gca ctt gga aat ggg         683
Leu Glu Ala Val Ala Cys Gln Glu Arg Asp Ala Ala Leu Gly Asn Gly
195             200             205 ggt ctc ggg agg ctc gct tcg tgc ttt ctt gac tct ctc gct aca ttg         731
Gly Leu Gly Arg Leu Ala Ser Cys Phe Leu Asp Ser Leu Ala Thr Leu
210             215             220             225 aat tat cct gca tgg ggt tat gga cta aga tac aag tat ggg tta ttc         779
Asn Tyr Pro Ala Trp Gly Tyr Gly Leu Arg Tyr Lys Tyr Gly Leu Phe
            230             235             240 aag caa atg att acc aag gat ggt caa gaa gaa gtt gct gag aat tgg         827
Lys Gln Met Ile Thr Lys Asp Gly Gln Glu Glu Val Ala Glu Asn Trp
    245             250             255 ctt gag att gct aat cca tgg gaa ctt gtg aga aat gat gtt tcc tat         875
Leu Glu Ile Ala Asn Pro Trp Glu Leu Val Arg Asn Asp Val Ser Tyr
260             265             270 tca ata aaa ttt tat gga aag gtg gtt tct gga tcg gat ggc aga agt         923
Ser Ile Lys Phe Tyr Gly Lys Val Val Ser Gly Ser Asp Gly Arg Ser
275             280             285 cat tgg act ggg gga gag gat atc agg gct gtt gcc tat gat gtt cct         971
His Trp Thr Gly Gly Glu Asp Ile Arg Ala Val Ala Tyr Asp Val Pro
290             295             300             305
```

```
att cct ggg tat caa act aaa acc act att aat ctt cga ttg tgg tgt      1019
Ile Pro Gly Tyr Gln Thr Lys Thr Thr Ile Asn Leu Arg Leu Trp Cys
            310                 315                 320 act act gta tca tct gaa gac ttt gac tta tct gct ttt aat gcg ggg      1067
Thr Thr Val Ser Ser Glu Asp Phe Asp Leu Ser Ala Phe Asn Ala Gly
        325                 330                 335 gaa cac gcc aaa gca aat gag gct cgt gcg aat gcg gaa aag atc tgt      1115
Glu His Ala Lys Ala Asn Glu Ala Arg Ala Asn Ala Glu Lys Ile Cys
            340                 345                 350 agc gta cta tac ccc ggg gat gaa tct atg gaa gga aag atc ctc cgt      1163
Ser Val Leu Tyr Pro Gly Asp Glu Ser Met Glu Gly Lys Ile Leu Arg
355                 360                 365 ctg aag caa caa tac acc cta tgt tcg gct tct ttg caa gac atc att      1211
Leu Lys Gln Gln Tyr Thr Leu Cys Ser Ala Ser Leu Gln Asp Ile Ile
370                 375                 380                 385 tca caa ttt gaa agg aga tca ggg gaa cat gta aat tgg gaa gaa ttt      1259
Ser Gln Phe Glu Arg Arg Ser Gly Glu His Val Asn Trp Glu Glu Phe
                390                 395                 400 cca gag aag gtg gct gtg cag atg aat gac act cat cca aca ttg tgt      1307
Pro Glu Lys Val Ala Val Gln Met Asn Asp Thr His Pro Thr Leu Cys
            405                 410                 415 ata cca gaa ctg atg agg ata cta ata gat gta aaa gga ctt gcc tgg      1355
Ile Pro Glu Leu Met Arg Ile Leu Ile Asp Val Lys Gly Leu Ala Trp
        420                 425                 430 aag gaa gct tgg aat ata acc caa aga act gtt gcg tat aca aat cat      1403
Lys Glu Ala Trp Asn Ile Thr Gln Arg Thr Val Ala Tyr Thr Asn His
    435                 440                 445 act gtt ttg ccg gag gca ttg gag aaa tgg agt ttt gaa ctt atg caa      1451
Thr Val Leu Pro Glu Ala Leu Glu Lys Trp Ser Phe Glu Leu Met Gln
450                 455                 460                 465 tcc ttg ctt cct cga cat gtt gag att ata gag aaa ata gac gag gag      1499
Ser Leu Leu Pro Arg His Val Glu Ile Ile Glu Lys Ile Asp Glu Glu
                470                 475                 480 cta gtt gat acc atc gtt tct gag tat ggt act gat gac ccc aaa ttg      1547
Leu Val Asp Thr Ile Val Ser Glu Tyr Gly Thr Asp Asp Pro Lys Leu
            485                 490                 495 ctg atg gga aaa ctg aat gag ttg aga ata ctg gag aat ttt cat ctt      1595
Leu Met Gly Lys Leu Asn Glu Leu Arg Ile Leu Glu Asn Phe His Leu
        500                 505                 510 ccc agt tcg gtt gcc agt ata atc aag gat aaa att acc tgt caa gtc      1643
Pro Ser Ser Val Ala Ser Ile Ile Lys Asp Lys Ile Thr Cys Gln Val
    515                 520                 525 gac gag gat aaa aaa att gaa att tct gat gaa gta gat gga cta gtt      1691
Asp Glu Asp Lys Lys Ile Glu Ile Ser Asp Glu Val Asp Gly Leu Val
530                 535                 540                 545 gtt gta gag gaa agt gaa gaa ggt gat ata gag aaa cag gca gtg gaa      1739
Val Val Glu Glu Ser Glu Glu Gly Asp Ile Glu Lys Gln Ala Val Glu
                550                 555                 560 gag cca gtt cca aaa cca gca aag ttg gtt cgg atg gct aac ctt tgc      1787
Glu Pro Val Pro Lys Pro Ala Lys Leu Val Arg Met Ala Asn Leu Cys
            565                 570                 575 ata gtt ggg ggt cat gca gta aat ggg gtt gcc gag att cat agc caa      1835
Ile Val Gly Gly His Ala Val Asn Gly Val Ala Glu Ile His Ser Gln
        580                 585                 590 atc gtg aag gaa caa gtt ttc cgt gac ttc ttc gag ttg tgg cca gag      1883
Ile Val Lys Glu Gln Val Phe Arg Asp Phe Phe Glu Leu Trp Pro Glu
    595                 600                 605 aaa ttt cag aac aaa aca aat ggg gtg act cca aga aga tgg atc cgg      1931
Lys Phe Gln Asn Lys Thr Asn Gly Val Thr Pro Arg Arg Trp Ile Arg
```

```
                    610                 615                 620                 625
ttt tgc aat cca gaa cta agc agt atc tta aca aaa tgg att ggg tct      1979
Phe Cys Asn Pro Glu Leu Ser Ser Ile Leu Thr Lys Trp Ile Gly Ser
                    630                 635                 640 gac gac tgg gtt ctt aac acc gaa aaa ctt gca gaa ctg cga aag ttt      2027
Asp Asp Trp Val Leu Asn Thr Glu Lys Leu Ala Glu Leu Arg Lys Phe
                645                 650                 655 gca gat aat aaa gat ctt cac act gaa tgg atg gaa gca aaa cgg aac      2075
Ala Asp Asn Lys Asp Leu His Thr Glu Trp Met Glu Ala Lys Arg Asn
            660                 665                 670 aac aaa cag aag gtt gtt tcg tta atc aaa gag aga aca ggt tac acg      2123
Asn Lys Gln Lys Val Val Ser Leu Ile Lys Glu Arg Thr Gly Tyr Thr
        675                 680                 685 gtc agc cca gat gca atg ttt gat att cag atc aag cgt att cat gaa      2171
Val Ser Pro Asp Ala Met Phe Asp Ile Gln Ile Lys Arg Ile His Glu
690                 695                 700                 705 tac aag cgg caa ctt atg aac ata ttg gga att gta tac cgc tac aaa      2219
Tyr Lys Arg Gln Leu Met Asn Ile Leu Gly Ile Val Tyr Arg Tyr Lys
                710                 715                 720 aaa atg aaa gaa atg agt gct gca gag agg aag gaa aaa tat gtt cca      2267
Lys Met Lys Glu Met Ser Ala Ala Glu Arg Lys Glu Lys Tyr Val Pro
                725                 730                 735 aga gtt tgt ata ttc gga gga aaa gct ttt gcc aca tat gtg cag gct      2315
Arg Val Cys Ile Phe Gly Gly Lys Ala Phe Ala Thr Tyr Val Gln Ala
            740                 745                 750 aaa aga ata gtg aaa ttt atc act gat gta gga gct aca att aat cac      2363
Lys Arg Ile Val Lys Phe Ile Thr Asp Val Gly Ala Thr Ile Asn His
        755                 760                 765 gat cct gaa att ggt gat cta ctg aag gtt gtg ttc atc ccc gat tac      2411
Asp Pro Glu Ile Gly Asp Leu Leu Lys Val Val Phe Ile Pro Asp Tyr
770                 775                 780                 785 aat gtt agt gtg gct gag tta ttg atc cct gca agt gaa ctt tca cag      2459
Asn Val Ser Val Ala Glu Leu Leu Ile Pro Ala Ser Glu Leu Ser Gln
                790                 795                 800 cat ata agc act gct ggg atg gag gca agt gga aca agc aat atg aag      2507
His Ile Ser Thr Ala Gly Met Glu Ala Ser Gly Thr Ser Asn Met Lys
                805                 810                 815 ttt tca atg aat gga tgt atc tta att ggg acc cta gat ggt gcc aat      2555
Phe Ser Met Asn Gly Cys Ile Leu Ile Gly Thr Leu Asp Gly Ala Asn
            820                 825                 830 gtt gag att aga gaa gaa gtc gga gaa gat aac ttc ttt ctg ttt ggc      2603
Val Glu Ile Arg Glu Glu Val Gly Glu Asp Asn Phe Phe Leu Phe Gly
        835                 840                 845 gct cga gca cat gat att gct ggc tta agg aag gaa aga gct gag ggc      2651
Ala Arg Ala His Asp Ile Ala Gly Leu Arg Lys Glu Arg Ala Glu Gly
850                 855                 860                 865 aag tat gtg ccg gac cca tgt ttt gaa gaa gta aag gag tat gtt aga      2699
Lys Tyr Val Pro Asp Pro Cys Phe Glu Glu Val Lys Glu Tyr Val Arg
                870                 875                 880 agt ggt gtc ttt ggt tca aac agt tat gat gaa ctg tta ggg tct tta      2747
Ser Gly Val Phe Gly Ser Asn Ser Tyr Asp Glu Leu Leu Gly Ser Leu
                885                 890                 895 gag gga aat gaa gga ttt gga cgt gct gat tat ttc ctt gtg ggc aaa      2795
Glu Gly Asn Glu Gly Phe Gly Arg Ala Asp Tyr Phe Leu Val Gly Lys
            900                 905                 910 gac ttc cct agt tat gta gaa tgc caa gaa caa gtt gac caa gca tat      2843
Asp Phe Pro Ser Tyr Val Glu Cys Gln Glu Gln Val Asp Gln Ala Tyr
        915                 920                 925 aga gat caa cag aaa tgg aca aga atg tca atc cta aat aca gct ggt      2891
```

```
Arg Asp Gln Gln Lys Trp Thr Arg Met Ser Ile Leu Asn Thr Ala Gly
930                 935                 940                 945 tca ttc aag ttt agc agc gac cga acg att cat caa tat gct aag gat        2939
Ser Phe Lys Phe Ser Ser Asp Arg Thr Ile His Gln Tyr Ala Lys Asp
                950                 955                 960 ata tgg aat atc cat cca gta aat ctg cca tga aattgaaaac aactggatgg      2992
Ile Trp Asn Ile His Pro Val Asn Leu Pro
                965                 970 ctcgccagag taaccatcat gctagaactc ttaaaagcgc ctctctctat attttttta       3052 atgaataatt ttggtcaaaa aaaaaaaaaa aaaaa                                 3088

<210> SEQ ID NO 12
<211> LENGTH: 971
<212> TYPE: PRT
<213> ORGANISM: Spinacia oleracea

<400> SEQUENCE: 12

Met Ala Thr Leu Pro Leu Ser Ser Thr Thr Pro Ser Thr Gly Arg Thr
1               5                   10                  15

Glu Asn Cys Phe Ser Ser Tyr Tyr Ser Ser Ser Ile Ser Arg Val Met
            20                  25                  30

Glu Phe Gly Leu Lys Asn Gly Cys Asn Ser Lys Leu Leu Phe Ser Ser
        35                  40                  45

Val Asn Tyr Lys Pro Met Ile Met Arg Gly Ser Arg Arg Cys Ile Val
    50                  55                  60

Ile Arg Asn Val Phe Ser Glu Ser Lys Pro Lys Ser Glu Glu Pro Ile
65                  70                  75                  80

Ile Glu Gln Glu Thr Pro Ser Ile Leu Asn Pro Leu Ser Asn Leu Ser
                85                  90                  95

Pro Asp Ser Ala Ser Arg Gln Ser Ser Ile Lys Tyr His Ala Glu Phe
            100                 105                 110

Thr Pro Leu Phe Ala Pro Asn Asp Phe Ser Leu Pro Lys Ala Phe Phe
        115                 120                 125

Ala Ala Ala Gln Ser Val Arg Asp Ser Leu Ile Ile Asn Trp Asn Ala
    130                 135                 140

Thr Tyr Ala His Tyr Glu Lys Met Asn Met Lys Gln Ala Tyr Tyr Leu
145                 150                 155                 160

Ser Met Glu Phe Leu Gln Gly Arg Ala Leu Leu Asn Ala Ile Gly Asn
                165                 170                 175

Leu Glu Leu Thr Asp Ala Tyr Gly Asp Ala Leu Lys Lys Leu Gly His
            180                 185                 190

Asn Leu Glu Ala Val Ala Cys Gln Glu Arg Asp Ala Ala Leu Gly Asn
        195                 200                 205

Gly Gly Leu Gly Arg Leu Ala Ser Cys Phe Leu Asp Ser Leu Ala Thr
    210                 215                 220

Leu Asn Tyr Pro Ala Trp Gly Tyr Gly Leu Arg Tyr Lys Tyr Gly Leu
225                 230                 235                 240

Phe Lys Gln Met Ile Thr Lys Asp Gly Gln Glu Glu Val Ala Glu Asn
                245                 250                 255

Trp Leu Glu Ile Ala Asn Pro Trp Glu Leu Val Arg Asn Asp Val Ser
            260                 265                 270

Tyr Ser Ile Lys Phe Tyr Gly Lys Val Val Ser Gly Ser Asp Gly Arg
        275                 280                 285

Ser His Trp Thr Gly Gly Glu Asp Ile Arg Ala Val Ala Tyr Asp Val
    290                 295                 300
```

-continued

```
Pro Ile Pro Gly Tyr Gln Thr Lys Thr Thr Ile Asn Leu Arg Leu Trp
305                 310                 315                 320

Cys Thr Thr Val Ser Ser Glu Asp Phe Asp Leu Ser Ala Phe Asn Ala
                325                 330                 335

Gly Glu His Ala Lys Ala Asn Glu Ala Arg Ala Asn Ala Glu Lys Ile
            340                 345                 350

Cys Ser Val Leu Tyr Pro Gly Asp Glu Ser Met Glu Gly Lys Ile Leu
            355                 360                 365

Arg Leu Lys Gln Gln Tyr Thr Leu Cys Ser Ala Ser Leu Gln Asp Ile
370                 375                 380

Ile Ser Gln Phe Glu Arg Arg Ser Gly Glu His Val Asn Trp Glu Glu
385                 390                 395                 400

Phe Pro Glu Lys Val Ala Val Gln Met Asn Asp Thr His Pro Thr Leu
                405                 410                 415

Cys Ile Pro Glu Leu Met Arg Ile Leu Ile Asp Val Lys Gly Leu Ala
            420                 425                 430

Trp Lys Glu Ala Trp Asn Ile Thr Gln Arg Thr Val Ala Tyr Thr Asn
            435                 440                 445

His Thr Val Leu Pro Glu Ala Leu Glu Lys Trp Ser Phe Glu Leu Met
    450                 455                 460

Gln Ser Leu Leu Pro Arg His Val Glu Ile Ile Glu Lys Ile Asp Glu
465                 470                 475                 480

Glu Leu Val Asp Thr Ile Val Ser Glu Tyr Gly Thr Asp Asp Pro Lys
                485                 490                 495

Leu Leu Met Gly Lys Leu Asn Glu Leu Arg Ile Leu Glu Asn Phe His
            500                 505                 510

Leu Pro Ser Ser Val Ala Ser Ile Ile Lys Asp Lys Ile Thr Cys Gln
            515                 520                 525

Val Asp Glu Asp Lys Lys Ile Glu Ile Ser Asp Glu Val Asp Gly Leu
530                 535                 540

Val Val Val Glu Glu Ser Glu Glu Gly Asp Ile Glu Lys Gln Ala Val
545                 550                 555                 560

Glu Glu Pro Val Pro Lys Pro Ala Lys Leu Val Arg Met Ala Asn Leu
                565                 570                 575

Cys Ile Val Gly Gly His Ala Val Asn Gly Val Ala Glu Ile His Ser
            580                 585                 590

Gln Ile Val Lys Glu Gln Val Phe Arg Asp Phe Phe Glu Leu Trp Pro
            595                 600                 605

Glu Lys Phe Gln Asn Lys Thr Asn Gly Val Thr Pro Arg Arg Trp Ile
610                 615                 620

Arg Phe Cys Asn Pro Glu Leu Ser Ser Ile Leu Thr Lys Trp Ile Gly
625                 630                 635                 640

Ser Asp Asp Trp Val Leu Asn Thr Glu Lys Leu Ala Glu Leu Arg Lys
                645                 650                 655

Phe Ala Asp Asn Lys Asp Leu His Thr Glu Trp Met Glu Ala Lys Arg
            660                 665                 670

Asn Asn Lys Gln Lys Val Val Ser Leu Ile Lys Glu Arg Thr Gly Tyr
            675                 680                 685

Thr Val Ser Pro Asp Ala Met Phe Asp Ile Gln Ile Lys Arg Ile His
    690                 695                 700

Glu Tyr Lys Arg Gln Leu Met Asn Ile Leu Gly Ile Val Tyr Arg Tyr
705                 710                 715                 720
```

-continued

```
Lys Lys Met Lys Glu Met Ser Ala Ala Glu Arg Lys Glu Lys Tyr Val
                725                 730                 735

Pro Arg Val Cys Ile Phe Gly Lys Ala Phe Ala Thr Tyr Val Gln
            740                 745                 750

Ala Lys Arg Ile Val Lys Phe Ile Thr Asp Val Gly Ala Thr Ile Asn
            755                 760                 765

His Asp Pro Glu Ile Gly Asp Leu Leu Lys Val Phe Ile Pro Asp
    770                 775                 780

Tyr Asn Val Ser Val Ala Glu Leu Leu Ile Pro Ala Ser Glu Leu Ser
785                 790                 795                 800

Gln His Ile Ser Thr Ala Gly Met Glu Ala Ser Gly Thr Ser Asn Met
                805                 810                 815

Lys Phe Ser Met Asn Gly Cys Ile Leu Ile Gly Thr Leu Asp Gly Ala
                820                 825                 830

Asn Val Glu Ile Arg Glu Glu Val Gly Glu Asp Asn Phe Phe Leu Phe
                835                 840                 845

Gly Ala Arg Ala His Asp Ile Ala Gly Leu Arg Lys Glu Arg Ala Glu
850                 855                 860

Gly Lys Tyr Val Pro Asp Pro Cys Phe Glu Val Lys Glu Tyr Val
865                 870                 875                 880

Arg Ser Gly Val Phe Gly Ser Asn Ser Tyr Asp Glu Leu Leu Gly Ser
                885                 890                 895

Leu Glu Gly Asn Glu Gly Phe Gly Arg Ala Asp Tyr Phe Leu Val Gly
                900                 905                 910

Lys Asp Phe Pro Ser Tyr Val Glu Cys Gln Glu Gln Val Asp Gln Ala
            915                 920                 925

Tyr Arg Asp Gln Gln Lys Trp Thr Arg Met Ser Ile Leu Asn Thr Ala
    930                 935                 940

Gly Ser Phe Lys Phe Ser Ser Asp Arg Thr Ile His Gln Tyr Ala Lys
945                 950                 955                 960

Asp Ile Trp Asn Ile His Pro Val Asn Leu Pro
                965                 970

<210> SEQ ID NO 13
<211> LENGTH: 2952
<212> TYPE: DNA
<213> ORGANISM: Zea mays
<220> FEATURE:
<221> NAME/KEY: CDS
<222> LOCATION: (1)..(2952)

<400> SEQUENCE: 13 ggc gac gac cac ctc gcc gcc gct gca gct cgc cac cgc ctc ccg ccc      48
Gly Asp Asp His Leu Ala Ala Ala Ala Ala Arg His Arg Leu Pro Pro
1               5                   10                  15 gca cgc ctc ctc ctc cgg cgg tgg cgg ggt tct cct ccg cgg gcg gtt      96
Ala Arg Leu Leu Leu Arg Arg Trp Arg Gly Ser Pro Pro Arg Ala Val
                20                  25                  30 ccg gag gtg ggg tcg cgc cgg gtc ggg gtc ggg gtc gag ggg cga ttg     144
Pro Glu Val Gly Ser Arg Arg Val Gly Val Gly Val Glu Gly Arg Leu
            35                  40                  45 cag cgg cgg gtg tcg gcg cgc agc gtg gcg agc gat cgg gac gtg caa     192
Gln Arg Arg Val Ser Ala Arg Ser Val Ala Ser Asp Arg Asp Val Gln
        50                  55                  60 ggc ccc gtc tcg ccc gcg gaa ggg ctt cca aat gtg cta aac tcc atc     240
Gly Pro Val Ser Pro Ala Glu Gly Leu Pro Asn Val Leu Asn Ser Ile
65                  70                  75                  80
```

-continued

| | | |
|---|---|---|
| ggc tca tct gcc att gca tca aac atc aag cac cat gca gag ttc gct<br>Gly Ser Ser Ala Ile Ala Ser Asn Ile Lys His His Ala Glu Phe Ala<br>                        85                    90                        95 | 288 |
| ccc ttg ttc tct cca gat cac ttt tct ccc ctg aaa gct tac cat gcg<br>Pro Leu Phe Ser Pro Asp His Phe Ser Pro Leu Lys Ala Tyr His Ala<br>                100                      105                      110 | 336 |
| act gct aaa agt gtc ctt gat gcg ctg ctg ata aac tgg aat gcg aca<br>Thr Ala Lys Ser Val Leu Asp Ala Leu Leu Ile Asn Trp Asn Ala Thr<br>        115                      120                      125 | 384 |
| tat gat tat tac aac aaa atg aat gta aaa caa gca tat tac ctg tcc<br>Tyr Asp Tyr Tyr Asn Lys Met Asn Val Lys Gln Ala Tyr Tyr Leu Ser<br>130                      135                      140 | 432 |
| atg gag ttt tta cag gga agg gct ctc aca aat gct att ggc aat cta<br>Met Glu Phe Leu Gln Gly Arg Ala Leu Thr Asn Ala Ile Gly Asn Leu<br>145                      150                      155                      160 | 480 |
| gag att act ggt gaa tat gca gaa gca tta aaa caa ctt gga caa aac<br>Glu Ile Thr Gly Glu Tyr Ala Glu Ala Leu Lys Gln Leu Gly Gln Asn<br>                    165                      170                      175 | 528 |
| ctg gag gat gtc gct agc cag gaa cca gat gct gcc ctg ggc aat ggt<br>Leu Glu Asp Val Ala Ser Gln Glu Pro Asp Ala Ala Leu Gly Asn Gly<br>                180                      185                      190 | 576 |
| ggt tta ggc cgc ctg gct tct tgt ttt ttg gat tct ttg gca aca tta<br>Gly Leu Gly Arg Leu Ala Ser Cys Phe Leu Asp Ser Leu Ala Thr Leu<br>        195                      200                      205 | 624 |
| aat tat cca gca ttg gga tat gga ctt cgc tat gaa tat ggc ctc ttt<br>Asn Tyr Pro Ala Leu Gly Tyr Gly Leu Arg Tyr Glu Tyr Gly Leu Phe<br>        210                      215                      220 | 672 |
| aag cag atc ata aca aag gat ggt cag gag gag att gct gag aat tgg<br>Lys Gln Ile Ile Thr Lys Asp Gly Gln Glu Glu Ile Ala Glu Asn Trp<br>225                      230                      235                      240 | 720 |
| ctt gag atg gga tat cct tgg gag gtt gta aga aat gat gtc tct tat<br>Leu Glu Met Gly Tyr Pro Trp Glu Val Val Arg Asn Asp Val Ser Tyr<br>                    245                      250                      255 | 768 |
| cct gtg aaa ttc tat ggt aaa gtg gtg gaa ggc act gat ggt agg aag<br>Pro Val Lys Phe Tyr Gly Lys Val Val Glu Gly Thr Asp Gly Arg Lys<br>                260                      265                      270 | 816 |
| cac tgg att gga gga gaa aat atc aag gct gtg gca cat gat gtc cct<br>His Trp Ile Gly Gly Glu Asn Ile Lys Ala Val Ala His Asp Val Pro<br>        275                      280                      285 | 864 |
| att cct ggc tac aaa act aga act acc aat aat ctg cgt ctt tgg tca<br>Ile Pro Gly Tyr Lys Thr Arg Thr Thr Asn Asn Leu Arg Leu Trp Ser<br>        290                      295                      300 | 912 |
| aca act gta cca gca caa gat ttt gac ttg gca gct ttt aat tct gga<br>Thr Thr Val Pro Ala Gln Asp Phe Asp Leu Ala Ala Phe Asn Ser Gly<br>305                      310                      315                      320 | 960 |
| gat cat acc aag gca tat gaa gct cat cta aac gct aaa aag ata tgc<br>Asp His Thr Lys Ala Tyr Glu Ala His Leu Asn Ala Lys Lys Ile Cys<br>                    325                      330                      335 | 1008 |
| cac ata ttg tat cct ggg gat gaa tca cta gag ggg aaa gtt ctc cgc<br>His Ile Leu Tyr Pro Gly Asp Glu Ser Leu Glu Gly Lys Val Leu Arg<br>                    340                      345                      350 | 1056 |
| ttg aag caa caa tat aca ttg tgt tca gcc tca cta cag gac atc att<br>Leu Lys Gln Gln Tyr Thr Leu Cys Ser Ala Ser Leu Gln Asp Ile Ile<br>        355                      360                      365 | 1104 |
| gct cgt ttt gag agt aga gct ggc gag tct ctc aac tgg gag gac ttc<br>Ala Arg Phe Glu Ser Arg Ala Gly Glu Ser Leu Asn Trp Glu Asp Phe<br>        370                      375                      380 | 1152 |
| ccc tcc aaa gtt gca gtg cag atg aat gac act cat cca aca cta tgc<br>Pro Ser Lys Val Ala Val Gln Met Asn Asp Thr His Pro Thr Leu Cys<br>385                      390                      395                      400 | 1200 |

```
att cct gag tta atg aga ata ctg atg gat gtt aag gga tta agc tgg    1248
Ile Pro Glu Leu Met Arg Ile Leu Met Asp Val Lys Gly Leu Ser Trp
            405                 410                 415 agt gag gca tgg agt att aca gaa aga acc gtg gca tac act aac cat    1296
Ser Glu Ala Trp Ser Ile Thr Glu Arg Thr Val Ala Tyr Thr Asn His
        420                 425                 430 aca gtg ctt cct gaa gct cta gag aag tgg agc ttg gac ata atg cag    1344
Thr Val Leu Pro Glu Ala Leu Glu Lys Trp Ser Leu Asp Ile Met Gln
    435                 440                 445 aaa ctt tta cct cga cat gtt gag ata ata gaa aca att gat gaa gag    1392
Lys Leu Leu Pro Arg His Val Glu Ile Ile Glu Thr Ile Asp Glu Glu
450                 455                 460 ctg ata aac aac ata gtc tca aaa tat gga acc aca gat act gaa ctg    1440
Leu Ile Asn Asn Ile Val Ser Lys Tyr Gly Thr Thr Asp Thr Glu Leu
465                 470                 475                 480 ttg aaa aag aag ctg aaa gag atg aga att ctg gat aat gtt gac ctt    1488
Leu Lys Lys Lys Leu Lys Glu Met Arg Ile Leu Asp Asn Val Asp Leu
            485                 490                 495 cca gct tcc att tcc caa cta ttt gtt aaa ccc aaa gac aaa aag gaa    1536
Pro Ala Ser Ile Ser Gln Leu Phe Val Lys Pro Lys Asp Lys Lys Glu
        500                 505                 510 tct cct gct aaa tca aag caa aag tta ctt gtt aaa tct ttg gag act    1584
Ser Pro Ala Lys Ser Lys Gln Lys Leu Leu Val Lys Ser Leu Glu Thr
    515                 520                 525 att gtt gag gtt gag gag aaa act gag ttg gaa gag gag gcg gag gtt    1632
Ile Val Glu Val Glu Glu Lys Thr Glu Leu Glu Glu Glu Ala Glu Val
530                 535                 540 cta tct gag ata gag gag gaa aaa ctt gaa tct gaa gaa gta gag gca    1680
Leu Ser Glu Ile Glu Glu Glu Lys Leu Glu Ser Glu Glu Val Glu Ala
545                 550                 555                 560 gaa gaa gcg agt tct gag gat gag tta gat cca ttt gta aag tct gat    1728
Glu Glu Ala Ser Ser Glu Asp Glu Leu Asp Pro Phe Val Lys Ser Asp
            565                 570                 575 cct aag tta cca aga gtt gtc cga atg gca aac ctc tgt gtt gtt ggt    1776
Pro Lys Leu Pro Arg Val Val Arg Met Ala Asn Leu Cys Val Val Gly
        580                 585                 590 ggg cat tca gta aat ggt gta gct gaa att cac agt gaa att gtg aaa    1824
Gly His Ser Val Asn Gly Val Ala Glu Ile His Ser Glu Ile Val Lys
    595                 600                 605 cag gat gtg ttc aac agc ttc tat gag atg tgg cca act aaa ttt cag    1872
Gln Asp Val Phe Asn Ser Phe Tyr Glu Met Trp Pro Thr Lys Phe Gln
610                 615                 620 aat aaa aca aat gga gtg act ccc agg cgt tgg atc cgg ttt tgt aat    1920
Asn Lys Thr Asn Gly Val Thr Pro Arg Arg Trp Ile Arg Phe Cys Asn
625                 630                 635                 640 cct gca tta agt gca tta att tca aag tgg att ggt tct gat gac tgg    1968
Pro Ala Leu Ser Ala Leu Ile Ser Lys Trp Ile Gly Ser Asp Asp Trp
            645                 650                 655 gtg ctt aat aca gac aaa ctg gca gaa ctg aag aag ttt gct gat aat    2016
Val Leu Asn Thr Asp Lys Leu Ala Glu Leu Lys Lys Phe Ala Asp Asn
        660                 665                 670 gaa gat ctg cat tca gag tgg cgt gct gct aag aag gct aac aaa atg    2064
Glu Asp Leu His Ser Glu Trp Arg Ala Ala Lys Lys Ala Asn Lys Met
    675                 680                 685 aag gtt att tct ctt ata agg gag aag aca gga tat att gtc agt cca    2112
Lys Val Ile Ser Leu Ile Arg Glu Lys Thr Gly Tyr Ile Val Ser Pro
690                 695                 700 gat gca atg ttt gat gtg cag gtg aaa agg ata cat gaa tat aag cgg    2160
Asp Ala Met Phe Asp Val Gln Val Lys Arg Ile His Glu Tyr Lys Arg
```

```
                705                 710                 715                 720
cag ctg cta aat atc ctt gga att gtc tac cgc tac aag aag atg aaa    2208
Gln Leu Leu Asn Ile Leu Gly Ile Val Tyr Arg Tyr Lys Lys Met Lys
                725                 730                 735 gaa atg agc aca gaa gaa aga gca aag agc ttt gtt cca agg gta tgc    2256
Glu Met Ser Thr Glu Glu Arg Ala Lys Ser Phe Val Pro Arg Val Cys
            740                 745                 750 ata ttc ggt ggg aaa gca ttt gcc aca tat ata cag gca aaa agg atc    2304
Ile Phe Gly Gly Lys Ala Phe Ala Thr Tyr Ile Gln Ala Lys Arg Ile
        755                 760                 765 gtt aaa ttt att aca gat gtg gca gct acc gtg aac cat gat tca gac    2352
Val Lys Phe Ile Thr Asp Val Ala Ala Thr Val Asn His Asp Ser Asp
    770                 775                 780 att gga gat ttg ttg aag gtc gta ttt gtt cca gac tat aat gtt agt    2400
Ile Gly Asp Leu Leu Lys Val Val Phe Val Pro Asp Tyr Asn Val Ser
785                 790                 795                 800 gtt gcc gag gca cta att cct gcc agt gaa ttg tca cag cat atc agt    2448
Val Ala Glu Ala Leu Ile Pro Ala Ser Glu Leu Ser Gln His Ile Ser
                805                 810                 815 act gct gga atg gaa gct agt ggg acc agt aac atg aag ttt gca atg    2496
Thr Ala Gly Met Glu Ala Ser Gly Thr Ser Asn Met Lys Phe Ala Met
            820                 825                 830 aac ggt tgc att ctt att gga act tta gat ggt gca aat gtg gag atc    2544
Asn Gly Cys Ile Leu Ile Gly Thr Leu Asp Gly Ala Asn Val Glu Ile
        835                 840                 845 aga gag gag gtt gga gaa gaa aac ttt ttc ctt ttt ggt gca gag gca    2592
Arg Glu Glu Val Gly Glu Glu Asn Phe Phe Leu Phe Gly Ala Glu Ala
    850                 855                 860 cat gaa att gct ggt ttg cgg aaa gaa aga gcc gag gga aag ttt gtg    2640
His Glu Ile Ala Gly Leu Arg Lys Glu Arg Ala Glu Gly Lys Phe Val
865                 870                 875                 880 cct gac cca aga ttt gag gag gtt aag gaa ttt gtc cgc agt ggt gtc    2688
Pro Asp Pro Arg Phe Glu Glu Val Lys Glu Phe Val Arg Ser Gly Val
                885                 890                 895 ttt ggg act tac agc tat gat gaa ttg atg ggg tct ttg gaa gga aat    2736
Phe Gly Thr Tyr Ser Tyr Asp Glu Leu Met Gly Ser Leu Glu Gly Asn
            900                 905                 910 gaa ggt tac gga cgt gca gat tat ttc ctt gtt ggc aag gac ttc ccc    2784
Glu Gly Tyr Gly Arg Ala Asp Tyr Phe Leu Val Gly Lys Asp Phe Pro
        915                 920                 925 agc tat att gaa tgc caa gaa aaa gtt gat gag gcg tac cga gat cag    2832
Ser Tyr Ile Glu Cys Gln Glu Lys Val Asp Glu Ala Tyr Arg Asp Gln
    930                 935                 940 aag tta tgg aca agg atg tct atc ctc aac acg gct ggc tca tcc aag    2880
Lys Leu Trp Thr Arg Met Ser Ile Leu Asn Thr Ala Gly Ser Ser Lys
945                 950                 955                 960 ttc agc agc gat agg acg att cat gag tac gcc aag gat atc tgg gat    2928
Phe Ser Ser Asp Arg Thr Ile His Glu Tyr Ala Lys Asp Ile Trp Asp
                965                 970                 975 atc agc cct gcc atc ctt ccc tag                                    2952
Ile Ser Pro Ala Ile Leu Pro
            980

<210> SEQ ID NO 14
<211> LENGTH: 983
<212> TYPE: PRT
<213> ORGANISM: Zea mays

<400> SEQUENCE: 14

Gly Asp Asp His Leu Ala Ala Ala Ala Ala Arg His Arg Leu Pro Pro
```

-continued

```
1               5               10              15
Ala Arg Leu Leu Leu Arg Arg Trp Arg Gly Ser Pro Pro Arg Ala Val
                20              25              30

Pro Glu Val Gly Ser Arg Arg Val Gly Val Gly Val Glu Gly Arg Leu
                35              40              45

Gln Arg Arg Val Ser Ala Arg Ser Val Ala Ser Asp Arg Asp Val Gln
 50              55              60

Gly Pro Val Ser Pro Ala Glu Gly Leu Pro Asn Val Leu Asn Ser Ile
 65              70              75              80

Gly Ser Ser Ala Ile Ala Ser Asn Ile Lys His His Ala Glu Phe Ala
                85              90              95

Pro Leu Phe Ser Pro Asp His Phe Ser Pro Leu Lys Ala Tyr His Ala
                100             105             110

Thr Ala Lys Ser Val Leu Asp Ala Leu Leu Ile Asn Trp Asn Ala Thr
                115             120             125

Tyr Asp Tyr Tyr Asn Lys Met Asn Val Lys Gln Ala Tyr Tyr Leu Ser
                130             135             140

Met Glu Phe Leu Gln Gly Arg Ala Leu Thr Asn Ala Ile Gly Asn Leu
145             150             155             160

Glu Ile Thr Gly Glu Tyr Ala Glu Ala Leu Lys Gln Leu Gly Gln Asn
                165             170             175

Leu Glu Asp Val Ala Ser Gln Glu Pro Asp Ala Ala Leu Gly Asn Gly
                180             185             190

Gly Leu Gly Arg Leu Ala Ser Cys Phe Leu Asp Ser Leu Ala Thr Leu
                195             200             205

Asn Tyr Pro Ala Leu Gly Tyr Gly Leu Arg Tyr Glu Tyr Gly Leu Phe
                210             215             220

Lys Gln Ile Ile Thr Lys Asp Gly Gln Glu Glu Ile Ala Glu Asn Trp
225             230             235             240

Leu Glu Met Gly Tyr Pro Trp Glu Val Val Arg Asn Asp Val Ser Tyr
                245             250             255

Pro Val Lys Phe Tyr Gly Lys Val Val Glu Gly Thr Asp Gly Arg Lys
                260             265             270

His Trp Ile Gly Gly Glu Asn Ile Lys Ala Val Ala His Asp Val Pro
                275             280             285

Ile Pro Gly Tyr Lys Thr Arg Thr Thr Asn Asn Leu Arg Leu Trp Ser
                290             295             300

Thr Thr Val Pro Ala Gln Asp Phe Asp Leu Ala Ala Phe Asn Ser Gly
305             310             315             320

Asp His Thr Lys Ala Tyr Glu Ala His Leu Asn Ala Lys Lys Ile Cys
                325             330             335

His Ile Leu Tyr Pro Gly Asp Glu Ser Leu Glu Gly Lys Val Leu Arg
                340             345             350

Leu Lys Gln Gln Tyr Thr Leu Cys Ser Ala Ser Leu Gln Asp Ile Ile
                355             360             365

Ala Arg Phe Glu Ser Arg Ala Gly Glu Ser Leu Asn Trp Glu Asp Phe
                370             375             380

Pro Ser Lys Val Ala Val Gln Met Asn Asp Thr His Pro Thr Leu Cys
385             390             395             400

Ile Pro Glu Leu Met Arg Ile Leu Met Asp Val Lys Gly Leu Ser Trp
                405             410             415

Ser Glu Ala Trp Ser Ile Thr Glu Arg Thr Val Ala Tyr Thr Asn His
                420             425             430
```

```
Thr Val Leu Pro Glu Ala Leu Glu Lys Trp Ser Leu Asp Ile Met Gln
        435                 440                 445

Lys Leu Leu Pro Arg His Val Glu Ile Ile Glu Thr Ile Asp Glu Glu
        450                 455                 460

Leu Ile Asn Asn Ile Val Ser Lys Tyr Gly Thr Thr Asp Thr Glu Leu
465                     470                 475                 480

Leu Lys Lys Lys Leu Lys Glu Met Arg Ile Leu Asp Asn Val Asp Leu
                485                 490                 495

Pro Ala Ser Ile Ser Gln Leu Phe Val Lys Pro Lys Asp Lys Lys Glu
                500                 505                 510

Ser Pro Ala Lys Ser Lys Gln Lys Leu Leu Val Lys Ser Leu Glu Thr
        515                 520                 525

Ile Val Glu Val Glu Glu Lys Thr Glu Leu Glu Glu Glu Ala Glu Val
        530                 535                 540

Leu Ser Glu Ile Glu Glu Glu Lys Leu Glu Ser Glu Glu Val Glu Ala
545                     550                 555                 560

Glu Glu Ala Ser Ser Glu Asp Glu Leu Asp Pro Phe Val Lys Ser Asp
                565                 570                 575

Pro Lys Leu Pro Arg Val Val Arg Met Ala Asn Leu Cys Val Val Gly
                580                 585                 590

Gly His Ser Val Asn Gly Val Ala Glu Ile His Ser Glu Ile Val Lys
        595                 600                 605

Gln Asp Val Phe Asn Ser Phe Tyr Glu Met Trp Pro Thr Lys Phe Gln
        610                 615                 620

Asn Lys Thr Asn Gly Val Thr Pro Arg Arg Trp Ile Arg Phe Cys Asn
625                     630                 635                 640

Pro Ala Leu Ser Ala Leu Ile Ser Lys Trp Ile Gly Ser Asp Asp Trp
                645                 650                 655

Val Leu Asn Thr Asp Lys Leu Ala Glu Leu Lys Lys Phe Ala Asp Asn
                660                 665                 670

Glu Asp Leu His Ser Glu Trp Arg Ala Ala Lys Lys Ala Asn Lys Met
        675                 680                 685

Lys Val Ile Ser Leu Ile Arg Glu Lys Thr Gly Tyr Ile Val Ser Pro
        690                 695                 700

Asp Ala Met Phe Asp Val Gln Val Lys Arg Ile His Glu Tyr Lys Arg
705                     710                 715                 720

Gln Leu Leu Asn Ile Leu Gly Ile Val Tyr Arg Tyr Lys Lys Met Lys
                725                 730                 735

Glu Met Ser Thr Glu Glu Arg Ala Lys Ser Phe Val Pro Arg Val Cys
                740                 745                 750

Ile Phe Gly Gly Lys Ala Phe Ala Thr Tyr Ile Gln Ala Lys Arg Ile
        755                 760                 765

Val Lys Phe Ile Thr Asp Val Ala Ala Thr Val Asn His Asp Ser Asp
        770                 775                 780

Ile Gly Asp Leu Leu Lys Val Val Phe Val Pro Asp Tyr Asn Val Ser
785                     790                 795                 800

Val Ala Glu Ala Leu Ile Pro Ala Ser Glu Leu Ser Gln His Ile Ser
                805                 810                 815

Thr Ala Gly Met Glu Ala Ser Gly Thr Ser Asn Met Lys Phe Ala Met
                820                 825                 830

Asn Gly Cys Ile Leu Ile Gly Thr Leu Asp Gly Ala Asn Val Glu Ile
        835                 840                 845
```

```
                        -continued

Arg Glu Glu Val Gly Glu Glu Asn Phe Phe Leu Phe Gly Ala Glu Ala
    850                 855                 860

His Glu Ile Ala Gly Leu Arg Lys Glu Arg Ala Gly Lys Phe Val
865                 870                 875                 880

Pro Asp Pro Arg Phe Glu Val Lys Glu Phe Val Arg Ser Gly Val
                885                 890                 895

Phe Gly Thr Tyr Ser Tyr Asp Glu Leu Met Gly Ser Leu Glu Gly Asn
                900                 905                 910

Glu Gly Tyr Gly Arg Ala Asp Tyr Phe Leu Val Gly Lys Asp Phe Pro
            915                 920                 925

Ser Tyr Ile Glu Cys Gln Glu Lys Val Asp Glu Ala Tyr Arg Asp Gln
    930                 935                 940

Lys Leu Trp Thr Arg Met Ser Ile Leu Asn Thr Ala Gly Ser Ser Lys
945                 950                 955                 960

Phe Ser Ser Asp Arg Thr Ile His Glu Tyr Ala Lys Asp Ile Trp Asp
                965                 970                 975

Ile Ser Pro Ala Ile Leu Pro
            980

<210> SEQ ID NO 15
<211> LENGTH: 3141
<212> TYPE: DNA
<213> ORGANISM: Oryza sativa
<220> FEATURE:
<221> NAME/KEY: CDS
<222> LOCATION: (2)..(2788)

<400> SEQUENCE: 15 g cgg agc gtg gcg agc gat cgg ggc gtg cag ggg tcg gtg tcg ccc gag      49
  Arg Ser Val Ala Ser Asp Arg Gly Val Gln Gly Ser Val Ser Pro Glu
  1               5                  10                  15 gaa gag att tca agt gtg cta aat tcc atc gat tcc tct acc att gca       97
Glu Glu Ile Ser Ser Val Leu Asn Ser Ile Asp Ser Ser Thr Ile Ala
            20                  25                  30 tca aac att aag cac cat gcg gag ttc aca cca gta ttc tct cca gag      145
Ser Asn Ile Lys His His Ala Glu Phe Thr Pro Val Phe Ser Pro Glu
        35                  40                  45 cac ttt tca cct ctg aag gct tac cat gca act gct aaa agt gtt ctt      193
His Phe Ser Pro Leu Lys Ala Tyr His Ala Thr Ala Lys Ser Val Leu
    50                  55                  60 gat act ctg ata atg aac tgg aat gca aca tat gac tat tac gac aga      241
Asp Thr Leu Ile Met Asn Trp Asn Ala Thr Tyr Asp Tyr Tyr Asp Arg
65                  70                  75                  80 aca aat gtg aag caa gcg tat tac ctg tcc atg gag ttt tta cag gga      289
Thr Asn Val Lys Gln Ala Tyr Tyr Leu Ser Met Glu Phe Leu Gln Gly
                85                  90                  95 aga gct ctc act aat gcc gtt ggt aac ctt gag cta act gga caa tac      337
Arg Ala Leu Thr Asn Ala Val Gly Asn Leu Glu Leu Thr Gly Gln Tyr
            100                 105                 110 gca gaa gca cta caa caa ctt gga cac agc cta gag gat gtt gct acc      385
Ala Glu Ala Leu Gln Gln Leu Gly His Ser Leu Glu Asp Val Ala Thr
        115                 120                 125 cag gag cca gat gct gcc ctt ggg aat ggt ggt cta ggc cgg tta gct      433
Gln Glu Pro Asp Ala Ala Leu Gly Asn Gly Gly Leu Gly Arg Leu Ala
    130                 135                 140 tcc tgt ttc ttg gat tct ctg gca acc cta aat tat cca gca tgg gga      481
Ser Cys Phe Leu Asp Ser Leu Ala Thr Leu Asn Tyr Pro Ala Trp Gly
145                 150                 155                 160 tat gga ctt cga tac aaa cat ggc ctc ttt aag caa atc ata acg aag      529
```

```
                Tyr Gly Leu Arg Tyr Lys His Gly Leu Phe Lys Gln Ile Ile Thr Lys
                            165                 170                 175 gat ggt cag gag gag gta gct gaa aat tgg ctc gag atg gga aat cct         577
Asp Gly Gln Glu Glu Val Ala Glu Asn Trp Leu Glu Met Gly Asn Pro
            180                 185                 190 tgg gag att gta aga acc gat gtc tcc tat cct gtg aag ttc tat ggt         625
Trp Glu Ile Val Arg Thr Asp Val Ser Tyr Pro Val Lys Phe Tyr Gly
            195                 200                 205 aaa gtg gtt gaa ggc act gat ggg agg atg cac tgg att gga gga gaa         673
Lys Val Val Glu Gly Thr Asp Gly Arg Met His Trp Ile Gly Gly Glu
    210                 215                 220 aat atc aag gtt gtt gct cat gat atc cct att cct ggc tac aag act         721
Asn Ile Lys Val Val Ala His Asp Ile Pro Ile Pro Gly Tyr Lys Thr
225                 230                 235                 240 aaa act acc aac aat ctt cgt ctt tgg tca aca aca gtg cca tca caa         769
Lys Thr Thr Asn Asn Leu Arg Leu Trp Ser Thr Thr Val Pro Ser Gln
            245                 250                 255 gat ttc gat ttg gaa gct ttt aat gct gga gat cat gca agt gca tat         817
Asp Phe Asp Leu Glu Ala Phe Asn Ala Gly Asp His Ala Ser Ala Tyr
            260                 265                 270 gaa gct cat cta aat gct gaa aag ata tgt cac gta ctg tat cct ggg         865
Glu Ala His Leu Asn Ala Glu Lys Ile Cys His Val Leu Tyr Pro Gly
            275                 280                 285 gac gaa tca cca gag ggg aaa gtt ctt cgc ctg aag caa caa tat aca         913
Asp Glu Ser Pro Glu Gly Lys Val Leu Arg Leu Lys Gln Gln Tyr Thr
    290                 295                 300 tta tgc tca gcc tca cta cag gat att att gct cgt ttc gag agg aga         961
Leu Cys Ser Ala Ser Leu Gln Asp Ile Ile Ala Arg Phe Glu Arg Arg
305                 310                 315                 320 gct ggt gat tct ctc agc tgg gag gac ttc ccc tct aaa gtt gca gtg         1009
Ala Gly Asp Ser Leu Ser Trp Glu Asp Phe Pro Ser Lys Val Ala Val
            325                 330                 335 cag atg aat gac act cac cca aca ctg tgc att cct gag ttg atg aga         1057
Gln Met Asn Asp Thr His Pro Thr Leu Cys Ile Pro Glu Leu Met Arg
            340                 345                 350 ata ttg att gat gtt aaa ggg tta agc tgg aat gag gct tgg agt atc         1105
Ile Leu Ile Asp Val Lys Gly Leu Ser Trp Asn Glu Ala Trp Ser Ile
            355                 360                 365 aca gaa aga act gtg gca tac aca aac cac acg gtg ctt cct gaa gct         1153
Thr Glu Arg Thr Val Ala Tyr Thr Asn His Thr Val Leu Pro Glu Ala
            370                 375                 380 ctg gag aag tgg agc ttg gac ata atg cag aaa ctt ctt cct cgg cat         1201
Leu Glu Lys Trp Ser Leu Asp Ile Met Gln Lys Leu Leu Pro Arg His
385                 390                 395                 400 gtt gaa atc ata gaa aaa att gat ggg gag ctg atg aac atc att atc         1249
Val Glu Ile Ile Glu Lys Ile Asp Gly Glu Leu Met Asn Ile Ile Ile
            405                 410                 415 tca aaa tac gga aca gaa gat act tca ctg tta aaa aag aag att aaa         1297
Ser Lys Tyr Gly Thr Glu Asp Thr Ser Leu Leu Lys Lys Lys Ile Lys
            420                 425                 430 gaa atg aga atc tta gac aac att gac cta cca gat tct att gcc aaa         1345
Glu Met Arg Ile Leu Asp Asn Ile Asp Leu Pro Asp Ser Ile Ala Lys
            435                 440                 445 cta ttt gtg aaa cca aaa gag aaa aaa gaa tct cct gct aaa ttg aaa         1393
Leu Phe Val Lys Pro Lys Glu Lys Lys Glu Ser Pro Ala Lys Leu Lys
            450                 455                 460 gag aaa ttg ctt gtc aaa tct ctg gag cct agt gtt gtg gtt gag gag         1441
Glu Lys Leu Leu Val Lys Ser Leu Glu Pro Ser Val Val Val Glu Glu
465                 470                 475                 480
```

```
aaa act gtg tcc aaa gta gag ata aac gag gac tct gag gag gtg gag    1489
Lys Thr Val Ser Lys Val Glu Ile Asn Glu Asp Ser Glu Glu Val Glu
            485                 490                 495 gta gac tct gaa gaa gtt gtg gag gca gaa aac gag gac tct gag gat    1537
Val Asp Ser Glu Glu Val Val Glu Ala Glu Asn Glu Asp Ser Glu Asp
        500                 505                 510 gag tta gat cca ttt gta aaa tca gat cct aaa tta cct aga gtt gtc    1585
Glu Leu Asp Pro Phe Val Lys Ser Asp Pro Lys Leu Pro Arg Val Val
            515                 520                 525 cga atg gct aac ctt tgt gtt gtt ggt ggg cat tcg gtt aat ggt gtg    1633
Arg Met Ala Asn Leu Cys Val Val Gly Gly His Ser Val Asn Gly Val
        530                 535                 540 gct gcg att cac agc gag att gtg aaa gaa gat gta ttc aac agc ttt    1681
Ala Ala Ile His Ser Glu Ile Val Lys Glu Asp Val Phe Asn Ser Phe
545                 550                 555                 560 tat gag atg tgg ccc gct aaa ttt caa aat aaa aca aat gga gtg act    1729
Tyr Glu Met Trp Pro Ala Lys Phe Gln Asn Lys Thr Asn Gly Val Thr
            565                 570                 575 cct aga cgt tgg att cgg ttt tgt aat cct gaa tta agt gca atc att    1777
Pro Arg Arg Trp Ile Arg Phe Cys Asn Pro Glu Leu Ser Ala Ile Ile
        580                 585                 590 tca aaa tgg ata gga tct gat gat tgg gtt ttg aac act gat aaa ctt    1825
Ser Lys Trp Ile Gly Ser Asp Asp Trp Val Leu Asn Thr Asp Lys Leu
            595                 600                 605 gct gaa tta aag aag ttt gct gat gat gag gat ctg caa tca gaa tgg    1873
Ala Glu Leu Lys Lys Phe Ala Asp Asp Glu Asp Leu Gln Ser Glu Trp
        610                 615                 620 cgt gct gct aaa aag gct aac aag gtg aag gtt gtt tct ctc ata aga    1921
Arg Ala Ala Lys Lys Ala Asn Lys Val Lys Val Val Ser Leu Ile Arg
625                 630                 635                 640 gaa aaa aca gga tat atc gtc agt cca gat gca atg ttt gac gtt cag    1969
Glu Lys Thr Gly Tyr Ile Val Ser Pro Asp Ala Met Phe Asp Val Gln
            645                 650                 655 gtg aaa agg atc cat gag tat aag cga cag ctg cta aat atc ctt gga    2017
Val Lys Arg Ile His Glu Tyr Lys Arg Gln Leu Leu Asn Ile Leu Gly
        660                 665                 670 att gtc tac cgc tac aag aag atg aaa gaa atg agt gca aaa gac aga    2065
Ile Val Tyr Arg Tyr Lys Lys Met Lys Glu Met Ser Ala Lys Asp Arg
            675                 680                 685 ata aat agc ttt gtt cca agg gta tgc ata ttt ggt ggg aaa gca ttt    2113
Ile Asn Ser Phe Val Pro Arg Val Cys Ile Phe Gly Gly Lys Ala Phe
        690                 695                 700 gcc act tac gta cag gca aag agg ata gtg aag ttt att aca gat gtt    2161
Ala Thr Tyr Val Gln Ala Lys Arg Ile Val Lys Phe Ile Thr Asp Val
705                 710                 715                 720 gca gct act gta aat cat gat cca gaa att gga gat cta ttg aag gtt    2209
Ala Ala Thr Val Asn His Asp Pro Glu Ile Gly Asp Leu Leu Lys Val
            725                 730                 735 gta ttt att cca gat tat aat gtt agt gtt gct gag gcg cta atc cct    2257
Val Phe Ile Pro Asp Tyr Asn Val Ser Val Ala Glu Ala Leu Ile Pro
        740                 745                 750 gcc agt gaa ttg tct cag cat atc agt act gct gga atg gaa gct agt    2305
Ala Ser Glu Leu Ser Gln His Ile Ser Thr Ala Gly Met Glu Ala Ser
            755                 760                 765 gga acc agc aac atg aag ttt gca atg aat gga tgt atc ctt att gga    2353
Gly Thr Ser Asn Met Lys Phe Ala Met Asn Gly Cys Ile Leu Ile Gly
        770                 775                 780 act ttg gat ggt gct aat gtg gaa atc aga gag gag gtt gga gag gaa    2401
Thr Leu Asp Gly Ala Asn Val Glu Ile Arg Glu Glu Val Gly Glu Glu
785                 790                 795                 800
```

-continued

| | |
|---|---|
| aac ttt ttc ctt ttt ggt gct gag gca cat gaa att gct ggt tta agg<br>Asn Phe Phe Leu Phe Gly Ala Glu Ala His Glu Ile Ala Gly Leu Arg<br>805 810 815 | 2449 |
| aaa gag aga gcc cag gga aag ttt gtg cct gac cca aga ttc gaa gag<br>Lys Glu Arg Ala Gln Gly Lys Phe Val Pro Asp Pro Arg Phe Glu Glu<br>820 825 830 | 2497 |
| gtt aag aga ttt gtc cgc agt ggg gtc ttt gga act tac aac tac gat<br>Val Lys Arg Phe Val Arg Ser Gly Val Phe Gly Thr Tyr Asn Tyr Asp<br>835 840 845 | 2545 |
| gac ttg atg ggt tct ctg gaa gga aat gaa ggt tat ggg cgt gca gac<br>Asp Leu Met Gly Ser Leu Glu Gly Asn Glu Gly Tyr Gly Arg Ala Asp<br>850 855 860 | 2593 |
| tat ttt ctt gtt ggt aaa gat ttc ccc agc tac att gaa tgc cag gag<br>Tyr Phe Leu Val Gly Lys Asp Phe Pro Ser Tyr Ile Glu Cys Gln Glu<br>865 870 875 880 | 2641 |
| aag gtt gat aaa gca tac cgc gat cag aaa cta tgg aca agg atg tca<br>Lys Val Asp Lys Ala Tyr Arg Asp Gln Lys Leu Trp Thr Arg Met Ser<br>885 890 895 | 2689 |
| atc ctc aac aca gcc agt tcc tcc aag ttc aac agc gac cgg acg att<br>Ile Leu Asn Thr Ala Ser Ser Ser Lys Phe Asn Ser Asp Arg Thr Ile<br>900 905 910 | 2737 |
| cac gag tac gcc aag gac atc tgg gac atc aag cct gtc atc ctg ccc<br>His Glu Tyr Ala Lys Asp Ile Trp Asp Ile Lys Pro Val Ile Leu Pro<br>915 920 925 | 2785 |
| tag acaggcaagg caagcactag ccactccctg ccagcgacct tcagagctaa | 2838 |
| ggtgcgcgca accggtgatg cgatgacagc atctgcctcc cagctctcct tggcaggaag | 2898 |
| gtttcgcttt gctcccagtt ttgagtagac agaagcaagt tcagttcagg cttcgataaa | 2958 |
| acgctggaac tatgcaaatt gtagccgtgt tgcctagcct ggaacaccct tgttttacct | 3018 |
| gtaatgtgta gcagcctctg ctgatcagct catgtgctat atggaattct gaagtgaaac | 3078 |
| catagttaaa agggatcggt tagtggcaaa aaaaaaaga aaaaaaaaaa aaaaaaaaaa | 3138 |
| aaa | 3141 |

<210> SEQ ID NO 16
<211> LENGTH: 928
<212> TYPE: PRT
<213> ORGANISM: Oryza sativa

<400> SEQUENCE: 16

Arg Ser Val Ala Ser Asp Arg Gly Val Gln Gly Ser Val Ser Pro Glu
1               5                   10                  15

Glu Glu Ile Ser Ser Val Leu Asn Ser Ile Asp Ser Ser Thr Ile Ala
            20                  25                  30

Ser Asn Ile Lys His His Ala Glu Phe Thr Pro Val Phe Ser Pro Glu
        35                  40                  45

His Phe Ser Pro Leu Lys Ala Tyr His Ala Thr Ala Lys Ser Val Leu
    50                  55                  60

Asp Thr Leu Ile Met Asn Trp Asn Ala Thr Tyr Asp Tyr Tyr Asp Arg
65                  70                  75                  80

Thr Asn Val Lys Gln Ala Tyr Tyr Leu Ser Met Glu Phe Leu Gln Gly
                85                  90                  95

Arg Ala Leu Thr Asn Ala Val Gly Asn Leu Glu Leu Thr Gly Gln Tyr
            100                 105                 110

Ala Glu Ala Leu Gln Gln Leu Gly His Ser Leu Glu Asp Val Ala Thr
        115                 120                 125

```
Gln Glu Pro Asp Ala Ala Leu Gly Asn Gly Gly Leu Gly Arg Leu Ala
    130                 135                 140

Ser Cys Phe Leu Asp Ser Leu Ala Thr Leu Asn Tyr Pro Ala Trp Gly
145                 150                 155                 160

Tyr Gly Leu Arg Tyr Lys His Gly Leu Phe Lys Gln Ile Ile Thr Lys
                165                 170                 175

Asp Gly Gln Glu Glu Val Ala Glu Asn Trp Leu Glu Met Gly Asn Pro
            180                 185                 190

Trp Glu Ile Val Arg Thr Asp Val Ser Tyr Pro Val Lys Phe Tyr Gly
        195                 200                 205

Lys Val Val Glu Gly Thr Asp Gly Arg Met His Trp Ile Gly Gly Glu
    210                 215                 220

Asn Ile Lys Val Val Ala His Asp Ile Pro Ile Pro Gly Tyr Lys Thr
225                 230                 235                 240

Lys Thr Thr Asn Asn Leu Arg Leu Trp Ser Thr Thr Val Pro Ser Gln
                245                 250                 255

Asp Phe Asp Leu Glu Ala Phe Asn Ala Gly Asp His Ala Ser Ala Tyr
            260                 265                 270

Glu Ala His Leu Asn Ala Glu Lys Ile Cys His Val Leu Tyr Pro Gly
        275                 280                 285

Asp Glu Ser Pro Glu Gly Lys Val Leu Arg Leu Lys Gln Gln Tyr Thr
    290                 295                 300

Leu Cys Ser Ala Ser Leu Gln Asp Ile Ile Ala Arg Phe Glu Arg Arg
305                 310                 315                 320

Ala Gly Asp Ser Leu Ser Trp Glu Asp Phe Pro Ser Lys Val Ala Val
                325                 330                 335

Gln Met Asn Asp Thr His Pro Thr Leu Cys Ile Pro Glu Leu Met Arg
            340                 345                 350

Ile Leu Ile Asp Val Lys Gly Leu Ser Trp Asn Glu Ala Trp Ser Ile
        355                 360                 365

Thr Glu Arg Thr Val Ala Tyr Thr Asn His Thr Val Leu Pro Glu Ala
    370                 375                 380

Leu Glu Lys Trp Ser Leu Asp Ile Met Gln Lys Leu Leu Pro Arg His
385                 390                 395                 400

Val Glu Ile Ile Glu Lys Ile Asp Gly Glu Leu Met Asn Ile Ile Ile
                405                 410                 415

Ser Lys Tyr Gly Thr Glu Asp Thr Ser Leu Leu Lys Lys Lys Ile Lys
            420                 425                 430

Glu Met Arg Ile Leu Asp Asn Ile Asp Leu Pro Asp Ser Ile Ala Lys
        435                 440                 445

Leu Phe Val Lys Pro Lys Glu Lys Lys Glu Ser Pro Ala Lys Leu Lys
    450                 455                 460

Glu Lys Leu Leu Val Lys Ser Leu Glu Pro Ser Val Val Glu Glu
465                 470                 475                 480

Lys Thr Val Ser Lys Val Glu Ile Asn Glu Asp Ser Glu Glu Val Glu
                485                 490                 495

Val Asp Ser Glu Glu Val Val Glu Ala Glu Asn Glu Asp Ser Glu Asp
            500                 505                 510

Glu Leu Asp Pro Phe Val Lys Ser Asp Pro Lys Leu Pro Arg Val Val
        515                 520                 525

Arg Met Ala Asn Leu Cys Val Val Gly Gly His Ser Val Asn Gly Val
    530                 535                 540

Ala Ala Ile His Ser Glu Ile Val Lys Glu Asp Val Phe Asn Ser Phe
```

```
                 545                 550                 555                 560
Tyr Glu Met Trp Pro Ala Lys Phe Gln Asn Lys Thr Asn Gly Val Thr
            565                 570                 575

Pro Arg Arg Trp Ile Arg Phe Cys Asn Pro Glu Leu Ser Ala Ile Ile
        580                 585                 590

Ser Lys Trp Ile Gly Ser Asp Asp Trp Val Leu Asn Thr Asp Lys Leu
    595                 600                 605

Ala Glu Leu Lys Lys Phe Ala Asp Asp Glu Asp Leu Gln Ser Glu Trp
610                 615                 620

Arg Ala Ala Lys Ala Asn Lys Val Lys Val Ser Leu Ile Arg
625                 630                 635                 640

Glu Lys Thr Gly Tyr Ile Val Ser Pro Asp Ala Met Phe Asp Val Gln
                645                 650                 655

Val Lys Arg Ile His Glu Tyr Lys Arg Gln Leu Leu Asn Ile Leu Gly
            660                 665                 670

Ile Val Tyr Arg Tyr Lys Lys Met Lys Glu Met Ser Ala Lys Asp Arg
        675                 680                 685

Ile Asn Ser Phe Val Pro Arg Val Cys Ile Phe Gly Gly Lys Ala Phe
    690                 695                 700

Ala Thr Tyr Val Gln Ala Lys Arg Ile Val Lys Phe Ile Thr Asp Val
705                 710                 715                 720

Ala Ala Thr Val Asn His Asp Pro Glu Ile Gly Asp Leu Leu Lys Val
                725                 730                 735

Val Phe Ile Pro Asp Tyr Asn Val Ser Val Ala Glu Ala Leu Ile Pro
            740                 745                 750

Ala Ser Glu Leu Ser Gln His Ile Ser Thr Ala Gly Met Glu Ala Ser
        755                 760                 765

Gly Thr Ser Asn Met Lys Phe Ala Met Asn Gly Cys Ile Leu Ile Gly
    770                 775                 780

Thr Leu Asp Gly Ala Asn Val Glu Ile Arg Glu Glu Val Gly Glu Glu
785                 790                 795                 800

Asn Phe Phe Leu Phe Gly Ala Glu Ala His Glu Ile Ala Gly Leu Arg
                805                 810                 815

Lys Glu Arg Ala Gln Gly Lys Phe Val Pro Asp Pro Arg Phe Glu Glu
            820                 825                 830

Val Lys Arg Phe Val Arg Ser Gly Val Phe Gly Thr Tyr Asn Tyr Asp
        835                 840                 845

Asp Leu Met Gly Ser Leu Glu Gly Asn Glu Gly Tyr Gly Arg Ala Asp
    850                 855                 860

Tyr Phe Leu Val Gly Lys Asp Phe Pro Ser Tyr Ile Glu Cys Gln Glu
865                 870                 875                 880

Lys Val Asp Lys Ala Tyr Arg Asp Gln Lys Leu Trp Thr Arg Met Ser
                885                 890                 895

Ile Leu Asn Thr Ala Ser Ser Lys Phe Asn Ser Asp Arg Thr Ile
            900                 905                 910

His Glu Tyr Ala Lys Asp Ile Trp Asp Ile Lys Pro Val Ile Leu Pro
        915                 920                 925

<210> SEQ ID NO 17
<211> LENGTH: 2856
<212> TYPE: DNA
<213> ORGANISM: Oryza sativa
<220> FEATURE:
<221> NAME/KEY: CDS
<222> LOCATION: (1)..(2856)
```

<400> SEQUENCE: 17

```
atg gcg acc gcc tcg gcg ccg ctg cag ctg gcc acc gcg tcc cgg ccg         48
Met Ala Thr Ala Ser Ala Pro Leu Gln Leu Ala Thr Ala Ser Arg Pro
1               5                   10                  15 ctc ccc gtc ggc gtc ggc tgc ggc gga gga gga ggg ggg ctc cac             96
Leu Pro Val Gly Val Gly Cys Gly Gly Gly Gly Gly Gly Leu His
            20                  25                  30 gtg ggt ggt gcc cgc ggc ggg ggc gcg gca ccg gcg cgg cgg cgg ctg        144
Val Gly Gly Ala Arg Gly Gly Gly Ala Ala Pro Ala Arg Arg Arg Leu
        35                  40                  45 gcg gtg cgg agc gtg gcg agc gat cgg ggc gtg cag ggg tcg gtg tcg        192
Ala Val Arg Ser Val Ala Ser Asp Arg Gly Val Gln Gly Ser Val Ser
50                  55                  60 ccc gag gaa gag att tca agt gtg cta aat tcc atc gat tcc tct acc        240
Pro Glu Glu Glu Ile Ser Ser Val Leu Asn Ser Ile Asp Ser Ser Thr
65                  70                  75                  80 att gca tca aac att aag cac cat gcg gag ttc aca cca gta ttc tct        288
Ile Ala Ser Asn Ile Lys His His Ala Glu Phe Thr Pro Val Phe Ser
                85                  90                  95 cca gag cac ttt tca cct ctg aag gct tac cat gca act gct aaa agt        336
Pro Glu His Phe Ser Pro Leu Lys Ala Tyr His Ala Thr Ala Lys Ser
            100                 105                 110 gtt ctt gat act ctg ata atg aac tgg aat gca aca tat gac tat tac        384
Val Leu Asp Thr Leu Ile Met Asn Trp Asn Ala Thr Tyr Asp Tyr Tyr
        115                 120                 125 gac aga aca aat gtg aag caa gcg tat tac ctg tcc atg gag ttt tta        432
Asp Arg Thr Asn Val Lys Gln Ala Tyr Tyr Leu Ser Met Glu Phe Leu
130                 135                 140 cag gga aga gct ctc act aat gcc gtt ggt aac ctt gag cta act gga        480
Gln Gly Arg Ala Leu Thr Asn Ala Val Gly Asn Leu Glu Leu Thr Gly
145                 150                 155                 160 caa tac gca gaa gca cta caa caa ctt gga cac agc cta gag gat gtt        528
Gln Tyr Ala Glu Ala Leu Gln Gln Leu Gly His Ser Leu Glu Asp Val
                165                 170                 175 gct acc cag gag cca gat gct gcc ctt ggg aat ggt ggt cta ggc cgg        576
Ala Thr Gln Glu Pro Asp Ala Ala Leu Gly Asn Gly Gly Leu Gly Arg
            180                 185                 190 tta gct tcc tgt ttc ttg gat tct ctg gca acc cta aat tat cca gca        624
Leu Ala Ser Cys Phe Leu Asp Ser Leu Ala Thr Leu Asn Tyr Pro Ala
        195                 200                 205 tgg gga tat gga ctt cga tac aaa cat ggc ctc ttt aaa gca aat cat        672
Trp Gly Tyr Gly Leu Arg Tyr Lys His Gly Leu Phe Lys Ala Asn His
210                 215                 220 acg aag gat ggt cag gag gag gta gct gaa aat tgg ctc gag atg gga        720
Thr Lys Asp Gly Gln Glu Glu Val Ala Glu Asn Trp Leu Glu Met Gly
225                 230                 235                 240 aat cct tgg gag att gta aga acc gat gtc tcc tat cct gtg aag ttc        768
Asn Pro Trp Glu Ile Val Arg Thr Asp Val Ser Tyr Pro Val Lys Phe
                245                 250                 255 tat ggt aaa gtg gtt gaa ggc act gat ggg agg atg cac tgg att gga        816
Tyr Gly Lys Val Val Glu Gly Thr Asp Gly Arg Met His Trp Ile Gly
            260                 265                 270 gga gaa aat atc aag gtt gtt gct cat gat atc cct att cct ggc tac        864
Gly Glu Asn Ile Lys Val Val Ala His Asp Ile Pro Ile Pro Gly Tyr
        275                 280                 285 aag act aaa act acc aac aat ctt cgt ctt tgg tca aca aca gtg cca        912
Lys Thr Lys Thr Thr Asn Asn Leu Arg Leu Trp Ser Thr Thr Val Pro
290                 295                 300
```

```
tca caa gat ttc gat ttg gaa gct ttt aat gct gga gat cat gca agt     960
Ser Gln Asp Phe Asp Leu Glu Ala Phe Asn Ala Gly Asp His Ala Ser
305                 310                 315                 320 gca tat gaa gct cat cta aat gct gaa aag cct cac tac agg gat att    1008
Ala Tyr Glu Ala His Leu Asn Ala Glu Lys Pro His Tyr Arg Asp Ile
                325                 330                 335 att gct cgt ttc gag agg aga gct ggt gat tct ctc agc tgg gag gac    1056
Ile Ala Arg Phe Glu Arg Arg Ala Gly Asp Ser Leu Ser Trp Glu Asp
            340                 345                 350 ttc ccc tct aaa gtt gca gtg cag atg aat gac act cac cca aca ctg    1104
Phe Pro Ser Lys Val Ala Val Gln Met Asn Asp Thr His Pro Thr Leu
        355                 360                 365 tgc att cct gag ttg atg aga ata ttg att gat gtt aaa ggg tta agc    1152
Cys Ile Pro Glu Leu Met Arg Ile Leu Ile Asp Val Lys Gly Leu Ser
    370                 375                 380 tgg aat gag gct tgg agt atc aca gaa aga act gtg gca tac aca aac    1200
Trp Asn Glu Ala Trp Ser Ile Thr Glu Arg Thr Val Ala Tyr Thr Asn
385                 390                 395                 400 cac acg gtg ctt cct gaa gct ctg gag aag tgg agc ttg gac ata atg    1248
His Thr Val Leu Pro Glu Ala Leu Glu Lys Trp Ser Leu Asp Ile Met
                405                 410                 415 cag aaa ctt ctt cct cgg cat gtt gaa atc ata gaa aaa att gat ggg    1296
Gln Lys Leu Leu Pro Arg His Val Glu Ile Ile Glu Lys Ile Asp Gly
            420                 425                 430 gag ctg atg aac atc att atc tca aaa tac gga aca gaa gat act tca    1344
Glu Leu Met Asn Ile Ile Ile Ser Lys Tyr Gly Thr Glu Asp Thr Ser
        435                 440                 445 ctg tta aaa aag aag att aaa gaa atg aga atc tta gac aac att gac    1392
Leu Leu Lys Lys Lys Ile Lys Glu Met Arg Ile Leu Asp Asn Ile Asp
    450                 455                 460 cta cca gat tct att gcc aaa cta ttt gtg aaa cca aaa gag aaa aaa    1440
Leu Pro Asp Ser Ile Ala Lys Leu Phe Val Lys Pro Lys Glu Lys Lys
465                 470                 475                 480 gaa tct cct gct aaa ttg aaa gag aaa ttg ctt gtc aaa tct ctg gag    1488
Glu Ser Pro Ala Lys Leu Lys Glu Lys Leu Leu Val Lys Ser Leu Glu
                485                 490                 495 cct agt gtt gtg gtt gag gag aaa act gtg tcc aaa gta gag ata aac    1536
Pro Ser Val Val Val Glu Glu Lys Thr Val Ser Lys Val Glu Ile Asn
            500                 505                 510 gag gac tct gag gag gtg gag gta gac tct gaa gaa gtt gtg gag gca    1584
Glu Asp Ser Glu Glu Val Glu Val Asp Ser Glu Glu Val Val Glu Ala
        515                 520                 525 gaa aac gag gac tct gag gat gag tta gat cca ttt gta aaa tca gat    1632
Glu Asn Glu Asp Ser Glu Asp Glu Leu Asp Pro Phe Val Lys Ser Asp
    530                 535                 540 cct aaa tta cct aga gtt gtc cga atg gct aac ctt tgt gtt gtt ggt    1680
Pro Lys Leu Pro Arg Val Val Arg Met Ala Asn Leu Cys Val Val Gly
545                 550                 555                 560 ggg cat tcg gtt aat ggt gtg gct gcg att cac agc gag att gtg aaa    1728
Gly His Ser Val Asn Gly Val Ala Ala Ile His Ser Glu Ile Val Lys
                565                 570                 575 gaa gat gta ttc aac agc ttt tat gag atg tgg ccc gct aaa ttt caa    1776
Glu Asp Val Phe Asn Ser Phe Tyr Glu Met Trp Pro Ala Lys Phe Gln
            580                 585                 590 aat aaa aca aat gga gtg act cct aga cgt tgg att cgg ttt tgt aat    1824
Asn Lys Thr Asn Gly Val Thr Pro Arg Arg Trp Ile Arg Phe Cys Asn
        595                 600                 605 cct gaa tta agt gca atc att tca aaa tgg ata gga tct gat gat tgg    1872
Pro Glu Leu Ser Ala Ile Ile Ser Lys Trp Ile Gly Ser Asp Asp Trp
    610                 615                 620
```

```
                                                        -continued gtt ttg aac act gat aaa ctt gct gaa tta aag aag ttt gct gat gat    1920
Val Leu Asn Thr Asp Lys Leu Ala Glu Leu Lys Lys Phe Ala Asp Asp
625                 630                 635                 640 gag gat ctg caa tca gaa tgg cgt gct gct aaa aag gct aac aag gtg    1968
Glu Asp Leu Gln Ser Glu Trp Arg Ala Ala Lys Lys Ala Asn Lys Val
            645                 650                 655 aag gtt gtt tct ctc ata aga gaa aaa aca gga tat atc gtc agt cca    2016
Lys Val Val Ser Leu Ile Arg Glu Lys Thr Gly Tyr Ile Val Ser Pro
        660                 665                 670 gat gca atg ttt gac gtt cag gtg aaa agg atc cat gag tat aag cga    2064
Asp Ala Met Phe Asp Val Gln Val Lys Arg Ile His Glu Tyr Lys Arg
    675                 680                 685 cag ctg cta aat atc ctt gga att gtc tac cgc tac aag aag atg aaa    2112
Gln Leu Leu Asn Ile Leu Gly Ile Val Tyr Arg Tyr Lys Lys Met Lys
690                 695                 700 gaa atg agt gca aaa gac aga ata aat agc ttt gtt cca agg gta tgc    2160
Glu Met Ser Ala Lys Asp Arg Ile Asn Ser Phe Val Pro Arg Val Cys
705                 710                 715                 720 ata ttt ggt ggg aaa gca ttt gcc act tac gta cag gca aag agg ata    2208
Ile Phe Gly Gly Lys Ala Phe Ala Thr Tyr Val Gln Ala Lys Arg Ile
            725                 730                 735 gtg aag ttt att aca gat gtt gca gct act gta aat cat gat cca gaa    2256
Val Lys Phe Ile Thr Asp Val Ala Ala Thr Val Asn His Asp Pro Glu
        740                 745                 750 att gga gat cta ttg aag gtt gta ttt att cca gat tat aat gtt agt    2304
Ile Gly Asp Leu Leu Lys Val Val Phe Ile Pro Asp Tyr Asn Val Ser
    755                 760                 765 gtt gct gag gcg cta atc cct gcc agt gaa ttg tct cag cat atc agt    2352
Val Ala Glu Ala Leu Ile Pro Ala Ser Glu Leu Ser Gln His Ile Ser
770                 775                 780 act gct gga atg gaa gct agt gga acc agc aac atg aag ttt gca atg    2400
Thr Ala Gly Met Glu Ala Ser Gly Thr Ser Asn Met Lys Phe Ala Met
785                 790                 795                 800 aat gga tgt atc ctt att gga act ttg gat ggt gct aat gtg gaa atc    2448
Asn Gly Cys Ile Leu Ile Gly Thr Leu Asp Gly Ala Asn Val Glu Ile
            805                 810                 815 aga gag gag gtt gga gag gaa aac ttt ttc ctt ttt ggt gct gag gca    2496
Arg Glu Glu Val Gly Glu Glu Asn Phe Phe Leu Phe Gly Ala Glu Ala
        820                 825                 830 cat gaa att gct ggt tta agg aaa gag aga gcc cag gga aag ttt gtg    2544
His Glu Ile Ala Gly Leu Arg Lys Glu Arg Ala Gln Gly Lys Phe Val
    835                 840                 845 cct gac cca aga ttc gaa gag gtt aag aga ttt gtc cgc agt ggg gtc    2592
Pro Asp Pro Arg Phe Glu Glu Val Lys Arg Phe Val Arg Ser Gly Val
850                 855                 860 ttt gga act tac aac tac gat gac ttg atg ggt tct ctg gaa gga aat    2640
Phe Gly Thr Tyr Asn Tyr Asp Asp Leu Met Gly Ser Leu Glu Gly Asn
865                 870                 875                 880 gaa ggt tat ggg cgt gca gac tat ttt ctt gtt ggt aaa gat ttc ccc    2688
Glu Gly Tyr Gly Arg Ala Asp Tyr Phe Leu Val Gly Lys Asp Phe Pro
            885                 890                 895 agc tac att gaa tgc cag gag aag gtt gat aaa gca tac cgc gat cag    2736
Ser Tyr Ile Glu Cys Gln Glu Lys Val Asp Lys Ala Tyr Arg Asp Gln
        900                 905                 910 aaa cta tgg aca agg atg tca atc ctc aac aca gcc agt tcc tcc aag    2784
Lys Leu Trp Thr Arg Met Ser Ile Leu Asn Thr Ala Ser Ser Ser Lys
    915                 920                 925 ttc aac agc gac cgg acg att cac gag tac gcc aag gac atc tgg gac    2832
Phe Asn Ser Asp Arg Thr Ile His Glu Tyr Ala Lys Asp Ile Trp Asp
```

```
                930             935             940
atc aag cct gtc atc ctg ccc tag                                          2856
Ile Lys Pro Val Ile Leu Pro
945                 950
```

<210> SEQ ID NO 18
<211> LENGTH: 951
<212> TYPE: PRT
<213> ORGANISM: Oryza sativa

<400> SEQUENCE: 18

```
Met Ala Thr Ala Ser Ala Pro Leu Gln Leu Ala Thr Ala Ser Arg Pro
1               5                   10                  15

Leu Pro Val Gly Val Gly Cys Gly Gly Gly Gly Gly Gly Gly Leu His
            20                  25                  30

Val Gly Gly Ala Arg Gly Gly Gly Ala Ala Pro Ala Arg Arg Arg Leu
        35                  40                  45

Ala Val Arg Ser Val Ala Ser Asp Arg Gly Val Gln Gly Ser Val Ser
    50                  55                  60

Pro Glu Glu Ile Ser Ser Val Leu Asn Ser Ile Asp Ser Ser Thr
65                  70                  75                  80

Ile Ala Ser Asn Ile Lys His His Ala Glu Phe Thr Pro Val Phe Ser
                85                  90                  95

Pro Glu His Phe Ser Pro Leu Lys Ala Tyr His Ala Thr Ala Lys Ser
            100                 105                 110

Val Leu Asp Thr Leu Ile Met Asn Trp Asn Ala Thr Tyr Asp Tyr Tyr
        115                 120                 125

Asp Arg Thr Asn Val Lys Gln Ala Tyr Tyr Leu Ser Met Glu Phe Leu
    130                 135                 140

Gln Gly Arg Ala Leu Thr Asn Ala Val Gly Asn Leu Glu Leu Thr Gly
145                 150                 155                 160

Gln Tyr Ala Glu Ala Leu Gln Gln Leu Gly His Ser Leu Glu Asp Val
                165                 170                 175

Ala Thr Gln Glu Pro Asp Ala Ala Leu Gly Asn Gly Gly Leu Gly Arg
            180                 185                 190

Leu Ala Ser Cys Phe Leu Asp Ser Leu Ala Thr Leu Asn Tyr Pro Ala
        195                 200                 205

Trp Gly Tyr Gly Leu Arg Tyr Lys His Gly Leu Phe Lys Ala Asn His
    210                 215                 220

Thr Lys Asp Gly Gln Glu Glu Val Ala Glu Asn Trp Leu Glu Met Gly
225                 230                 235                 240

Asn Pro Trp Glu Ile Val Arg Thr Asp Val Ser Tyr Pro Val Lys Phe
                245                 250                 255

Tyr Gly Lys Val Val Glu Gly Thr Asp Gly Arg Met His Trp Ile Gly
            260                 265                 270

Gly Glu Asn Ile Lys Val Val Ala His Asp Ile Pro Ile Pro Gly Tyr
        275                 280                 285

Lys Thr Lys Thr Thr Asn Asn Leu Arg Leu Trp Ser Thr Thr Val Pro
    290                 295                 300

Ser Gln Asp Phe Asp Leu Glu Ala Phe Asn Ala Gly Asp His Ala Ser
305                 310                 315                 320

Ala Tyr Glu Ala His Leu Asn Ala Glu Lys Pro His Tyr Arg Asp Ile
                325                 330                 335

Ile Ala Arg Phe Glu Arg Arg Ala Gly Asp Ser Leu Ser Trp Glu Asp
            340                 345                 350
```

```
Phe Pro Ser Lys Val Ala Val Gln Met Asn Asp Thr His Pro Thr Leu
            355                 360                 365

Cys Ile Pro Glu Leu Met Arg Ile Leu Ile Asp Val Lys Gly Leu Ser
        370                 375                 380

Trp Asn Glu Ala Trp Ser Ile Thr Glu Arg Thr Val Ala Tyr Thr Asn
385                 390                 395                 400

His Thr Val Leu Pro Glu Ala Leu Glu Lys Trp Ser Leu Asp Ile Met
                405                 410                 415

Gln Lys Leu Leu Pro Arg His Val Glu Ile Glu Lys Ile Asp Gly
            420                 425                 430

Glu Leu Met Asn Ile Ile Ile Ser Lys Tyr Gly Thr Glu Asp Thr Ser
        435                 440                 445

Leu Leu Lys Lys Lys Ile Lys Glu Met Arg Ile Leu Asp Asn Ile Asp
    450                 455                 460

Leu Pro Asp Ser Ile Ala Lys Leu Phe Val Lys Pro Lys Glu Lys Lys
465                 470                 475                 480

Glu Ser Pro Ala Lys Leu Lys Glu Lys Leu Leu Val Lys Ser Leu Glu
                485                 490                 495

Pro Ser Val Val Val Glu Glu Lys Thr Val Ser Lys Val Glu Ile Asn
            500                 505                 510

Glu Asp Ser Glu Glu Val Glu Val Asp Ser Glu Glu Val Val Glu Ala
        515                 520                 525

Glu Asn Glu Asp Ser Glu Asp Glu Leu Asp Pro Phe Val Lys Ser Asp
    530                 535                 540

Pro Lys Leu Pro Arg Val Val Arg Met Ala Asn Leu Cys Val Val Gly
545                 550                 555                 560

Gly His Ser Val Asn Gly Val Ala Ala Ile His Ser Glu Ile Val Lys
                565                 570                 575

Glu Asp Val Phe Asn Ser Phe Tyr Glu Met Trp Pro Ala Lys Phe Gln
            580                 585                 590

Asn Lys Thr Asn Gly Val Thr Pro Arg Arg Trp Ile Arg Phe Cys Asn
        595                 600                 605

Pro Glu Leu Ser Ala Ile Ile Ser Lys Trp Ile Gly Ser Asp Asp Trp
    610                 615                 620

Val Leu Asn Thr Asp Lys Leu Ala Glu Leu Lys Lys Phe Ala Asp Asp
625                 630                 635                 640

Glu Asp Leu Gln Ser Glu Trp Arg Ala Ala Lys Lys Ala Asn Lys Val
                645                 650                 655

Lys Val Val Ser Leu Ile Arg Glu Lys Thr Gly Tyr Ile Val Ser Pro
            660                 665                 670

Asp Ala Met Phe Asp Val Gln Val Lys Arg Ile His Glu Tyr Lys Arg
        675                 680                 685

Gln Leu Leu Asn Ile Leu Gly Ile Val Tyr Arg Tyr Lys Lys Met Lys
    690                 695                 700

Glu Met Ser Ala Lys Asp Arg Ile Asn Ser Phe Val Pro Arg Val Cys
705                 710                 715                 720

Ile Phe Gly Gly Lys Ala Phe Ala Thr Tyr Val Gln Ala Lys Arg Ile
                725                 730                 735

Val Lys Phe Ile Thr Asp Val Ala Ala Thr Val Asn His Asp Pro Glu
            740                 745                 750

Ile Gly Asp Leu Leu Lys Val Val Phe Ile Pro Asp Tyr Asn Val Ser
        755                 760                 765
```

-continued

```
Val Ala Glu Ala Leu Ile Pro Ala Ser Glu Leu Ser Gln His Ile Ser
    770                 775                 780
Thr Ala Gly Met Glu Ala Ser Gly Thr Ser Asn Met Lys Phe Ala Met
785                 790                 795                 800
Asn Gly Cys Ile Leu Ile Gly Thr Leu Asp Gly Ala Asn Val Glu Ile
                805                 810                 815
Arg Glu Glu Val Gly Glu Glu Asn Phe Phe Leu Phe Gly Ala Glu Ala
            820                 825                 830
His Glu Ile Ala Gly Leu Arg Lys Glu Arg Ala Gln Gly Lys Phe Val
        835                 840                 845
Pro Asp Pro Arg Phe Glu Glu Val Lys Arg Phe Val Arg Ser Gly Val
    850                 855                 860
Phe Gly Thr Tyr Asn Tyr Asp Asp Leu Met Gly Ser Leu Glu Gly Asn
865                 870                 875                 880
Glu Gly Tyr Gly Arg Ala Asp Tyr Phe Leu Val Gly Lys Asp Phe Pro
                885                 890                 895
Ser Tyr Ile Glu Cys Gln Glu Lys Val Asp Lys Ala Tyr Arg Asp Gln
            900                 905                 910
Lys Leu Trp Thr Arg Met Ser Ile Leu Asn Thr Ala Ser Ser Ser Lys
        915                 920                 925
Phe Asn Ser Asp Arg Thr Ile His Glu Tyr Ala Lys Asp Ile Trp Asp
    930                 935                 940
Ile Lys Pro Val Ile Leu Pro
945                 950

<210> SEQ ID NO 19
<211> LENGTH: 2856
<212> TYPE: DNA
<213> ORGANISM: Triticum aestivum
<220> FEATURE:
<221> NAME/KEY: CDS
<222> LOCATION: (58)..(2556)

<400> SEQUENCE: 19
cgccacctcc cccgcacaca ccgagtgctc gtgctcgacg caattcccca ccccgcg          57 atg agt gcg gcg gac aag gtg aag ccg gcg gcc agc ccc gcg tcg gag       105
Met Ser Ala Ala Asp Lys Val Lys Pro Ala Ala Ser Pro Ala Ser Glu
1               5                   10                  15 gac ccc tcc gcc atc gcc ggc aac atc tcc tac cac gcg cag tac agc       153
Asp Pro Ser Ala Ile Ala Gly Asn Ile Ser Tyr His Ala Gln Tyr Ser
            20                  25                  30 ccc cac ttc tcg ccg ctc gcc ttc ggc ccc gag cag gcc ttc tac gcc       201
Pro His Phe Ser Pro Leu Ala Phe Gly Pro Glu Gln Ala Phe Tyr Ala
        35                  40                  45 acc gcc gag agc gtc cgc gac cac ctc ctc cag aga tgg aac gac acc       249
Thr Ala Glu Ser Val Arg Asp His Leu Leu Gln Arg Trp Asn Asp Thr
    50                  55                  60 tac ctg cat ttc cac aag acg gat ccc aag cag acc tac tac ctc tcc       297
Tyr Leu His Phe His Lys Thr Asp Pro Lys Gln Thr Tyr Tyr Leu Ser
65                  70                  75                  80 atg gag tac ctg cag ggc cgc gcg ctc acc aac gcc gtc ggc aac ctc       345
Met Glu Tyr Leu Gln Gly Arg Ala Leu Thr Asn Ala Val Gly Asn Leu
                85                  90                  95 gcc atc acc ggc gcc tac gct gac gcc ctg aag aag ttc ggc tac gag       393
Ala Ile Thr Gly Ala Tyr Ala Asp Ala Leu Lys Lys Phe Gly Tyr Glu
            100                 105                 110 ctc gag gcc atc gct gga cag gag aga gat gcg gct ctg gga aat ggt       441
Leu Glu Ala Ile Ala Gly Gln Glu Arg Asp Ala Ala Leu Gly Asn Gly
```

```
                115                 120                 125
ggc ttg ggc agg ctt gca tct tgc ttt ttg gat tca atg gca acg ctg      489
Gly Leu Gly Arg Leu Ala Ser Cys Phe Leu Asp Ser Met Ala Thr Leu
130                 135                 140 aac ttg cct tct tgg ggc tat ggc ctt cgt tac cgt tat ggc ctg ttc      537
Asn Leu Pro Ser Trp Gly Tyr Gly Leu Arg Tyr Arg Tyr Gly Leu Phe
145                 150                 155                 160 aag cag cgc att gcc aag gaa gga caa gaa gaa atc gct gaa gat tgg      585
Lys Gln Arg Ile Ala Lys Glu Gly Gln Glu Glu Ile Ala Glu Asp Trp
                165                 170                 175 ctt gat aag ttt agc cca tgg gag att gtc agg cat gat gtt gta tac      633
Leu Asp Lys Phe Ser Pro Trp Glu Ile Val Arg His Asp Val Val Tyr
            180                 185                 190 cca atc aga ttt ttc ggc cat gtc gag att tcg cca gat gga aag cgg      681
Pro Ile Arg Phe Phe Gly His Val Glu Ile Ser Pro Asp Gly Lys Arg
        195                 200                 205 aaa tgg gcc ggt gga gaa gtt ctg aac gct tta gcc tat gat gtg cca      729
Lys Trp Ala Gly Gly Glu Val Leu Asn Ala Leu Ala Tyr Asp Val Pro
    210                 215                 220 att cct ggg tac aag aca aaa aat gca atc agt ctt cgc ctt tgg gat      777
Ile Pro Gly Tyr Lys Thr Lys Asn Ala Ile Ser Leu Arg Leu Trp Asp
225                 230                 235                 240 gca aca gct act gct gag gat ttc aac tta ttt cag ttc aat gat ggc      825
Ala Thr Ala Thr Ala Glu Asp Phe Asn Leu Phe Gln Phe Asn Asp Gly
                245                 250                 255 cag tat gag tca gct gct caa ctt cac tcg agg gca cag cag ata tgt      873
Gln Tyr Glu Ser Ala Ala Gln Leu His Ser Arg Ala Gln Gln Ile Cys
            260                 265                 270 gct gtt ctc tat ccc ggt gat gct aca gaa gaa ggg aag ctt ctg aga      921
Ala Val Leu Tyr Pro Gly Asp Ala Thr Glu Glu Gly Lys Leu Leu Arg
        275                 280                 285 tta aag cag cag tat ttc ctt tgc agc gca tca ctt cag gat att att      969
Leu Lys Gln Gln Tyr Phe Leu Cys Ser Ala Ser Leu Gln Asp Ile Ile
    290                 295                 300 ttc aga ttt aaa gaa aga aaa gct gac aga gtt tca ggg aag tgg agt     1017
Phe Arg Phe Lys Glu Arg Lys Ala Asp Arg Val Ser Gly Lys Trp Ser
305                 310                 315                 320 gag ttc cct tcc aaa gtt gct gtt caa atg aat gac act cat cca act     1065
Glu Phe Pro Ser Lys Val Ala Val Gln Met Asn Asp Thr His Pro Thr
                325                 330                 335 ctt gcc att cct gag cta atg agg ttg ctt atg gac gtg gag gga ctt     1113
Leu Ala Ile Pro Glu Leu Met Arg Leu Leu Met Asp Val Glu Gly Leu
            340                 345                 350 ggt tgg gac gaa gcc tgg gct gtc aca aat aag acg gtt gct tac acc     1161
Gly Trp Asp Glu Ala Trp Ala Val Thr Asn Lys Thr Val Ala Tyr Thr
        355                 360                 365 aat cac acg gtt ctt cct gaa gct ctt gag aaa tgg tca cag gct gta     1209
Asn His Thr Val Leu Pro Glu Ala Leu Glu Lys Trp Ser Gln Ala Val
    370                 375                 380 atg aag aaa ttg ctt cca cgt cac atg gaa atc att gag gaa att gac     1257
Met Lys Lys Leu Leu Pro Arg His Met Glu Ile Ile Glu Glu Ile Asp
385                 390                 395                 400 aag cgg ttt aga gaa atg gta atc tcc acc cgg aag gat atg gag gga     1305
Lys Arg Phe Arg Glu Met Val Ile Ser Thr Arg Lys Asp Met Glu Gly
                405                 410                 415 aag atc gaa tcg atg agg gtt tta gat aac aat ccc gag aag cca gta     1353
Lys Ile Glu Ser Met Arg Val Leu Asp Asn Asn Pro Glu Lys Pro Val
            420                 425                 430 gtg cgg atg gcg aat ttg tgt gtt gtg gct ggg cat acg gtg aat gga     1401
```

```
Val Arg Met Ala Asn Leu Cys Val Ala Gly His Thr Val Asn Gly
        435                 440                 445 gtg gcc gag ttg cac agc aac atc ttg aaa caa gag ctg ttt gca gat      1449
Val Ala Glu Leu His Ser Asn Ile Leu Lys Gln Glu Leu Phe Ala Asp
        450                 455                 460 tat gtc tct att tgg cct aac aaa ttc cag aac aaa act aat gga att      1497
Tyr Val Ser Ile Trp Pro Asn Lys Phe Gln Asn Lys Thr Asn Gly Ile
465                 470                 475                 480 aca cca cgt aga tgg ctc cgt ttt tgc aac cct gag ttg agt gaa ata      1545
Thr Pro Arg Arg Trp Leu Arg Phe Cys Asn Pro Glu Leu Ser Glu Ile
                485                 490                 495 gtc act aaa tgg cta aaa aca gat cag tgg aca agc aac ctt gat ctt      1593
Val Thr Lys Trp Leu Lys Thr Asp Gln Trp Thr Ser Asn Leu Asp Leu
        500                 505                 510 ctc acc ggg ctt cgg aaa ttc gca gat gat gaa aaa cta cat gct gag      1641
Leu Thr Gly Leu Arg Lys Phe Ala Asp Asp Glu Lys Leu His Ala Glu
        515                 520                 525 tgg gca gca gcc aag ctg gcc agc aaa aag cgc cta gcc aag cat gta      1689
Trp Ala Ala Ala Lys Leu Ala Ser Lys Lys Arg Leu Ala Lys His Val
        530                 535                 540 ttg gat gtg act ggt gtt aca att gac cca gat agc ctt ttt gat ata      1737
Leu Asp Val Thr Gly Val Thr Ile Asp Pro Asp Ser Leu Phe Asp Ile
545                 550                 555                 560 caa att aaa cgc atc cac gaa tac aag aga cag ctg atg aac att ttg      1785
Gln Ile Lys Arg Ile His Glu Tyr Lys Arg Gln Leu Met Asn Ile Leu
                565                 570                 575 gga gct gtg tac aga tac aag aag tta aag gaa atg agc gca gca gac      1833
Gly Ala Val Tyr Arg Tyr Lys Lys Leu Lys Glu Met Ser Ala Ala Asp
                580                 585                 590 agg cag aag gtt aca ccg cgc act gtc atg gta gga ggg aaa gca ttt      1881
Arg Gln Lys Val Thr Pro Arg Thr Val Met Val Gly Gly Lys Ala Phe
        595                 600                 605 gca aca tac acc aac gcc aaa aga ata gtg aaa ttg gta aat gat gtt      1929
Ala Thr Tyr Thr Asn Ala Lys Arg Ile Val Lys Leu Val Asn Asp Val
        610                 615                 620 ggt gct gtg gtt aac aac gat gct gac gtc aac aaa tat ctg aag gtg      1977
Gly Ala Val Val Asn Asn Asp Ala Asp Val Asn Lys Tyr Leu Lys Val
625                 630                 635                 640 gtg ttc att cca aac tac aat gta tca gtg gct gaa gtg ctc att cct      2025
Val Phe Ile Pro Asn Tyr Asn Val Ser Val Ala Glu Val Leu Ile Pro
                645                 650                 655 ggc agt gaa ctg tca cag cac atc agt act gca ggc atg gaa gca agt      2073
Gly Ser Glu Leu Ser Gln His Ile Ser Thr Ala Gly Met Glu Ala Ser
                660                 665                 670 gga aca agt aac atg aag ttc tct ctg aat ggc tgt gtt atc att gga      2121
Gly Thr Ser Asn Met Lys Phe Ser Leu Asn Gly Cys Val Ile Ile Gly
        675                 680                 685 act ctc gat gga gcc aat gtt gaa atc aga gaa gaa gtg gga caa gac      2169
Thr Leu Asp Gly Ala Asn Val Glu Ile Arg Glu Glu Val Gly Gln Asp
        690                 695                 700 aac ttc ttc ctt ttc ggt gcc aaa gca gat cag gtt gct ggt ctg agg      2217
Asn Phe Phe Leu Phe Gly Ala Lys Ala Asp Gln Val Ala Gly Leu Arg
705                 710                 715                 720 aag gat aga gaa aat ggc ttg ttc aag cca gac cca cgc ttc gaa gaa      2265
Lys Asp Arg Glu Asn Gly Leu Phe Lys Pro Asp Pro Arg Phe Glu Glu
                725                 730                 735 gcc aag cag ttt atc agg agt ggt gct ttc ggc acc tac gac tac act      2313
Ala Lys Gln Phe Ile Arg Ser Gly Ala Phe Gly Thr Tyr Asp Tyr Thr
                740                 745                 750
```

-continued

```
cct ctc ttg gat tcc ctt gaa ggg aac act gga ttt ggg cgt ggt gac        2361
Pro Leu Leu Asp Ser Leu Glu Gly Asn Thr Gly Phe Gly Arg Gly Asp
            755                 760                 765 tac ttc ctt gtt ggc tat gac ttt cca agc tac att gat gca cag gcc        2409
Tyr Phe Leu Val Gly Tyr Asp Phe Pro Ser Tyr Ile Asp Ala Gln Ala
770                 775                 780 cgg gtt gat gaa gcc tac aag gac aag aag aaa tgg gtc aag atg tcc        2457
Arg Val Asp Glu Ala Tyr Lys Asp Lys Lys Lys Trp Val Lys Met Ser
785                 790                 795                 800 atc ttg aac acg gct gga agc ggc aag ttc agc agc gac cgc acc atc        2505
Ile Leu Asn Thr Ala Gly Ser Gly Lys Phe Ser Ser Asp Arg Thr Ile
                805                 810                 815 gac caa tat gcg aag gag atc tgg ggc att tcg gct tgc cct gtt cca        2553
Asp Gln Tyr Ala Lys Glu Ile Trp Gly Ile Ser Ala Cys Pro Val Pro
            820                 825                 830 tga agaggagacg tgatcaagag gtgatggatg atgatgcgtg gcagtaataa              2606
ggaccttata ctggtccatg gtgaataacc cctgcttccg ttgtagctga aagaatgaa        2666 gcaacgtacg aagcctgttg tgttgtgtat tctgctgcac ttttgaagtg catagaggat       2726 gcgactttc ttttgttctt tttcttttttt ggtctgtaac catactattt tgatcctgaa       2786
ccggaatggc ggaatcatcc aggttctcaa taaaatagtt caagttttga ttaaaaaaaa       2846
aaaaaaaaaa                                                              2856
```

<210> SEQ ID NO 20
<211> LENGTH: 832
<212> TYPE: PRT
<213> ORGANISM: Triticum aestivum

<400> SEQUENCE: 20

```
Met Ser Ala Ala Asp Lys Val Lys Pro Ala Ala Ser Pro Ala Ser Glu
1               5                   10                  15

Asp Pro Ser Ala Ile Ala Gly Asn Ile Ser Tyr His Ala Gln Tyr Ser
            20                  25                  30

Pro His Phe Ser Pro Leu Ala Phe Gly Pro Glu Gln Ala Phe Tyr Ala
        35                  40                  45

Thr Ala Glu Ser Val Arg Asp His Leu Leu Gln Arg Trp Asn Asp Thr
    50                  55                  60

Tyr Leu His Phe His Lys Thr Asp Pro Lys Gln Thr Tyr Tyr Leu Ser
65                  70                  75                  80

Met Glu Tyr Leu Gln Gly Arg Ala Leu Thr Asn Ala Val Gly Asn Leu
                85                  90                  95

Ala Ile Thr Gly Ala Tyr Ala Asp Ala Leu Lys Lys Phe Gly Tyr Glu
            100                 105                 110

Leu Glu Ala Ile Ala Gly Gln Glu Arg Asp Ala Ala Leu Gly Asn Gly
        115                 120                 125

Gly Leu Gly Arg Leu Ala Ser Cys Phe Leu Asp Ser Met Ala Thr Leu
    130                 135                 140

Asn Leu Pro Ser Trp Gly Tyr Gly Leu Arg Tyr Arg Tyr Gly Leu Phe
145                 150                 155                 160

Lys Gln Arg Ile Ala Lys Glu Gly Gln Glu Glu Ile Ala Glu Asp Trp
                165                 170                 175

Leu Asp Lys Phe Ser Pro Trp Glu Ile Val Arg His Asp Val Val Tyr
            180                 185                 190

Pro Ile Arg Phe Phe Gly His Val Glu Ile Ser Pro Asp Gly Lys Arg
        195                 200                 205
```

```
Lys Trp Ala Gly Gly Glu Val Leu Asn Ala Leu Ala Tyr Asp Val Pro
    210                 215                 220

Ile Pro Gly Tyr Lys Thr Lys Asn Ala Ile Ser Leu Arg Leu Trp Asp
225                 230                 235                 240

Ala Thr Ala Thr Ala Glu Asp Phe Asn Leu Phe Gln Phe Asn Asp Gly
                245                 250                 255

Gln Tyr Glu Ser Ala Ala Gln Leu His Ser Arg Ala Gln Gln Ile Cys
            260                 265                 270

Ala Val Leu Tyr Pro Gly Asp Ala Thr Glu Glu Gly Lys Leu Leu Arg
        275                 280                 285

Leu Lys Gln Gln Tyr Phe Leu Cys Ser Ala Ser Leu Gln Asp Ile Ile
    290                 295                 300

Phe Arg Phe Lys Glu Arg Lys Ala Asp Arg Val Ser Gly Lys Trp Ser
305                 310                 315                 320

Glu Phe Pro Ser Lys Val Ala Val Gln Met Asn Asp Thr His Pro Thr
                325                 330                 335

Leu Ala Ile Pro Glu Leu Met Arg Leu Leu Met Asp Val Glu Gly Leu
            340                 345                 350

Gly Trp Asp Glu Ala Trp Ala Val Thr Asn Lys Thr Val Ala Tyr Thr
        355                 360                 365

Asn His Thr Val Leu Pro Glu Ala Leu Glu Lys Trp Ser Gln Ala Val
    370                 375                 380

Met Lys Lys Leu Leu Pro Arg His Met Glu Ile Ile Glu Glu Ile Asp
385                 390                 395                 400

Lys Arg Phe Arg Glu Met Val Ile Ser Thr Arg Lys Asp Met Glu Gly
                405                 410                 415

Lys Ile Glu Ser Met Arg Val Leu Asp Asn Pro Glu Lys Pro Val
            420                 425                 430

Val Arg Met Ala Asn Leu Cys Val Val Ala Gly His Thr Val Asn Gly
        435                 440                 445

Val Ala Glu Leu His Ser Asn Ile Leu Lys Gln Glu Leu Phe Ala Asp
    450                 455                 460

Tyr Val Ser Ile Trp Pro Asn Lys Phe Gln Asn Lys Thr Asn Gly Ile
465                 470                 475                 480

Thr Pro Arg Arg Trp Leu Arg Phe Cys Asn Pro Glu Leu Ser Glu Ile
                485                 490                 495

Val Thr Lys Trp Leu Lys Thr Asp Gln Trp Thr Ser Asn Leu Asp Leu
            500                 505                 510

Leu Thr Gly Leu Arg Lys Phe Ala Asp Asp Glu Lys Leu His Ala Glu
        515                 520                 525

Trp Ala Ala Ala Lys Leu Ala Ser Lys Lys Arg Leu Ala Lys His Val
    530                 535                 540

Leu Asp Val Thr Gly Val Thr Ile Asp Pro Asp Ser Leu Phe Asp Ile
545                 550                 555                 560

Gln Ile Lys Arg Ile His Glu Tyr Lys Arg Gln Leu Met Asn Ile Leu
                565                 570                 575

Gly Ala Val Tyr Arg Tyr Lys Lys Leu Lys Glu Met Ser Ala Ala Asp
            580                 585                 590

Arg Gln Lys Val Thr Pro Arg Thr Val Met Val Gly Gly Lys Ala Phe
        595                 600                 605

Ala Thr Tyr Thr Asn Ala Lys Arg Ile Val Lys Leu Val Asn Asp Val
    610                 615                 620

Gly Ala Val Val Asn Asn Asp Ala Asp Val Asn Lys Tyr Leu Lys Val
```

-continued

```
            625                 630                 635                 640
Val Phe Ile Pro Asn Tyr Asn Val Ser Val Ala Glu Val Leu Ile Pro
                645                 650                 655
Gly Ser Glu Leu Ser Gln His Ile Ser Thr Ala Gly Met Glu Ala Ser
                660                 665                 670
Gly Thr Ser Asn Met Lys Phe Ser Leu Asn Gly Cys Val Ile Ile Gly
                675                 680                 685
Thr Leu Asp Gly Ala Asn Val Glu Ile Arg Glu Val Gly Gln Asp
                690                 695                 700
Asn Phe Leu Phe Gly Ala Lys Ala Asp Gln Val Ala Gly Leu Arg
705                 710                 715                 720
Lys Asp Arg Glu Asn Gly Leu Phe Lys Pro Asp Pro Arg Phe Glu Glu
                725                 730                 735
Ala Lys Gln Phe Ile Arg Ser Gly Ala Phe Gly Thr Tyr Asp Tyr Thr
                740                 745                 750
Pro Leu Leu Asp Ser Leu Glu Gly Asn Thr Gly Phe Gly Arg Gly Asp
                755                 760                 765
Tyr Phe Leu Val Gly Tyr Asp Phe Pro Ser Tyr Ile Asp Ala Gln Ala
                770                 775                 780
Arg Val Asp Glu Ala Tyr Lys Asp Lys Lys Trp Val Lys Met Ser
785                 790                 795                 800
Ile Leu Asn Thr Ala Gly Ser Gly Lys Phe Ser Ser Asp Arg Thr Ile
                805                 810                 815
Asp Gln Tyr Ala Lys Glu Ile Trp Gly Ile Ser Ala Cys Pro Val Pro
                820                 825                 830

<210> SEQ ID NO 21
<211> LENGTH: 2884
<212> TYPE: DNA
<213> ORGANISM: Citrus hybrid cultivar
<220> FEATURE:
<221> NAME/KEY: CDS
<222> LOCATION: (48)..(2570)

<400> SEQUENCE: 21
cggcacgagc tgaaacaagc aagtaattcg gtaatttgtg gaatcaa atg gcg gat          56
                                                    Met Ala Asp
                                                    1 gcg aaa gca aac gga aag aat gag gcg gcc aaa ctg gcg aaa att ccg         104
Ala Lys Ala Asn Gly Lys Asn Glu Ala Ala Lys Leu Ala Lys Ile Pro
    5                  10                  15 gcg gct gcg aat cca ttg gct aat gaa cca tcg gcg att gca tca aat         152
Ala Ala Ala Asn Pro Leu Ala Asn Glu Pro Ser Ala Ile Ala Ser Asn
20                  25                  30                  35 ata agt tac cac gtg cag tac agt cct cat ttc tcg ccg act aag ttc         200
Ile Ser Tyr His Val Gln Tyr Ser Pro His Phe Ser Pro Thr Lys Phe
                40                  45                  50 gag ccg gag caa gct ttc ttt gcc acg gcg gag gtt gtc cgc gat cgt         248
Glu Pro Glu Gln Ala Phe Phe Ala Thr Ala Glu Val Val Arg Asp Arg
            55                  60                  65 ctt att caa caa tgg aat gag aca tac cac cat ttt aat aaa gtt gat         296
Leu Ile Gln Gln Trp Asn Glu Thr Tyr His His Phe Asn Lys Val Asp
        70                  75                  80 ccg aag caa aca tac tac cta tca atg gaa ttt ctt caa gga agg act         344
Pro Lys Gln Thr Tyr Tyr Leu Ser Met Glu Phe Leu Gln Gly Arg Thr
    85                  90                  95 ttg act aat gca att ggc agt ttg gac att cag aat gca tat gct gat         392
Leu Thr Asn Ala Ile Gly Ser Leu Asp Ile Gln Asn Ala Tyr Ala Asp
    100                 105                 110
```

```
                          -continued
     100             105             110             115
gct tta aat aat ttg ggg cat gtc ctt gag gag ata gct gaa cag gaa     440
Ala Leu Asn Asn Leu Gly His Val Leu Glu Glu Ile Ala Glu Gln Glu
            120             125             130 aaa gat gct gca cta gga aat ggt ggg ctg ggc agg cta gct tca tgc     488
Lys Asp Ala Ala Leu Gly Asn Gly Gly Leu Gly Arg Leu Ala Ser Cys
        135             140             145 ttc tta gac tcc atg gca aca ttg aat ttg cct gca tgg ggt tat ggt     536
Phe Leu Asp Ser Met Ala Thr Leu Asn Leu Pro Ala Trp Gly Tyr Gly
        150             155             160 ttg aga tac cgg tat ggg ctg ttc aag cag aag atc acc aag cag ggt     584
Leu Arg Tyr Arg Tyr Gly Leu Phe Lys Gln Lys Ile Thr Lys Gln Gly
    165             170             175 caa gaa gaa gtt gct gaa gat tgg ctt gag aaa ttt agt cct tgg gaa     632
Gln Glu Glu Val Ala Glu Asp Trp Leu Glu Lys Phe Ser Pro Trp Glu
180             185             190             195 gtt gtc agg cat gat gtg gta ttt ccg gtc aga ttt ttt ggg agt gtt     680
Val Val Arg His Asp Val Val Phe Pro Val Arg Phe Phe Gly Ser Val
                200             205             210 atg gtt aat cca aat gga acg aga aaa tgg gtt ggg ggt gaa gtt gtc     728
Met Val Asn Pro Asn Gly Thr Arg Lys Trp Val Gly Gly Glu Val Val
        215             220             225 caa gcc gta gct tat gat ata cca att cca ggg tac aaa acc aag aac     776
Gln Ala Val Ala Tyr Asp Ile Pro Ile Pro Gly Tyr Lys Thr Lys Asn
        230             235             240 act atc agt ctt cgt ctc tgg gac gct aaa gct agc gct gag gat ttc     824
Thr Ile Ser Leu Arg Leu Trp Asp Ala Lys Ala Ser Ala Glu Asp Phe
    245             250             255 aat tta ttt cag ttt aat gat gga caa tac gaa tct gct gca cag ctt     872
Asn Leu Phe Gln Phe Asn Asp Gly Gln Tyr Glu Ser Ala Ala Gln Leu
260             265             270             275 cat tct cga gct caa cag att tgt gct gtg ctc tac ccc ggg gat tct     920
His Ser Arg Ala Gln Gln Ile Cys Ala Val Leu Tyr Pro Gly Asp Ser
                280             285             290 act gaa gaa ggg aag ctt tta agg ctg aaa caa caa ttc ttt ctc tgc     968
Thr Glu Glu Gly Lys Leu Leu Arg Leu Lys Gln Gln Phe Phe Leu Cys
        295             300             305 agt gct tca ctt cag gat atg att ctt aga ttc aag gag agg aaa agt    1016
Ser Ala Ser Leu Gln Asp Met Ile Leu Arg Phe Lys Glu Arg Lys Ser
        310             315             320 gga agg cag tgg tct gaa ttt ccc agc aag gta gct gta caa ctg aat    1064
Gly Arg Gln Trp Ser Glu Phe Pro Ser Lys Val Ala Val Gln Leu Asn
    325             330             335 gat act cat cca aca ctt gca att cca gag ttg atg cga ttg cta atg    1112
Asp Thr His Pro Thr Leu Ala Ile Pro Glu Leu Met Arg Leu Leu Met
340             345             350             355 gat gag gaa gga ctt gga tgg gat gaa gca tgg gat ata aca aca agg    1160
Asp Glu Glu Gly Leu Gly Trp Asp Glu Ala Trp Asp Ile Thr Thr Arg
                360             365             370 act gtt gct tat acc aat cac aca gta ctt cct gaa gca ctt gag aag    1208
Thr Val Ala Tyr Thr Asn His Thr Val Leu Pro Glu Ala Leu Glu Lys
        375             380             385 tgg tca caa gca gta atg tgg aag ctt ctt cct cgc cat atg gaa ata    1256
Trp Ser Gln Ala Val Met Trp Lys Leu Leu Pro Arg His Met Glu Ile
        390             395             400 att gaa gag att gac aag aga ttc att gca atg gtc cgc tcc aca agg    1304
Ile Glu Glu Ile Asp Lys Arg Phe Ile Ala Met Val Arg Ser Thr Arg
    405             410             415 agt gac ctt gag agt aag att ccc agc atg tgc atc ttg gat aat aat    1352
```

```
                Ser Asp Leu Glu Ser Lys Ile Pro Ser Met Cys Ile Leu Asp Asn Asn
                420             425                 430                 435 ccc aaa aag ccg gtt gtt agg atg gca aac tta tgt gta gta tct gcg          1400
Pro Lys Lys Pro Val Val Arg Met Ala Asn Leu Cys Val Val Ser Ala
                440                 445                 450 cat acg gta aat ggt gtt gct cag ttg cac agt gat atc tta aag gcc          1448
His Thr Val Asn Gly Val Ala Gln Leu His Ser Asp Ile Leu Lys Ala
                455                 460                 465 gac ttg ttc gct gac tat gtt tct cta tgg cca aac aaa ctc caa aat          1496
Asp Leu Phe Ala Asp Tyr Val Ser Leu Trp Pro Asn Lys Leu Gln Asn
                470                 475                 480 aaa act aat ggc att act cct cgt cga tgg ctc cgg ttt tgc aat cct          1544
Lys Thr Asn Gly Ile Thr Pro Arg Arg Trp Leu Arg Phe Cys Asn Pro
                485                 490                 495 gag ctc agc aaa att atc aca aaa tgg tta aaa acc gat cag tgg gtt          1592
Glu Leu Ser Lys Ile Ile Thr Lys Trp Leu Lys Thr Asp Gln Trp Val
500                 505                 510                 515 acg aac ctt gac ctg ctt gta ggt ctt cgt cag ttt gct gac aac aca          1640
Thr Asn Leu Asp Leu Leu Val Gly Leu Arg Gln Phe Ala Asp Asn Thr
                520                 525                 530 gaa ctc caa gct gaa tgg gaa tct gct aag atg gcc agt aag aaa cat          1688
Glu Leu Gln Ala Glu Trp Glu Ser Ala Lys Met Ala Ser Lys Lys His
                535                 540                 545 ttg gca gac tac ata tgg cga gta acc ggt gta acg att gat cct aat          1736
Leu Ala Asp Tyr Ile Trp Arg Val Thr Gly Val Thr Ile Asp Pro Asn
                550                 555                 560 agc tta ttt gac ata caa gtc aag cgc att cat gaa tac aag aga caa          1784
Ser Leu Phe Asp Ile Gln Val Lys Arg Ile His Glu Tyr Lys Arg Gln
565                 570                 575 ctg cta aat att ttg ggc gca atc tac aga tac aag aag ttg aag gag          1832
Leu Leu Asn Ile Leu Gly Ala Ile Tyr Arg Tyr Lys Lys Leu Lys Glu
580                 585                 590                 595 atg agc cct cag gag cgg aag aaa act act cca cgc acc att atg ttt          1880
Met Ser Pro Gln Glu Arg Lys Lys Thr Thr Pro Arg Thr Ile Met Phe
                600                 605                 610 gga ggg aaa gca ttt gca aca tat aca aac gca aaa aga ata gta aag          1928
Gly Gly Lys Ala Phe Ala Thr Tyr Thr Asn Ala Lys Arg Ile Val Lys
                615                 620                 625 ttg gtt aat gat gtt ggt gaa gtc gtc aac acc gat cct gag gtc aat          1976
Leu Val Asn Asp Val Gly Glu Val Val Asn Thr Asp Pro Glu Val Asn
                630                 635                 640 agt tat ttg aag gtg gta ttt gtt cca aat tac aat gtc tct gtt gcg          2024
Ser Tyr Leu Lys Val Val Phe Val Pro Asn Tyr Asn Val Ser Val Ala
                645                 650                 655 gag ttg ctt att cca gga agt gag cta tct cag cat att agc aca gca          2072
Glu Leu Leu Ile Pro Gly Ser Glu Leu Ser Gln His Ile Ser Thr Ala
660                 665                 670                 675 ggc atg gag gca agt ggc aca agc aac atg aaa ttt tct cta aat ggt          2120
Gly Met Glu Ala Ser Gly Thr Ser Asn Met Lys Phe Ser Leu Asn Gly
                680                 685                 690 tgc ctc att ata gga aca ttg gat gga gct aat gtg gaa atc agg cag          2168
Cys Leu Ile Ile Gly Thr Leu Asp Gly Ala Asn Val Glu Ile Arg Gln
                695                 700                 705 gag ata gga gag gag aat ttc ttt ctc ttt ggt gca gga gca gac caa          2216
Glu Ile Gly Glu Glu Asn Phe Phe Leu Phe Gly Ala Gly Ala Asp Gln
                710                 715                 720 gtc cct aag ctg cgg aag gaa aga gaa gat gga ttg ttc aaa cca gat          2264
Val Pro Lys Leu Arg Lys Glu Arg Glu Asp Gly Leu Phe Lys Pro Asp
                725                 730                 735
```

| | | | | | | | | | | | | | | | | |
|---|---|---|---|---|---|---|---|---|---|---|---|---|---|---|---|---|
| cct | cgg | ttt | gaa | gag | gcc | aag | caa | ttt | ata | aga | agt | gga | gca | ttt | gga | 2312 |
| Pro | Arg | Phe | Glu | Glu | Ala | Lys | Gln | Phe | Ile | Arg | Ser | Gly | Ala | Phe | Gly | |
| 740 | | | | 745 | | | | | 750 | | | | | 755 | | |
| agc | tat | gac | tac | aac | ccg | ctt | ctt | gat | tcc | ctg | gag | ggg | aac | act | ggt | 2360 |
| Ser | Tyr | Asp | Tyr | Asn | Pro | Leu | Leu | Asp | Ser | Leu | Glu | Gly | Asn | Thr | Gly | |
| | | | | 760 | | | | | 765 | | | | | 770 | | |
| tat | ggt | cgt | ggt | gat | tat | ttt | cta | gtt | ggt | tat | gac | ttc | cca | agt | tac | 2408 |
| Tyr | Gly | Arg | Gly | Asp | Tyr | Phe | Leu | Val | Gly | Tyr | Asp | Phe | Pro | Ser | Tyr | |
| | | | 775 | | | | | 780 | | | | | 785 | | | |
| tta | gag | gct | cag | gac | aga | gtt | gac | caa | gct | tac | aag | gac | cgg | aag | aag | 2456 |
| Leu | Glu | Ala | Gln | Asp | Arg | Val | Asp | Gln | Ala | Tyr | Lys | Asp | Arg | Lys | Lys | |
| | | | 790 | | | | | 795 | | | | | 800 | | | |
| tgg | ctg | aag | atg | tct | ata | tta | agt | aca | gct | ggc | agt | ggg | aaa | ttc | agc | 2504 |
| Trp | Leu | Lys | Met | Ser | Ile | Leu | Ser | Thr | Ala | Gly | Ser | Gly | Lys | Phe | Ser | |
| | 805 | | | | | 810 | | | | | 815 | | | | | |
| agt | gat | cgc | aca | att | gca | cag | tat | gct | aag | gaa | atc | tgg | aac | ata | aca | 2552 |
| Ser | Asp | Arg | Thr | Ile | Ala | Gln | Tyr | Ala | Lys | Glu | Ile | Trp | Asn | Ile | Thr | |
| 820 | | | | 825 | | | | | 830 | | | | | 835 | | |
| gaa | tgc | cgt | aca | tca | tga | ttcaagtgca | | aaaaaatttc | | atgtgcaata | | | | | | 2600 |
| Glu | Cys | Arg | Thr | Ser | | | | | | | | | | | | |
| | | | 840 | | | | | | | | | | | | | | ggttatataa tttcttggaa ggatgtatta agatgggaag aaaatgaaag gaaatccaca 2660 atctgtgggg atcattaaat aaacctgtct ctccgtctta accatcattt gtttactcaa 2720 acatcgctct gtcagataag ttttaagttg taatttctta acaattcta tctttataag 2780 aatttccagg ttttgaagaa ttacatcatt tgtcattact gataatagta cgaaggaatt 2840 atgatacacc attttttttt tgttttaaaa aaaaaaaaaa aaaa 2884

<210> SEQ ID NO 22
<211> LENGTH: 840
<212> TYPE: PRT
<213> ORGANISM: Citrus hybrid cultivar

<400> SEQUENCE: 22

Met Ala Asp Ala Lys Ala Asn Gly Lys Asn Glu Ala Ala Lys Leu Ala
1               5                   10                  15

Lys Ile Pro Ala Ala Ala Asn Pro Leu Ala Asn Glu Pro Ser Ala Ile
            20                  25                  30

Ala Ser Asn Ile Ser Tyr His Val Gln Tyr Ser Pro His Phe Ser Pro
        35                  40                  45

Thr Lys Phe Glu Pro Glu Gln Ala Phe Phe Ala Thr Ala Glu Val Val
    50                  55                  60

Arg Asp Arg Leu Ile Gln Gln Trp Asn Glu Thr Tyr His His Phe Asn
65                  70                  75                  80

Lys Val Asp Pro Lys Gln Thr Tyr Tyr Leu Ser Met Glu Phe Leu Gln
                85                  90                  95

Gly Arg Thr Leu Thr Asn Ala Ile Gly Ser Leu Asp Ile Gln Asn Ala
            100                 105                 110

Tyr Ala Asp Ala Leu Asn Asn Leu Gly His Val Leu Glu Glu Ile Ala
        115                 120                 125

Glu Gln Glu Lys Asp Ala Ala Leu Gly Asn Gly Gly Leu Gly Arg Leu
    130                 135                 140

Ala Ser Cys Phe Leu Asp Ser Met Ala Thr Leu Asn Leu Pro Ala Trp
145                 150                 155                 160

Gly Tyr Gly Leu Arg Tyr Arg Tyr Gly Leu Phe Lys Gln Lys Ile Thr
                165                 170                 175

```
Lys Gln Gly Gln Glu Glu Val Ala Glu Asp Trp Leu Glu Lys Phe Ser
            180                 185                 190

Pro Trp Glu Val Val Arg His Asp Val Val Phe Pro Val Arg Phe Phe
        195                 200                 205

Gly Ser Val Met Val Asn Pro Asn Gly Thr Arg Lys Trp Val Gly Gly
        210                 215                 220

Glu Val Val Gln Ala Val Ala Tyr Asp Ile Pro Ile Pro Gly Tyr Lys
225                 230                 235                 240

Thr Lys Asn Thr Ile Ser Leu Arg Leu Trp Asp Ala Lys Ala Ser Ala
            245                 250                 255

Glu Asp Phe Asn Leu Phe Gln Phe Asn Asp Gly Gln Tyr Glu Ser Ala
            260                 265                 270

Ala Gln Leu His Ser Arg Ala Gln Gln Ile Cys Ala Val Leu Tyr Pro
            275                 280                 285

Gly Asp Ser Thr Glu Glu Gly Lys Leu Leu Arg Leu Lys Gln Gln Phe
        290                 295                 300

Phe Leu Cys Ser Ala Ser Leu Gln Asp Met Ile Leu Arg Phe Lys Glu
305                 310                 315                 320

Arg Lys Ser Gly Arg Gln Trp Ser Glu Phe Pro Ser Lys Val Ala Val
                325                 330                 335

Gln Leu Asn Asp Thr His Pro Thr Leu Ala Ile Pro Glu Leu Met Arg
            340                 345                 350

Leu Leu Met Asp Glu Glu Gly Leu Gly Trp Asp Glu Ala Trp Asp Ile
            355                 360                 365

Thr Thr Arg Thr Val Ala Tyr Thr Asn His Thr Val Leu Pro Glu Ala
        370                 375                 380

Leu Glu Lys Trp Ser Gln Ala Val Met Trp Lys Leu Pro Arg His
385                 390                 395                 400

Met Glu Ile Ile Glu Glu Ile Asp Lys Arg Phe Ile Ala Met Val Arg
            405                 410                 415

Ser Thr Arg Ser Asp Leu Glu Ser Lys Ile Pro Ser Met Cys Ile Leu
            420                 425                 430

Asp Asn Asn Pro Lys Lys Pro Val Val Arg Met Ala Asn Leu Cys Val
            435                 440                 445

Val Ser Ala His Thr Val Asn Gly Val Ala Gln Leu His Ser Asp Ile
450                 455                 460

Leu Lys Ala Asp Leu Phe Ala Asp Tyr Val Ser Leu Trp Pro Asn Lys
465                 470                 475                 480

Leu Gln Asn Lys Thr Asn Gly Ile Thr Pro Arg Arg Trp Leu Arg Phe
                485                 490                 495

Cys Asn Pro Glu Leu Ser Lys Ile Ile Thr Lys Trp Leu Lys Thr Asp
            500                 505                 510

Gln Trp Val Thr Asn Leu Asp Leu Leu Val Gly Leu Arg Gln Phe Ala
        515                 520                 525

Asp Asn Thr Glu Leu Gln Ala Glu Trp Glu Ser Ala Lys Met Ala Ser
        530                 535                 540

Lys Lys His Leu Ala Asp Tyr Ile Trp Arg Val Thr Gly Val Thr Ile
545                 550                 555                 560

Asp Pro Asn Ser Leu Phe Asp Ile Gln Val Lys Arg Ile His Glu Tyr
            565                 570                 575

Lys Arg Gln Leu Leu Asn Ile Leu Gly Ala Ile Tyr Arg Tyr Lys Lys
            580                 585                 590

Leu Lys Glu Met Ser Pro Gln Glu Arg Lys Lys Thr Thr Pro Arg Thr
```

```
                595             600             605
Ile Met Phe Gly Gly Lys Ala Phe Ala Thr Tyr Thr Asn Ala Lys Arg
    610             615             620
Ile Val Lys Leu Val Asn Asp Val Gly Glu Val Val Asn Thr Asp Pro
625             630             635             640
Glu Val Asn Ser Tyr Leu Lys Val Val Phe Val Pro Asn Tyr Asn Val
                645             650             655
Ser Val Ala Glu Leu Leu Ile Pro Gly Ser Glu Leu Ser Gln His Ile
            660             665             670
Ser Thr Ala Gly Met Glu Ala Ser Gly Thr Ser Asn Met Lys Phe Ser
            675             680             685
Leu Asn Gly Cys Leu Ile Ile Gly Thr Leu Asp Gly Ala Asn Val Glu
        690             695             700
Ile Arg Gln Glu Ile Gly Glu Glu Asn Phe Phe Leu Phe Gly Ala Gly
705             710             715             720
Ala Asp Gln Val Pro Lys Leu Arg Lys Glu Arg Glu Asp Gly Leu Phe
                725             730             735
Lys Pro Asp Pro Arg Phe Glu Glu Ala Lys Gln Phe Ile Arg Ser Gly
            740             745             750
Ala Phe Gly Ser Tyr Asp Tyr Asn Pro Leu Leu Asp Ser Leu Glu Gly
            755             760             765
Asn Thr Gly Tyr Gly Arg Gly Asp Tyr Phe Leu Val Gly Tyr Asp Phe
        770             775             780
Pro Ser Tyr Leu Glu Ala Gln Asp Arg Val Asp Gln Ala Tyr Lys Asp
785             790             795             800
Arg Lys Lys Trp Leu Lys Met Ser Ile Leu Ser Thr Ala Gly Ser Gly
                805             810             815
Lys Phe Ser Ser Asp Arg Thr Ile Ala Gln Tyr Ala Lys Glu Ile Trp
            820             825             830
Asn Ile Thr Glu Cys Arg Thr Ser
            835             840

<210> SEQ ID NO 23
<211> LENGTH: 2526
<212> TYPE: DNA
<213> ORGANISM: Oryza sativa
<220> FEATURE:
<221> NAME/KEY: CDS
<222> LOCATION: (1)..(2526)

<400> SEQUENCE: 23 atg ccg gag agc aac ggc gcc gcg tgc ggc gcg gcg gag aag gtg aag      48
Met Pro Glu Ser Asn Gly Ala Ala Cys Gly Ala Ala Glu Lys Val Lys
1               5                   10                  15 ccg gcg gcc agc ccc gcg tcg gag gag ccg gcc gcc atc gcc ggt aac      96
Pro Ala Ala Ser Pro Ala Ser Glu Glu Pro Ala Ala Ile Ala Gly Asn
            20                  25                  30 atc tcc ttc cac gcg cag tac agc ccc cac ttc tcg ccg ctc gcg ttc     144
Ile Ser Phe His Ala Gln Tyr Ser Pro His Phe Ser Pro Leu Ala Phe
        35                  40                  45 ggc ccc gag cag gcc ttc tac tcc acc gcc gag agc gtc cgc gat cac     192
Gly Pro Glu Gln Ala Phe Tyr Ser Thr Ala Glu Ser Val Arg Asp His
    50                  55                  60 ctc gtc cag aga tgg aac gag acg tac ttg cat ttc cac aag acg gat     240
Leu Val Gln Arg Trp Asn Glu Thr Tyr Leu His Phe His Lys Thr Asp
65                  70                  75                  80 ccg aag cag acg tac tac ctc tcc atg gag tac ctg cag ggc cgc gcg     288
```

```
                Pro Lys Gln Thr Tyr Tyr Leu Ser Met Glu Tyr Leu Gln Gly Arg Ala
                                85                  90                  95 ctc acc aac gcc gtc ggc aac ctc ggc atc acc ggc gcc tac gcg gag            336
Leu Thr Asn Ala Val Gly Asn Leu Gly Ile Thr Gly Ala Tyr Ala Glu
            100                 105                 110 gcc gtg aag aag ttc ggg tac gag ctc gag gcc ctc gtc ggg cag gaa            384
Ala Val Lys Lys Phe Gly Tyr Glu Leu Glu Ala Leu Val Gly Gln Glu
        115                 120                 125 aaa gat gca gct ctg gga aat ggt ggc ttg ggt agg ctc gca tct tgc            432
Lys Asp Ala Ala Leu Gly Asn Gly Gly Leu Gly Arg Leu Ala Ser Cys
    130                 135                 140 ttt ttg gat tcg atg gca aca cta aat ttg cct gct tgg gga tat ggt            480
Phe Leu Asp Ser Met Ala Thr Leu Asn Leu Pro Ala Trp Gly Tyr Gly
145                 150                 155                 160 ctg cgg tac cga tat ggt cta ttc aaa caa tgc atc acc aag gaa ggc            528
Leu Arg Tyr Arg Tyr Gly Leu Phe Lys Gln Cys Ile Thr Lys Glu Gly
                165                 170                 175 cag gaa gaa att gct gaa gat tgg ctt gag aag ttc agc cca tgg gaa            576
Gln Glu Glu Ile Ala Glu Asp Trp Leu Glu Lys Phe Ser Pro Trp Glu
            180                 185                 190 att gtc agg cat gac att gta tac cca atc aga ttt ttt ggc cac gtt            624
Ile Val Arg His Asp Ile Val Tyr Pro Ile Arg Phe Phe Gly His Val
        195                 200                 205 gag att ttg cca gat gga tct cgt aaa tgg gtg ggg gga gaa gtt ctc            672
Glu Ile Leu Pro Asp Gly Ser Arg Lys Trp Val Gly Gly Glu Val Leu
    210                 215                 220 aat gct tta gca tat gat gtg cca att cct ggg tac aag aca aaa aat            720
Asn Ala Leu Ala Tyr Asp Val Pro Ile Pro Gly Tyr Lys Thr Lys Asn
225                 230                 235                 240 gca atc agt ctt cgt ctt tgg gac gca aaa gct agt gcg gag gat ttt            768
Ala Ile Ser Leu Arg Leu Trp Asp Ala Lys Ala Ser Ala Glu Asp Phe
                245                 250                 255 aac tta ttt caa ttc aat gat ggc cag tat gag tcc gct gct caa ctt            816
Asn Leu Phe Gln Phe Asn Asp Gly Gln Tyr Glu Ser Ala Ala Gln Leu
            260                 265                 270 cat gct agg gca caa cag ata tgt gcc gtt ctc tat ccc ggt gat gct            864
His Ala Arg Ala Gln Gln Ile Cys Ala Val Leu Tyr Pro Gly Asp Ala
        275                 280                 285 aca gaa gaa gga aag ctt ctc aga ctg aag caa cag tat ttc ctt tgc            912
Thr Glu Glu Gly Lys Leu Leu Arg Leu Lys Gln Gln Tyr Phe Leu Cys
    290                 295                 300 agt gca tcg ctt cag gat att ttt ttc agg ttt aaa gaa agg aaa gct            960
Ser Ala Ser Leu Gln Asp Ile Phe Phe Arg Phe Lys Glu Arg Lys Ala
305                 310                 315                 320 gac aga gtt tct ggg aaa tgg agt gag ttc cct gca aaa gtt gct gtt           1008
Asp Arg Val Ser Gly Lys Trp Ser Glu Phe Pro Ala Lys Val Ala Val
                325                 330                 335 caa ttg aat gac act cac cca act ctt gcg att cct gag ctg atg agg           1056
Gln Leu Asn Asp Thr His Pro Thr Leu Ala Ile Pro Glu Leu Met Arg
            340                 345                 350 cta ctc atg gat gtg gag gga ctt ggt tgg gat gaa gca tgg gat atc           1104
Leu Leu Met Asp Val Glu Gly Leu Gly Trp Asp Glu Ala Trp Asp Ile
        355                 360                 365 aca aat aaa aca att gcc tac acc aat cac act gtt ctt cct gaa gcc           1152
Thr Asn Lys Thr Ile Ala Tyr Thr Asn His Thr Val Leu Pro Glu Ala
    370                 375                 380 ctt gag aaa tgg tcg cag att gta atg agg aaa tta ctt cca cga cac           1200
Leu Glu Lys Trp Ser Gln Ile Val Met Arg Lys Leu Leu Pro Arg His
385                 390                 395                 400
```

```
atg gaa att atc gag gaa att gac aag cgg ttc aag gaa atg gta atc        1248
Met Glu Ile Ile Glu Glu Ile Asp Lys Arg Phe Lys Glu Met Val Ile
            405                 410                 415 tcc acc cgg aag gaa atg gag gga aag att gac tcc atg aga atc tta        1296
Ser Thr Arg Lys Glu Met Glu Gly Lys Ile Asp Ser Met Arg Ile Leu
        420                 425                 430 gac aac tca aat cct cag aag cca gta gtg cgc atg gca aat ttg tgc        1344
Asp Asn Ser Asn Pro Gln Lys Pro Val Val Arg Met Ala Asn Leu Cys
    435                 440                 445 gta gtg tct gcc cat acg gta aat gga gtg gct gag tta cac agc aac        1392
Val Val Ser Ala His Thr Val Asn Gly Val Ala Glu Leu His Ser Asn
450                 455                 460 att ttg aag gaa gag ctt ttt gca gac tat ctc tct ata tgg ccc aac        1440
Ile Leu Lys Glu Glu Leu Phe Ala Asp Tyr Leu Ser Ile Trp Pro Asn
465                 470                 475                 480 aaa ttt cag aac aaa aca aat gga att aca cct cgt aga tgg ctc cgt        1488
Lys Phe Gln Asn Lys Thr Asn Gly Ile Thr Pro Arg Arg Trp Leu Arg
            485                 490                 495 ttc tgc aac cca gag ttg agt gaa ata gta aca aaa tgg cta aaa aca        1536
Phe Cys Asn Pro Glu Leu Ser Glu Ile Val Thr Lys Trp Leu Lys Thr
        500                 505                 510 gat cag tgg aca agc aac ctt gat ctt ctt acc gga ctt cgg aaa ttt        1584
Asp Gln Trp Thr Ser Asn Leu Asp Leu Leu Thr Gly Leu Arg Lys Phe
    515                 520                 525 gca gat gat gaa aag ctt cat gct gag tgg gca tca gct aag ttg gct        1632
Ala Asp Asp Glu Lys Leu His Ala Glu Trp Ala Ser Ala Lys Leu Ala
530                 535                 540 agc aaa aaa cgc cta gcc aag cat gtg ttg gat gtg aca ggt gtt aca        1680
Ser Lys Lys Arg Leu Ala Lys His Val Leu Asp Val Thr Gly Val Thr
545                 550                 555                 560 atc gac cca aat agc ctt ttt gat ata caa att aaa cgc att cat gag        1728
Ile Asp Pro Asn Ser Leu Phe Asp Ile Gln Ile Lys Arg Ile His Glu
            565                 570                 575 tac aag aga cag ctg cta aac att ttg gga gct gtt tac aga tac aag        1776
Tyr Lys Arg Gln Leu Leu Asn Ile Leu Gly Ala Val Tyr Arg Tyr Lys
        580                 585                 590 aag tta aag gga atg agt gca gag gag aga caa aaa gtt acg cca cgc        1824
Lys Leu Lys Gly Met Ser Ala Glu Glu Arg Gln Lys Val Thr Pro Arg
    595                 600                 605 act gtc atg ata ggg gga aaa gca ttc gcg act tac acc aat gcc aaa        1872
Thr Val Met Ile Gly Gly Lys Ala Phe Ala Thr Tyr Thr Asn Ala Lys
610                 615                 620 aga ata gta aaa ttg gta aat gat gtt ggt gct gtg gtg aac aat gat        1920
Arg Ile Val Lys Leu Val Asn Asp Val Gly Ala Val Val Asn Asn Asp
625                 630                 635                 640 cct gat gtt aat aaa tac cta aag gtg gtg ttc att ccc aac tac aat        1968
Pro Asp Val Asn Lys Tyr Leu Lys Val Val Phe Ile Pro Asn Tyr Asn
            645                 650                 655 gta tct gtg gcc gag gtg ctc att cct ggg agt gaa ctg tca cag cac        2016
Val Ser Val Ala Glu Val Leu Ile Pro Gly Ser Glu Leu Ser Gln His
        660                 665                 670 atc agt acc gca ggc atg gaa gca agt gga acg agt aat atg aaa ttc        2064
Ile Ser Thr Ala Gly Met Glu Ala Ser Gly Thr Ser Asn Met Lys Phe
    675                 680                 685 tct ctg aat ggt tgt gtt atc att ggt act ctt gat gga gct aat gtt        2112
Ser Leu Asn Gly Cys Val Ile Ile Gly Thr Leu Asp Gly Ala Asn Val
690                 695                 700 gag ata aga gag gaa gtg gga caa gaa aat ttc ttc ctt ttt ggt gcc        2160
Glu Ile Arg Glu Glu Val Gly Gln Glu Asn Phe Phe Leu Phe Gly Ala
705                 710                 715                 720
```

-continued

```
aag gca gat caa gtt gct ggg ctg agg aag gat aga gag aat ggc ttg      2208
Lys Ala Asp Gln Val Ala Gly Leu Arg Lys Asp Arg Glu Asn Gly Leu
            725                 730                 735 ttc aaa cca gac cca cgt ttt gaa gaa gcc aag cag ctt ata agg agt      2256
Phe Lys Pro Asp Pro Arg Phe Glu Glu Ala Lys Gln Leu Ile Arg Ser
        740                 745                 750 ggt gct ttt ggc acc tat gac tat gct ccc ctc ttg gat tct ctt gaa      2304
Gly Ala Phe Gly Thr Tyr Asp Tyr Ala Pro Leu Leu Asp Ser Leu Glu
    755                 760                 765 gga aat tct gga ttt ggt cgt ggt gat tat ttc ctc gtt ggc tat gat      2352
Gly Asn Ser Gly Phe Gly Arg Gly Asp Tyr Phe Leu Val Gly Tyr Asp
770                 775                 780 ttc cca agc tat att gat gca cag gcc cag gtt gat gaa gcc tac aag      2400
Phe Pro Ser Tyr Ile Asp Ala Gln Ala Gln Val Asp Glu Ala Tyr Lys
785                 790                 795                 800 gat aag aaa aaa tgg atc aag atg tct ata ctg aac aca gct gga agt      2448
Asp Lys Lys Lys Trp Ile Lys Met Ser Ile Leu Asn Thr Ala Gly Ser
            805                 810                 815 ggc aaa ttc agc agc gac cgt act atc gct cag tat gca aag gaa ata      2496
Gly Lys Phe Ser Ser Asp Arg Thr Ile Ala Gln Tyr Ala Lys Glu Ile
        820                 825                 830 tgg ggc att act gct agc cct gtc tcc taa                              2526
Trp Gly Ile Thr Ala Ser Pro Val Ser
    835                 840

<210> SEQ ID NO 24
<211> LENGTH: 841
<212> TYPE: PRT
<213> ORGANISM: Oryza sativa

<400> SEQUENCE: 24

Met Pro Glu Ser Asn Gly Ala Ala Cys Gly Ala Ala Glu Lys Val Lys
1               5                   10                  15

Pro Ala Ala Ser Pro Ala Ser Glu Glu Pro Ala Ala Ile Ala Gly Asn
            20                  25                  30

Ile Ser Phe His Ala Gln Tyr Ser Pro His Phe Ser Pro Leu Ala Phe
        35                  40                  45

Gly Pro Glu Gln Ala Phe Tyr Ser Thr Ala Glu Ser Val Arg Asp His
    50                  55                  60

Leu Val Gln Arg Trp Asn Glu Thr Tyr Leu His Phe His Lys Thr Asp
65                  70                  75                  80

Pro Lys Gln Thr Tyr Tyr Leu Ser Met Glu Tyr Leu Gln Gly Arg Ala
                85                  90                  95

Leu Thr Asn Ala Val Gly Asn Leu Gly Ile Thr Gly Ala Tyr Ala Glu
            100                 105                 110

Ala Val Lys Lys Phe Gly Tyr Glu Leu Glu Ala Leu Val Gly Gln Glu
        115                 120                 125

Lys Asp Ala Ala Leu Gly Asn Gly Leu Gly Arg Leu Ala Ser Cys
    130                 135                 140

Phe Leu Asp Ser Met Ala Thr Leu Asn Leu Pro Ala Trp Gly Tyr Gly
145                 150                 155                 160

Leu Arg Tyr Arg Tyr Gly Leu Phe Lys Gln Cys Ile Thr Lys Glu Gly
                165                 170                 175

Gln Glu Glu Ile Ala Glu Asp Trp Leu Glu Lys Phe Ser Pro Trp Glu
            180                 185                 190

Ile Val Arg His Asp Ile Val Tyr Pro Ile Arg Phe Phe Gly His Val
        195                 200                 205
```

-continued

```
Glu Ile Leu Pro Asp Gly Ser Arg Lys Trp Val Gly Gly Glu Val Leu
    210                 215                 220
Asn Ala Leu Ala Tyr Asp Val Pro Ile Pro Gly Tyr Lys Thr Lys Asn
225                 230                 235                 240
Ala Ile Ser Leu Arg Leu Trp Asp Ala Lys Ala Ser Ala Glu Asp Phe
                245                 250                 255
Asn Leu Phe Gln Phe Asn Asp Gly Gln Tyr Glu Ser Ala Ala Gln Leu
            260                 265                 270
His Ala Arg Ala Gln Gln Ile Cys Ala Val Leu Tyr Pro Gly Asp Ala
        275                 280                 285
Thr Glu Glu Gly Lys Leu Leu Arg Leu Lys Gln Gln Tyr Phe Leu Cys
    290                 295                 300
Ser Ala Ser Leu Gln Asp Ile Phe Phe Arg Phe Lys Glu Arg Lys Ala
305                 310                 315                 320
Asp Arg Val Ser Gly Lys Trp Ser Glu Phe Pro Ala Lys Val Ala Val
                325                 330                 335
Gln Leu Asn Asp Thr His Pro Thr Leu Ala Ile Pro Glu Leu Met Arg
            340                 345                 350
Leu Leu Met Asp Val Glu Gly Leu Gly Trp Asp Glu Ala Trp Asp Ile
        355                 360                 365
Thr Asn Lys Thr Ile Ala Tyr Thr Asn His Thr Val Leu Pro Glu Ala
    370                 375                 380
Leu Glu Lys Trp Ser Gln Ile Val Met Arg Lys Leu Leu Pro Arg His
385                 390                 395                 400
Met Glu Ile Ile Glu Glu Ile Asp Lys Arg Phe Lys Glu Met Val Ile
                405                 410                 415
Ser Thr Arg Lys Glu Met Glu Gly Lys Ile Asp Ser Met Arg Ile Leu
            420                 425                 430
Asp Asn Ser Asn Pro Gln Lys Pro Val Val Arg Met Ala Asn Leu Cys
        435                 440                 445
Val Val Ser Ala His Thr Val Asn Gly Val Ala Glu Leu His Ser Asn
    450                 455                 460
Ile Leu Lys Glu Glu Leu Phe Ala Asp Tyr Leu Ser Ile Trp Pro Asn
465                 470                 475                 480
Lys Phe Gln Asn Lys Thr Asn Gly Ile Thr Pro Arg Arg Trp Leu Arg
                485                 490                 495
Phe Cys Asn Pro Glu Leu Ser Glu Ile Val Thr Lys Trp Leu Lys Thr
            500                 505                 510
Asp Gln Trp Thr Ser Asn Leu Asp Leu Leu Thr Gly Leu Arg Lys Phe
        515                 520                 525
Ala Asp Asp Glu Lys Leu His Ala Glu Trp Ala Ser Ala Lys Leu Ala
    530                 535                 540
Ser Lys Lys Arg Leu Ala Lys His Val Leu Asp Val Thr Gly Val Thr
545                 550                 555                 560
Ile Asp Pro Asn Ser Leu Phe Asp Ile Gln Ile Lys Arg Ile His Glu
                565                 570                 575
Tyr Lys Arg Gln Leu Leu Asn Ile Leu Gly Ala Val Tyr Arg Tyr Lys
            580                 585                 590
Lys Leu Lys Gly Met Ser Ala Glu Glu Arg Gln Lys Val Thr Pro Arg
        595                 600                 605
Thr Val Met Ile Gly Gly Lys Ala Phe Ala Thr Tyr Thr Asn Ala Lys
    610                 615                 620
```

```
Arg Ile Val Lys Leu Val Asn Asp Val Gly Ala Val Asn Asn Asp
625                 630                 635                 640

Pro Asp Val Asn Lys Tyr Leu Lys Val Phe Ile Pro Asn Tyr Asn
            645                 650                 655

Val Ser Val Ala Glu Val Leu Ile Pro Gly Ser Glu Leu Ser Gln His
            660                 665                 670

Ile Ser Thr Ala Gly Met Glu Ala Ser Gly Thr Ser Asn Met Lys Phe
            675                 680                 685

Ser Leu Asn Gly Cys Val Ile Ile Gly Thr Leu Asp Gly Ala Asn Val
            690                 695                 700

Glu Ile Arg Glu Val Gly Gln Glu Asn Phe Leu Phe Gly Ala
705                 710                 715                 720

Lys Ala Asp Gln Val Ala Gly Leu Arg Lys Asp Arg Glu Asn Gly Leu
            725                 730                 735

Phe Lys Pro Asp Pro Arg Phe Glu Glu Ala Lys Gln Leu Ile Arg Ser
            740                 745                 750

Gly Ala Phe Gly Thr Tyr Asp Tyr Ala Pro Leu Leu Asp Ser Leu Glu
            755                 760                 765

Gly Asn Ser Gly Phe Gly Arg Gly Asp Tyr Phe Leu Val Gly Tyr Asp
            770                 775                 780

Phe Pro Ser Tyr Ile Asp Ala Gln Ala Gln Val Asp Glu Ala Tyr Lys
785                 790                 795                 800

Asp Lys Lys Lys Trp Ile Lys Met Ser Ile Leu Asn Thr Ala Gly Ser
            805                 810                 815

Gly Lys Phe Ser Ser Asp Arg Thr Ile Ala Gln Tyr Ala Lys Glu Ile
            820                 825                 830

Trp Gly Ile Thr Ala Ser Pro Val Ser
            835                 840

<210> SEQ ID NO 25
<211> LENGTH: 2910
<212> TYPE: DNA
<213> ORGANISM: Vicia faba
<220> FEATURE:
<221> NAME/KEY: CDS
<222> LOCATION: (155)..(2683)

<400> SEQUENCE: 25
tcatctcaca ctcacatgag gtagcaattc cattccttca aatatcttca catatgcttc     60
caaatccaga ttctttttaa tctcttttt tttccatttc ttcaaacaac tcgtttcgtt    120
gctacctttc tttactctca taaggatttg aaaa atg ggt ttt aaa gta gaa act   175
                                     Met Gly Phe Lys Val Glu Thr
                                      1               5 aat ggt ggt gat ggt tct tta gtt tct gct aaa gtt cca cct ctg gct    223
Asn Gly Gly Asp Gly Ser Leu Val Ser Ala Lys Val Pro Pro Leu Ala
        10                  15                  20 aat cca ttg gct gaa aaa cct gat gag att gct tct aac atc agt tat    271
Asn Pro Leu Ala Glu Lys Pro Asp Glu Ile Ala Ser Asn Ile Ser Tyr
 25                  30                  35 cat gct cag tat act cct cat ttt tca cct ttc aaa ttt cag ctt caa    319
His Ala Gln Tyr Thr Pro His Phe Ser Pro Phe Lys Phe Gln Leu Gln
40                  45                  50                  55 caa gct tac tat gca act gca gag agt gtt cgt gat cgt ctc att cag    367
Gln Ala Tyr Tyr Ala Thr Ala Glu Ser Val Arg Asp Arg Leu Ile Gln
                60                  65                  70 caa tgg aat gaa aca tac tta cat ttt cac aaa gtt gat ccc aag caa    415
Gln Trp Asn Glu Thr Tyr Leu His Phe His Lys Val Asp Pro Lys Gln
```

-continued

```
                    75                      80                      85
aca tac tac tta tca atg gag ttc ctt caa ggt cga gct ttg acc aat          463
Thr Tyr Tyr Leu Ser Met Glu Phe Leu Gln Gly Arg Ala Leu Thr Asn
            90                      95                     100 gcc att gga aat ctc aat atc caa gat gca tat gct gat gct ttg cgc          511
Ala Ile Gly Asn Leu Asn Ile Gln Asp Ala Tyr Ala Asp Ala Leu Arg
105                     110                     115 aaa ttt gga ctt gaa ctt gaa gaa ata aca gag cag gag aag gat gca          559
Lys Phe Gly Leu Glu Leu Glu Glu Ile Thr Glu Gln Glu Lys Asp Ala
        120                     125                     130             135 gca cta gga aat ggt ggt ctt ggt agg ctt gct tct tgc ttt ctg gat          607
Ala Leu Gly Asn Gly Gly Leu Gly Arg Leu Ala Ser Cys Phe Leu Asp
                    140                     145                     150 tcc atg gca aca ctt aat ttg cct gct tgg ggg tac ggt ttg agg tat          655
Ser Met Ala Thr Leu Asn Leu Pro Ala Trp Gly Tyr Gly Leu Arg Tyr
                155                     160                     165 cgg tac gga cta ttt aag cag ata atc aca aaa gaa ggt cag gag gaa          703
Arg Tyr Gly Leu Phe Lys Gln Ile Ile Thr Lys Glu Gly Gln Glu Glu
            170                     175                     180 gtt gct gag gac tgg ctt gag aag ttt agc cct tgg gaa att gtg agg          751
Val Ala Glu Asp Trp Leu Glu Lys Phe Ser Pro Trp Glu Ile Val Arg
185                     190                     195 cat gac gtt ttg tac ccg atc aga ttc ttt ggc cag gtt gag gtt aac          799
His Asp Val Leu Tyr Pro Ile Arg Phe Phe Gly Gln Val Glu Val Asn
200                     205                     210                     215 cct gat gga agc cga caa tgg ata ggc gga gaa gtt att caa gca cta          847
Pro Asp Gly Ser Arg Gln Trp Ile Gly Gly Glu Val Ile Gln Ala Leu
                    220                     225                     230 gct tat gat gtg ccg att cct gga tac cag acc aag aac acc atc agt          895
Ala Tyr Asp Val Pro Ile Pro Gly Tyr Gln Thr Lys Asn Thr Ile Ser
                235                     240                     245 ctt cgc ctc tgg gaa gcg aaa gca tgc gct gat gat ttc gat ttg ttt          943
Leu Arg Leu Trp Glu Ala Lys Ala Cys Ala Asp Asp Phe Asp Leu Phe
            250                     255                     260 tta ttc aac gat ggg caa ctt gaa tct gct tca gtt ctt cac tca cga          991
Leu Phe Asn Asp Gly Gln Leu Glu Ser Ala Ser Val Leu His Ser Arg
265                     270                     275 gcg caa cag att tgc tcg gtt ttg tat cct ggt gat gcc aca gaa ggt         1039
Ala Gln Gln Ile Cys Ser Val Leu Tyr Pro Gly Asp Ala Thr Glu Gly
280                     285                     290                     295 ggg aaa ctc cta cgg ctg aag cag cag tac ttt ctc tgc agt gca tca         1087
Gly Lys Leu Leu Arg Leu Lys Gln Gln Tyr Phe Leu Cys Ser Ala Ser
                    300                     305                     310 ctc caa gac ata att tcc cga ttc aag gag agg agg caa gga cct tgg         1135
Leu Gln Asp Ile Ile Ser Arg Phe Lys Glu Arg Arg Gln Gly Pro Trp
                315                     320                     325 aac tgg tct gag ttc cca aca aag gtt gct gta caa ttg aac gat acc         1183
Asn Trp Ser Glu Phe Pro Thr Lys Val Ala Val Gln Leu Asn Asp Thr
            330                     335                     340 cac cca acc ctt tca ata ccg gag ttg atg cga tta cta atg gat gat         1231
His Pro Thr Leu Ser Ile Pro Glu Leu Met Arg Leu Leu Met Asp Asp
345                     350                     355 gaa ggg ctt gga tgg gat gaa gca tgg gct gtg aca tca aag aca gtt         1279
Glu Gly Leu Gly Trp Asp Glu Ala Trp Ala Val Thr Ser Lys Thr Val
360                     365                     370                     375 gct tac act aat cac act gtc ctc cct gaa gcg ctg gag aaa tgg tct         1327
Ala Tyr Thr Asn His Thr Val Leu Pro Glu Ala Leu Glu Lys Trp Ser
                    380                     385                     390 caa cct gtt atg tgg aaa ctg ctt cct cgt cac atg gaa atc ata gag         1375
```

-continued

```
Gln Pro Val Met Trp Lys Leu Leu Pro Arg His Met Glu Ile Ile Glu
            395                 400                 405 gaa atc gac aga cga ttc gtt gca ttg ata agt aaa acc cgt ttg gac    1423
Glu Ile Asp Arg Arg Phe Val Ala Leu Ile Ser Lys Thr Arg Leu Asp
410                 415                 420 ctt gag gac gaa gtt tcc aac atg cgc att tta gac aat aat ctt cag    1471
Leu Glu Asp Glu Val Ser Asn Met Arg Ile Leu Asp Asn Asn Leu Gln
    425                 430                 435 aaa cca gta gtt cgg atg gcg aat ttg tgt gtt gtt tct tct cat act    1519
Lys Pro Val Val Arg Met Ala Asn Leu Cys Val Val Ser Ser His Thr
440                 445                 450                 455 gtg aat ggt gtt gcc cag tta cac agt gat ata ttg aag tca gaa tta    1567
Val Asn Gly Val Ala Gln Leu His Ser Asp Ile Leu Lys Ser Glu Leu
                460                 465                 470 ttt gca agt tat gtt tca ata tgg cca aca aaa ttc caa aat aaa act    1615
Phe Ala Ser Tyr Val Ser Ile Trp Pro Thr Lys Phe Gln Asn Lys Thr
            475                 480                 485 aat ggc att acg cct cga aga tgg atc aat ttc tgc agt cct gag cta    1663
Asn Gly Ile Thr Pro Arg Arg Trp Ile Asn Phe Cys Ser Pro Glu Leu
490                 495                 500 agc agg ata atc aca aag tgg tta aaa act gat aaa tgg gta acc aat    1711
Ser Arg Ile Ile Thr Lys Trp Leu Lys Thr Asp Lys Trp Val Thr Asn
    505                 510                 515 ctt gac cta tta aca ggt ctt cgt gag ttt gct gac aac gaa gat cta    1759
Leu Asp Leu Leu Thr Gly Leu Arg Glu Phe Ala Asp Asn Glu Asp Leu
520                 525                 530                 535 caa gca gag tgg ctg tct gca aag agg gct aat aag cag cgc tta gca    1807
Gln Ala Glu Trp Leu Ser Ala Lys Arg Ala Asn Lys Gln Arg Leu Ala
                540                 545                 550 cag tat gtt ctg caa gtg aca ggg gag aac att gac cct gat agt cta    1855
Gln Tyr Val Leu Gln Val Thr Gly Glu Asn Ile Asp Pro Asp Ser Leu
            555                 560                 565 ttt gac att caa gtc aag cgt atc cac gaa tac aag agg cag ctg cta    1903
Phe Asp Ile Gln Val Lys Arg Ile His Glu Tyr Lys Arg Gln Leu Leu
570                 575                 580 aac att ctt ggt gtg atc tat aga tat aaa aag tta aag gag atg agc    1951
Asn Ile Leu Gly Val Ile Tyr Arg Tyr Lys Lys Leu Lys Glu Met Ser
    585                 590                 595 cct gaa gaa cgg aaa agt aca act gca cgc acg gtc atg att gga gga    1999
Pro Glu Glu Arg Lys Ser Thr Thr Ala Arg Thr Val Met Ile Gly Gly
600                 605                 610                 615 aag gca ttt gca acg tac aca aat gct aaa cgg ata gtc aag ctt gtc    2047
Lys Ala Phe Ala Thr Tyr Thr Asn Ala Lys Arg Ile Val Lys Leu Val
                620                 625                 630 gat gat gtt ggt tct gtt gta aac agt gat cct gaa gtc aat agc tac    2095
Asp Asp Val Gly Ser Val Val Asn Ser Asp Pro Glu Val Asn Ser Tyr
            635                 640                 645 ttg aag gtt gtg ttt gtg cca aat tac aac gta tca gtg gcg gag gtg    2143
Leu Lys Val Val Phe Val Pro Asn Tyr Asn Val Ser Val Ala Glu Val
650                 655                 660 ctt atc cca ggg agc gag cta tcg cag cat atc agc act gca gga atg    2191
Leu Ile Pro Gly Ser Glu Leu Ser Gln His Ile Ser Thr Ala Gly Met
    665                 670                 675 gaa gca agt ggc acg agc aac atg aaa ttt gct ttg aac cgg gtg ctt    2239
Glu Ala Ser Gly Thr Ser Asn Met Lys Phe Ala Leu Asn Arg Val Leu
680                 685                 690                 695 ata ata ggt aca tta gat gga gct aat gtc gaa atc cgg gag gag att    2287
Ile Ile Gly Thr Leu Asp Gly Ala Asn Val Glu Ile Arg Glu Glu Ile
                700                 705                 710
```

```
ggt gag gag aat ttt ttc ctg ttt ggt gca aca gcg gat gaa gtc cct    2335
Gly Glu Glu Asn Phe Phe Leu Phe Gly Ala Thr Ala Asp Glu Val Pro
            715                 720                 725 cga ctc agg aag gaa aga gag aat gga ctg ttc aag ccg gat cct cga    2383
Arg Leu Arg Lys Glu Arg Glu Asn Gly Leu Phe Lys Pro Asp Pro Arg
        730                 735                 740 ttc gaa gag gca aag aag ttt ata agg agt ggg gtg ttt gga agc tac    2431
Phe Glu Glu Ala Lys Lys Phe Ile Arg Ser Gly Val Phe Gly Ser Tyr
    745                 750                 755 gac tac aac cca ttg ctc gat tca ttg gaa gga aat tct ggt tat ggt    2479
Asp Tyr Asn Pro Leu Leu Asp Ser Leu Glu Gly Asn Ser Gly Tyr Gly
760                 765                 770                 775 cgc gga gat tac ttt ctt gtt ggt tat gac ttc cca agc tac atg gat    2527
Arg Gly Asp Tyr Phe Leu Val Gly Tyr Asp Phe Pro Ser Tyr Met Asp
                780                 785                 790 gct cag gaa aaa gta gac gaa gca tat cgt gat aag aaa agg tgg cta    2575
Ala Gln Glu Lys Val Asp Glu Ala Tyr Arg Asp Lys Lys Arg Trp Leu
            795                 800                 805 aaa atg tct att tta agc act gct ggg agt ggg aag ttc agc agt gac    2623
Lys Met Ser Ile Leu Ser Thr Ala Gly Ser Gly Lys Phe Ser Ser Asp
        810                 815                 820 agg aca att gct cag tat gct aag gaa att tgg aac atc gaa gaa tgc    2671
Arg Thr Ile Ala Gln Tyr Ala Lys Glu Ile Trp Asn Ile Glu Glu Cys
    825                 830                 835 cgg gta cca taa tttcaaggct ctgtaatagta ctagagcatt gaaattaatg       2723
Arg Val Pro
840 acagtatata gtcatgaata aaaagaaca taatttcta tatttgattt tagtatgcca    2783 tatcaggttt caactgtatt attattatag taagtgtcgt ttctctcgat gcatctgctt  2843 ctacattatg aaaatatatt tgtatcatga tattttttat attggtttaa tttcaattca  2903 atcttcc                                                            2910

<210> SEQ ID NO 26
<211> LENGTH: 842
<212> TYPE: PRT
<213> ORGANISM: Vicia faba

<400> SEQUENCE: 26

Met Gly Phe Lys Val Glu Thr Asn Gly Gly Asp Gly Ser Leu Val Ser
1               5                   10                  15

Ala Lys Val Pro Pro Leu Ala Asn Pro Leu Ala Glu Lys Pro Asp Glu
            20                  25                  30

Ile Ala Ser Asn Ile Ser Tyr His Ala Gln Tyr Thr Pro His Phe Ser
        35                  40                  45

Pro Phe Lys Phe Gln Leu Gln Gln Ala Tyr Tyr Ala Thr Ala Glu Ser
    50                  55                  60

Val Arg Asp Arg Leu Ile Gln Gln Trp Asn Glu Thr Tyr Leu His Phe
65                  70                  75                  80

His Lys Val Asp Pro Lys Gln Thr Tyr Tyr Leu Ser Met Glu Phe Leu
            85                  90                  95

Gln Gly Arg Ala Leu Thr Asn Ala Ile Gly Asn Leu Asn Ile Gln Asp
        100                 105                 110

Ala Tyr Ala Asp Ala Leu Arg Lys Phe Gly Leu Glu Leu Glu Glu Ile
    115                 120                 125

Thr Glu Gln Glu Lys Asp Ala Ala Leu Gly Asn Gly Gly Leu Gly Arg
130                 135                 140
```

-continued

```
Leu Ala Ser Cys Phe Leu Asp Ser Met Ala Thr Leu Asn Leu Pro Ala
145                 150                 155                 160

Trp Gly Tyr Gly Leu Arg Tyr Arg Tyr Gly Leu Phe Lys Gln Ile Ile
                165                 170                 175

Thr Lys Glu Gly Gln Glu Glu Val Ala Glu Asp Trp Leu Glu Lys Phe
            180                 185                 190

Ser Pro Trp Glu Ile Val Arg His Asp Val Leu Tyr Pro Ile Arg Phe
        195                 200                 205

Phe Gly Gln Val Glu Val Asn Pro Asp Gly Ser Arg Gln Trp Ile Gly
    210                 215                 220

Gly Glu Val Ile Gln Ala Leu Ala Tyr Asp Val Pro Ile Pro Gly Tyr
225                 230                 235                 240

Gln Thr Lys Asn Thr Ile Ser Leu Arg Leu Trp Glu Ala Lys Ala Cys
                245                 250                 255

Ala Asp Asp Phe Asp Leu Phe Leu Phe Asn Asp Gly Gln Leu Glu Ser
            260                 265                 270

Ala Ser Val Leu His Ser Arg Ala Gln Gln Ile Cys Ser Val Leu Tyr
        275                 280                 285

Pro Gly Asp Ala Thr Glu Gly Gly Lys Leu Leu Arg Leu Lys Gln Gln
    290                 295                 300

Tyr Phe Leu Cys Ser Ala Ser Leu Gln Asp Ile Ile Ser Arg Phe Lys
305                 310                 315                 320

Glu Arg Arg Gln Gly Pro Trp Asn Trp Ser Glu Phe Pro Thr Lys Val
                325                 330                 335

Ala Val Gln Leu Asn Asp Thr His Pro Thr Leu Ser Ile Pro Glu Leu
            340                 345                 350

Met Arg Leu Leu Met Asp Asp Glu Gly Leu Gly Trp Asp Glu Ala Trp
        355                 360                 365

Ala Val Thr Ser Lys Thr Val Ala Tyr Thr Asn His Thr Val Leu Pro
    370                 375                 380

Glu Ala Leu Glu Lys Trp Ser Gln Pro Val Met Trp Lys Leu Leu Pro
385                 390                 395                 400

Arg His Met Glu Ile Ile Glu Glu Ile Asp Arg Arg Phe Val Ala Leu
                405                 410                 415

Ile Ser Lys Thr Arg Leu Asp Leu Glu Asp Glu Val Ser Asn Met Arg
            420                 425                 430

Ile Leu Asp Asn Asn Leu Gln Lys Pro Val Val Arg Met Ala Asn Leu
        435                 440                 445

Cys Val Val Ser Ser His Thr Val Asn Gly Val Ala Gln Leu His Ser
    450                 455                 460

Asp Ile Leu Lys Ser Glu Leu Phe Ala Ser Tyr Val Ser Ile Trp Pro
465                 470                 475                 480

Thr Lys Phe Gln Asn Lys Thr Asn Gly Ile Thr Pro Arg Arg Trp Ile
                485                 490                 495

Asn Phe Cys Ser Pro Glu Leu Ser Arg Ile Ile Thr Lys Trp Leu Lys
            500                 505                 510

Thr Asp Lys Trp Val Thr Asn Leu Asp Leu Leu Thr Gly Leu Arg Glu
        515                 520                 525

Phe Ala Asp Asn Glu Asp Leu Gln Ala Glu Trp Leu Ser Ala Lys Arg
    530                 535                 540

Ala Asn Lys Gln Arg Leu Ala Gln Tyr Val Leu Gln Val Thr Gly Glu
545                 550                 555                 560

Asn Ile Asp Pro Asp Ser Leu Phe Asp Ile Gln Val Lys Arg Ile His
```

-continued

```
                565                 570                 575
Glu Tyr Lys Arg Gln Leu Leu Asn Ile Leu Gly Val Ile Tyr Arg Tyr
            580                 585                 590
Lys Lys Leu Lys Glu Met Ser Pro Glu Arg Lys Ser Thr Thr Ala
        595                 600                 605
Arg Thr Val Met Ile Gly Gly Lys Ala Phe Ala Thr Tyr Thr Asn Ala
            610                 615                 620
Lys Arg Ile Val Lys Leu Val Asp Asp Val Gly Ser Val Val Asn Ser
625                 630                 635                 640
Asp Pro Glu Val Asn Ser Tyr Leu Lys Val Val Phe Val Pro Asn Tyr
                645                 650                 655
Asn Val Ser Val Ala Glu Val Leu Ile Pro Gly Ser Glu Leu Ser Gln
                660                 665                 670
His Ile Ser Thr Ala Gly Met Glu Ala Ser Gly Thr Ser Asn Met Lys
            675                 680                 685
Phe Ala Leu Asn Arg Val Leu Ile Ile Gly Thr Leu Asp Gly Ala Asn
        690                 695                 700
Val Glu Ile Arg Glu Glu Ile Gly Glu Glu Asn Phe Phe Leu Phe Gly
705                 710                 715                 720
Ala Thr Ala Asp Glu Val Pro Arg Leu Arg Lys Glu Arg Glu Asn Gly
                725                 730                 735
Leu Phe Lys Pro Asp Pro Arg Phe Glu Glu Ala Lys Lys Phe Ile Arg
            740                 745                 750
Ser Gly Val Phe Gly Ser Tyr Asp Tyr Asn Pro Leu Leu Asp Ser Leu
        755                 760                 765
Glu Gly Asn Ser Gly Tyr Gly Arg Gly Asp Tyr Phe Leu Val Gly Tyr
    770                 775                 780
Asp Phe Pro Ser Tyr Met Asp Ala Gln Glu Lys Val Asp Glu Ala Tyr
785                 790                 795                 800
Arg Asp Lys Lys Arg Trp Leu Lys Met Ser Ile Leu Ser Thr Ala Gly
                805                 810                 815
Ser Gly Lys Phe Ser Ser Asp Arg Thr Ile Ala Gln Tyr Ala Lys Glu
            820                 825                 830
Ile Trp Asn Ile Glu Glu Cys Arg Val Pro
        835                 840

<210> SEQ ID NO 27
<211> LENGTH: 2526
<212> TYPE: DNA
<213> ORGANISM: Arabidopsis thaliana
<220> FEATURE:
<221> NAME/KEY: CDS
<222> LOCATION: (1)..(2526)

<400> SEQUENCE: 27 atg gca aac gcc aat gga aaa gct gcg act agt tta ccg gag aaa atc      48
Met Ala Asn Ala Asn Gly Lys Ala Ala Thr Ser Leu Pro Glu Lys Ile
1               5                   10                  15 tcg gct aag gcg aat ccg gag gcc gat gat gct acg gag atc gct ggg      96
Ser Ala Lys Ala Asn Pro Glu Ala Asp Asp Ala Thr Glu Ile Ala Gly
                20                  25                  30 aat atc gtc tac cac gcc aag tac agt cca cat ttc tct cca ttg aag     144
Asn Ile Val Tyr His Ala Lys Tyr Ser Pro His Phe Ser Pro Leu Lys
            35                  40                  45 ttc ggg cct gag caa gct ctc tac gct acc gca gag agt ctt cgc gat     192
Phe Gly Pro Glu Gln Ala Leu Tyr Ala Thr Ala Glu Ser Leu Arg Asp
        50                  55                  60
```

```
cgt ctc att cag ctg tgg aat gag act tat gtt cat ttt aac aaa gtt    240
Arg Leu Ile Gln Leu Trp Asn Glu Thr Tyr Val His Phe Asn Lys Val
65                  70                  75                  80 gat cca aaa caa act tat tac ttg tca atg gag tat ctc caa ggt cgt    288
Asp Pro Lys Gln Thr Tyr Tyr Leu Ser Met Glu Tyr Leu Gln Gly Arg
                85                  90                  95 gct ttg acc aat gcc att ggg aat ttg aac ctt caa ggt cca tat gct    336
Ala Leu Thr Asn Ala Ile Gly Asn Leu Asn Leu Gln Gly Pro Tyr Ala
            100                 105                 110 gat gca ctg cgt acg ctg ggt tat gag ctt gag gag ata gct gag cag    384
Asp Ala Leu Arg Thr Leu Gly Tyr Glu Leu Glu Glu Ile Ala Glu Gln
        115                 120                 125 gag aaa gat gca gct cta gga aat ggt ggg tta ggg aga ctt gcc tcg    432
Glu Lys Asp Ala Ala Leu Gly Asn Gly Gly Leu Gly Arg Leu Ala Ser
    130                 135                 140 tgt ttc ttg gat tcg atg gcc acc cta aat ctg cct gct tgg ggt tat    480
Cys Phe Leu Asp Ser Met Ala Thr Leu Asn Leu Pro Ala Trp Gly Tyr
145                 150                 155                 160 ggt ttg agg tac aga cat ggg ttg ttt aag caa ata atc aca aag aaa    528
Gly Leu Arg Tyr Arg His Gly Leu Phe Lys Gln Ile Ile Thr Lys Lys
                165                 170                 175 ggt caa gaa gag att cca gag gac tgg ctt gag aaa ttc agc cca tgg    576
Gly Gln Glu Glu Ile Pro Glu Asp Trp Leu Glu Lys Phe Ser Pro Trp
            180                 185                 190 gaa att gtg agg cac gac gtg gta ttc cct gtc aga ttt ttc ggc aag    624
Glu Ile Val Arg His Asp Val Val Phe Pro Val Arg Phe Phe Gly Lys
        195                 200                 205 gtg caa gta aat ccg gat gga tca agg aaa tgg gta gat ggt gat gtt    672
Val Gln Val Asn Pro Asp Gly Ser Arg Lys Trp Val Asp Gly Asp Val
    210                 215                 220 gta caa gct ctt gct tat gac gtg cca atc ccg gga tat ggc aca aag    720
Val Gln Ala Leu Ala Tyr Asp Val Pro Ile Pro Gly Tyr Gly Thr Lys
225                 230                 235                 240 aac aca atc agt ctc cgt ctc tgg gaa gca aaa gct aga gct gag gat    768
Asn Thr Ile Ser Leu Arg Leu Trp Glu Ala Lys Ala Arg Ala Glu Asp
                245                 250                 255 ctt gat ctt ttt cag ttc aac gaa gga gaa tat gaa ttg gct gca cag    816
Leu Asp Leu Phe Gln Phe Asn Glu Gly Glu Tyr Glu Leu Ala Ala Gln
            260                 265                 270 ctt cat tct cga gct caa cag att tgc act gtt tta tat cca gga gat    864
Leu His Ser Arg Ala Gln Gln Ile Cys Thr Val Leu Tyr Pro Gly Asp
        275                 280                 285 gct acc gag aat ggg aag tta tta cgg tta aaa cag cag ttc ttt ctc    912
Ala Thr Glu Asn Gly Lys Leu Leu Arg Leu Lys Gln Gln Phe Phe Leu
    290                 295                 300 tgc agt gct tcg ctt cag gat att ata tca aga ttt cac gag agg agc    960
Cys Ser Ala Ser Leu Gln Asp Ile Ile Ser Arg Phe His Glu Arg Ser
305                 310                 315                 320 acc act gaa ggc agc cgg aaa tgg tca gag ttt cca agt aaa gtt gct   1008
Thr Thr Glu Gly Ser Arg Lys Trp Ser Glu Phe Pro Ser Lys Val Ala
                325                 330                 335 gtt caa atg aat gac aca cac cca act ctt gca ata cct gag ctc atg   1056
Val Gln Met Asn Asp Thr His Pro Thr Leu Ala Ile Pro Glu Leu Met
            340                 345                 350 cga ttg cta atg gat gac aat gga ctt gga tgg gat gag gct tgg gat   1104
Arg Leu Leu Met Asp Asp Asn Gly Leu Gly Trp Asp Glu Ala Trp Asp
        355                 360                 365 gtg aca tca aag acc gtt gct tac acc aat cac act gtc ctt cct gaa   1152
Val Thr Ser Lys Thr Val Ala Tyr Thr Asn His Thr Val Leu Pro Glu
```

-continued

```
                370                     375                     380
gcg ttg gag aaa tgg tca caa tct ttg atg tgg aag ctt ctt cct cgt       1200
Ala Leu Glu Lys Trp Ser Gln Ser Leu Met Trp Lys Leu Leu Pro Arg
385                     390                     395                 400 cat atg gaa ata ata gaa gag att gac aag agg ttt gtt caa acc att       1248
His Met Glu Ile Ile Glu Glu Ile Asp Lys Arg Phe Val Gln Thr Ile
                405                     410                     415 cgc gat aca aga gtt gat ctg gag gat aag att tca agt ttg agc atc       1296
Arg Asp Thr Arg Val Asp Leu Glu Asp Lys Ile Ser Ser Leu Ser Ile
                    420                     425                     430 tta gat aac aat cca caa aag cct gtg gtg aga atg gct aac tta tgt       1344
Leu Asp Asn Asn Pro Gln Lys Pro Val Val Arg Met Ala Asn Leu Cys
                435                     440                     445 gtt gta tcc tcg cat acg gtg aat ggc gtt gct cag tta cac agt gat       1392
Val Val Ser Ser His Thr Val Asn Gly Val Ala Gln Leu His Ser Asp
                    450                     455                     460 atc ttg aag gct gag tta ttc gca gac tat gtc tct ata tgg cca aac       1440
Ile Leu Lys Ala Glu Leu Phe Ala Asp Tyr Val Ser Ile Trp Pro Asn
465                     470                     475                 480 aag ttt caa aac aag act aat ggc atc aca cct cga agg tgg tta cgt       1488
Lys Phe Gln Asn Lys Thr Asn Gly Ile Thr Pro Arg Arg Trp Leu Arg
                485                     490                     495 ttc tgc agc cct gag ctc agt gat ata atc aca aag tgg tta aag act       1536
Phe Cys Ser Pro Glu Leu Ser Asp Ile Ile Thr Lys Trp Leu Lys Thr
                    500                     505                     510 gac aaa tgg att acc gat ctt gac cta ctt acc ggt ctt cgc cag ttt       1584
Asp Lys Trp Ile Thr Asp Leu Asp Leu Leu Thr Gly Leu Arg Gln Phe
                515                     520                     525 gcg gac aat gaa gaa ctc caa tct gaa tgg gct tct gca aag aca gcc       1632
Ala Asp Asn Glu Glu Leu Gln Ser Glu Trp Ala Ser Ala Lys Thr Ala
                    530                     535                     540 aat aag aaa cgt ttg gct caa tat ata gag cgt gtg act ggt gtg agt       1680
Asn Lys Lys Arg Leu Ala Gln Tyr Ile Glu Arg Val Thr Gly Val Ser
545                     550                     555                 560 atc gat cca aca agc tta ttt gac ata caa gtt aag cgt atc cac gaa       1728
Ile Asp Pro Thr Ser Leu Phe Asp Ile Gln Val Lys Arg Ile His Glu
                565                     570                     575 tac aag agg cag ctg atg aac att ctt gga gta gta tac aga ttc aag       1776
Tyr Lys Arg Gln Leu Met Asn Ile Leu Gly Val Val Tyr Arg Phe Lys
                    580                     585                     590 aaa cta aag gag atg aag cct gag gag agg aag aaa aca gtt cct cgt       1824
Lys Leu Lys Glu Met Lys Pro Glu Glu Arg Lys Lys Thr Val Pro Arg
                595                     600                     605 act gtc atg att ggg ggt aaa gca ttt gcc acc tat aca aat gca aaa       1872
Thr Val Met Ile Gly Gly Lys Ala Phe Ala Thr Tyr Thr Asn Ala Lys
                    610                     615                     620 cgg ata gtg aag ctg gtg aat gat gtt ggt gat gtt gtt aac agc gat       1920
Arg Ile Val Lys Leu Val Asn Asp Val Gly Asp Val Val Asn Ser Asp
625                     630                     635                 640 cca gag gtc aac gaa tac cta aag gtg gta ttt gtt cca aac tac aat       1968
Pro Glu Val Asn Glu Tyr Leu Lys Val Val Phe Val Pro Asn Tyr Asn
                645                     650                     655 gtc act gta gcg gag atg cta ata ccc gga agt gag cta tct caa cac       2016
Val Thr Val Ala Glu Met Leu Ile Pro Gly Ser Glu Leu Ser Gln His
                    660                     665                     670 atc agc aca gca ggc atg gag gca agt ggt acc agc aat atg aaa ttc       2064
Ile Ser Thr Ala Gly Met Glu Ala Ser Gly Thr Ser Asn Met Lys Phe
675                     680                     685 gct ctc aac ggt tgt ctt att ata gga acc ctt gat ggg gct aat gtt       2112
Ala Leu Asn Gly Cys Leu Ile Ile Gly Thr Leu Asp Gly Ala Asn Val
```

```
Ala Leu Asn Gly Cys Leu Ile Ile Gly Thr Leu Asp Gly Ala Asn Val
        690                 695                 700 gag ata aga gag gag gtt ggc gaa gaa aat ttc ttt ctt ttt ggt gca        2160
Glu Ile Arg Glu Glu Val Gly Glu Glu Asn Phe Phe Leu Phe Gly Ala
705                 710                 715                 720 acg gcc gat cag gtc cct cga ctg cgt aaa gaa cga gaa gac gga ctg        2208
Thr Ala Asp Gln Val Pro Arg Leu Arg Lys Glu Arg Glu Asp Gly Leu
            725                 730                 735 ttc aaa ccc gat cct cgg ttc gaa gag gca aag cag ttt gtc aaa agt        2256
Phe Lys Pro Asp Pro Arg Phe Glu Glu Ala Lys Gln Phe Val Lys Ser
        740                 745                 750 gga gtg ttt ggg agc tac gat tat ggt cca ctc ctt gat tct ctt gag        2304
Gly Val Phe Gly Ser Tyr Asp Tyr Gly Pro Leu Leu Asp Ser Leu Glu
    755                 760                 765 ggt aac aca ggt ttt gga cgt ggt gat tac ttc ctg gtt ggg tat gac        2352
Gly Asn Thr Gly Phe Gly Arg Gly Asp Tyr Phe Leu Val Gly Tyr Asp
770                 775                 780 ttc ccc agc tac atg gac gct cag gcc aaa gtt gac gaa gct tat aag        2400
Phe Pro Ser Tyr Met Asp Ala Gln Ala Lys Val Asp Glu Ala Tyr Lys
785                 790                 795                 800 gac cgg aag ggg tgg ctg aaa atg tcg ata ttg agc aca gcc ggg tca        2448
Asp Arg Lys Gly Trp Leu Lys Met Ser Ile Leu Ser Thr Ala Gly Ser
            805                 810                 815 gga aag ttc agc agt gac cgt aca ata gct cag tat gcc aaa gag att        2496
Gly Lys Phe Ser Ser Asp Arg Thr Ile Ala Gln Tyr Ala Lys Glu Ile
        820                 825                 830 tgg aac att gag gct tgt cct gtt ccc taa                                2526
Trp Asn Ile Glu Ala Cys Pro Val Pro
    835                 840

<210> SEQ ID NO 28
<211> LENGTH: 841
<212> TYPE: PRT
<213> ORGANISM: Arabidopsis thaliana

<400> SEQUENCE: 28

Met Ala Asn Ala Asn Gly Lys Ala Ala Thr Ser Leu Pro Glu Lys Ile
1               5                   10                  15

Ser Ala Lys Ala Asn Pro Glu Ala Asp Asp Ala Thr Glu Ile Ala Gly
            20                  25                  30

Asn Ile Val Tyr His Ala Lys Tyr Ser Pro His Phe Ser Pro Leu Lys
        35                  40                  45

Phe Gly Pro Glu Gln Ala Leu Tyr Ala Thr Ala Glu Ser Leu Arg Asp
    50                  55                  60

Arg Leu Ile Gln Leu Trp Asn Glu Thr Tyr Val His Phe Asn Lys Val
65                  70                  75                  80

Asp Pro Lys Gln Thr Tyr Tyr Leu Ser Met Glu Tyr Leu Gln Gly Arg
                85                  90                  95

Ala Leu Thr Asn Ala Ile Gly Asn Leu Asn Leu Gln Gly Pro Tyr Ala
            100                 105                 110

Asp Ala Leu Arg Thr Leu Gly Tyr Glu Leu Glu Glu Ile Ala Glu Gln
        115                 120                 125

Glu Lys Asp Ala Ala Leu Gly Asn Gly Leu Gly Arg Leu Ala Ser
    130                 135                 140

Cys Phe Leu Asp Ser Met Ala Thr Leu Asn Leu Pro Ala Trp Gly Tyr
145                 150                 155                 160

Gly Leu Arg Tyr Arg His Gly Leu Phe Lys Gln Ile Ile Thr Lys Lys
                165                 170                 175
```

-continued

```
Gly Gln Glu Glu Ile Pro Glu Asp Trp Leu Glu Lys Phe Ser Pro Trp
            180                 185                 190

Glu Ile Val Arg His Asp Val Phe Pro Val Arg Phe Phe Gly Lys
        195                 200                 205

Val Gln Val Asn Pro Asp Gly Ser Arg Lys Trp Val Asp Gly Asp Val
        210                 215                 220

Val Gln Ala Leu Ala Tyr Asp Val Pro Ile Pro Gly Tyr Gly Thr Lys
225                 230                 235                 240

Asn Thr Ile Ser Leu Arg Leu Trp Glu Ala Lys Ala Arg Ala Glu Asp
                245                 250                 255

Leu Asp Leu Phe Gln Phe Asn Glu Gly Glu Tyr Glu Leu Ala Ala Gln
            260                 265                 270

Leu His Ser Arg Ala Gln Gln Ile Cys Thr Val Leu Tyr Pro Gly Asp
        275                 280                 285

Ala Thr Glu Asn Gly Lys Leu Leu Arg Leu Lys Gln Gln Phe Phe Leu
    290                 295                 300

Cys Ser Ala Ser Leu Gln Asp Ile Ile Ser Arg Phe His Glu Arg Ser
305                 310                 315                 320

Thr Thr Glu Gly Ser Arg Lys Trp Ser Glu Phe Pro Ser Lys Val Ala
                325                 330                 335

Val Gln Met Asn Asp Thr His Pro Thr Leu Ala Ile Pro Glu Leu Met
            340                 345                 350

Arg Leu Leu Met Asp Asp Asn Gly Leu Gly Trp Asp Glu Ala Trp Asp
        355                 360                 365

Val Thr Ser Lys Thr Val Ala Tyr Thr Asn His Thr Val Leu Pro Glu
    370                 375                 380

Ala Leu Glu Lys Trp Ser Gln Ser Leu Met Trp Lys Leu Leu Pro Arg
385                 390                 395                 400

His Met Glu Ile Ile Glu Glu Ile Asp Lys Arg Phe Val Gln Thr Ile
                405                 410                 415

Arg Asp Thr Arg Val Asp Leu Glu Asp Lys Ile Ser Ser Leu Ser Ile
            420                 425                 430

Leu Asp Asn Asn Pro Gln Lys Pro Val Val Arg Met Ala Asn Leu Cys
        435                 440                 445

Val Val Ser Ser His Thr Val Asn Gly Val Ala Gln Leu His Ser Asp
    450                 455                 460

Ile Leu Lys Ala Glu Leu Phe Ala Asp Tyr Val Ser Ile Trp Pro Asn
465                 470                 475                 480

Lys Phe Gln Asn Lys Thr Asn Gly Ile Thr Pro Arg Arg Trp Leu Arg
                485                 490                 495

Phe Cys Ser Pro Glu Leu Ser Asp Ile Ile Thr Lys Trp Leu Lys Thr
            500                 505                 510

Asp Lys Trp Ile Thr Asp Leu Asp Leu Leu Thr Gly Leu Arg Gln Phe
        515                 520                 525

Ala Asp Asn Glu Glu Leu Gln Ser Glu Trp Ala Ser Ala Lys Thr Ala
    530                 535                 540

Asn Lys Lys Arg Leu Ala Gln Tyr Ile Glu Arg Val Thr Gly Val Ser
545                 550                 555                 560

Ile Asp Pro Thr Ser Leu Phe Asp Ile Gln Val Lys Arg Ile His Glu
                565                 570                 575

Tyr Lys Arg Gln Leu Met Asn Ile Leu Gly Val Val Tyr Arg Phe Lys
            580                 585                 590
```

```
Lys Leu Lys Glu Met Lys Pro Glu Glu Arg Lys Lys Thr Val Pro Arg
        595                 600                 605

Thr Val Met Ile Gly Gly Lys Ala Phe Ala Thr Tyr Thr Asn Ala Lys
    610                 615                 620

Arg Ile Val Lys Leu Val Asn Asp Val Gly Asp Val Val Asn Ser Asp
625                 630                 635                 640

Pro Glu Val Asn Glu Tyr Leu Lys Val Phe Val Pro Asn Tyr Asn
                645                 650                 655

Val Thr Val Ala Glu Met Leu Ile Pro Gly Ser Glu Leu Ser Gln His
            660                 665                 670

Ile Ser Thr Ala Gly Met Glu Ala Ser Gly Thr Ser Asn Met Lys Phe
        675                 680                 685

Ala Leu Asn Gly Cys Leu Ile Ile Gly Thr Leu Asp Gly Ala Asn Val
    690                 695                 700

Glu Ile Arg Glu Glu Val Gly Glu Glu Asn Phe Phe Leu Phe Gly Ala
705                 710                 715                 720

Thr Ala Asp Gln Val Pro Arg Leu Arg Lys Glu Arg Glu Asp Gly Leu
                725                 730                 735

Phe Lys Pro Asp Pro Arg Phe Glu Glu Ala Lys Gln Phe Val Lys Ser
            740                 745                 750

Gly Val Phe Gly Ser Tyr Asp Tyr Gly Pro Leu Leu Asp Ser Leu Glu
        755                 760                 765

Gly Asn Thr Gly Phe Gly Arg Gly Asp Tyr Phe Leu Val Gly Tyr Asp
    770                 775                 780

Phe Pro Ser Tyr Met Asp Ala Gln Ala Lys Val Asp Glu Ala Tyr Lys
785                 790                 795                 800

Asp Arg Lys Gly Trp Leu Lys Met Ser Ile Leu Ser Thr Ala Gly Ser
                805                 810                 815

Gly Lys Phe Ser Ser Asp Arg Thr Ile Ala Gln Tyr Ala Lys Glu Ile
            820                 825                 830

Trp Asn Ile Glu Ala Cys Pro Val Pro
        835                 840

<210> SEQ ID NO 29
<211> LENGTH: 2655
<212> TYPE: DNA
<213> ORGANISM: Solanum tuberosum
<220> FEATURE:
<221> NAME/KEY: CDS
<222> LOCATION: (12)..(2528)

<400> SEQUENCE: 29
gtttattttc c atg gaa ggt ggt gca aaa tcg aat gat gta tca gca gca      50
           Met Glu Gly Gly Ala Lys Ser Asn Asp Val Ser Ala Ala
             1               5                  10 cct att gct caa cca ctt tct gaa gac cct act gac att gca tct aat       98
Pro Ile Ala Gln Pro Leu Ser Glu Asp Pro Thr Asp Ile Ala Ser Asn
         15                  20                  25 atc aag tat cat gct caa tat act cct cat ttt tct cct ttc aag ttt      146
Ile Lys Tyr His Ala Gln Tyr Thr Pro His Phe Ser Pro Phe Lys Phe
 30                  35                  40                  45 gag cca cta caa gca tac tat gct gct act gct gac agt gtt cgt gat      194
Glu Pro Leu Gln Ala Tyr Tyr Ala Ala Thr Ala Asp Ser Val Arg Asp
                 50                  55                  60 cgc ttg atc aaa caa tgg aat gac acc tat ctt cat tat gac aaa gtt      242
Arg Leu Ile Lys Gln Trp Asn Asp Thr Tyr Leu His Tyr Asp Lys Val
             65                  70                  75
```

```
aat cca aag caa aca tac tac tta tca atg gag tat ctc cag ggg cga      290
Asn Pro Lys Gln Thr Tyr Tyr Leu Ser Met Glu Tyr Leu Gln Gly Arg
        80                  85                  90 gct ttg aca aat gca gtt gga aac tta gac atc cac aat gca tat gct      338
Ala Leu Thr Asn Ala Val Gly Asn Leu Asp Ile His Asn Ala Tyr Ala
 95                 100                 105 gat gct tta aac aaa ctg ggt cag cag ctt gag gag gtc gtt gag cag      386
Asp Ala Leu Asn Lys Leu Gly Gln Gln Leu Glu Glu Val Val Glu Gln
110                 115                 120                 125 gaa aaa gat gca gca tta gga aat ggt ggt tta gga agg ctc gct tca      434
Glu Lys Asp Ala Ala Leu Gly Asn Gly Gly Leu Gly Arg Leu Ala Ser
                130                 135                 140 tgc ttt ctt gat tcc atg gcc aca ttg aac ctt cca gca tgg ggt tat      482
Cys Phe Leu Asp Ser Met Ala Thr Leu Asn Leu Pro Ala Trp Gly Tyr
            145                 150                 155 ggc ttg agg tac aga tat gga ctt ttt aag cag ctt atc aca aag gct      530
Gly Leu Arg Tyr Arg Tyr Gly Leu Phe Lys Gln Leu Ile Thr Lys Ala
        160                 165                 170 ggg caa gaa gaa gtt cct gaa gat tgg ttg gag aaa ttt agt ccc tgg      578
Gly Gln Glu Glu Val Pro Glu Asp Trp Leu Glu Lys Phe Ser Pro Trp
175                 180                 185 gaa att gta agg cat gat gtt gtc ttt cct atc agg ttt ttt ggt cat      626
Glu Ile Val Arg His Asp Val Val Phe Pro Ile Arg Phe Phe Gly His
190                 195                 200                 205 gtt gaa gtc ctc cct tct ggc tcg cga aaa tgg gtt ggt gga gag gtc      674
Val Glu Val Leu Pro Ser Gly Ser Arg Lys Trp Val Gly Gly Glu Val
                210                 215                 220 cta cag gct ctt gca tat gat gtg cca att cca gga tac aga act aaa      722
Leu Gln Ala Leu Ala Tyr Asp Val Pro Ile Pro Gly Tyr Arg Thr Lys
            225                 230                 235 aac act aat agt ctt cgt ctc tgg gaa gcc aaa gca agc tct gag gat      770
Asn Thr Asn Ser Leu Arg Leu Trp Glu Ala Lys Ala Ser Ser Glu Asp
        240                 245                 250 ttc aac ttg ttt ctg ttt aat gat gga cag tat gat gct gct gca cag      818
Phe Asn Leu Phe Leu Phe Asn Asp Gly Gln Tyr Asp Ala Ala Ala Gln
    255                 260                 265 ctt cat tct agg gct cag cag att tgt gct gtt ctc tac cct ggg gat      866
Leu His Ser Arg Ala Gln Gln Ile Cys Ala Val Leu Tyr Pro Gly Asp
270                 275                 280                 285 gct aca gag aat gga aaa ctc tta cgg cta aag caa caa ttt ttt ctg      914
Ala Thr Glu Asn Gly Lys Leu Leu Arg Leu Lys Gln Gln Phe Phe Leu
                290                 295                 300 tgc agt gca tcg ctt cag gat att att gcc aga ttc aaa gag aga gaa      962
Cys Ser Ala Ser Leu Gln Asp Ile Ile Ala Arg Phe Lys Glu Arg Glu
            305                 310                 315 gat gga aag ggt tct cac cag tgg tct gaa ttc ccc aag aag gtt gcg     1010
Asp Gly Lys Gly Ser His Gln Trp Ser Glu Phe Pro Lys Lys Val Ala
        320                 325                 330 ata caa cta aat gac aca cat cca act ctt acg att cca gag ctg atg     1058
Ile Gln Leu Asn Asp Thr His Pro Thr Leu Thr Ile Pro Glu Leu Met
    335                 340                 345 cgg ttg cta atg gat gat gaa gga ctt ggg tgg gat gaa tct tgg aat     1106
Arg Leu Leu Met Asp Asp Glu Gly Leu Gly Trp Asp Glu Ser Trp Asn
350                 355                 360                 365 atc act act agg aca att gcc tat acg aat cat aca gtc cta cct gaa     1154
Ile Thr Thr Arg Thr Ile Ala Tyr Thr Asn His Thr Val Leu Pro Glu
                370                 375                 380 gca ctt gaa aaa tgg tct cag gca gtc atg tgg aag ctc ctt cct aga     1202
Ala Leu Glu Lys Trp Ser Gln Ala Val Met Trp Lys Leu Leu Pro Arg
            385                 390                 395
```

```
cat atg gaa atc att gaa gaa att gac aaa cgg ttt gtt gct aca ata      1250
His Met Glu Ile Ile Glu Glu Ile Asp Lys Arg Phe Val Ala Thr Ile
        400                 405                 410 atg tca gaa aga cct gat ctt gag aat aag atg cct agc atg cgc att      1298
Met Ser Glu Arg Pro Asp Leu Glu Asn Lys Met Pro Ser Met Arg Ile
415                 420                 425 ttg gat cac aac gcc aca aaa cct gtt gtg cat atg gct aac ttg tgt      1346
Leu Asp His Asn Ala Thr Lys Pro Val Val His Met Ala Asn Leu Cys
430                 435                 440                 445 gtt gtc tct tca cat acg gta aat ggt gtt gcc cag ctg cat agt gac      1394
Val Val Ser Ser His Thr Val Asn Gly Val Ala Gln Leu His Ser Asp
                450                 455                 460 atc ctg aag gct gag tta ttt gct gat tat gtc tct gta tgg ccc acc      1442
Ile Leu Lys Ala Glu Leu Phe Ala Asp Tyr Val Ser Val Trp Pro Thr
            465                 470                 475 aag ttc cag aat aag acc aat ggt ata act cct cgt agg tgg atc cga      1490
Lys Phe Gln Asn Lys Thr Asn Gly Ile Thr Pro Arg Arg Trp Ile Arg
        480                 485                 490 ttt tgt agt cct gag ctg agt cat ata att acc aag tgg tta aaa aca      1538
Phe Cys Ser Pro Glu Leu Ser His Ile Ile Thr Lys Trp Leu Lys Thr
495                 500                 505 gat caa tgg gtg acg aac ctc gaa ctg ctt gct aat ctt cgg gag ttt      1586
Asp Gln Trp Val Thr Asn Leu Glu Leu Leu Ala Asn Leu Arg Glu Phe
510                 515                 520                 525 gct gat aat tcg gag ctc cat gct gaa tgg gaa tca gcc aag atg gcc      1634
Ala Asp Asn Ser Glu Leu His Ala Glu Trp Glu Ser Ala Lys Met Ala
                530                 535                 540 aac aag cag cgt ttg gca cag tat ata ctg cat gtg aca ggt gtg agc      1682
Asn Lys Gln Arg Leu Ala Gln Tyr Ile Leu His Val Thr Gly Val Ser
            545                 550                 555 atc gat cca aat tcc ctt ttt gac ata caa gtc aaa cgt atc cat gaa      1730
Ile Asp Pro Asn Ser Leu Phe Asp Ile Gln Val Lys Arg Ile His Glu
        560                 565                 570 tac aaa agg cag ctt cta aat att ctg ggc gtc atc tat aga tac aag      1778
Tyr Lys Arg Gln Leu Leu Asn Ile Leu Gly Val Ile Tyr Arg Tyr Lys
575                 580                 585 aag ctt aag gga atg agc cct gaa gaa agg aaa aat aca act cct cgc      1826
Lys Leu Lys Gly Met Ser Pro Glu Glu Arg Lys Asn Thr Thr Pro Arg
590                 595                 600                 605 aca gtc atg att gga gga aaa gca ttt gca aca tac aca aat gca aaa      1874
Thr Val Met Ile Gly Gly Lys Ala Phe Ala Thr Tyr Thr Asn Ala Lys
                610                 615                 620 cga att gtc aag ctc gtg act gat gtt ggc gac gtt gtc aat agt gac      1922
Arg Ile Val Lys Leu Val Thr Asp Val Gly Asp Val Val Asn Ser Asp
            625                 630                 635 cct gac gtc aat gac tat ttg aag gtg gtt ttt gtt ccc aac tac aat      1970
Pro Asp Val Asn Asp Tyr Leu Lys Val Val Phe Val Pro Asn Tyr Asn
        640                 645                 650 gta tct gtg gca gag atg ctt att ccg gga agt gag cta tca caa cac      2018
Val Ser Val Ala Glu Met Leu Ile Pro Gly Ser Glu Leu Ser Gln His
655                 660                 665 atc agt act gca ggc atg gaa gca agt gga aca agc aac atg aaa ttt      2066
Ile Ser Thr Ala Gly Met Glu Ala Ser Gly Thr Ser Asn Met Lys Phe
670                 675                 680                 685 gcc ctt aat gga tgc ctt atc att ggg aca cta gat ggg gcc aat gtg      2114
Ala Leu Asn Gly Cys Leu Ile Ile Gly Thr Leu Asp Gly Ala Asn Val
                690                 695                 700 gaa att agg gag gaa att gga gaa gat aac ttc ttt ctt ttt ggt gca      2162
Glu Ile Arg Glu Glu Ile Gly Glu Asp Asn Phe Phe Leu Phe Gly Ala
```

-continued

```
                    705                 710                 715
aca gct gat gaa gtt cct caa ctg cgc aaa gat cga gag aat gga ctg    2210
Thr Ala Asp Glu Val Pro Gln Leu Arg Lys Asp Arg Glu Asn Gly Leu
        720                 725                 730 ttc aaa cct gat cct cgg ttt gaa gag gca aaa caa ttt att agg tct    2258
Phe Lys Pro Asp Pro Arg Phe Glu Glu Ala Lys Gln Phe Ile Arg Ser
    735                 740                 745 gga gca ttt ggg acg tat gat tat aat ccc ctc ctt gaa tca ctg gaa    2306
Gly Ala Phe Gly Thr Tyr Asp Tyr Asn Pro Leu Leu Glu Ser Leu Glu
750                 755                 760                 765 ggg aac tcg gga tat ggt cgt gga gac tat ttt ctt gtt ggt cat gat    2354
Gly Asn Ser Gly Tyr Gly Arg Gly Asp Tyr Phe Leu Val Gly His Asp
                770                 775                 780 ttt ccg agc tac atg gat gct cag gca agg gtt gat gaa gct tac aag    2402
Phe Pro Ser Tyr Met Asp Ala Gln Ala Arg Val Asp Glu Ala Tyr Lys
            785                 790                 795 gac agg aaa aga tgg ata aag atg tct ata ctg agc act agt ggg agt    2450
Asp Arg Lys Arg Trp Ile Lys Met Ser Ile Leu Ser Thr Ser Gly Ser
        800                 805                 810 ggc aaa ttt agt agt gac cgt aca att tct caa tat gca aaa gag atc    2498
Gly Lys Phe Ser Ser Asp Arg Thr Ile Ser Gln Tyr Ala Lys Glu Ile
    815                 820                 825 tgg aac att gcc gag tgt cgc gtg cct tga gcacacttct gaacctggta      2548
Trp Asn Ile Ala Glu Cys Arg Val Pro
830                 835 tctaataagg atctaatgtt cattgtttac tagcatatga ataatgtaag ttcaagcaca  2608
acatgctttc ttatttccta ctgctctcaa gaagcagtta tttgttg                2655

<210> SEQ ID NO 30
<211> LENGTH: 838
<212> TYPE: PRT
<213> ORGANISM: Solanum tuberosum

<400> SEQUENCE: 30

Met Glu Gly Gly Ala Lys Ser Asn Asp Val Ser Ala Ala Pro Ile Ala
1               5                   10                  15

Gln Pro Leu Ser Glu Asp Pro Thr Asp Ile Ala Ser Asn Ile Lys Tyr
            20                  25                  30

His Ala Gln Tyr Thr Pro His Phe Ser Pro Phe Lys Phe Glu Pro Leu
        35                  40                  45

Gln Ala Tyr Tyr Ala Ala Thr Ala Asp Ser Val Arg Asp Arg Leu Ile
    50                  55                  60

Lys Gln Trp Asn Asp Thr Tyr Leu His Tyr Asp Lys Val Asn Pro Lys
65                  70                  75                  80

Gln Thr Tyr Tyr Leu Ser Met Glu Tyr Leu Gln Gly Arg Ala Leu Thr
                85                  90                  95

Asn Ala Val Gly Asn Leu Asp Ile His Asn Ala Tyr Ala Asp Ala Leu
            100                 105                 110

Asn Lys Leu Gly Gln Gln Leu Glu Glu Val Val Glu Gln Glu Lys Asp
        115                 120                 125

Ala Ala Leu Gly Asn Gly Gly Leu Gly Arg Leu Ala Ser Cys Phe Leu
    130                 135                 140

Asp Ser Met Ala Thr Leu Asn Leu Pro Ala Trp Gly Tyr Gly Leu Arg
145                 150                 155                 160

Tyr Arg Tyr Gly Leu Phe Lys Gln Leu Ile Thr Lys Ala Gly Gln Glu
                165                 170                 175
```

-continued

```
Glu Val Pro Glu Asp Trp Leu Glu Lys Phe Ser Pro Trp Glu Ile Val
            180                 185                 190

Arg His Asp Val Val Phe Pro Ile Arg Phe Gly His Val Glu Val
            195                 200             205

Leu Pro Ser Gly Ser Arg Lys Trp Val Gly Glu Val Leu Gln Ala
210                 215                 220

Leu Ala Tyr Asp Val Pro Ile Pro Gly Tyr Arg Thr Lys Asn Thr Asn
225                 230                 235                 240

Ser Leu Arg Leu Trp Glu Ala Lys Ala Ser Ser Glu Asp Phe Asn Leu
                245                 250                 255

Phe Leu Phe Asn Asp Gly Gln Tyr Asp Ala Ala Gln Leu His Ser
                260                 265                 270

Arg Ala Gln Gln Ile Cys Ala Val Leu Tyr Pro Gly Asp Ala Thr Glu
            275                 280                 285

Asn Gly Lys Leu Leu Arg Leu Lys Gln Gln Phe Phe Leu Cys Ser Ala
            290                 295                 300

Ser Leu Gln Asp Ile Ile Ala Arg Phe Lys Glu Arg Glu Asp Gly Lys
305                 310                 315                 320

Gly Ser His Gln Trp Ser Glu Phe Pro Lys Lys Val Ala Ile Gln Leu
                325                 330                 335

Asn Asp Thr His Pro Thr Leu Thr Ile Pro Glu Leu Met Arg Leu Leu
            340                 345                 350

Met Asp Asp Glu Gly Leu Gly Trp Asp Glu Ser Trp Asn Ile Thr Thr
            355                 360                 365

Arg Thr Ile Ala Tyr Thr Asn His Thr Val Leu Pro Glu Ala Leu Glu
370                 375                 380

Lys Trp Ser Gln Ala Val Met Trp Lys Leu Leu Pro Arg His Met Glu
385                 390                 395                 400

Ile Ile Glu Glu Ile Asp Lys Arg Phe Val Ala Thr Ile Met Ser Glu
                405                 410                 415

Arg Pro Asp Leu Glu Asn Lys Met Pro Ser Met Arg Ile Leu Asp His
                420                 425                 430

Asn Ala Thr Lys Pro Val Val His Met Ala Asn Leu Cys Val Val Ser
            435                 440                 445

Ser His Thr Val Asn Gly Val Ala Gln Leu His Ser Asp Ile Leu Lys
            450                 455                 460

Ala Glu Leu Phe Ala Asp Tyr Val Ser Val Trp Pro Thr Lys Phe Gln
465                 470                 475                 480

Asn Lys Thr Asn Gly Ile Thr Pro Arg Arg Trp Ile Arg Phe Cys Ser
                485                 490                 495

Pro Glu Leu Ser His Ile Ile Thr Lys Trp Leu Lys Thr Asp Gln Trp
                500                 505                 510

Val Thr Asn Leu Glu Leu Leu Ala Asn Leu Arg Glu Phe Ala Asp Asn
            515                 520                 525

Ser Glu Leu His Ala Glu Trp Glu Ser Ala Lys Met Ala Asn Lys Gln
            530                 535                 540

Arg Leu Ala Gln Tyr Ile Leu His Val Thr Gly Val Ser Ile Asp Pro
545                 550                 555                 560

Asn Ser Leu Phe Asp Ile Gln Val Lys Arg Ile His Glu Tyr Lys Arg
                565                 570                 575

Gln Leu Leu Asn Ile Leu Gly Val Ile Tyr Arg Tyr Lys Lys Leu Lys
                580                 585                 590

Gly Met Ser Pro Glu Glu Arg Lys Asn Thr Thr Pro Arg Thr Val Met
```

-continued

```
             595                 600                 605
Ile Gly Gly Lys Ala Phe Ala Thr Tyr Thr Asn Ala Lys Arg Ile Val
        610                 615                 620

Lys Leu Val Thr Asp Val Gly Asp Val Val Asn Ser Asp Pro Asp Val
625                 630                 635                 640

Asn Asp Tyr Leu Lys Val Val Phe Val Pro Asn Tyr Asn Val Ser Val
                645                 650                 655

Ala Glu Met Leu Ile Pro Gly Ser Glu Leu Ser Gln His Ile Ser Thr
            660                 665                 670

Ala Gly Met Glu Ala Ser Gly Thr Ser Asn Met Lys Phe Ala Leu Asn
        675                 680                 685

Gly Cys Leu Ile Ile Gly Thr Leu Asp Gly Ala Asn Val Glu Ile Arg
    690                 695                 700

Glu Glu Ile Gly Glu Asp Asn Phe Phe Leu Phe Gly Ala Thr Ala Asp
705                 710                 715                 720

Glu Val Pro Gln Leu Arg Lys Asp Arg Glu Asn Gly Leu Phe Lys Pro
                725                 730                 735

Asp Pro Arg Phe Glu Glu Ala Lys Gln Phe Ile Arg Ser Gly Ala Phe
            740                 745                 750

Gly Thr Tyr Asp Tyr Asn Pro Leu Leu Glu Ser Leu Glu Gly Asn Ser
        755                 760                 765

Gly Tyr Gly Arg Gly Asp Tyr Phe Leu Val Gly His Asp Phe Pro Ser
    770                 775                 780

Tyr Met Asp Ala Gln Ala Arg Val Asp Glu Ala Tyr Lys Asp Arg Lys
785                 790                 795                 800

Arg Trp Ile Lys Met Ser Ile Leu Ser Thr Ser Gly Ser Gly Lys Phe
                805                 810                 815

Ser Ser Asp Arg Thr Ile Ser Gln Tyr Ala Lys Glu Ile Trp Asn Ile
            820                 825                 830

Ala Glu Cys Arg Val Pro
        835

<210> SEQ ID NO 31
<211> LENGTH: 1618
<212> TYPE: DNA
<213> ORGANISM: Ipomoea batatas
<220> FEATURE:
<221> NAME/KEY: CDS
<222> LOCATION: (2)..(1618)

<400> SEQUENCE: 31 c ttg gga agg ctt gct tct tgc ttt ctt gat tcc atg gca aca tta aac      49
  Leu Gly Arg Leu Ala Ser Cys Phe Leu Asp Ser Met Ala Thr Leu Asn
  1               5                  10                  15 ttg cca gcc tgg ggt tat gga ttg agg tac aaa cat gga ctg ttc aag       97
Leu Pro Ala Trp Gly Tyr Gly Leu Arg Tyr Lys His Gly Leu Phe Lys
                20                  25                  30 caa cgt atc acc aaa gca gga caa gag gag att gct gaa gat tgg ctg      145
Gln Arg Ile Thr Lys Ala Gly Gln Glu Glu Ile Ala Glu Asp Trp Leu
            35                  40                  45 gag aaa ttc agt ccc tgg gaa gtt gca agg cat gac att gtc ttc ccc      193
Glu Lys Phe Ser Pro Trp Glu Val Ala Arg His Asp Ile Val Phe Pro
    50                  55                  60 atc aga ttt ttt ggt cac gtt gag gtt gat cct agt ggc tcc cgg aaa      241
Ile Arg Phe Phe Gly His Val Glu Val Asp Pro Ser Gly Ser Arg Lys
65                  70                  75                  80 tgg gtt ggt ggt gag gtc ata cag gct gtt gca tat gat gtt cct att      289
```

```
            Trp Val Gly Gly Glu Val Ile Gln Ala Val Ala Tyr Asp Val Pro Ile
                         85                  90                  95 cct ggg tat aaa aca aag aat act att agt ctt cga cta tgg gaa gcc         337
Pro Gly Tyr Lys Thr Lys Asn Thr Ile Ser Leu Arg Leu Trp Glu Ala
                100                 105                 110 aaa gcc agt gca gag gac tta aac tta tct caa ttt aat gat ggg caa         385
Lys Ala Ser Ala Glu Asp Leu Asn Leu Ser Gln Phe Asn Asp Gly Gln
            115                 120                 125 tat gaa tct gct aca ctg ctt cat tct cgg gct cat cag att tgt gct         433
Tyr Glu Ser Ala Thr Leu Leu His Ser Arg Ala His Gln Ile Cys Ala
130                 135                 140 gtc ctt tac cct ggg gat gca acg gaa agt gga aaa ctt tta cga ctt         481
Val Leu Tyr Pro Gly Asp Ala Thr Glu Ser Gly Lys Leu Leu Arg Leu
145                 150                 155                 160 aaa caa caa ttt ttg ctg tgt agt gca tct ctt cag gac atc ata ttc         529
Lys Gln Gln Phe Leu Leu Cys Ser Ala Ser Leu Gln Asp Ile Ile Phe
                165                 170                 175 aga ttt aag gag agg aat gat ggg aag ggc act ctt gat tgg tcc aca         577
Arg Phe Lys Glu Arg Asn Asp Gly Lys Gly Thr Leu Asp Trp Ser Thr
            180                 185                 190 ttc ccc aca aaa gtt gca gta caa ctg aat gac aca cat cct acg ctc         625
Phe Pro Thr Lys Val Ala Val Gln Leu Asn Asp Thr His Pro Thr Leu
        195                 200                 205 tcg att ccg gag ctg atg cgg tta ttg atg gat gat gaa gga ctt gga         673
Ser Ile Pro Glu Leu Met Arg Leu Leu Met Asp Asp Glu Gly Leu Gly
210                 215                 220 tgg gat gaa gca tgg gat ata acc act agg aca atc gct tat aca aat         721
Trp Asp Glu Ala Trp Asp Ile Thr Thr Arg Thr Ile Ala Tyr Thr Asn
225                 230                 235                 240 cat acc gtc cta cct gaa gca cta gaa aaa tgg tca caa gca gtc atg         769
His Thr Val Leu Pro Glu Ala Leu Glu Lys Trp Ser Gln Ala Val Met
                245                 250                 255 tgg aaa ctt ctt cca cgg cat atg gaa atc att gag gaa atc gac aag         817
Trp Lys Leu Leu Pro Arg His Met Glu Ile Ile Glu Glu Ile Asp Lys
            260                 265                 270 cgg ttt att gca atg ata caa tca aag ata cct aat ctt gag agt aag         865
Arg Phe Ile Ala Met Ile Gln Ser Lys Ile Pro Asn Leu Glu Ser Lys
        275                 280                 285 atc tct gcc ata tgc att ttg gat cac aat ccc cag aag cct gtt gtg         913
Ile Ser Ala Ile Cys Ile Leu Asp His Asn Pro Gln Lys Pro Val Val
290                 295                 300 cgt atg gct aat ttg tgt gtc atc tct tcg cat acg gtg aat ggt gtt         961
Arg Met Ala Asn Leu Cys Val Ile Ser Ser His Thr Val Asn Gly Val
305                 310                 315                 320 gcc cag cta cac agt gat atc ttg aag gat gaa tta ttc atc gac tat        1009
Ala Gln Leu His Ser Asp Ile Leu Lys Asp Glu Leu Phe Ile Asp Tyr
                325                 330                 335 gtc tct atc tgg ccc acc aaa ttc cag aac aaa acc aac ggc ata aca        1057
Val Ser Ile Trp Pro Thr Lys Phe Gln Asn Lys Thr Asn Gly Ile Thr
            340                 345                 350 cca cgg cgg tgg ctt agg ttt tgc aat ccc gag ctg agt gat ata atc        1105
Pro Arg Arg Trp Leu Arg Phe Cys Asn Pro Glu Leu Ser Asp Ile Ile
        355                 360                 365 acc aag tgg tta aaa act gat gaa tgg gtg act aat ctt gat ttg ctt        1153
Thr Lys Trp Leu Lys Thr Asp Glu Trp Val Thr Asn Leu Asp Leu Leu
370                 375                 380 act aat ctg cgg aag ttt gct gac gat gaa caa ctc cat gct caa tgg        1201
Thr Asn Leu Arg Lys Phe Ala Asp Asp Glu Gln Leu His Ala Gln Trp
385                 390                 395                 400
```

-continued

```
gag tct gcc aag atg gca agc aag caa cga ttg gcg cag tac ata ctg    1249
Glu Ser Ala Lys Met Ala Ser Lys Gln Arg Leu Ala Gln Tyr Ile Leu
            405                 410                 415 cga gta acc ggt gtg cgt gtt gac cca aat aca cta ttt gac ata caa    1297
Arg Val Thr Gly Val Arg Val Asp Pro Asn Thr Leu Phe Asp Ile Gln
        420                 425                 430 gtc aag cgc att cac gaa tac aaa agg cag cta cta aat gta ttg ggt    1345
Val Lys Arg Ile His Glu Tyr Lys Arg Gln Leu Leu Asn Val Leu Gly
    435                 440                 445 gta gtc tac cgg tac aag aaa ctg aag gag atg aaa ccc gaa gag cgt    1393
Val Val Tyr Arg Tyr Lys Lys Leu Lys Glu Met Lys Pro Glu Glu Arg
450                 455                 460 aag aat aca aca gca cgc act gtc atg ctc ggg gga aaa gca ttt gcg    1441
Lys Asn Thr Thr Ala Arg Thr Val Met Leu Gly Gly Lys Ala Phe Ala
465                 470                 475                 480 acc tat aca aat gca aaa agg atc atc aag ctt gtg acg gat gtt ggg    1489
Thr Tyr Thr Asn Ala Lys Arg Ile Ile Lys Leu Val Thr Asp Val Gly
            485                 490                 495 gat gtt gtc aat agt gat cct gag gtc aat agc tat ttg aag gta gtc    1537
Asp Val Val Asn Ser Asp Pro Glu Val Asn Ser Tyr Leu Lys Val Val
        500                 505                 510 ttt gta ccc aat tac aac gta tct gtg gca gaa gtg ctt att ccg gga    1585
Phe Val Pro Asn Tyr Asn Val Ser Val Ala Glu Val Leu Ile Pro Gly
    515                 520                 525 agt gag ctt tca cag cac atc agc aca gct ggc                        1618
Ser Glu Leu Ser Gln His Ile Ser Thr Ala Gly
530                 535
```

<210> SEQ ID NO 32
<211> LENGTH: 539
<212> TYPE: PRT
<213> ORGANISM: Ipomoea batatas

<400> SEQUENCE: 32

```
Leu Gly Arg Leu Ala Ser Cys Phe Leu Asp Ser Met Ala Thr Leu Asn
1               5                   10                  15

Leu Pro Ala Trp Gly Tyr Gly Leu Arg Tyr Lys His Gly Leu Phe Lys
            20                  25                  30

Gln Arg Ile Thr Lys Ala Gly Gln Glu Ile Ala Glu Asp Trp Leu
        35                  40                  45

Glu Lys Phe Ser Pro Trp Glu Val Ala Arg His Asp Ile Val Phe Pro
    50                  55                  60

Ile Arg Phe Phe Gly His Val Glu Val Asp Pro Ser Gly Ser Arg Lys
65                  70                  75                  80

Trp Val Gly Gly Glu Val Ile Gln Ala Val Ala Tyr Asp Val Pro Ile
                85                  90                  95

Pro Gly Tyr Lys Thr Lys Asn Thr Ile Ser Leu Arg Leu Trp Glu Ala
            100                 105                 110

Lys Ala Ser Ala Glu Asp Leu Asn Leu Ser Gln Phe Asn Asp Gly Gln
        115                 120                 125

Tyr Glu Ser Ala Thr Leu Leu His Ser Arg Ala His Gln Ile Cys Ala
    130                 135                 140

Val Leu Tyr Pro Gly Asp Ala Thr Glu Ser Gly Lys Leu Leu Arg Leu
145                 150                 155                 160

Lys Gln Gln Phe Leu Leu Cys Ser Ala Ser Leu Gln Asp Ile Ile Phe
                165                 170                 175

Arg Phe Lys Glu Arg Asn Asp Gly Lys Gly Thr Leu Asp Trp Ser Thr
            180                 185                 190
```

```
Phe Pro Thr Lys Val Ala Val Gln Leu Asn Asp Thr His Pro Thr Leu
            195                 200                 205

Ser Ile Pro Glu Leu Met Arg Leu Leu Met Asp Asp Glu Gly Leu Gly
    210                 215                 220

Trp Asp Glu Ala Trp Asp Ile Thr Thr Arg Thr Ile Ala Tyr Thr Asn
225                 230                 235                 240

His Thr Val Leu Pro Glu Ala Leu Glu Lys Trp Ser Gln Ala Val Met
                245                 250                 255

Trp Lys Leu Leu Pro Arg His Met Glu Ile Ile Glu Glu Ile Asp Lys
            260                 265                 270

Arg Phe Ile Ala Met Ile Gln Ser Lys Ile Pro Asn Leu Glu Ser Lys
        275                 280                 285

Ile Ser Ala Ile Cys Ile Leu Asp His Asn Pro Gln Lys Pro Val Val
    290                 295                 300

Arg Met Ala Asn Leu Cys Val Ile Ser His Thr Val Asn Gly Val
305                 310                 315                 320

Ala Gln Leu His Ser Asp Ile Leu Lys Asp Glu Leu Phe Ile Asp Tyr
                325                 330                 335

Val Ser Ile Trp Pro Thr Lys Phe Gln Asn Lys Thr Asn Gly Ile Thr
            340                 345                 350

Pro Arg Arg Trp Leu Arg Phe Cys Asn Pro Glu Leu Ser Asp Ile Ile
        355                 360                 365

Thr Lys Trp Leu Lys Thr Asp Glu Trp Val Thr Asn Leu Asp Leu Leu
370                 375                 380

Thr Asn Leu Arg Lys Phe Ala Asp Asp Glu Gln Leu His Ala Gln Trp
385                 390                 395                 400

Glu Ser Ala Lys Met Ala Ser Lys Gln Arg Leu Ala Gln Tyr Ile Leu
                405                 410                 415

Arg Val Thr Gly Val Arg Val Asp Pro Asn Thr Leu Phe Asp Ile Gln
            420                 425                 430

Val Lys Arg Ile His Glu Tyr Lys Arg Gln Leu Leu Asn Val Leu Gly
        435                 440                 445

Val Val Tyr Arg Tyr Lys Lys Leu Lys Glu Met Lys Pro Glu Glu Arg
    450                 455                 460

Lys Asn Thr Thr Ala Arg Thr Val Met Leu Gly Gly Lys Ala Phe Ala
465                 470                 475                 480

Thr Tyr Thr Asn Ala Lys Arg Ile Ile Lys Leu Val Thr Asp Val Gly
                485                 490                 495

Asp Val Val Asn Ser Asp Pro Glu Val Asn Ser Tyr Leu Lys Val Val
            500                 505                 510

Phe Val Pro Asn Tyr Asn Val Ser Val Ala Glu Val Leu Ile Pro Gly
        515                 520                 525

Ser Glu Leu Ser Gln His Ile Ser Thr Ala Gly
    530                 535

<210> SEQ ID NO 33
<211> LENGTH: 2754
<212> TYPE: DNA
<213> ORGANISM: Artificial sequence
<220> FEATURE:
<223> OTHER INFORMATION: a mutant of a potato type L alpha-glucan
      phosphorylase
<220> FEATURE:
<221> NAME/KEY: CDS
<222> LOCATION: (1)..(2751)
<220> FEATURE:
```

-continued

```
<221> NAME/KEY: mat_peptide
<222> LOCATION: (4)..(2751)

<400> SEQUENCE: 33
```

| | | | | | | | | | | | | | | | | |
|---|---|---|---|---|---|---|---|---|---|---|---|---|---|---|---|---|
| atg | acc | ttg | agt | gag | aaa | att | cac | cat | ccc | att | act | gaa | caa | ggt | ggt | 48 |
| Met | Thr | Leu | Ser | Glu | Lys | Ile | His | His | Pro | Ile | Thr | Glu | Gln | Gly | Gly | |
| -1 | 1 | | | | 5 | | | | | 10 | | | | | 15 | |
| gag | agc | gac | ctg | agt | tct | ttt | gct | cct | gat | gcc | gca | tct | att | acc | tca | 96 |
| Glu | Ser | Asp | Leu | Ser | Ser | Phe | Ala | Pro | Asp | Ala | Ala | Ser | Ile | Thr | Ser | |
| | | | | 20 | | | | | 25 | | | | | 30 | | |
| agt | atc | aaa | tac | cat | gca | gaa | ctc | aca | cct | gta | ttc | tct | cct | gaa | agg | 144 |
| Ser | Ile | Lys | Tyr | His | Ala | Glu | Leu | Thr | Pro | Val | Phe | Ser | Pro | Glu | Arg | |
| | | | 35 | | | | | 40 | | | | | 45 | | | |
| ttt | gag | ctc | cct | aag | gca | ttc | ttt | gca | aca | gct | caa | agt | gtt | cgt | gat | 192 |
| Phe | Glu | Leu | Pro | Lys | Ala | Phe | Phe | Ala | Thr | Ala | Gln | Ser | Val | Arg | Asp | |
| | | 50 | | | | | 55 | | | | | 60 | | | | |
| tcg | ctc | ctt | att | aat | tgg | aat | gct | acg | tat | gat | att | tat | gaa | aag | ctg | 240 |
| Ser | Leu | Leu | Ile | Asn | Trp | Asn | Ala | Thr | Tyr | Asp | Ile | Tyr | Glu | Lys | Leu | |
| | 65 | | | | | 70 | | | | | 75 | | | | | |
| aac | atg | aag | caa | gcg | tac | tat | cta | tcc | atg | gaa | ttt | ctg | cag | ggt | aga | 288 |
| Asn | Met | Lys | Gln | Ala | Tyr | Tyr | Leu | Ser | Met | Glu | Phe | Leu | Gln | Gly | Arg | |
| 80 | | | | | 85 | | | | | 90 | | | | | 95 | |
| gca | ttg | tta | aat | gca | att | ggt | aat | ctg | gag | ctt | act | ggt | gca | ttt | gcg | 336 |
| Ala | Leu | Leu | Asn | Ala | Ile | Gly | Asn | Leu | Glu | Leu | Thr | Gly | Ala | Phe | Ala | |
| | | | | 100 | | | | | 105 | | | | | 110 | | |
| gaa | gct | ttg | aaa | aac | ctt | ggt | cac | aat | cta | gaa | aat | gtg | gct | tct | cag | 384 |
| Glu | Ala | Leu | Lys | Asn | Leu | Gly | His | Asn | Leu | Glu | Asn | Val | Ala | Ser | Gln | |
| | | | 115 | | | | | 120 | | | | | 125 | | | |
| gaa | cca | gat | gct | gct | ctt | gga | agt | ggg | ggt | ttg | gga | cgg | ctt | gct | tcc | 432 |
| Glu | Pro | Asp | Ala | Ala | Leu | Gly | Ser | Gly | Gly | Leu | Gly | Arg | Leu | Ala | Ser | |
| | | 130 | | | | | 135 | | | | | 140 | | | | |
| tgt | ttt | ctg | gac | tct | ttg | gca | aca | cta | aac | tac | cca | gca | tgg | ggc | tat | 480 |
| Cys | Phe | Leu | Asp | Ser | Leu | Ala | Thr | Leu | Asn | Tyr | Pro | Ala | Trp | Gly | Tyr | |
| | 145 | | | | | 150 | | | | | 155 | | | | | |
| gga | ctt | agg | tac | aag | tat | ggt | tta | ttt | aag | caa | cgg | att | aca | aaa | gat | 528 |
| Gly | Leu | Arg | Tyr | Lys | Tyr | Gly | Leu | Phe | Lys | Gln | Arg | Ile | Thr | Lys | Asp | |
| 160 | | | | | 165 | | | | | 170 | | | | | 175 | |
| ggt | cag | gag | gag | gtg | gct | gaa | gat | tgg | ctt | gaa | att | ggc | agt | cca | tgg | 576 |
| Gly | Gln | Glu | Glu | Val | Ala | Glu | Asp | Trp | Leu | Glu | Ile | Gly | Ser | Pro | Trp | |
| | | | | 180 | | | | | 185 | | | | | 190 | | |
| gaa | gtt | gtg | agg | aat | gat | gtt | tca | tat | cct | atc | aaa | ttc | tat | gga | aaa | 624 |
| Glu | Val | Val | Arg | Asn | Asp | Val | Ser | Tyr | Pro | Ile | Lys | Phe | Tyr | Gly | Lys | |
| | | | 195 | | | | | 200 | | | | | 205 | | | |
| gtc | tct | aca | gga | tca | gat | gga | aag | agg | tat | tgg | att | ggt | gga | gag | gat | 672 |
| Val | Ser | Thr | Gly | Ser | Asp | Gly | Lys | Arg | Tyr | Trp | Ile | Gly | Gly | Glu | Asp | |
| | | 210 | | | | | 215 | | | | | 220 | | | | |
| ata | aag | gca | gtt | gcg | tat | gat | gtt | ccc | ata | cca | ggg | tat | aag | acc | aga | 720 |
| Ile | Lys | Ala | Val | Ala | Tyr | Asp | Val | Pro | Ile | Pro | Gly | Tyr | Lys | Thr | Arg | |
| | 225 | | | | | 230 | | | | | 235 | | | | | |
| acc | aca | atc | agc | ctt | cga | ctg | tgg | tct | aca | cag | gtt | cca | tca | gcg | gat | 768 |
| Thr | Thr | Ile | Ser | Leu | Arg | Leu | Trp | Ser | Thr | Gln | Val | Pro | Ser | Ala | Asp | |
| 240 | | | | | 245 | | | | | 250 | | | | | 255 | |
| ttt | gat | tta | tct | gct | ttc | aat | gct | gga | gag | cac | acc | aaa | gca | tgt | gaa | 816 |
| Phe | Asp | Leu | Ser | Ala | Phe | Asn | Ala | Gly | Glu | His | Thr | Lys | Ala | Cys | Glu | |
| | | | | 260 | | | | | 265 | | | | | 270 | | |
| gcc | caa | gca | aac | gct | gag | aag | ata | tgt | tac | ata | ctc | tac | cct | ggg | gat | 864 |
| Ala | Gln | Ala | Asn | Ala | Glu | Lys | Ile | Cys | Tyr | Ile | Leu | Tyr | Pro | Gly | Asp | |
| | | | 275 | | | | | 280 | | | | | 285 | | | |
| gaa | tca | gag | gag | gga | aag | atc | ctt | cgg | ttg | aag | caa | caa | tat | acc | tta | 912 |
| Glu | Ser | Glu | Glu | Gly | Lys | Ile | Leu | Arg | Leu | Lys | Gln | Gln | Tyr | Thr | Leu | |

-continued

```
             290                 295                 300
tgc tcg gct tct ctc caa gat att att tct cga ttt gag agg aga tca      960
Cys Ser Ala Ser Leu Gln Asp Ile Ile Ser Arg Phe Glu Arg Arg Ser
305                 310                 315 ggt gat cgt att aag tgg gaa gag ttt cct gaa aaa gtt gct gtg cag     1008
Gly Asp Arg Ile Lys Trp Glu Glu Phe Pro Glu Lys Val Ala Val Gln
320                 325                 330                 335 atg aat gac act cac cct aca ctt tgt atc cct gag ctg atg aga ata     1056
Met Asn Asp Thr His Pro Thr Leu Cys Ile Pro Glu Leu Met Arg Ile
            340                 345                 350 ttg ata gat ctg aag ggc ttg aat tgg aat gaa gct tgg aat att act     1104
Leu Ile Asp Leu Lys Gly Leu Asn Trp Asn Glu Ala Trp Asn Ile Thr
                355                 360                 365 caa aga act gtg gcc tac aca aac cat act gtt ttg cct gag gca ctg     1152
Gln Arg Thr Val Ala Tyr Thr Asn His Thr Val Leu Pro Glu Ala Leu
370                 375                 380 gag aaa tgg agt tat gaa ttg atg cag aaa ctg ctt ccc aga cat gtc     1200
Glu Lys Trp Ser Tyr Glu Leu Met Gln Lys Leu Leu Pro Arg His Val
385                 390                 395 gaa atc att gag gcg att gac gag gag ctg gta cat gaa att gta tta     1248
Glu Ile Ile Glu Ala Ile Asp Glu Glu Leu Val His Glu Ile Val Leu
400                 405                 410                 415 aaa tat ggt tca atg gat ctg aac aaa ttg gag gaa aag ttg act aca     1296
Lys Tyr Gly Ser Met Asp Leu Asn Lys Leu Glu Glu Lys Leu Thr Thr
                420                 425                 430 atg aga atc tta gaa aat ttt gat ctt ccc agt cct gtt gct gaa tta     1344
Met Arg Ile Leu Glu Asn Phe Asp Leu Pro Ser Pro Val Ala Glu Leu
                435                 440                 445 ttt att aag cct gaa atc tca gtt gat gat gat act gaa aca gta gaa     1392
Phe Ile Lys Pro Glu Ile Ser Val Asp Asp Asp Thr Glu Thr Val Glu
                450                 455                 460 gtc cat gac aaa gtt gaa gct tcc gat aaa gtt gtg act aat gat gaa     1440
Val His Asp Lys Val Glu Ala Ser Asp Lys Val Val Thr Asn Asp Glu
465                 470                 475 gat gac act ggt aag aaa act agt gtg aag ata gaa gca gct gca gaa     1488
Asp Asp Thr Gly Lys Lys Thr Ser Val Lys Ile Glu Ala Ala Ala Glu
480                 485                 490                 495 aaa gac att gac aag aaa act ccc gtg agt ccg gaa cca gct gtt ata     1536
Lys Asp Ile Asp Lys Lys Thr Pro Val Ser Pro Glu Pro Ala Val Ile
                500                 505                 510 cca cct aag aag gta cgc atg gcc aac ttg tgt gtt gtg ggc ggc cat     1584
Pro Pro Lys Lys Val Arg Met Ala Asn Leu Cys Val Val Gly Gly His
                515                 520                 525 gct gtt aat gga gtt gct gag atc cat agt gaa att gtg aag gag gag     1632
Ala Val Asn Gly Val Ala Glu Ile His Ser Glu Ile Val Lys Glu Glu
                530                 535                 540 gtt ttc aat gac ttc tat gag ctc tgg ccg gaa aag ttc caa aac aaa     1680
Val Phe Asn Asp Phe Tyr Glu Leu Trp Pro Glu Lys Phe Gln Asn Lys
545                 550                 555 aca aat gga gtg act cca aga aga tgg att cgt ttc tgc aat cct cct     1728
Thr Asn Gly Val Thr Pro Arg Arg Trp Ile Arg Phe Cys Asn Pro Pro
560                 565                 570                 575 ctt agt gcc atc ata act aag tgg act ggt aca gag gat tgg gtc ctg     1776
Leu Ser Ala Ile Ile Thr Lys Trp Thr Gly Thr Glu Asp Trp Val Leu
                580                 585                 590 aaa act gaa aag ttg gca gaa ttg cag aag ttt gct gat aat gaa gat     1824
Lys Thr Glu Lys Leu Ala Glu Leu Gln Lys Phe Ala Asp Asn Glu Asp
                595                 600                 605 ctt caa aat gag tgg agg gaa gca aaa agg agc aac aag att aaa gtt     1872
```

```
Leu Gln Asn Glu Trp Arg Glu Ala Lys Arg Ser Asn Lys Ile Lys Val
        610                 615                 620 gtc tcc ttt ctc aaa gaa aag aca ggg tat tct gtt gtc cca gat gca    1920
Val Ser Phe Leu Lys Glu Lys Thr Gly Tyr Ser Val Val Pro Asp Ala
625                 630                 635 atg ttt gat att cag gta aaa cgc att cat gag tac aag cga caa ctg    1968
Met Phe Asp Ile Gln Val Lys Arg Ile His Glu Tyr Lys Arg Gln Leu
640                 645                 650                 655 tta aat atc ttc ggc atc gtt tat cgg tat aag aag atg aaa gaa atg    2016
Leu Asn Ile Phe Gly Ile Val Tyr Arg Tyr Lys Lys Met Lys Glu Met
                660                 665                 670 aca gct gca gaa aga aag act aac ttc gtt cct cga gta tgc ata ttt    2064
Thr Ala Ala Glu Arg Lys Thr Asn Phe Val Pro Arg Val Cys Ile Phe
            675                 680                 685 ggg gga aaa gct ttt gcc aca tat gtg caa gcc aag agg att gta aaa    2112
Gly Gly Lys Ala Phe Ala Thr Tyr Val Gln Ala Lys Arg Ile Val Lys
        690                 695                 700 ttt atc ata gat gtt ggt gct act ata aat cat gat cca gaa atc ggt    2160
Phe Ile Ile Asp Val Gly Ala Thr Ile Asn His Asp Pro Glu Ile Gly
705                 710                 715 gat ctg ttg aag gta gtc ttt gtg cca gat tac aat gtc agt gtt gct    2208
Asp Leu Leu Lys Val Val Phe Val Pro Asp Tyr Asn Val Ser Val Ala
720                 725                 730                 735 gaa ttg cta att cct gct agc gat cta tca gaa cat atc agt acg gct    2256
Glu Leu Leu Ile Pro Ala Ser Asp Leu Ser Glu His Ile Ser Thr Ala
                740                 745                 750 gga atg gag gcc agt gga acc agt aat atg aag ttt gca atg aat ggt    2304
Gly Met Glu Ala Ser Gly Thr Ser Asn Met Lys Phe Ala Met Asn Gly
            755                 760                 765 tgt atc caa att ggt aca ttg gat ggc gct aat gtt gaa ata agg gaa    2352
Cys Ile Gln Ile Gly Thr Leu Asp Gly Ala Asn Val Glu Ile Arg Glu
        770                 775                 780 gag gtt gga gaa gaa aac ttc ttt ctc ttt ggt gct caa gct cat gaa    2400
Glu Val Gly Glu Glu Asn Phe Phe Leu Phe Gly Ala Gln Ala His Glu
785                 790                 795 att gca ggg ctt aga aaa gaa aga gct gac gga aag ttt gta cct gat    2448
Ile Ala Gly Leu Arg Lys Glu Arg Ala Asp Gly Lys Phe Val Pro Asp
800                 805                 810                 815 gaa cgt ttt gaa gag gtg aag gaa ttt gtt aga agc ggt gct ttt ggc    2496
Glu Arg Phe Glu Glu Val Lys Glu Phe Val Arg Ser Gly Ala Phe Gly
                820                 825                 830 tct tat aac tat gat gac cta att gga tcg ttg gaa gga aat gaa ggt    2544
Ser Tyr Asn Tyr Asp Asp Leu Ile Gly Ser Leu Glu Gly Asn Glu Gly
            835                 840                 845 ttt ggc cgt gct gac tat ttc ctt gtg ggc aag gac ttc ccc agt tac    2592
Phe Gly Arg Ala Asp Tyr Phe Leu Val Gly Lys Asp Phe Pro Ser Tyr
        850                 855                 860 ata gaa tgc caa gag aaa gtt gat gag gca tat cgc gac cag aaa agg    2640
Ile Glu Cys Gln Glu Lys Val Asp Glu Ala Tyr Arg Asp Gln Lys Arg
865                 870                 875 tgg aca acg atg tca atc ttg aat aca gcg gga tcg tac aag ttc agc    2688
Trp Thr Thr Met Ser Ile Leu Asn Thr Ala Gly Ser Tyr Lys Phe Ser
880                 885                 890                 895 agt gac aga aca atc cat gaa tat gcc aaa gac att tgg aac att gaa    2736
Ser Asp Arg Thr Ile His Glu Tyr Ala Lys Asp Ile Trp Asn Ile Glu
                900                 905                 910 gct gtg gaa ata gca taa                                            2754
Ala Val Glu Ile Ala
            915
```

```
<210> SEQ ID NO 34
<211> LENGTH: 917
<212> TYPE: PRT
<213> ORGANISM: Artificial sequence
<220> FEATURE:
<223> OTHER INFORMATION: Synthetic Construct

<400> SEQUENCE: 34

Met Thr Leu Ser Glu Lys Ile His His Pro Ile Thr Glu Gln Gly Gly
 -1  1           5                  10                  15

Glu Ser Asp Leu Ser Ser Phe Ala Pro Asp Ala Ala Ser Ile Thr Ser
                 20                  25                  30

Ser Ile Lys Tyr His Ala Glu Leu Thr Pro Val Phe Ser Pro Glu Arg
             35                  40                  45

Phe Glu Leu Pro Lys Ala Phe Phe Ala Thr Ala Gln Ser Val Arg Asp
         50                  55                  60

Ser Leu Leu Ile Asn Trp Asn Ala Thr Tyr Asp Ile Tyr Glu Lys Leu
     65                  70                  75

Asn Met Lys Gln Ala Tyr Tyr Leu Ser Met Glu Phe Leu Gln Gly Arg
 80                  85                  90                  95

Ala Leu Leu Asn Ala Ile Gly Asn Leu Glu Leu Thr Gly Ala Phe Ala
                100                 105                 110

Glu Ala Leu Lys Asn Leu Gly His Asn Leu Glu Asn Val Ala Ser Gln
                115                 120                 125

Glu Pro Asp Ala Ala Leu Gly Ser Gly Gly Leu Gly Arg Leu Ala Ser
            130                 135                 140

Cys Phe Leu Asp Ser Leu Ala Thr Leu Asn Tyr Pro Ala Trp Gly Tyr
145                 150                 155

Gly Leu Arg Tyr Lys Tyr Gly Leu Phe Lys Gln Arg Ile Thr Lys Asp
160                 165                 170                 175

Gly Gln Glu Glu Val Ala Glu Asp Trp Leu Glu Ile Gly Ser Pro Trp
                180                 185                 190

Glu Val Val Arg Asn Asp Val Ser Tyr Pro Ile Lys Phe Tyr Gly Lys
            195                 200                 205

Val Ser Thr Gly Ser Asp Gly Lys Arg Tyr Trp Ile Gly Gly Glu Asp
        210                 215                 220

Ile Lys Ala Val Ala Tyr Asp Val Pro Ile Pro Gly Tyr Lys Thr Arg
225                 230                 235

Thr Thr Ile Ser Leu Arg Leu Trp Ser Thr Gln Val Pro Ser Ala Asp
240                 245                 250                 255

Phe Asp Leu Ser Ala Phe Asn Ala Gly Glu His Thr Lys Ala Cys Glu
                260                 265                 270

Ala Gln Ala Asn Ala Glu Lys Ile Cys Tyr Ile Leu Tyr Pro Gly Asp
            275                 280                 285

Glu Ser Glu Glu Gly Lys Ile Leu Arg Leu Lys Gln Gln Tyr Thr Leu
        290                 295                 300

Cys Ser Ala Ser Leu Gln Asp Ile Ile Ser Arg Phe Glu Arg Arg Ser
305                 310                 315

Gly Asp Arg Ile Lys Trp Glu Glu Phe Pro Glu Lys Val Ala Val Gln
320                 325                 330                 335

Met Asn Asp Thr His Pro Thr Leu Cys Ile Pro Glu Leu Met Arg Ile
                340                 345                 350

Leu Ile Asp Leu Lys Gly Leu Asn Trp Asn Glu Ala Trp Asn Ile Thr
            355                 360                 365
```

```
Gln Arg Thr Val Ala Tyr Thr Asn His Thr Val Leu Pro Glu Ala Leu
        370                 375                 380

Glu Lys Trp Ser Tyr Glu Leu Met Gln Lys Leu Leu Pro Arg His Val
        385                 390                 395

Glu Ile Ile Glu Ala Ile Asp Glu Glu Leu Val His Glu Ile Val Leu
400                 405                 410                 415

Lys Tyr Gly Ser Met Asp Leu Asn Lys Leu Glu Glu Lys Leu Thr Thr
                420                 425                 430

Met Arg Ile Leu Glu Asn Phe Asp Leu Pro Ser Pro Val Ala Glu Leu
            435                 440                 445

Phe Ile Lys Pro Glu Ile Ser Val Asp Asp Thr Glu Thr Val Glu
        450                 455                 460

Val His Asp Lys Val Glu Ala Ser Asp Lys Val Val Thr Asn Asp Glu
        465                 470                 475

Asp Asp Thr Gly Lys Lys Thr Ser Val Lys Ile Glu Ala Ala Glu
480                 485                 490                 495

Lys Asp Ile Asp Lys Lys Thr Pro Val Ser Pro Glu Pro Ala Val Ile
                500                 505                 510

Pro Pro Lys Lys Val Arg Met Ala Asn Leu Cys Val Val Gly Gly His
            515                 520                 525

Ala Val Asn Gly Val Ala Glu Ile His Ser Glu Ile Val Lys Glu Glu
        530                 535                 540

Val Phe Asn Asp Phe Tyr Glu Leu Trp Pro Glu Lys Phe Gln Asn Lys
        545                 550                 555

Thr Asn Gly Val Thr Pro Arg Arg Trp Ile Arg Phe Cys Asn Pro Pro
560                 565                 570                 575

Leu Ser Ala Ile Ile Thr Lys Trp Thr Gly Thr Glu Asp Trp Val Leu
                580                 585                 590

Lys Thr Glu Lys Leu Ala Glu Leu Gln Lys Phe Ala Asp Asn Glu Asp
            595                 600                 605

Leu Gln Asn Glu Trp Arg Glu Ala Lys Arg Ser Asn Lys Ile Lys Val
        610                 615                 620

Val Ser Phe Leu Lys Glu Lys Thr Gly Tyr Ser Val Val Pro Asp Ala
        625                 630                 635

Met Phe Asp Ile Gln Val Lys Arg Ile His Glu Tyr Lys Arg Gln Leu
640                 645                 650                 655

Leu Asn Ile Phe Gly Ile Val Tyr Arg Tyr Lys Lys Met Lys Glu Met
                660                 665                 670

Thr Ala Ala Glu Arg Lys Thr Asn Phe Val Pro Arg Val Cys Ile Phe
            675                 680                 685

Gly Gly Lys Ala Phe Ala Thr Tyr Val Gln Ala Lys Arg Ile Val Lys
        690                 695                 700

Phe Ile Ile Asp Val Gly Ala Thr Ile Asn His Asp Pro Glu Ile Gly
        705                 710                 715

Asp Leu Leu Lys Val Val Phe Val Pro Asp Tyr Asn Val Ser Val Ala
720                 725                 730                 735

Glu Leu Leu Ile Pro Ala Ser Asp Leu Ser Glu His Ile Ser Thr Ala
                740                 745                 750

Gly Met Glu Ala Ser Gly Thr Ser Asn Met Lys Phe Ala Met Asn Gly
            755                 760                 765

Cys Ile Gln Ile Gly Thr Leu Asp Gly Ala Asn Val Glu Ile Arg Glu
        770                 775                 780

Glu Val Gly Glu Glu Asn Phe Phe Leu Phe Gly Ala Gln Ala His Glu
```

```
              785                 790                 795
Ile Ala Gly Leu Arg Lys Glu Arg Ala Asp Gly Lys Phe Val Pro Asp
800                 805                 810                 815

Glu Arg Phe Glu Glu Val Lys Glu Phe Val Arg Ser Gly Ala Phe Gly
                    820                 825                 830

Ser Tyr Asn Tyr Asp Asp Leu Ile Gly Ser Leu Glu Gly Asn Glu Gly
                    835                 840                 845

Phe Gly Arg Ala Asp Tyr Phe Leu Val Gly Lys Asp Phe Pro Ser Tyr
                    850                 855                 860

Ile Glu Cys Gln Glu Lys Val Asp Glu Ala Tyr Arg Asp Gln Lys Arg
865                 870                 875

Trp Thr Thr Met Ser Ile Leu Asn Thr Ala Gly Ser Tyr Lys Phe Ser
880                 885                 890                 895

Ser Asp Arg Thr Ile His Glu Tyr Ala Lys Asp Ile Trp Asn Ile Glu
                    900                 905                 910

Ala Val Glu Ile Ala
                915

<210> SEQ ID NO 35
<211> LENGTH: 797
<212> TYPE: PRT
<213> ORGANISM: Escherichia coli

<400> SEQUENCE: 35

Met Ser Gln Pro Ile Phe Asn Asp Lys Gln Phe Gln Glu Ala Leu Ser
1               5                   10                  15

Arg Gln Trp Gln Arg Tyr Gly Leu Asn Ser Ala Ala Glu Met Thr Pro
            20                  25                  30

Arg Gln Trp Trp Leu Ala Val Ser Glu Ala Leu Ala Glu Met Leu Arg
        35                  40                  45

Ala Gln Pro Phe Ala Lys Pro Val Ala Asn Gln Arg His Val Asn Tyr
    50                  55                  60

Ile Ser Met Glu Phe Leu Ile Gly Arg Leu Thr Gly Asn Asn Leu Leu
65                  70                  75                  80

Asn Leu Gly Trp Tyr Gln Asp Val Gln Asp Ser Leu Lys Ala Tyr Asp
                85                  90                  95

Ile Asn Leu Thr Asp Leu Leu Glu Glu Ile Asp Pro Ala Leu Gly
            100                 105                 110

Asn Gly Gly Leu Gly Arg Leu Ala Ala Cys Phe Leu Asp Ser Met Ala
        115                 120                 125

Thr Val Gly Gln Ser Ala Thr Gly Tyr Gly Leu Asn Tyr Gln Tyr Gly
    130                 135                 140

Leu Phe Arg Gln Ser Phe Val Asp Gly Lys Gln Val Glu Ala Pro Asp
145                 150                 155                 160

Asp Trp His Arg Ser Asn Tyr Pro Trp Phe Arg His Asn Glu Ala Leu
                165                 170                 175

Asp Val Gln Val Gly Ile Gly Gly Lys Val Thr Lys Asp Gly Arg Trp
            180                 185                 190

Glu Pro Glu Phe Thr Ile Thr Gly Gln Ala Trp Asp Leu Pro Val Val
        195                 200                 205

Gly Tyr Arg Asn Gly Val Ala Gln Pro Leu Arg Leu Trp Gln Ala Thr
    210                 215                 220

His Ala His Pro Phe Asp Leu Thr Lys Phe Asn Asp Gly Asp Phe Leu
225                 230                 235                 240
```

-continued

```
Arg Ala Glu Gln Gln Gly Ile Asn Ala Glu Lys Leu Thr Lys Val Leu
                245                 250                 255

Tyr Pro Asn Asp Asn His Thr Ala Gly Lys Lys Leu Arg Leu Met Gln
            260                 265                 270

Gln Tyr Phe Gln Cys Ala Cys Ser Val Ala Asp Ile Leu Arg Arg His
        275                 280                 285

His Leu Ala Gly Arg Glu Leu His Glu Leu Ala Asp Tyr Glu Val Ile
    290                 295                 300

Gln Leu Asn Asp Thr His Pro Thr Ile Ala Ile Pro Glu Leu Leu Arg
305                 310                 315                 320

Val Leu Ile Asp Glu His Gln Met Ser Trp Asp Ala Trp Ala Ile
                325                 330                 335

Thr Ser Lys Thr Phe Ala Tyr Thr Asn His Thr Leu Met Pro Glu Ala
                340                 345                 350

Leu Glu Arg Trp Asp Val Lys Leu Val Lys Gly Leu Leu Pro Arg His
            355                 360                 365

Met Gln Ile Ile Asn Glu Ile Asn Thr Arg Phe Lys Thr Leu Val Glu
    370                 375                 380

Lys Thr Trp Pro Gly Asp Glu Lys Val Trp Ala Lys Leu Ala Val Val
385                 390                 395                 400

His Asp Lys Gln Val His Met Ala Asn Leu Cys Val Val Gly Gly Phe
                405                 410                 415

Ala Val Asn Gly Val Ala Ala Leu His Ser Asp Leu Val Val Lys Asp
            420                 425                 430

Leu Phe Pro Glu Tyr His Gln Leu Trp Pro Asn Lys Phe His Asn Val
        435                 440                 445

Thr Asn Gly Ile Thr Pro Arg Arg Trp Ile Lys Gln Cys Asn Pro Ala
    450                 455                 460

Leu Ala Ala Leu Leu Asp Lys Ser Leu Gln Lys Glu Trp Ala Asn Asp
465                 470                 475                 480

Leu Asp Gln Leu Ile Asn Leu Val Lys Leu Ala Asp Asp Ala Lys Phe
                485                 490                 495

Arg Asp Leu Tyr Arg Val Ile Lys Gln Ala Asn Lys Val Arg Leu Ala
            500                 505                 510

Glu Phe Val Lys Val Arg Thr Gly Ile Asp Ile Asn Pro Gln Ala Ile
        515                 520                 525

Phe Asp Ile Gln Ile Lys Arg Leu His Glu Tyr Lys Arg Gln His Leu
    530                 535                 540

Asn Leu Leu His Ile Leu Ala Leu Tyr Lys Glu Ile Arg Glu Asn Pro
545                 550                 555                 560

Gln Ala Asp Arg Val Pro Arg Val Phe Leu Phe Gly Ala Lys Ala Ala
                565                 570                 575

Pro Gly Tyr Tyr Leu Ala Lys Asn Ile Ile Phe Ala Ile Asn Lys Val
            580                 585                 590

Ala Asp Val Ile Asn Asn Asp Pro Leu Val Gly Asp Lys Leu Lys Val
        595                 600                 605

Val Phe Leu Pro Asp Tyr Cys Val Ser Ala Ala Glu Lys Leu Ile Pro
    610                 615                 620

Ala Ala Asp Ile Ser Glu Gln Ile Ser Thr Ala Gly Lys Glu Ala Ser
625                 630                 635                 640

Gly Thr Gly Asn Met Lys Leu Ala Leu Asn Gly Ala Leu Thr Val Gly
                645                 650                 655

Thr Leu Asp Gly Ala Asn Val Glu Ile Ala Glu Lys Val Gly Glu Glu
```

```
                    660             665             670
Asn Ile Phe Ile Phe Gly His Thr Val Lys Gln Val Lys Ala Ile Leu
                675             680             685
Ala Lys Gly Tyr Asp Pro Val Lys Trp Arg Lys Lys Asp Lys Val Leu
            690             695             700
Asp Ala Val Leu Lys Glu Leu Glu Ser Gly Lys Tyr Ser Asp Gly Asp
705             710             715             720
Lys His Ala Phe Asp Gln Met Leu His Ser Ile Gly Lys Gln Gly Gly
                725             730             735
Asp Pro Tyr Leu Val Met Ala Asp Phe Ala Ala Tyr Val Glu Ala Gln
                740             745             750
Lys Gln Val Asp Val Leu Tyr Arg Asp Gln Glu Ala Trp Thr Arg Ala
                755             760             765
Ala Ile Leu Asn Thr Ala Arg Cys Gly Met Phe Ser Ser Asp Arg Ser
                770             775             780
Ile Arg Asp Tyr Gln Ala Arg Ile Trp Gln Ala Lys Arg
785             790             795

<210> SEQ ID NO 36
<211> LENGTH: 37
<212> TYPE: DNA
<213> ORGANISM: Artificial sequence
<220> FEATURE:
<223> OTHER INFORMATION: sequence of connection portion of plasmid and
      gene

<400> SEQUENCE: 36
acccaaatcg ataggaggaa aacatatgac cttgagt                           37

<210> SEQ ID NO 37
<211> LENGTH: 38
<212> TYPE: DNA
<213> ORGANISM: Artificial sequence
<220> FEATURE:
<223> OTHER INFORMATION: sequence of connection portion of plasmid and
      gene

<400> SEQUENCE: 37
gcataagagg gggaagtgaa tgaaaaggta ccttcggg                          38

<210> SEQ ID NO 38
<211> LENGTH: 41
<212> TYPE: DNA
<213> ORGANISM: Artificial sequence
<220> FEATURE:
<223> OTHER INFORMATION: primer sequence

<400> SEQUENCE: 38
aaatcgatag gaggaaaaca tatgaccttg agtgagaaaa t                      41

<210> SEQ ID NO 39
<211> LENGTH: 29
<212> TYPE: DNA
<213> ORGANISM: Artificial sequence
<220> FEATURE:
<223> OTHER INFORMATION: primer sequence

<400> SEQUENCE: 39
gaaggtacct ttcattcac ttccccctc                                     29

<210> SEQ ID NO 40
<211> LENGTH: 32
```

```
<212> TYPE: DNA
<213> ORGANISM: Artificial sequence
<220> FEATURE:
<223> OTHER INFORMATION: primer sequence

<400> SEQUENCE: 40
ttcggatcct caccttgagt gagaaaattc ac                                    32

<210> SEQ ID NO 41
<211> LENGTH: 29
<212> TYPE: DNA
<213> ORGANISM: Artificial sequence
<220> FEATURE:
<223> OTHER INFORMATION: primer sequence

<400> SEQUENCE: 41
ttcggatcct tttcattcac ttccccctc                                        29

<210> SEQ ID NO 42
<211> LENGTH: 71
<212> TYPE: DNA
<213> ORGANISM: Artificial Sequence
<220> FEATURE:
<223> OTHER INFORMATION: primer sequence

<400> SEQUENCE: 42
aaatcgatag gaggaaaaca tatggcaaac gccaatggaa aagctgcgac tagtttaccg      60
gagaaaatct c                                                          71

<210> SEQ ID NO 43
<211> LENGTH: 59
<212> TYPE: DNA
<213> ORGANISM: Artificial sequence
<220> FEATURE:
<223> OTHER INFORMATION: primer sequence

<400> SEQUENCE: 43
gaaggtacct tagggaacag acaagcctca atgttccaa atctctttgg catactgag        59

<210> SEQ ID NO 44
<211> LENGTH: 9
<212> TYPE: PRT
<213> ORGANISM: Solanum tuberosum

<400> SEQUENCE: 44

His Ala Glu Phe Thr Pro Val Phe Ser
1               5

<210> SEQ ID NO 45
<211> LENGTH: 9
<212> TYPE: PRT
<213> ORGANISM: Oryza sativa

<400> SEQUENCE: 45

His Ala Gln Tyr Ser Pro His Phe Ser
1               5

<210> SEQ ID NO 46
<211> LENGTH: 8
<212> TYPE: PRT
<213> ORGANISM: Solanum tuberosum

<400> SEQUENCE: 46

Ala Leu Gly Asn Gly Gly Leu Gly
1               5
```

```
<210> SEQ ID NO 47
<211> LENGTH: 9
<212> TYPE: PRT
<213> ORGANISM: Solanum tuberosum

<400> SEQUENCE: 47

Arg Ile Val Lys Phe Ile Thr Asp Val
1               5

<210> SEQ ID NO 48
<211> LENGTH: 9
<212> TYPE: PRT
<213> ORGANISM: Oryza sativa

<400> SEQUENCE: 48

Arg Ile Val Lys Leu Val Asn Asp Val
1               5
```

METHOD OF HEAT-STABILIZING α-GLUCAN PHOSPHORYLASE(GP)

TECHNICAL FIELD

The present invention relates to thermostable α-glucan phosphorylase and a gene encoding said thermostable α-glucan phosphorylase. Further, the present invention relates to a method for producing thermostable α-glucan phosphorylase.

BACKGROUND ART

α-glucan phosphorylase (hereinafter, also referred to as GP) is an enzyme utilized in, for example, synthesis of glucose-1-phosphate (hereinafter, also referred to as G-1-P), and glucan synthesis. G-1-P is utilized, for example, as a medical antibacterial agent, an anti-tumor agent (as a platinum complex), a drug for treating heart disease (as an amine salt), or a substrate for glucan synthesis. GP is widely distributed in plants, for example in tubers such as potatoes; animals, for example in rabbit muscle; and microorganisms such as yeast.

Among the above, plant-derived GP is useful because it generally has the ability to synthesize glucans having a high molecular weight.

Various GPs can be used to produce G-1-P or glucans, inter alia, potato-derived GP is used in many cases because a relatively large amount of the enzyme is easily obtained.

In industrial production of G-1-P or a glucan using GP, it is necessary to essentially remove other enzyme activity derived from contamination of GP, particularly, phosphatase activity and amylase activity *Escherichia coli* and *Bacillus subtilis* are desirable hosts to express a GP gene when producing large amounts of GP. However, as shown in FIG. 4 and FIG. 5, *Escherichia coli* has amylase activity and phosphatase activity, and *Bacillus subtilis* has amylase activity. However, as shown in FIGS. 4 and 5, enzymes expressed by these hosts cannot be inactivated by heat treatment at 55° C., but can be almost completely inactivated by heat treatment at 60° C. Therefore, a plant-derived GP having heat resistance whereby it's activity is not lost, even after heat treatment at 60° C., has been desired.

For reference, specific numerical values of amylase activity and phosphatase activity in cell extracts from various bacteria (*Escherichia coli* TG-1 strain, *Escherichia coli* BL21 strain, and *Bacillus subtilis* ANA-1 strain) before and after heating are shown in the following Table 1.

TABLE 1

| | Phosphatase activity (%) | | Amylase activity (%) | | |
|---|---|---|---|---|---|
| | TG-1 | BL21 | TG-1 | BL21 | ANA-1 |
| Before heating | 100 | 100 | 100 | 100 | 100 |
| 50° C. | 99.1 | 98.6 | 21.6 | 28.6 | 33.8 |
| 55° C. | 60.9 | 74.5 | 9.1 | 9.7 | 19.8 |
| 60° C. | 2.9 | 3.1 | 0.4 | 0 | 3.0 |
| 65° C. | 2.5 | 2.0 | 0.9 | 0 | 2.4 |

However, a plant-derived GP which can synthesize high molecular weight glucans, and has thermostability, particularly, GP which can maintain sufficient activity at high temperatures (e.g. 60° C. to 75° C.), is not known. Regarding GP derived from organisms other than plants, GP having high thermostability, GP expressed by extreme thermophilic bacteria (*Thermus aquaticus*, *Thermococcus litoralis*, *Aquifex aeolicus* and the like) has been reported. However, since such the above GP is derived from organisms other than plants, it is unable to synthesize high molecular weight glucans, and is thus less useful.

GPs are classified into two groups based on homology between amino acid sequences, (see Non-Patent Document 1). GP having 30% or more identity to potato-derived GP is classified as being a group A GP, and a GP having less than 30% identity to potato-derived GP and having 30% or more identity to GP of *Thermus aquaticus* is classified a being a group B GP.

A glucan produced using GP derived from *Thermus* belonging to a group B has a considerably lower molecular weight when compared with a glucan produced using potato-derived GP which is classified as a group A GP. For this reason, there is the problem that high molecular weight glucans cannot be obtained using GP derived from *Thermus*.

In order to solve these problems, a plant-derived GP which is advantageous for industrial utilization, and has high thermostability, is required.

Theoretical methods for making a general enzyme more thermostable, such as proline theory and amino acid substitution based on enzyme steric structure information have been tried, but have not necessarily succeeded. For this reason, methods based upon random mutation, or methods using a combination of random mutation and theoretical methodology is currently being carried out. However, in any of these methods, every protein must be characterized by trial and error.

Regarding enzymes other than GP, it has been reported that, once the position of a particular amino acid(s) involved in improving the thermostability of an enzyme is, determined, an enzyme can be made thermostable by substitution of the specified amino acid residue(s) with other amino acid residues (for example see Non-Patent Documents 3 to 5).

An example of GP having improved thermostability has been reported with regard to *Escherichia coli* maltodextrin phosphorylase (see Non-Patent Document 2). In this document, thermostable *Escherichia coli* maltodextrin phosphorylase is disclosed. Maltodextrin phosphorylase is one type of GP. In this GP having improved thermostability, asparagine at position 133 is substituted with alanine. This asparagine at position 133 is present at an active site, and is a binding site for pyridoxal 5'-phosphate which is a coenzyme essential in the enzymatic reaction. In this GP having improved thermostability, thermostability is improved by about 15° C., and the optimal reaction temperature is elevated from about 45° C. to about 60° C., and the GP is denatured at about 67° C., as compared with natural GP. However, this *Escherichia coli* GP, similar to *Thermus*-derived GP, does not have the ability to synthesize high molecular weight glucans h. Further, the enzyme activity at optimal temperatures for the GP having improved thermostability described in this document, is lower than the enzyme activity at an optimal temperature of natural GP. That is, due to mutation, the ability to synthesize a glucan thereof, is lowered. For this reason, this document teaches that substitution at position 133 is not preferable, at least from the viewpoint of glucan synthesizing ability.

Usually, an enzyme protein is unstable, and is sensitive to physical factors such as pH, temperature etc, as well as proteases, and thus may be easily degraded. Among enzymes, there are also enzymes which become more unstable, and therefore easily degraded, at high degrees of purification. For this reason, enzymes must be prepared at as low as possible temperatures, and must be prepared before every use. Degradation of an enzyme can be suppressed by freezing and storing. However, proteins are degraded upon thawing in some cases, and handling is therefore difficult when an enzyme is stored frozen and subsequently thawed. Generally, when an enzyme is degraded, the steric structure changes, and the nature of the enzyme with regard to optimal pH, pH stability, reaction rate, substrate affinity, and the like, similarly changes. Occasionally the enzyme activity is lowered, or inactivated. As such, degradation of an enzyme protein greatly influences enzyme reaction. For this reason, for industries that utilizing enzymes, it is desirable to use enzymes that have excellent stability as far as possible.

It has been known that natural potato type L GP is also easily degraded and, even when purified GP is refrigerated and stored, it gradually degrades from the point of purification. When degradation of a GP protein can be suppressed, it becomes possible to prepare a large amount of GP and store it long term, thus increasing production efficiency, which is a significant advantage in terms of both storage and use of an enzyme. For this reason, it is also preferable to provide GP which can be stored long term, without degradation.

(Non-Patent Document 1)

Takeshi Takaha, et el., "Structure and Properties of *Thermus aqaticus* α-Glucan Phosphorylase Expressed in *Escherichia coli*", J. Appl. Glycosi., 2001, Vol. 48, No. 1, pp. 71-78

(Non-Patent Document 2)

Richard Grieβler, et al., "Mechanism of thermal denaturation of maltodextrin phosphorylase from *Escherichia coli*", Biochem. J., 2000, 346, pp. 255-263

(Non-Patent Document 3)

Martin Lehmann and Markus Wyss, "Engineering proteins for thermostability: the use of sequence alignments versus rational design and directed evolution", Current Opinion in Biotechnology, 2001, 12, pp. 371-375

(Non-Patent Document 4)

M. Lehmann, et al., "The consensus concept for thermostability engineering of proteins", Biochemica Biophysica Acta, 2000, 1543, pp. 408-415

(Non-Patent Document 5)

Junichi Miyazaki, et al., "Ancestral Residues Stabilizing 3-Isopropylmalate Dehydrogenase of an Extreme Thermophile: Experimental Evidence Supporting the Thermophilic Common Ancestor Hypothesis", J. Biochem, 2001, 129, pp. 777-782

DISCLOSURE OF THE INVENTION

Problems to be Solved by the Invention

The present invention intends to solve the aforementioned problems, and an object of the present of invention is to provide a plant-derived α-glucan phosphorylase which has better thermostability than the conventional α-glucan phosphorylase. More particularly, an object of the present invention is to provide a plant-derived α-glucan phosphorylase having excellent storage stability in addition to thermostability.

Means for Solving the Problems

As a result of diligent studies to solve the aforementioned problems, the present inventors found that a plant-derived GP having improved thermostability is obtained by substituting an amino acid residue at a particular position in the amino acid sequence of a plant-derived GP. Based on these findings, the present inventors completed the present invention.

In order to solve the aforementioned problems, the present inventors continued to intensively study and, as a result, finally found that by substituting an amino acid residue in a specific position of the amino acid sequence of a plant derived GP, made the aforementioned discovery, which resulted in completion of the present of invention based thereon.

An α-glucan phosphorylase having, improved thermostability according to the present invention is an α-glucan phosphorylase having improved thermostability which is obtained by modifying a natural α-glucan phosphorylase, wherein the natural α-glucan phosphorylase is derived from a plant, and the α-glucan phosphorylase having improved thermostability has an amino acid residue which is different from that of the natural α-glucan phosphorylase in at least one position selected from the group consisting of:

a position corresponding to position 4 in the motif sequence 1L: H-A-E-F -T-P-V-F-S (SEQ ID NO 44) or a position corresponding to position 4 in the motif sequence 1H: A-A-Q-Y-S-P-H-F-S (SEQ ID NO: 45);

a position corresponding to position 4 in the motif sequence 2: A-L-G-N-G -G-L-G (SEQ ID NO: 46); and a position corresponding to position 7 in the motif sequence 3L: R-I-V-K-F -I-T-D-V (SEQ ID NO: 47) or a position corresponding to position 7 in the motif sequence 3H: R-I-V-K-L-V-N-D-V (SEQ ID NO: 48); and wherein the enzyme activity of the α-glucan phosphorylase having improved thermostability at 37° C., after heating in a 20 mM citrate buffer (pH 6.7) at 60° C. for 10 minutes, is 20% or more of enzyme activity at 37° C. of the α-glucan phosphorylase having improved thermostability before the heating.

In one embodiment, the natural α-glucan phosphorylase can have an amino acid residue which is different from an amino acid residue of the natural α-glucan phosphorylase at a position corresponding to position 4 in the motif sequence 1L; or a position corresponding to position 4 in the motif sequence 1H; or a position corresponding to position 7 in the motif sequence 3L; or a position corresponding to position 7 in the motif sequence 3H.

In one embodiment, the amino acid sequence of a natural α-glucan phosphorylase can have at least 50% identity with an amino acid sequence selected from the group consisting of position 1 to position 916 of SEQ ID NO: 2; position 1 to position 912 of SEQ ID NO: 4; position 1 to position 893 of SEQ ID NO: 6; position 1 to position 939 of SEQ ID NO: 8; position 1 to position 962 of SEQ ID NO: 10; position 1 to position 971 of SEQ ID NO: 12; position 1 to position 983 of SEQ ID NO: 14; position 1 to position 928 of SEQ ID NO: 16; position 1 to position 951 of SEQ ID NO: 18; position 1 to position 832 of SEQ ID NO: 20; position 1 to position 840 of SEQ ID NO: 22; position 1 to position 841 of SEQ ID NO: 24; position 1 to position 842 of SEQ ID NO: 26; position 1 to position 841 of SEQ ID NO: 28; and position 1 to position 838 of SEQ ID NO: 30.

In one embodiment, the amino acid sequence of a natural α-glucan phosphorylase can be encoded by a nucleic acid molecule which hybridizes under stringent conditions to a nucleic acid molecule consisting of a base sequence encoding an amino acid sequence selected from the group consisting of: position 1 to position 916 of SEQ ID NO: 2; position 1 to position 912 of SEQ ID NO: 4; position 1 to position 893 of SEQ ID NO: 6; position 1 to position 939 of SEQ ID NO: 8; position 1 to position 962 of SEQ ID NO: 10, position 1 to position 971 of SEQ ID NO: 12, position 1 to position 983 of SEQ ID NO: 14; position 1 to position 928 of SEQ ID NO: 16; position 1 to position 951 of SEQ ID NO: 18; position 1 to position 832 of SEQ ID NO: 20; position 1 to position 840 of SEQ ID NO: 22; position 1 to position 841 of SEQ ID NO: 24; position 1 to position 842 of SEQ ID NO: 26, position 1 to position 841 of SEQ ID NO: 28; and position 1 to position 838 of SEQ ID NO: 30.

In one embodiment, the natural α-glucan phosphorylase can be a type L α-glucan phosphorylase, and can have an amino acid residue which is different from that of the natural α-glucan phosphorylase in at least one position selected from the group consisting of: a position corresponding to position 4 in the motif sequence 1L; a position corresponding to position 4 in the motif sequence 2; and a position corresponding to position 7 in the motif sequence 3L.

In one embodiment, the natural α-glucan phosphorylase can be type H α-glucan phosphorylase, and can have an amino acid residue which is different from that of the natural α-glucan phosphorylase in at least one position selected from the group consisting of: a position corresponding to position 4 in the motif sequence 1H; a position corresponding to position 4 in the motif sequence 2; and a position corresponding to position 7 in the motif sequence 3H.

In one embodiment, the amino acid sequence of the natural α-glucan phosphorylase can be selected from the group consisting of: position 1 to position 916 of SEQ ID NO: 2; position 1 to position 912 of SEQ ID NO: 4; position 1 to position 893 of SEQ ID NO: 6; position 1 to position 939 of SEQ ID NO: 8; position 1 to position 962 of SEQ ID NO: 10; position 1 to position 971 of SEQ ID NO: 12; position 1 to position 983 of SEQ ID NO: 14; position 1 to position 928 of SEQ ID NO: 16; position 1 to position 951 of SEQ ID NO: 18; position 1 to position 832 of SEQ ID NO: 20; position 1 to position 840 of SEQ ID NO: 22; position 1 to position 841 of SEQ ID NO: 24; position 1 to position 842 of SEQ ID NO: 26; position 1 to position 841 of SEQ ID NO: 28; and position 1 to position 838 of SEQ ID NO: 30.

In one embodiment, the natural α-glucan phosphorylase can be derived from potato or *Arabidopsis thaliana*.

In one embodiment, the α-glucan phosphorylase according to the present invention can have an amino acid residue which is different from the amino acid residue of the natural α-glucan phosphorylase in at least two positions selected from the group consisting of: a position corresponding to position 4 in the motif sequence 1L or a position corresponding to position 4 in the motif sequence 1H; a position corresponding to position 4 in the motif sequence 2, and a position corresponding to position 7 in the motif sequence 3L or a position corresponding to position 7 in the motif sequence 3H.

In one embodiment, a α-glucan phosphorylase according to the present invention can have an amino acid residue which is different from an amino acid residue of a natural α-glucan phosphorylase in a position corresponding to position 4 in the motif sequence 1L or a position corresponding to position 4 in the motif sequence 1H; a position corresponding to position 4 in the motif sequence 2; and a position corresponding to position 7 in the motif sequence 3L or a position corresponding to position 7 in the motif sequence 3H.

In one embodiment, an amino acid residue at a position corresponding to position 4 in the motif sequence 1L or a position corresponding to position 4 in the motif sequence 1H can be selected from the group consisting of I, L and V.

In one embodiment, an amino acid residue at a position corresponding to position 4 in the motif sequence 1L or a position corresponding to position 4 in the motif sequence 1H can be selected from the group consisting of I and L.

In one embodiment, an amino acid residue at a position corresponding to position 4 in the motif sequence 2 can be selected from the group consisting of A, C, D, E, G, H, I, L, M, F, S, T, V and Y.

In one embodiment, an amino acid residue at a position corresponding to position 4 in the motif sequence 2 can be selected from the group consisting of C, G, S and V.

In one embodiment, an amino acid residue at a position corresponding to position 7 in the motif sequence 3L or a position corresponding to position 7 in the motif sequence 3H can be selected from the group consisting of C, I, L, V and W.

In one embodiment, an amino acid residue at a position corresponding to position 7 in the motif sequence 3L or a position corresponding to position 7 in the motif sequence 3H can be selected from the group consisting of C, I, L and V.

In one embodiment, the enzyme activity of the α-glucan phosphorylase having improved thermostability at 37° C., after heating in a 20 mM citrate buffer (pH 6.7) at 60° C. for 10 minutes, can be 30% or more of the enzyme activity of the α-glucan phosphorylase having improved thermostability at 37° C., before heating.

In one embodiment, the enzyme activity of the α-glucan phosphorylase having improved thermostability at 37° C., after heating in a 20 mM citrate buffer (pH 6.7) at 65° C. for 2 minutes, is 10% or more of enzyme activity of the α-glucan phosphorylase having improved thermostability at 37° C., before heating.

In one embodiment, the α-glucan phosphorylase having improved thermostability can have improved storage stability as compared with natural α-glucan phosphorylase.

The method of the invention is a method for producing α-glucan phosphorylase having improved thermostability, comprising:

modifying a first nucleic acid molecule comprising a base sequence encoding a first α-glucan phosphorylase to obtain a second nucleic acid molecule comprising a modified base sequence;

making an expression vector comprising the second nucleic acid molecule;

introducing the expression vector into a cell to express α-glucan phosphorylase having improved thermostability; and recovering the expressed α-glucan phosphorylase having improved thermostability, wherein the first α-glucan phosphorylase is derived from a plant, the α-glucan phosphorylase having improved thermostability has an amino acid residue which is different from an amino acid residue of the first α-glucan phosphorylase in at least one position selected from the group consisting of:

a position corresponding to position 4 in the motif sequence 1L: H-A-E-F -T-P-V-F-S (SEQ ID NO 44) or a position corresponding to position 4 in the motif sequence 1H: H-A-A-Q-Y-S-P-H-F-S (SEQ ID NO: 45);

a position corresponding to position 4 in the motif sequence 2: A-L-G-N-G -G-L-G (SEQ ID NO: 46); and a position corresponding to position 7 in the motif sequence 3L: R-I-V-K-F -I-T-D-V (SEQ ID NO: 47) or a position corresponding to position 7 in the motif sequence 3H: R-I-V-K-L-V-N-D-V (SEQ ID NO: 48);

and wherein the enzyme activity of the α-glucan phosphorylase having improved thermostability at 37° C., after heating in a 20 mM citrate buffer (pH 6.7) at 60° C. for 10 minutes, is 20% or more of the enzyme activity of the α-glucan phosphorylase having improved thermostability at 37° C., before heating.

In one embodiment, an amino acid residue of the α-glucan phosphorylase having improved thermostability at a position corresponding to position 4 in the motif sequence 1L or a position corresponding to position 4 in the motif sequence 1H; or a position corresponding to position 7 in the motif sequence 3L or a position corresponding to position 7 in the motif sequence 3H, can be different from the amino acid residue of the first α-glucan phosphorylase.

In one embodiment, the first α-glucan phosphorylase can be a type L α-glucan phosphorylase, and can have an amino acid residue which is different from that of the natural α-glucan phosphorylase in at least one position selected from the group consisting of: a position corresponding to position 4 in the motif sequence 1L; a position corresponding to position 4 in the motif sequence 2; and a position corresponding to position 7 in the motif sequence 3L.

In one embodiment, the first α-glucan phosphorylase can be a type H α-glucan phosphorylase, and can have an amino acid residue which is different from that of the natural α-glucan phosphorylase in at least one position selected from the group consisting of: a position corresponding to position 4 in the motif sequence 1H; a position corresponding to position 4 in the motif sequence 2; and a position corresponding to position 7 in the motif sequence 3H.

In one embodiment, the first α-glucan phosphorylase can be derived from potato or *Arabidopsis thaliana*.

A nucleic acid molecule of the present invention comprises a base sequence encoding the α-glucan phosphorylase having improved thermostability.

A vector of the present invention comprises the nucleic acid molecule.

A cell of the present invention comprises the nucleic acid molecule.

A method of synthesizing a glucan of the invention comprises reacting a reaction solution containing the α-glucan phosphorylase having improved thermostability, a sucrose phosphorylase, sucrose, a primer, and inorganic phosphoric acid or glucose-1-phosphate to produce a glucan.

In one embodiment, the reaction can be performed at a temperature of 60° C. to 75° C.

Another method of synthesizing a glucan of the invention comprises reacting a reaction solution containing the α-glucan phosphorylase having improved thermostability, a primer, and glucose-1-phosphate to produce a glucan.

In one embodiment, the reaction can be performed at a temperature of 60° C. to 75° C.

A method of synthesizing glucose-1-phosphate of the invention comprises reacting a reaction solution containing α-glucan phosphorylase having improved thermostability according to claim 1, a glucan and inorganic phosphoric acid to produce glucose-1-phosphate.

In one embodiment, the reaction can be performed at a temperature of 60° C. to 75° C.

The α-glucan phosphorylase having improved thermostability according to the present invention is an α-glucan phosphorylase having improved thermostability which is obtained by modifying a plant-derived natural α-glucan phosphorylase, wherein the α-glucan phosphorylase having improved thermostability has an amino acid residue which is different from an amino acid residue of the natural α-glucan phosphorylase at;
    a position corresponding to position 4 in the motif sequence 1L: H-A-E-F -T-P-V-F-S (SEQ ID NO 44) or a position corresponding to position 4 in the motif sequence 1H: H-A-Q-Y-S-P-H-F-S (SEQ ID NO: 45);
    a position corresponding to position 4 in the motif sequence 2: A-L-G-N-G -G-L-G (SEQ ID NO: 46); and
    a position corresponding to position 7 in the motif sequence 3L: R-I-V-K-F -I-T-D-V (SEQ ID NO: 47) or a position corresponding to position 7 in the motif sequence 3H: R-l-V-K-L-V-N-D-V (SEQ ID NO: 48);

wherein the enzyme activity of the α-glucan phosphorylase having improved thermostability at 37° C., after heating in a 20 mM citrate buffer (pH 6.7) at 60° C. for 10 minutes, is 20% or more of enzyme activity of the α-glucan phosphorylase having improved thermostability at 37° C., before heating, and the α-glucan phosphorylase having improved thermostability has the ability to synthesize an amylose having a weight average molecular weight of 600 kDa or more.

Another α-glucan phosphorylase having improved thermostability according to the present invention is an α-glucan phosphorylase having improved thermostability which is obtained by modifying a natural α-glucan phosphorylase, wherein the natural α-glucan phosphorylase is derived from a plant, the α-glucan phosphorylase having improved thermostability has an amino acid residue which is different from that of the natural α-glucan phosphorylase in at least one position selected from the group consisting of: a position corresponding to phenylalanine at position 39 (F39); a position corresponding to asparagine at position 135 (N135); and a position corresponding to threonine at position 706 (T706) of an amino acid sequence of SEQ ID NO: 2; and wherein the enzyme activity of the α-glucan phosphorylase having improved thermostability at 37° C., after heating in a 20 mM citrate buffer (pH 6.7) at 60° C. for 10 minutes, is 20% or more of enzyme activity of the α-glucan phosphorylase having improved thermostability at 37° C., before heating.

In one embodiment, the α-glucan phosphorylase having improved thermostability has an amino acid residue which is different from an amino acid residue of the natural α-glucan phosphorylase at a position corresponding to phenylalanine at position 39 (F39); or a position corresponding to threonine at position 706 (T706) in an amino acid sequence of SEQ ID NO: 2.

In one embodiment, an amino acid sequence of the natural α-glucan phosphorylase has at least 50% identity to an amino acid sequence selected from the group consisting of: position 1 to position 916 of SEQ ID NO: 2; position 1 to position 912 of SEQ ID NO:4; position 1 to position 893 of SEQ ID NO: 6; position 1 to position 939 of SEQ ID NO:8; position 1 to position 962 of SEQ ID NO: 10; position 1 to position 971 of SEQ ID NO:12; position 1 to position 983 of SEQ ID NO: 14; position 1 to position 928 of SEQ ID NO: 16; position 1 to position 951 of SEQ ID NO: 18; position 1 to position 832 of SEQ ID NO:20; position 1 to position 840 of SEQ ID NO: 22; position 1 to position 841 of SEQ ID NO:24; position 1 to position 842 of SEQ ID NO: 26; position 1 to position 841 of SEQ ID NO:28; and position 1 to position 838 of SEQ ID NO: 30.

In one embodiment, the amino acid sequence of the natural α-glucan phosphorylase is encoded by a nucleic acid molecule which hybridizes under stringent condition to a nucleic acid molecule consisting of a base sequence encoding an amino acids sequence selected from the group consisting of: position 1 to position 916 of SEQ ID NO: 2; position 1 to position 912 of SEQ ID NO:4; position 1 to position 893 of SEQ ID NO: 6; position 1 to position 939 of SEQ ID NO:8; position 1 to position 962 of SEQ ID NO: 10; position 1 to position 971 of SEQ ID NO:12; position 1 to position 983 of SEQ ID NO: 14; position 1 to position 928 of SEQ ID NO: 16; position 1 to position 951 of SEQ ID NO: 18; position 1 to position 832 of SEQ ID NO:20; position 1 to position 840 of SEQ ID NO: 22 position 1 to position 841 of SEQ ID NO:24; position 1 to position 842 of SEQ ID NO: 26; position 1 to position 841 of SEQ ID NO:28; and position 1 to position 838 of SEQ ID NO: 30.

In one embodiment, the base sequence is selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO. 25, SEQ ID NO: 27 and SEQ ID NO: 29.

In one embodiment, the natural α-glucan phosphorylase is a type L α-glucan phosphorylase.

In one embodiment, the natural α-glucan phosphorylase is a type H α-glucan phosphorylase.

In one embodiment, an amino acid sequence of the natural α-glucan phosphorylase is selected from the group consisting of: position 1 to position 916 of SEQ ID NO: 2; position 1 to position 912 of SEQ ID NO:4; position 1 to position 893 of SEQ ID NO: 6; position 1 to position 939 of SEQ ID NO:8; position 1 to position 962 of SEQ ID NO: 10; position 1 to position 971 of SEQ ID NO:12; position 1 to position 983 of SEQ ID NO: 14; position 1 to position 928 of SEQ ID NO: 16; position 1 to position 951 SEQ ID NO: 18; position 1 to position 832 of SEQ ID NO:20; position 1 to position 840 of SEQ ID NO: 22; position 1 to position 841 of SEQ ID NO:24; position 1 to position 842 of SEQ ID NO: 26; position 1 to position 841 of SEQ ID NO:28; and position 1 to position 838 of SEQ ID NO: 30.

In one embodiment, the natural α-glucan phosphorylase is derived from potato or *Arabidopsis thaliana*.

In one embodiment, the α-glucan phosphorylase having improved thermostability has an amino acid residue which is different from an amino acid residue of the natural α-glucan phosphorylase in at least two positions selected from the group consisting of: a position corresponding to phenylalanine at position 39 (F39); a position corresponding to asparagine at position 135 (N135); and a position corresponding to threonine at position 706 (T706) in an amino acid sequence of SEQ ID NO: 2.

In one embodiment, the α-glucan phosphorylase having improved thermostability has an amino acid residue which is different from an amino acid residue of the natural α-glucan phosphorylase at a position corresponding to phenylalanine at position 39 (F39); a position corresponding to asparagine at position 135 (N135); and a position corresponding to threonine at position 706 (T706) in an amino acid sequence of SEQ ID NO: 2.

In one embodiment, an amino acid residue at a position corresponding to the F39 is selected from the group consisting of isoleucine, valine and leucine.

In one embodiment, an amino acid residue at a position corresponding to F39 is isoleucine or leucine.

In one embodiment, an amino acid residue at a position corresponding to the N135 is selected from the group consisting of alanine, cysteine, aspartic acid, glutamic acid, glycine, histidine, isoleucine, leucine, methionine, phenylalanine, serine, threonine, valine and tyrosine.

In one embodiment, an amino acid residue at a position corresponding to N135 is cysteine, glycine, serine or valine.

In one embodiment, an amino acid residue at a position corresponding to T706 is selected from the group consisting of cysteine, isoleucine, leucine, valine and tryptophan.

In one embodiment, an amino acid residue at a position corresponding to T706 is cysteine, isoleucine, leucine or valine.

In one embodiment, the enzyme activity of the α-glucan phosphorylase having improved thermostability at 37° C., after heating in a 20 mM citrate buffer (pH 6.7) at 60° C. for 10 minutes, is 30% or more of enzyme activity of the α-glucan phosphorylase having improved thermostability at 37° C., before heating.

In one embodiment, the enzyme activity of the α-glucan phosphorylase having improved thermostability at 37° C., after heating in a 20 mM citrate buffer (pH 6.7) at 65° C. for 2 minutes, is 10% or more of enzyme activity of the α-glucan phosphorylase having improved thermostability at 37° C., before heating.

A method for producing an α-glucan phosphorylase having improved thermostability according to the present invention comprises modifying a first nucleic acid molecule comprising a base sequence encoding first α-glucan phosphorylase to obtain a second nucleic acid molecule comprising a modified base sequence; preparing an expression vector comprising the second nucleic acid molecule; introducing the expression vector into a cell to express an α-glucan phosphorylase having improved thermostability, and recovering the expressed α-glucan phosphorylase having improved thermostability, wherein the first α-glucan phosphorylase is derived from a plant, the α-glucan phosphorylase having improved thermostability has an amino acid residue which is different from an amino acid residue of the first α-glucan phosphorylase in at least one position selected from the group consisting of a position corresponding to phenylalanine at position 39 (F39), a position corresponding to asparagine at position 135 (N135) and a position corresponding to threonine at position 706 (T706) in the amino acid sequence set forth in SEQ ID NO: 2, and wherein the enzyme activity of the α-glucan phosphorylase having improved thermostability at 37° C., after heating in a 20 mM citrate buffer (pH 6.7) at 60° C. for 10 minutes, is 20% or more of enzyme activity at 37° C. of the α-glucan phosphorylase having improved thermostability at 37° C., before heating.

In one embodiment, an amino acid residue of the α-glucan phosphorylase having improved thermostability at a position corresponding to phenylalanine at position 39 (F39); or a position corresponding to threonine at position 706 (T706); in the amino acid sequence offset forth in SEQ ID NO: 2, is different from an amino acid residue of the first α-glucan phosphorylase.

In one embodiment, the first α-glucan phosphorylase is a type L α-glucan phosphorylase.

In one embodiment, the first α-glucan phosphorylase is a type H α-glucan phosphorylase.

In one embodiment, the first α-glucan phosphorylase is derived from potato or *Arabidopsis thaliana*.

A nucleic acid molecule of the present invention comprises abase sequence encoding the α-glucan phosphorylase having improved thermostability.

A vector of the present invention comprises the nucleic acid molecule.

A cell of the present invention comprises the nucleic acid molecule.

A method of synthesizing a glucan of the present invention comprises reacting a reaction solution containing the α-glucan phosphorylase having improved thermostability, a sucrose phosphorylase, sucrose, a primer, inorganic phosphoric acid or glucose-1-phosphate to produce a glucan.

In one embodiment, the reaction is performed at a temperature of 60° C. to 75° C.

A method of synthesizing a glucan of the present invention comprises reacting a reaction solution containing the α-glucan phosphorylase having improved thermostability, a primer, and glucose-1-phosphate.

In one embodiment, the reaction is performed at a temperature of 60° C. to 75° C.

A method of synthesizing glucose-1-phosphate of the present invention comprises reacting a reaction solution containing the α-glucan phosphorylase having improved thermostability, a glucan and inorganic phosphoric acid to produce glucose-1-phosphate.

In one embodiment, the reaction is performed at a temperature of 60° C. to 75° C.

An α-glucan phosphorylase having improved thermostability according to the present invention is an α-glucan phosphorylase having improved thermostability obtained by modifying a plant-derived natural α-glucan phosphorylase, wherein the α-glucan phosphorylase having improved thermostability has an amino acid residue which is different from an amino acid residue of the natural α-glucan phosphorylase in at least one position selected from the group consisting of: a position corresponding to phenylalanine at position 39 (F39); a position corresponding to asparagine at position 135 (N135); and a position corresponding to threonine at position 706 (T706) in the amino acid sequence offset forth in SEQ ID NO: 2, wherein the enzyme activity of α-glucan phosphorylase having improved thermostability at 37° C., after heating in a 20 mM citrate buffer (pH 6.7) at 60° C. for 10 minutes, is 20% or more of enzyme activity of α-glucan phosphorylase having improved thermostability at 37° C., before heating, and the α-glucan phosphorylase having improved thermostability has the ability to synthesize amylase having an weight average molecular weight of 600 kDa or more.

EFFECT OF THE INVENTION

According to the present invention, a plant-derived GP enzyme having excellent thermostability at high temperatures, (e.g. 60° C. or higher) was obtained.

According to the α-glucan phosphorylase having improved thermostability of the present invention, a glucan synthesizing reaction is possible at high temperature conditions (e.g. 60° C. or higher), under which natural GP enzymes cannot react.

The claimed invention attains the advantage that, when a gene encoding the α-glucan phosphorylase having improved thermostability of the present invention (e.g. a gene encoding GP having improved thermostability, obtained by improving thermostability of potato-derived GP) is highly expressed in mesophilic bacterium host, such as *Escherichia coli*, contaminating enzymes derived from the host bacterium can be simply removed by heating the bacterial cell extract containing an enzyme having improved thermostability at 60° C. according to the present invention. In particular, amylase activity and phosphatase activity, which pose great problems during industrial utilization of GP enzymes, can be considerably reduced by heat treatment. Therefore, the method of the present invention is advantageous in terms of enzyme purification.

The method of the present invention is effective not only in potato-derived GP and *Arabidopsis thaliana*-derived GP, but can also be suitably applied to improving the thermostability of other group A GP, exhibiting high homology to an amino acid sequence of potato-derived GP or *Arabidopsis thaliana*-derived GP.

Therefore, other organism-derived GP having improved thermostability which has an amino acid residue which is different from that of a natural α-glucan phosphorylase in at least one position selected from the group consisting of:

a position corresponding to position 4 in the motif sequence 1L: H-A-E-F -T-P-V-F-S (SEQ ID NO 44) or a position corresponding to position 4 in the motif sequence 1H: H-A-Q-Y-S-P-H-F-S (SEQ ID NO: 45);

a position corresponding to position 4 in the motif sequence 2: A-L-G-N-G -G-L-G (SEQ ID NO: 46); and a position corresponding to position 7 in the motif sequence 3L: R-l-V-K-F -I-T-D-V (SEQ ID NO: 47) or a position corresponding to position 7 in the motif sequence 3H: R-I-V-K-L-V-N-D-V (SEQ ID NO: 48) can be obtained.

Other organism-derived GP having improved thermostability can be obtained, which have an amino acid residue which is different from an amino acid residue of a natural α-glucan phosphorylase in at least one position selected from the group consisting of: a position corresponding to phenylalanine at position 39 (F39); a position corresponding to asparagine at position 135 (N135); and a position corresponding to threonine at position 706 (T706) in an amino acid sequence of SEQ ID NO: 2.

According to the present invention, GP having improved thermostability which has improved storage stability is also provided.

BRIEF DESCRIPTION OF THE DRAWINGS

FIG. 1A: FIG. 1A is a view showing the amino acid sequences of α-glucan phosphorylases derived from various plants, which were aligned using multiple alignment of GENETYX-Win Ver.4.0.

FIG. 1B: FIG. 1B is a continuation view from FIG. 1A. Positions of motif sequences 1 and 2 are shown.

FIG. 1C: FIG. 1C is a continuation view from FIG. 1B.

FIG. 1D: FIG. 1D is a continuation view from FIG. 1C.

FIG. 1E: FIG. 1E is a continuation view from FIG. 1D.

FIG. 1F: FIG. 1F is a continuation view from FIG. 1E.

FIG. 1G: FIG. 1G is a continuation view from FIG. 1F. The position of motif sequence 3 is shown.

FIG. 1H: FIG. 1H is a continuation view from FIG. 1G.

FIG. 1I: FIG. 1I is a continuation view from FIG. 1H.

FIG. 2: FIG. 2 is a schematic view of an insertion site of an α-glucan phosphorylase gene in a plasmid.

FIG. 3 is a graph showing remaining enzymatic activity (%) when various α-glucan phosphorylases having improved thermostability are incubated at 60° C. for 30 minutes or at 65° C. for 2 minutes.

FIG. 4 is a graph showing remaining enzymatic activity (%) of phosphatase after various bacteria (*Escherichia coli* TG-1 and *Escherichia coli* BL21) are heated at 50° C., 55° C., 60° C. or 65° C. for 30 minutes.

FIG. 5 is a graph showing remaining enzymatic activity (%) of amylase after various bacteria (*Escherichia coli* TG-1, *Escherichia coli* BL21 and *Bacillus subtilis* ANA-1) are heated at 50° C., 55° C., 60° C. or 65° C. for 30 minutes.

FIG. 6 is a graph showing a change in specific enzymatic activity over time of a GP enzyme having improved thermostability (triple mutant (F39L+N135S+T706I)), and a natural potato type L GP enzyme.

FIG. 7 is a graph showing the amount of amylose synthesized when a GP enzyme having improved thermostability (triple mutant (F39L+N135S+T706I)) and a natural potato type L GP enzyme are retained at 37° C., 50° C., 55° C. or 60° C. for 18 hours.

FIG. 8 is a graph showing remaining activity after natural potato type L GP and GPs, substituted with various amino acids at F39, are incubated at 60° C. for 10 minutes or at 65° C. for 2 minutes.

FIG. 9 is a graph showing remaining activity after natural potato type L GP and GPs, substituted with various amino acids at N135, are incubated at 60° C. for 10 minutes or at 65° C. for 2 minutes.

FIG. 10 is a graph showing remaining activity after natural potato type L GP and GPs, substituted with various amino acids at T706, are incubated at 60° C. for 10 minutes or at 65° C. for 2 minutes.

FIG. 11 is a graph showing remaining activity after natural potato type H GP and triple mutant (Y36L+N133S+T628I) potato type H GP are incubated at 58° C. for 10 minutes, 60° C. for 10 minutes or at 65° C. for 2 minutes.

FIG. 12 is a graph showing remaining enzymatic activity after natural Arabidopsis thaliana type H GP and triple mutant (Y40L+N136S+N631I) Arabidopsis thaliana type H GP are incubated at 58° C. for 10 minutes, at 60° C. for 10 minutes or at 65° C. for 2 minutes.

FIG. 13: FIG. 13 is a polyacrylamide gel electrophoresis photograph, showing the molecular weights of natural potato type L GP and seven kinds of GPs having improved thermostability immediately after purification and after storage at 4° C. for 5 months. Lane 1 indicates natural potato type L (Wild type) GP, lane 2 indicates F39L GP, lane 3 indicates N135S GP, lane 4 indicates T706I GP, lane 5 indicates F39L+N135S GP, lane 6 indicates F39L+T706I GP, lane 7 indicates N135S+T706I GP, and lane 8 indicates F39L+N135S+T706I GP.

BESTS MODE FOR CARRYING OUT THE INVENTION

Figure 3:
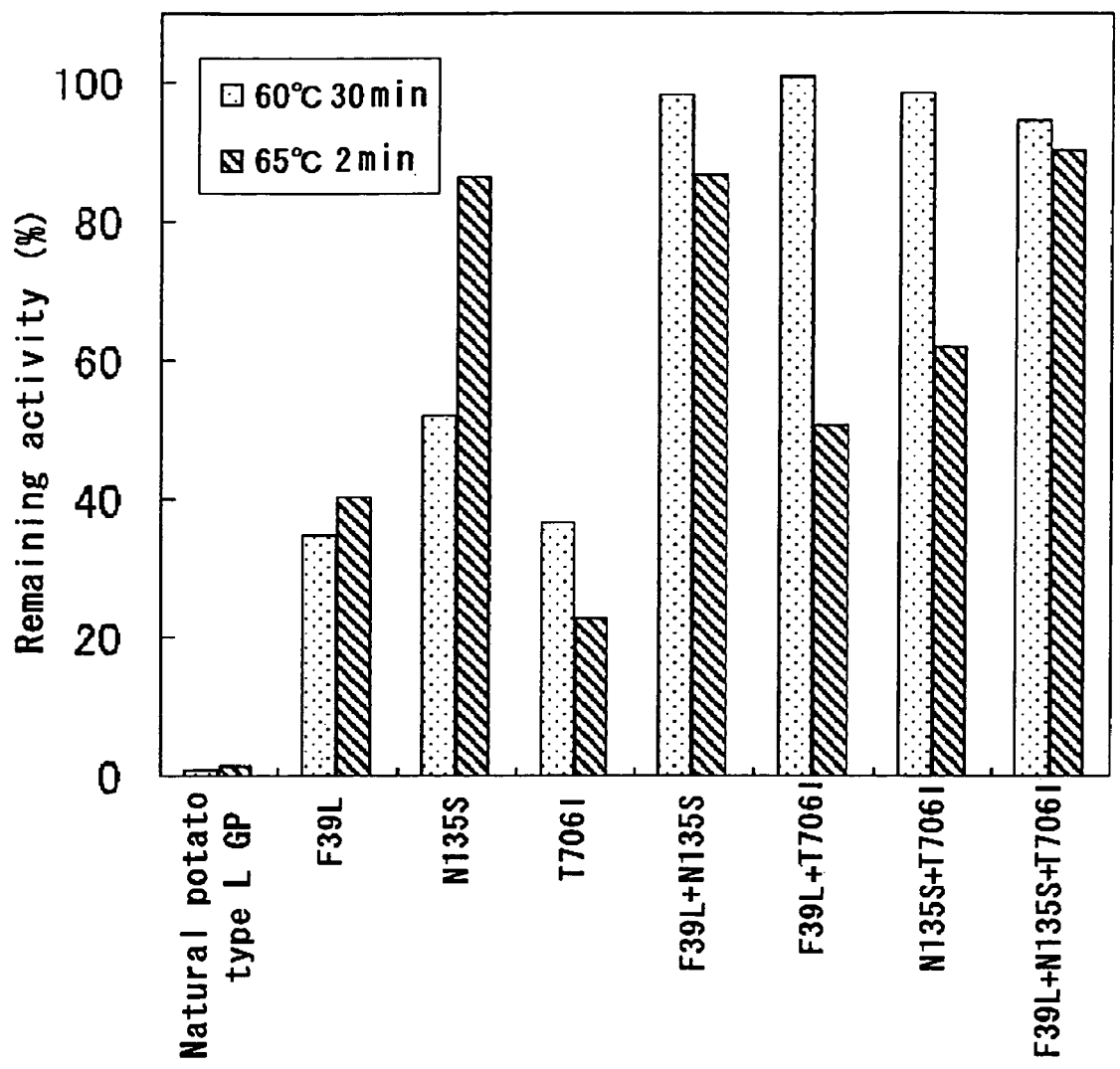
FIG. 3.
Figure 4:
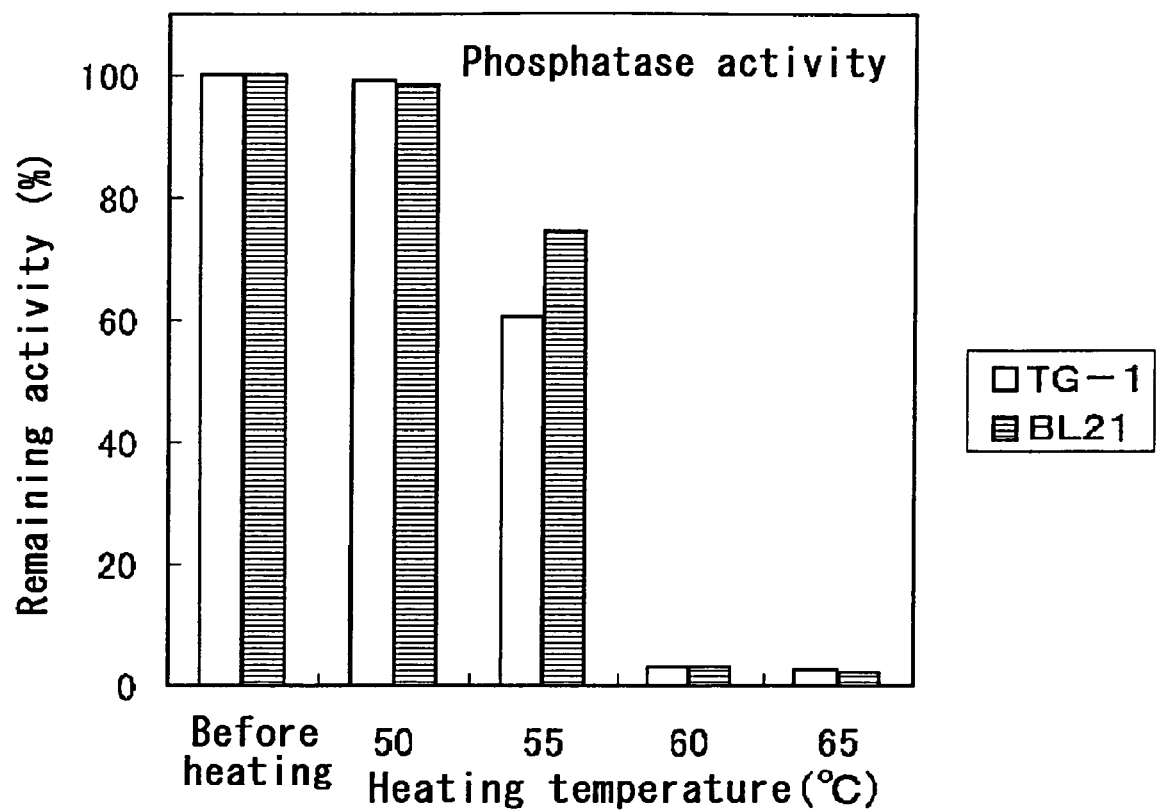
FIG. 4.
Figure 5:
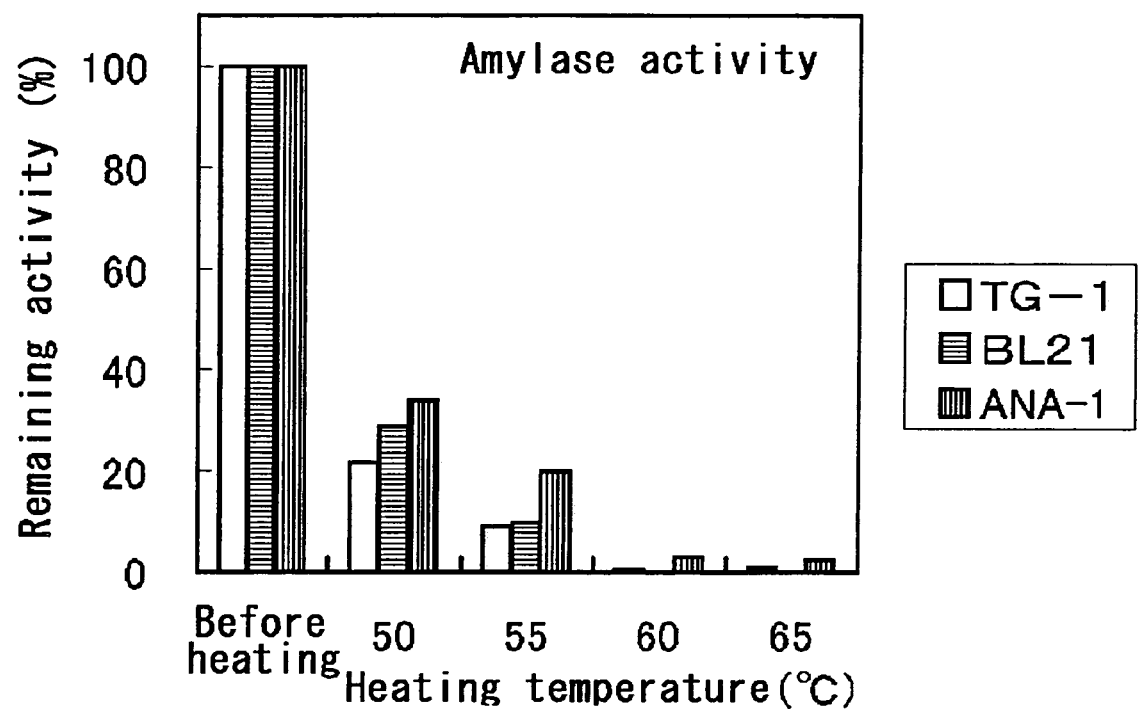
FIG. 5.

The present invention will be explained below. It should be understood that throughout the present specification, terms used in the present specification are used so as to have the meanings normally used in the art, unless otherwise specifically indicated.

(1. α-Glucan Phosphorylase)

In the present specification, "α-glucan phosphorylase" and "GP" are used exchangeably unless otherwise specifically indicated, and mean an enzyme having α-glucan phosphorylase activity. α-glucan phosphorylase is classified into EC2.4.1.1. α-glucan phosphorylase activity refers to the activity of catalyzing a reaction making glucose-1-phosphate and a partial degradation product of α-1,4-glucan from inorganic phosphoric acid and α-1,4-glucan, or a reverse reaction thereof. α-glucan phosphorylase is called phosphorylase, starch phosphorylase, glycogen phosphorylase, maltodextrin phosphorylase, and the like, in some cases. α-glucan phosphorylase can also catalyze a α-1,4-glucan synthesis reaction which is the reverse reaction of phosphorolysis. In which direction any particular reaction progresses depend on the amount of a substrate. In vivo, since the amount of inorganic phosphoric acid is large, the reaction of glucan phosphorylase proceeds towards the direction of phosphorolysis. When the amount of inorganic phosphoric acid is small, the reaction proceeds towards the synthesis of α-1,4-glucan.

It seems that all known α-glucan phosphorylases need pyridoxal 5'-phosphate for activation, and share a similar catalytic mechanism. Although enzymes derived from different origins are different with respect to preference of substrate and form of regulation, all α-glucan phosphorylases belong to a large group including many α-glucan phosphorylases. This large group includes glycogen phosphorylase derived from bacteria, yeast and animals, starch phosphorylase derived from plants, and maltodextrin phosphorylase derived from bacteria.

It has been reported that a minimum primer molecule for a glucan synthesis reaction of α-glucan phosphorylase is maltotetraose. It has been also reported that a minimum substrate effective for a glucan degradation reaction is maltopentaose. Generally, it has been thought that these are characteristics common to α-glucan phosphorylases. However, in recent years, it has been reported that α-glucan phosphorylase derived from *Thermus thermophilus* and α-glucan phosphorylase derived from *Thermococcus litoralis* have different substrate specificity from that of other α-glucan phosphorylases. Regarding these α-glucan phosphorylases, a minimum primer for glucan synthesis is maltotriose, and a minimum substrate for glucan degradation is maltotetraose.

It is thought that α-glucan phosphorylase is ubiquitously present in various plants, animals and bacteria which can store starch or glycogen.

Examples of a plant producing α-glucan phosphorylase include root and tuber crops such as potatoes (also referred to as Irish potato), sweet potatoes, yam, taro, and cassava; vegetables such as cabbage, and spinach; cereals such as corn, rice, wheat, barley, rye, and foxtail millet; beans such as Fava beans, peas, soybeans, adzuki beans, and mottled kidney beans; experimental plants such as *Arabidopsis thaliana*; Citrus hybrid cultivar, algae, and the like.

An organism producing α-glucan phosphorylase is not limited to the above examples.

It is preferable that a first α-glucan phosphorylase used in the method of the present invention is a natural α-glucan phosphorylase, and is derived from a plant. Generally, natural α-glucan phosphorylase derived from a plant has the ability to synthesize amylose having a high molecular weight. However, the thermostability of these α-glucan phosphorylases is low. For this reason, they cannot catalyse reactions at high temperatures (e.g. about 60° C. or higher). For this reason, when a reaction is performed at about 30° C. to about 40° C., which is the optimal reaction temperature of GP derived from plants (e.g. potato), the problem of contamination with various microbes or aging of the glucan arises, and glucan or G-1-P can not be effectively produced.

Plant α-glucan phosphorylases are classified into types L and type H, depending on their affinity for glycogen. Type L α-glucan phosphorylase refers to α-glucan phosphorylases having a low affinity for glycogen. Generally, type L α-glucan phosphorylases prefer maltodextrin, amylase and amylopectin over glycogen as a substrate (Hiroyuki Mori, et al., "A Chimeric α-Glucan phosphorylase of Plant Type L and H Isozymes", The Journal of Biological Chemistry, 1993, vol. 268, No. 8, pp. 5574-5581). Type H α-glucan phosphorylase refers to α-glucan phosphorylases having high affinity for glycogen. Generally, type H α-glucan phosphorylases have extremely high affinity for various glucans, including glycogen.

For example, according to Toshio Fukui, et al., Biochemistry of Vitamin B6, 1987, pp.267-276, the Km (Michaelis constant) of potato leaf-derived type L α-glucan phosphorylase for glycogen is $1.4 \times 10^{-3}$(M), while the Km of potato leaf-derived type H α-glucan phosphorylase for production of glycogen is $4 \times 10^{-6}$(M). In addition, the Km of a main component of potato tuber-derived α-glucan phosphorylase for production of glycogen is $2.4 \times 10^{-3}$(M), and this is classified as type L. The Km of a minor component α-glucan phosphorylase for production of glycogen is $1 \times 10^{-6}$(M), and this is classified as type H.

As known in the art, the Michaelis constant is one of the kinetic parameters determined from the dependency of an initial rate in an enzymatic reaction on substrate concentration. The Michaelis constant is the substrate concentration at a time when the initial rate becomes ½ the maximum rate, $V_{max}$. The Michaelis constant has the units of concentration. The Michaelis constant is peculiar to a enzyme under a specific set of measurement conditions. This constant is a measure indicating the affinity of an enzyme for a substrate. As a Michaelis constant becomes smaller, affinity for a substrate becomes greater.

Type L α-glucan phosphorylase and type H α-glucan phosphorylase have, for example, the following difference in properties.

TABLE 2

|  | Type L GP | Type H GP |
|---|---|---|
| Cross reactivity of antibody to a main component of potato tuber-derived GP | Presence | Absence |
| Cross reactivity of antibody to a minor component of potato tuber-derived GP | Absence | Presence |
| Sensitivity to proteolysis | High | Low |
| Location | Plastid (amyloplast or chloroplast) | Cytosol |

In a particular embodiment, it is further preferable that an α-glucan phosphorylase used in the method according to the present invention is a type L α-glucan phosphorylase. Potato Type L α-glucan phosphorylase is longer than potato type H glucan phosphorylase, and comprises an amino acid sequence of 78 residues not seen in type H, inserted into a central region of the polypeptide chain. For this reason, for example, the molecular weight of a subunit of potato leaf-derived type L α-glucan phosphorylase is about 104,000 Da, and the molecular weight of a subunit of potato leaf-derived type H α-glucan phosphorylase is about 94,000 Da. The molecular weight of a subunit of a main component of potato tuber-derived α-glucan phosphorylase is about 104,000 Da, and the molecular weight of a subunit of a minor component of potato tuber-derived α-glucan phosphorylase is about 94,000 Da. Whether a particular α-glucan phosphorylase is type L or type H can be determined by the presence of a region homologous with this amino acid sequence of 78 residues, without actually measuring affinity.

Generally, type L and type H are determined by comprehensively reviewing a number of properties such as enzyme activity, molecular weight, substrate specificity, location of enzyme, homology of a primary sequence, and the presence of an inserted sequence. Therefore, generally, a boundary between type L and type H is not clear in some cases, but for convenience, in the present invention, whether α-glucan phosphorylase is a type L or type H can be determined by the presence of a transit peptide in α-glucan phosphorylase. The characteristics of a transit peptide sequence are known in the art. Sequences that encode a transit peptide are type L, and sequences that do not encode a transit peptide are type H.

Examples of plants producing type L α-glucan phosphorylase include potatoes (also refers to as Irish potatoes), sweet potatoes, Fava beans, *Arabidopsis thaliana*, spinach, corn and rice.

In another embodiment, a first (natural) α-glucan phosphorylase used in the method of the present invention is preferably a type H α-glucan phosphorylase. Examples of plants producing type H α-glucan phosphorylase include potatoes, wheat, Citrus hybrid cultivar, rice, Fava beans, *Arabidopsis thaliana*, and sweet potatoes.

The cDNA sequence of a natural type L α-glucan phosphorylase, derived from potato, is set forth in SEQ ID NO: 1, and the amino acid sequence encoded thereby is set forth in position 1 to position 916 of SEQ ID NO: 2.

The cDNA sequence of a natural type L α-glucan phosphorylase, derived from sweet potato, is set forth in SEQ ID NO: 3, and the amino acid sequence encoded thereby is set forth in position 1 to position 912 of SEQ ID NO: 4.

The cDNA sequence of another natural type L α-glucan phosphorylase, derived from potato, is set forth in SEQ ID NO: 5, and the amino acid sequence encoded thereby is set forth in position 1 to position 893 of SEQ ID NO: 6.

A cDNA sequence of a natural type L α-glucan phosphorylase, derived from Fava bean, is set forth in SEQ ID NO: 7, and the amino acid sequence encoded thereby is set forth in position 1 to position 939 of SEQ ID NO: 8.

The cDNA sequence of a natural type L α-glucan phosphorylase, derived from of *Arabidopsis thaliana*, is set forth in SEQ ID NO: 9, and the amino acid sequence encoded thereby is set forth in position 1 to position 962 of SEQ ID NO: 10.

The cDNA sequence of a natural type L α-glucan phosphorylase, derived from spinach, is set forth in SEQ ID NO: 11, and the amino acid sequence encoded thereby is set forth in position 1 to position 971 of SEQ ID NO: 12.

The cDNA sequence of a natural type L α-glucan phosphorylase, derived from corn is set forth in SEQ ID NO: 13, and the amino acid sequence encoded thereby is set forth in position 1 to position 983 of SEQ ID NO: 14.

The cDNA sequence of a natural type L α-glucan phosphorylase, derived from rice, is set forth in SEQ ID NO: 15, and the amino acid sequence encoded thereby is set forth in position 1 to position 928 of SEQ ID NO: 16.

The cDNA sequence of another natural type L α-glucan phosphorylase, derived from rice, is set forth in SEQ ID NO: 17, and the amino acid sequence encoded thereby is set forth in position 1 to position 951 of SEQ ID NO: 18.

The cDNA sequence of a natural type H α-glucan phosphorylase, derived from wheat, is set forth in SEQ ID NO: 19, and the amino acid sequence encoded thereby is set forth in position 1 to position 832 of SEQ ID NO: 20.

The cDNA sequence of a natural type H α-glucan phosphorylase, derived from a Citrus hybrid cultivar, is set forth in SEQ ID NO: 21, and the amino acid sequence encoded thereby is set forth in position 1 to position 840 of SEQ ID NO: 22.

The cDNA sequence of a natural type H α-glucan phosphorylase, derived from rice, is set forth in SEQ ID NO: 23, and the amino acid sequence encoded thereby is set forth in position 1 to position 841 of SEQ ID NO: 24.

The cDNA sequence of a natural type H α-glucan phosphorylase, derived from Fava bean, is set forth in SEQ ID NO: 25, and the amino acid sequence encoded thereby is set forth in position 1 to position 842 of SEQ ID NO: 26.

The cDNA sequence of a natural type H α-glucan phosphorylase, derived from *Arabidopsis thaliana*, is set forth in SEQ ID NO: 27, and the amino acid sequence encoded thereby is set forth in position 1 to position 841 of SEQ ID NO: 28.

The cDNA sequence of a natural type H α-glucan phosphorylase, derived from potato is set forth in SEQ ID NO: 29, and the amino acid sequence encoded thereby is set forth in position 1 to position 838 of SEQ ID NO: 30.

The partial sequence of a cDNA of a natural type H α-glucan phosphorylase, derived from sweet potato is set forth in SEQ ID NO: 31, and the amino acid sequence encoded thereby is set forth in SEQ ID NO: 32. A complete sequence of a natural type H α-glucan phosphorylase, derived from sweet potato, can be obtained by conventional methods using this partial sequence.

A first (natural) α-glucan phosphorylase used in the method according to the present invention is preferably derived from a plant, and is preferably derived from potato, sweet potato, Fava bean, *Arabidopsis thaliana*, spinach, corn, rice, wheat or a Citrus hybrid cultivar, is more preferably derived from potato, sweet potato, Fava bean, *Arabidopsis thaliana*, spinach, corn or rice, and is most preferably derived from potato. It is preferable that the first (natural) α-glucan phosphorylase used in the method according to the present invention is a type L α-glucan phosphorylase. The first (natural) α-glucan phosphorylase used in the method of the present invention is preferably an α-glucan phosphorylase of type L, L2 or H derived from potato, type L or H derived from sweet potato, type L or H derived from Fava bean, type L or H derived from *Arabidopsis thaliana*, type L derived from spinach, type L derived from corn, type L or H derived from rice, type H derived from wheat, or type H derived from a Citrus hybrid cultivar, is more preferably α-glucan phosphorylase of type L or L2 derived from potato, type L derived from sweet potato, type L derived from Fava bean, type L derived from *Arabidopsis thaliana*, type L derived from spinach, type L derived from corn, or type L derived from rice, and is most preferably α-glucan phosphorylase of type L derived from potato.

In the present specification, an enzyme "derived from" an organism, means not only that the enzyme is directly isolated from the organism, but also refers to an enzyme obtained by utilizing the organism in any form. For example, when a gene encoding an enzyme obtained from an organism is introduced into *Escherichia coli*, and the expressed enzyme is subsequently isolated from *Escherichia coli*, the enzyme is referred to as being "derived from" the organism.

A gene encoding potato-derived type L GP can be prepared, for example, by the following procedure.

Firstly, as described by Takaha et al. (Journal of Biological Chemistry, Vol. 268, pp. 1391-1396, 1993), an mRNA is prepared from a potato tuber using well-known methods, and a cDNA library is prepared using a commercially available kit, and the like.

Then, based on the known GP gene sequence (database GenBank accession number D00520), PCR primers are prepared, and PCR is performed using the aforementioned cDNA library as a template. For example, when:

```
PCR primer 1:                           (SEQ ID NO: 38)
5'AAATCGATAGGAGGAAAACAT ATG ACC TTG AGT GAG
AAA AT 3' and

PCR primer 2:                           (SEQ ID NO: 39)
5'GAAGGTACCTTTTCATTCACTTCCCCCTC3'
``` are used as PCR primers, a gene can be amplified under the following conditions.

30 cycles of a PCR reaction is performed, one cycle being 30 seconds at 94° C., 1 minute at 50° C., and 3 minutes at 72° C.

The underlined portion of the PCR primer 1 corresponds to a structural gene sequence at the N-terminal region of a type L GP mature protein, and the underlined portion of the PCR primer 2 corresponds to the base sequence immediately after the termination codon of a type L GP structural gene.

Alternatively, a GP gene can be also prepared directly by chemical synthesis, based on the known GP gene sequence information, without preparation of a cDNA library. A method of synthesizing a gene is described, for example, in Te'o, et al. (FEMS Microbiological Letters, vol. 190, pp. 13-19, 2000).

The resulting GP gene can be inserted into a suitable vector by methods well-known to those skilled in the art. For example, as a vector for *Escherichia coli*, pMW118 (manufactured by Nippon Gene Co., Ltd.), pUC18 (manufactured by TAKARA BIO), pKK233-2 (manufactured by Amersham-Pharmacia-Biotech), pET3d (manufactured by STRATAGENE) and the like, can be used and, as a vector for *Bacillus subtilis*, pUB110 (which can be purchased from American Type Culture Collection), and pHY300PLK (manufactured by TAKARABIO) and the like, can be used.

For example, when a gene is amplified using PCR primers 1 and 2, a plasmid having a sequence shown in FIG. 2 can be selected by inserting the amplified gene into plasmid pMW118 which has been cut with SmaI in advance. This is used to transform, for example, *Escherichia coli* TG-1, an ampicillin resistant strain is then selected, and the resulting recombinant plasmid-harboring strain is cultured, and by extracting a plasmid, a GP gene can thereby be obtained.

(2. Improving the Thermostability of α-Glucan Phosphorylase)

A method according to the present invention includes modifying a first nucleic acid molecule comprising a base sequence encoding a first α-glucan phosphorylase to obtain a second nucleic acid molecule containing a modified base sequence; preparing an expression vector comprising the second nucleic acid molecule; introducing the expression vector into a cell, to express an α-glucan phosphorylase having improved thermostability; and recovering the expressed α-glucan phosphorylase having improved thermostability.

(2.1 Isolation of Nucleic Acid Molecule Comprising Base Sequence Encoding First (Natural) α-Glucan Phosphorylase)

A nucleic acid molecule comprising a base sequence encoding α-glucan phosphorylase having improved thermostability according to the present invention is also within the scope of the present invention. Such a nucleic acid molecule can be obtained by using methods known in the art, based on the disclosure of the present specification.

A nucleic acid molecule comprising a base sequence encoding natural α-glucan phosphorylase can be isolated directly from a plant producing a naturally occurring α-glucan phosphorylase, as described above.

For example, firstly, natural α-glucan phosphorylase is isolated from potato, *Arabidopsis thaliana*, spinach or the like. To exemplify a procedure for potato-derived α-glucan phosphorylase, firstly, 1.4 kg of commercially available potato tubers are peeled. The tuber, a skin of which has been removed, is mashed in a juicer to obtain a fluid mash. Then, this fluid mash is filtered with a gauge to obtain a filtrate. To the filtrate is added a Tris buffer (pH 7.0) to a final concentration of 100 mM, to obtain an enzyme solution. This enzyme solution is further heated in a water bath at 55° C. for further 10 minutes, after which the liquid temperature reaches 50° C. After heating, this enzyme solution is centrifuged at 8,500 rpm for 20 minutes using a centrifuge (AVANTI J-25I manufactured by BECKMANN) to remove insoluble proteins, and thus obtaining a supernatant.

Ammonium sulfate is added to the supernatant to a final concentration of 100 g/L, and this is allowed to stand at 4° C. for 2 hours to precipitate proteins. Then, a centrifuge (AVANTI J-25I manufactured by BECKMANN) is used to centrifuge the solution at 8,500 rpm for 20 minutes, to remove insoluble proteins. Further, ammonium sulfate is added to the resulting supernatant to a final concentration of 250 g/L, and this is allowed to stand at 4° C. for 2 hours to precipitate proteins. Then, a centrifuge (AVANTI J-25I manufactured by BECKMANN) is used to centrifuge the solution at 8,500 rpm for 20 minutes, to recover insoluble proteins.

The recovered insoluble proteins are suspended in 150 ml of 25 mM Tris buffer (pH 7.0). The suspended enzyme solution is dialyzed overnight against the same buffer. The sample after dialysis is adsorbed onto an anion exchange resin Q-Sepharose (manufactured by Pharmacia) which has been pre-equilibrated, and they washed with a buffer containing 200 mM sodium chloride. Subsequently, the proteins are eluted with a buffer containing 400 mM sodium chloride, and the eluate is recovered to obtain a partially purified potato tuber-derived glucan phosphorylase-containing solution.

Depending on the purchased potato, an α-glucan phosphorylase-containing solution obtained at this stage, can be used in trypsin treatment, but further purification is necessary in some cases. In such cases, if necessary, the purified potato α-glucan phosphorylase-containing solution can be obtained by combining a fraction from gel filtration chromatography using, for example, Sephacryl S-200HR (manufactured by Pharmacia), and a fraction from hydrophobic chromatography using, for example, Phenyl-TOYOPEARL650M (manufactured by Tosoh Corporation). Purification of α-glucan phosphorylase from other plant species can be performed similarly.

The thus obtained purified α-glucan phosphorylase is treated with trypsin, the resulting trypsin treated fragment is separated by HPLC, and the amino acid sequence of the N-terminus of each of the separated peptide fragments is determined using a peptide sequencer. Then, using synthetic oligonucleotide probes prepared based on the identified amino acid sequence, a suitable genome library or a cDNA library is screened, thereby, a nucleic acid molecule (also referred to as a gene) comprising a base sequence encoding natural α-glucan phosphorylase can be obtained. Fundamental strategies for preparing oligonucleotide probes and a DNA library, and screening them by hybridization of nucleic acids, are well-known to those skilled in the art. For example, see Sambrook, et al., Molecular Cloning: A Laboratory Manual (1989); DNA Cloning, vol. I and II (edited by D. N. Glover, 1985); Oligonucleotide Synthesis (edited by M. J. Gait, 1984); Nucleic Acid Hybridization (edited by B. D. Hames & S. J. Higgins, 1984).

Alternatively, based on homology to a base sequence of certain α-glucan phosphorylases for which a base sequence encoding α-glucan phosphorylase is known, for example, a cDNA library or a genome library is screened by hybridization using nucleic acid probes containing at least a part of this base sequence, thereby, a nucleic acid molecule containing the base sequence of another kind of α-glucan phosphorylase may be acquired. Such methods are known in the art.

Alternatively, degenerate primers corresponding to a region which is conserved in the amino acid sequence of various α-glucan phosphorylases are prepared, and PCR is performed using, for example, a cDNA library or a genome library of an objective species as a template, a base sequence of α-glucan phosphorylase derived from the species may be acquired. Such methods are known in the art.

When a genome library or a cDNA library is screened, the resulting nucleic acid molecule can be subcloned using methods well-known to the person skilled in the art. For example, by mixing λ phage containing an objective gene, suitable *Escherichia coli* and suitable helper phage, a plasmid containing an objective gene can be easily obtained. Thereafter, by transforming suitable *Escherichia coli* using a solution containing a plasmid, an objective gene can be subcloned. By culturing the resulting transformants, a plasmid DNA may be obtained, for example, by an alkaline SDS method, and the base sequence of an objective gene can be determined. A method of determining a base sequence is well-known to those skilled in the art. Further, by using PCR primers synthesized based on a base sequence of a DNA fragment, and using a polymerase chain reaction (PCR) employing the genomic DNA or the cDNA of potato as a template, an α-glucan phosphorylase gene may be directly amplified.

In the present specification, the "nucleic acid molecule" may consist only of natural nucleotides, may contain non-natural nucleotides, or may consist of only non-natural nucleotides. Examples of a non-natural nucleotide include derivatized nucleotides (also refers to as nucleotide analogs). The derivatized nucleotide and the "nucleotide analog" refer to those nucleotides which are different from naturally occurring nucleotides, but have a similar function to that of the original nucleotide. Such derivatized nucleotides and nucleotide analogs are well-known in the art. Examples of such derivatized nucleotides and nucleotide analogs include, but are not limited to phosphorothioate, phosphoramidate, methylphosphonate, chiral methylphosphonate, 2-O-methylribonucleotide, and peptide-nucleic acid (PNA).

(2.2 Modification of the First Nucleic Acid Molecule Comprising a Base Sequence Encoding First α-Glucan Phosphorylase)

A first nucleic acid molecule comprising a base sequence encoding a first α-glucan phosphorylase is modified to obtain a second nucleic acid containing a modified base sequence. A first nucleic acid molecule can be a nucleic acid molecule having a base sequence encoding a natural α-glucan phosphorylase, obtained as in the above (2.1). The first nucleic acid molecule may also be a nucleic acid molecule comprising a base sequence encoding α-glucan phosphorylase which has substantially the same enzyme activity as the enzyme activity of natural α-glucan phosphorylase, and in which 1 or a few or more amino acids are substituted, deleted or added to a base sequence encoding natural α-glucan phosphorylase. The "has substantially the same enzyme activity" refers to the enzyme activity when α-glucan phosphorylase after modification is measured under the same conditions as that of α-glucan phosphorylase before modification is within ±20%, preferably within ±10%, more preferably within ±5% of enzyme activity of α-glucan phosphorylase before modification.

Modification can be performed by carrying out site-directed mutagenesis, mutagenesis using a mutagen (treatment of a subject gene with a mutagenic agent such as nitrite, ultraviolet-ray treatment), or error prone PCR. It is preferable to use site-directed mutagenesis from the viewpoint that the objective mutation is easily obtained, because the objective modification can be introduced at an object site when site-directed mutagenesis is used. Alternatively, a nucleic acid molecule having an objective sequence may be directly synthesized. Such chemical synthesis methods are well-known in the art.

The present inventors found out that, by substituting an amino acid residue at a particular position in the amino acid sequence of a natural α-glucan phosphorylase derived from a plant, with another amino acid residue, the thermostability of the resulting α-glucan phosphorylase is improved. Such a particular position can be determined by aligning any of the following motif sequences, or the amino acid sequence of SEQ ID NO: 2, and a comparison subject amino acid sequence:

motif sequence 1L: H-A-E-F-T-P-V-F-S (SEQ ID NO: 44) or a motif sequence 1H: H-A-Q-Y-S-P-H-F-S (SEQ ID NO: 45), motif sequence 2: A-L-G-N-G-G-L-G (SEQ ID NO: 46), and motif sequence 3L: R-I-V-K-F-l-T-D-V (SEQ ID NO: 47) or motif sequence 3H:R -I-V-K-L-V-N-D-V (SEQ ID NO: 48).

The motif sequences 1L, 2 and 3L are present in the amino acid sequence (SEQ ID NO: 2) of potato-derived type L α-glucan phosphorylase. These motif sequences are present in the following positions in potato type L α-glucan phosphorylase: motif sequence 1L: position 36 to position 44 of the amino acid sequence set forth in SEQ ID NO: 2; motif sequence 2: position 132 to 1 position 39 of the amino acid sequence set forth in SEQ ID NO: 2; motif sequence 3L: position 700 to position 708 of the amino acid sequence set forth in SEQ ID NO: 2. The motif sequences 1H, 2 and 3H are present in the amino acid sequence of rice-derived type H α-glucan phosphorylase. These motif sequences are present in the following positions in rice type H α-glucan phosphorylase: motif sequence 1H: position 36 to position 44 of the amino acid sequence set forth in SEQ ID NO: 24; motif sequence 2: position 132 to position 139 of the amino acid sequence set forth in SEQ ID NO: 24; motif sequence 3H: position 625 to position 633 of the amino acid sequence set forth in SEQ ID NO: 24. Generally, natural α-glucan phosphorylase has these motif sequences, or sequences having high homology to them. The position of these motif sequences in other plant-derived α-glucan phosphorylases can be easily determined by those skilled in the art.

In the method according to the present invention, a nucleic acid molecule comprising a base sequence encoding a first α-glucan phosphorylase is modified so that α-glucan phosphorylase having improved thermostability, encoded by a modified nucleic acid molecule having an amino acid residue which is different from an amino acid residue of the natural α-glucan phosphorylase in at least one position selected from the group consisting of: a position corresponding to phenylalanine at position 342 (F39); a position corresponding to asparagine at position 135 (N135); and a position corresponding to threonine at position 706 (T706) in an amino acid sequence of SEQ ID NO: 2. Preferably, a nucleic acid molecule comprising a base sequence encoding the first α-glucan phosphorylase is modified so that an amino acid sequence at a position corresponding to phenylalanine at position 309 (F39) or a position corresponding to threonine at position 706 (T706) of an amino acid sequence set forth in SEQ ID NO: 2, of α-glucan phosphorylase having improved thermostability, encoded by a modified nucleic acid molecule is different from that of the natural α-glucan phosphorylase.

The "position corresponding to phenylalanine at position 39 (P39) of an amino acid sequence of SEQ ID NO: 2" as used in the present specification refers to a position which is aligned with phenylalanine at position 39 as set forth in SEQ ID NO: 2, when a subject amino acid sequence and an amino acid sequence of SEQ ID NO: 2 are aligned so that homology between the two sequences is highest, if necessary, by inserting a gap into one of sequences. When a gap is introduced into SEQ ID NO: 2, the gap is not counted when calculating the number of amino acid residues. More preferably, the above phrase refers to position which is aligned with phenylalanine at position 39 of SEQ ID NO: 2 when an amino acid sequence of SEQ ID NO: 2 and a subject amino acid sequence are aligned under the condition of GAP Penalty (Peptide): Insert=−10, Extend=−3, gap Extend on top position: setted (checked), Match Mode: Local Match using a score table of default, in multiple alignment of GENETYX-WIN Ver.4.0. A score table of default with respect to an amino acid is shown in the following Table 3.

TABLE 3

| | C | S | T | P | A | G | N | D | E | Q | H | R | K | M | I | L | V | F | Y | W | B | Z | X |
|---|---|---|---|---|---|---|---|---|---|---|---|---|---|---|---|---|---|---|---|---|---|---|---|
| C | 12, | | | | | | | | | | | | | | | | | | | | | | |
| S | 0, | 2, | | | | | | | | | | | | | | | | | | | | | |
| T | −2, | 1, | 3, | | | | | | | | | | | | | | | | | | | | |
| P | −3, | 1, | 0, | 6, | | | | | | | | | | | | | | | | | | | |
| A | −2, | 1, | 1, | 1, | 2, | | | | | | | | | | | | | | | | | | |
| G | −3, | 1, | 0, | −1, | 1, | 5, | | | | | | | | | | | | | | | | | |
| N | −4, | 1, | 0, | −1, | 0, | 0, | 2, | | | | | | | | | | | | | | | | |
| D | −5, | 0, | 0, | −1, | 0, | 1, | 2, | 4, | | | | | | | | | | | | | | | |
| E | −5, | 0, | 0, | −1, | 0, | 0, | 1, | 3, | 4, | | | | | | | | | | | | | | |
| Q | −5, | −1, | −1, | 0, | 0, | −1, | 1, | 2, | 2, | 4, | | | | | | | | | | | | | |
| H | −3, | −1, | −1, | 0, | −1, | −2, | 2, | 1, | 1, | 3, | 6, | | | | | | | | | | | | |
| R | −4, | 0, | −1, | 0, | −2, | −3, | 0, | −1, | −1, | 1, | 2, | 6, | | | | | | | | | | | |
| K | −5, | 0, | 0, | −1, | −1, | −2, | 1, | 0, | 0, | 1, | 0, | 3, | 5, | | | | | | | | | | |
| M | −5, | −2, | −1, | −2, | −1, | −3, | −2, | −3, | −2, | −1, | −2, | 0, | 0, | 6, | | | | | | | | | |
| I | −2, | −1, | 0, | −2, | −1, | −3, | −2, | −2, | −2, | −2, | −2, | −2, | −2, | 2, | 5, | | | | | | | | |
| L | −6, | −3, | −2, | −3, | −2, | −4, | −3, | −4, | −3, | −2, | −2, | −3, | −3, | 4, | 2, | 6, | | | | | | | |
| V | −2, | −1, | 0, | −1, | 0, | −1, | −2, | −2, | −2, | −2, | −2, | −2, | −2, | 2, | 4, | 2, | 4, | | | | | | |
| F | −4, | −3, | −3, | −5, | −4, | −5, | −4, | −6, | −5, | −5, | −2, | −4, | −5, | 0, | 1, | 2, | −1, | 9, | | | | | |
| Y | 0, | −3, | −3, | −5, | −3, | −5, | −2, | −4, | −4, | −4, | 0, | −4, | −4, | −2, | −1, | −1, | −2, | 7, | 10, | | | | |
| W | −8, | −2, | −5, | −6, | −6, | −7, | −4, | −7, | −7, | −5, | −3, | 2, | −3, | −4, | −5, | −2, | −6, | 0, | 0, | 17, | | | |
| B | −4, | 0, | 0, | −1, | 0, | 0, | 2, | 3, | 2, | 1, | 1, | −1, | 1, | −2, | −2, | −3, | −2, | −5, | −3, | −5, | 2, | | |
| Z | −5, | 0, | −1, | 0, | 0, | −1, | 1, | 3, | 3, | 3, | 2, | 0, | 0, | −2, | −2, | −3, | −2, | −5, | −4, | −6, | 2, | 3, | |
| X | 0, | 0, | 0, | 0, | 0, | 0, | 0, | 0, | 0, | 0, | 0, | 0, | 0, | 0, | 0, | 0, | 0, | 0, | 0, | 0, | 0, | 0, | 0 |

The multiple alignment of GENETYX-WIN Ver.4.0 is based on the following algorithm. In this alignment program, all possible pairs of sequences are aligned, two sequence alignment is performed as a round robin (pair wise alignment) and, among that, sequences of a combination having a high conservation ratio (score in pair wise alignment) are determined as common sequences, a hypothetical sequence is produced from common sequences (a common part remains as it is and, with respect to non-common parts, any one of the sequences is selected). A round robin between all sequences except for the sequence constituting the hypothetical sequence, and a hypothetical sequence is generated by the same procedure until the final hypothetical sequence is produced. Thereafter, by applying information on insertion and shift of GAP used to produce the hypothetical sequence, to the original sequence, to constitute a whole, and the multiple alignment is completed. A calculation equation for this pair wise alignment is as follows.

When sequences a and b, each having a sequence length of m or n, and respective sequences are expressed as:

$a = a1\ a2\ a3 \ldots am$ $b = b1\ b2\ b3 \ldots bm,$ a GAP penalty g is indicated by the following equation:

$-g = s(ai, \phi) = a(\phi, bj).$

An equation for obtaining an alignment score is as follows:

$G(0,0) = 0$ $G(i,0) = i(-g)$ $G(0,j) = j(-g)$ $-gk = -[\alpha + \beta(k-1)]$ $E(i,j) = \{G(i-1,j) - \alpha, E(i-1,j) - \beta\}$ $F(i,j) = \max\{G(i,j-1) - \alpha, F(i,j-1) - \beta\}$ $G(i,j) = \max\{E(i,j), G(i-1,j-1) + s(ai,bj), F(i,j)\}$ $\alpha$ is the GAP insertion penalty, and $\beta$ is the GAP extension penalty. E, F and G are a score matrix and, based on this, a pass matrix is produced.

A position corresponding to asparagine at position 135 (N135) and a position corresponding to threonine at position 706 (T706) are similarly construed.

In multiple alignments of GENETYX-WIN Ver.4.0, under the aforementioned condition, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30 were aligned with SEQ ID NO: 2. As a result, phenylalanine or tyrosine was aligned at a position corresponding to phenylalanine at position 39 (F39) of the amino acid sequence set forth in SEQ ID NO: 2, asparagine was aligned at a position corresponding to asparagine at position 135 (N135) of an amino acid sequence of SEQ ID NO: 2, and threonine, asparagine or aspartic acid was aligned at a position corresponding to threonine at position 706 (T706) of the amino acid sequence set forth in SEQ ID NO: 2. Results of this alignment are shown in FIG. 1A to FIG. 1I. In FIG. 1A to FIG. 1I, "potato type L" represents the amino acid sequence (SEQ ID NO: 2) of a potato-derived type L α-glucan phosphorylase. "Potato type L2" represents the amino acid sequence (SEQ ID NO: 6) of a potato-derived second type L α-glucan phosphorylase. "Sweet potato type L" represents the amino acid sequence (SEQ ID NO: 4) of a sweet potato-derived type L α-glucan phosphorylase. "Fava bean type L" represents the amino acid sequence (SEQ ID NO: 8) of a Fava bean-derived type L α-glucan phosphorylase. "*Arabidopsis thaliana* type L" represents the amino acid sequence (SEQ ID NO: 10) of *Arabidopsis thaliana*-derived type L α-glucan phosphorylase. "Spinach" represents the amino acid sequence (SEQ ID NO: 12) of a spinach-derived type L α-glucan phosphorylase. "Rice type L" represents the amino acid sequence (SEQ ID NO: 16) of a rice-derived type L α-glucan phosphorylase. "Rice type L2" represents the amino acid sequence (SEQ ID NO: 18) of a rice-derived second type L α-glucan phosphorylase. "Corn type L" represents the amino acid sequence (SEQ ID NO: 14) of a corn-derived type L α-glucan phosphorylase. "Potato type H" represents the amino acid sequence (SEQ ID NO: 30) of a potato-derived type H α-glucan phosphorylase. "Fava bean type H" represents the amino acid sequence (SEQ ID NO: 26) of a Fava bean-derived type H α-glucan phosphorylase. "*Arabidopsis thaliana* type H" represents the amino acid sequence (SEQ ID NO: 28) of an *Arabidopsis thaliana*-derived type H α-glucan phosphorylase. "Rice type H" represents the amino acid sequence (SEQ ID NO: 24) of a rice-derived type Hα-glucan phosphorylase. "Wheat" represents the amino acid sequence (SEQ ID NO: 20) of a wheat-derived type H α-glucan phosphorylase. "Citrus type H" represents the amino acid sequence (SEQ ID NO: 22) of a Citrus hybrid cultivar-derived type H α-glucan phosphorylase. "*E. coli* MalQ" represents the amino acid sequence (SEQ ID NO: 35) of an *Escherichia coli*-derived maltodextrin phosphorylase. Maltodextrin phosphorylase is one kind of α-glucan phosphorylases.

For example, in sweet potato-derived type L α-glucan phosphorylase, a position corresponding to phenylalanine at position 39 (F39) of an amino acid sequence of SEQ ID NO: 2 is position 39 of an amino acid sequence of SEQ ID NO: 4, position corresponding to asparagine at position 135 (N135) of the amino acid sequence set forth in SEQ ID NO: 2 is position 135 of an amino acid sequence set forth in SEQ ID NO: 4, and a position corresponding to threonine at position 706 (T706) of the amino acid sequence set forth in SEQ ID NO: 2 is position 702 of the amino acid sequence set forth in SEQ ID NO: 4.

For example, in potato-derived second type L α-glucan phosphorylase, a position corresponding to F39 of an amino acid sequence set forth in SEQ ID NO: 2 is position 11 of the amino acid sequence set forth in SEQ ID NO: 6, a position corresponding to N135 of the amino acid sequence set forth in SEQ ID NO: 2 is position 107 of the amino acid sequence set forth in SEQ ID NO: 6, and a position corresponding to T706 of the amino acid sequence set forth in SEQ ID NO: 2 is position 683 of the amino acid sequence set forth in SEQ ID NO: 6.

For example, in Fava bean-derived type L α-glucan phosphorylase, a position corresponding to F39 of the amino acid sequence set forth in SEQ ID NO: 2 is position 43 of the amino acid sequence set forth in SEQ ID NO: 8, a position corresponding to N135 of the amino acid sequence set forth in SEQ ID NO: 2 is position 139 of the amino acid sequence set forth in SEQ ID NO: 8, and a position corresponding to T706 of the amino acid sequence set forth in SEQ ID NO: 2 is position 729 of the amino acid sequence set forth in SEQ ID NO: 8.

For example, in *Arabidopsis thaliana*-derived type L α-glucan phosphorylase, a position corresponding to F39 of the amino acid sequence set forth in SEQ ID NO: 2 is position 106 of the amino acid sequence set forth in SEQ ID NO: 10, a position corresponding to N135 of the amino acid sequence set forth in SEQ ID NO: 2 is position 202 of the amino acid sequence set forth in SEQ ID NO: 10, and the position corresponding to T706 of the amino acid sequence set forth in SEQ ID NO: 2 is position 752 of the amino acid sequence set forth in SEQ ID NO: 10.

For example, in spinach-derived type L α-glucan phosphorylase, a position corresponding to F39 of the amino acid sequence set forth in SEQ ID NO: 2 is position 112 of the amino acid sequence set forth in SEQ ID NO: 12, a position corresponding to N135 of the amino acid sequence set forth in SEQ ID NO: 2 is position 208 of the amino acid sequence set forth in SEQ ID NO: 12, and a position corresponding to T706 of the amino acid sequence of SEQ ID NO: 2 is position 761 of the amino acid sequence set forth in SEQ ID NO: 12.

For example, in corn-derived type L α-glucan phosphorylase, a position corresponding to F39 of the amino acid sequence set forth in SEQ ID NO: 2 is position 95 of the amino acid sequence set forth in SEQ ID NO: 14, a position corresponding to N135 of the amino acid sequence set forth in SEQ ID NO: 2 is position 191 of the amino acid sequence set forth in SEQ ID NO: 14, and a position corresponding to T706 of the amino acid sequence set forth in SEQ ID NO: 2 is position 773 of the amino acid sequence set forth in SEQ ID NO: 14.

For example, in rice-derived type L α-glucan phosphorylase, a position corresponding to F39 of an amino acid sequence of SEQ ID NO: 2 is position 41 of the amino acid sequence set forth in SEQ ID NO: 16, a position corresponding to N135 of the amino acid sequence set forth in SEQ ID NO: 2 is position 137 of the amino acid sequence set forth in SEQ ID NO: 16, and a position corresponding to T706 of the amino acid sequence set forth in SEQ ID NO: 2 is position 718 of the amino acid sequence set forth in SEQ ID NO: 16.

For example, in another rice-derived type L α-glucan phosphorylase, a position corresponding to F39 of the amino acid sequence set forth in SEQ ID NO: 2 is position 91 of the amino acid sequence set forth in SEQ ID NO: 18, a position corresponding to N135 of the amino acid sequence set forth in SEQ ID NO: 2 is position 187 of the amino acid sequence set forth in SEQ ID NO: 18, and a position corresponding to T706 of the amino acid sequence set forth in SEQ ID NO: 2 is position 741 of the amino acid sequence set forth in SEQ ID NO: 18.

For example, in wheat-derived type H α-glucan phosphorylase, a position corresponding to F39 of the amino acid sequence set forth in SEQ ID NO: 2 is position 31 of the amino acid sequence set forth in SEQ ID NO: 20, a position corresponding to N135 of the amino acid sequence set forth in SEQ ID NO: 2 is position 127 of the amino acid sequence set forth in SEQ ID NO: 20, and a position corresponding to T706 of the amino acid sequence set forth in SEQ ID NO: 2 is a position 622 of the amino acid sequence set forth in SEQ ID NO: 20.

For example, in a Citrus hybrid cultivar-derived type H α-glucan phosphorylase, a position corresponding to F39 of the amino acid sequence set forth in SEQ ID NO: 2 is position 42 of the amino acid sequence set forth in SEQ ID NO: 22, a position corresponding to N135 of the amino acid sequence set forth in SEQ ID NO: 2 is a position 138 of the amino acid sequence set forth in SEQ ID NO: 22, and a position corresponding to T706 of the amino acid sequence set forth in SEQ ID NO: 2 is position 630 of the amino acid sequence set forth in SEQ ID NO: 22.

For example, in rice-derived type H α-glucan phosphorylase, a position corresponding to F39 of the amino acid sequence set forth in SEQ ID NO: 2 is position 39 of the amino acid sequence set forth in SEQ ID NO: 24, a position corresponding to N135 of the amino acid sequence set forth in SEQ ID NO: 2 is position 135 of set forth in amino acid sequence set forth in EQ ID NO: 24, and a position corresponding to T706 of the amino acid sequence set forth in SEQ ID NO: 2 is position 631 of the amino acid sequence set forth in SEQ ID NO: 24.

For example, in Fava bean-derived type H α-glucan phosphorylase, a position corresponding to F39 of an amino acid sequence of SEQ ID NO: 2 is position 43 of the amino acid sequence set forth in SEQ ID NO: 26, a position corresponding to N135 of the amino acid sequence set forth in SEQ ID NO: 2 is position 139 of the amino acid sequence set forth in SEQ ID NO: 26, and a position corresponding to T706 of the amino acid sequence set forth in SEQ ID NO: 2 is position 632 of the amino acid sequence set forth in SEQ ID NO: 26.

For example, in *Arabidopsis thaliana*-derived type H α-glucan phosphorylase, a position corresponding to F39 of the amino acid sequence set forth in SEQ ID NO: 2 is position 40 of the amino acid sequence set forth in SEQ ID NO: 28, a position corresponding to N135 of the amino acid sequence set forth in SEQ ID NO: 2 is position 136 of the amino acid sequence set forth in SEQ ID NO: 28, and a position corresponding to T706 of the amino acid sequence set forth in SEQ ID NO: 2 is position 631 of the amino acid sequence set forth in SEQ ID NO: 28.

For example, in potato-derived type H α-glucan phosphorylase, a position corresponding to F39 of the amino acid sequence set forth in SEQ ID NO: 2 is position 36 of the amino acid sequence set forth in SEQ ID NO: 30, a position corresponding to N135 of the amino acid sequence set forth in SEQ ID NO: 2 is position 133 of the amino acid sequence set forth in SEQ ID NO: 30, and a position corresponding to T706 of the amino acid sequence set forth in SEQ ID NO: 2 is position 628 of the amino acid sequence set forth in SEQ ID NO: 30.

A position of an amino acid residue which improves thermostability can be determined by not only alignment with the sequences 916 amino acid residues set forth in SEQ ID NO: 2, but also by alignment with one or more sequences selected from the group consisting of the aforementioned motif sequences 1L or 1H, 2, and 3L or 3H. As far as the heretofore known plant-derived α-glucan phosphorylases were aligned, the thus determined position is the same in either the case where SEQ ID NO: 2 is used and the case where motif sequences 1L or 1H, 2, and 3L or 3H are used.

The motif sequence 1L is well conserved in type L α-glucan phosphorylases, while the motif sequence 1H is well conserved in type H α-glucan phosphorylase. It can be said that a position corresponding to phenylalanine at position 39 (F39) of the amino acid sequence set forth in SEQ ID NO: 2 is a position corresponding to position 4 in the motif sequence 1L or 1H.

The motif sequence 2 is commonly conserved in type L and type H α-glucan phosphorylases. It can be said that a position corresponding to asparagine at position 135 (N135) of the amino acid sequence set forth in SEQ ID NO: 2 is a position corresponding to position 4 in the motif sequence 2.

The motif sequence 3L is well conserved in type L α-glucan phosphorylases, while the motif sequence 3H is well conserved in type H α-glucan phosphorylases. It can be said that a position corresponding to threonine at position 706 (T706) of the amino acid sequence set forth in SEQ ID NO: 2 is a position corresponding to position 7 in the motif sequence 3L or 3H.

In this manner, the position of an amino acid residue which improves thermostability can be also specified using the motif sequences. A position of an amino acid residue which improves thermostability can be at least one position selected from the group consisting of a position corresponding to position 4 in a motif sequence 1 L: H -A-E-F-T-P-V-F-S (SEQ ID NO 44) or a position corresponding to position 4 in a motif sequence 1H: H-A-Q-Y-S-P-H-F-S (SEQ ID NO: 45); a position corresponding to position 4 in a motif sequence 2: A-L-G-N-G-G-L-G (SEQ ID NO: 46); and a position corresponding to position 7 in a motif sequence 3L: R-I-V-K-F-l-T-D-V (SEQ ID NO: 47) or a position corresponding to position 7 in a motif sequence 3H: R-I-V-K-L-V-N-D-V (SEQ ID NO: 48).

Therefore, in the method according to the present invention, it can be said that a nucleic acid molecule comprising a base sequence encoding first α-glucan phosphorylase is modified so that α-glucan phosphorylase having improved thermostability, encoded by a modified nucleic acid has an amino acid residue which is different from an amino acid residue of the natural α-glucan phosphorylase in at least one position selected from the group consisting of a position corresponding to position 4 in a motif sequence 1L: H-A-E-F-T-P-V-F-S (SEQ ID NO 44) or a position corresponding to position 4 in a motif sequence 1H: H-A-Q-Y-S-P-H-F-S (SEQ ID NO: 45); a position corresponding to position 4 in a motif sequence 2: A-L-G-N-G-G-L-G (SEQ ID NO: 46); and a position corresponding to position 7 in a motif sequence 3L: R -I-V-K-F-l-T-D-V (SEQ ID NO: 47) or a position corresponding to position 7 in a motif sequence 3H: R-l-V-K-L-V-N-D-V (SEQ ID NO: 48).

In the present specification, the "motif sequence" refers to a partial sequence which is seen between amino acid sequences of a plurality of proteins, and is commonly or highly conserved. Generally, the motif sequence has particular function in many cases, but in the present specification, even when a particular function is not identified, as long as the sequences is conserved between a plurality of amino acid sequences, this is called motif sequence.

An amino acid residue "at position 4 in a motif sequence 1L" refers to an amino acid residue which is fourth when counted in order, when the amino acid residue at an N-terminus (left end) of the motif sequence 1L is taken to be position 1. "position 4 in a motif sequence 1H", "position 4 in a motif sequence 2", "position 7 in a motif sequence 3L", "position 7 in a motif sequence 3H", and the like are similar.

These motif sequences are generally well conserved in plant α-glucan phosphorylases. The motif sequences 1L or 1H and 3L or 3H are well conserved in α-glucan plant phosphorylases, but are not conserved in α-glucan phosphorylases derived from animals, microorganisms, or the like. Motif sequence 2 is well conserved in α-glucan phosphorylases of almost all organisms such as plants, animals and microorganisms. The motif sequence 2 contains an amino acid residue which is presumed to be involved in binding of a substrate and binding of pyridoxal 5'-phosphate which is a coenzyme, and is a part of the regions essential for activity. The positions of motif sequences 1L and 1H, and the position of the motif sequence 2 are shown in FIG. 1B. The positions of motif sequences 3L and 3H are shown in FIG. 1G.

As used herein, "a position corresponding to position 4 in a motif sequence 1L: H-A-E-F-T-P-V-F-S (SEQ ID NO 44) or a position corresponding to position 4 in a motif sequence 1H: H-A-Q-Y-S-P-H-F-S (SEQ ID NO: 45)" refers to position which is aligned with amino acid residue at position 4 in the motif sequence 1L or the motif sequence 1H when a subject amino acid sequence and the motif sequence 1L or the motif sequence 1H are aligned, without inserting a gap, so that homology between sequences is greatest. More preferably, it refers to the position which is aligned with the amino acid residue at position 4 in the motif sequence 1L or the motif sequence 1H when maximum matching of GENETYX-WIN Ver.4.0 (Genetics Co., Ltd.) is performed under no gap condition.

A position corresponding to position 4 in motif sequence 2, and a position corresponding to position 7 in motif sequence 3L and a position corresponding to position 7 in motif sequence 3H are similarly construed.

Maximum matching of GENETYX-WIN Ver.4.0 is as follows: while substitution and deletion are considered, sequence data to be analyzed, and sequence data to be compared are aligned so that amino acid pairs matching between these sequences become greatest, thereupon, Matches, Mismatches, and Gaps are scored, respectively, a sum is calculated, and alignment at the lowest sum is outputted (Reference: Takashi, K., and Gotoh, O. 1984. Sequence Relationships among Various 4.5 S RNA Species J. Biochem. 92:1173-1177). Preferably, alignment is performed under the condition of Matches=−1; Mismatches=1; Gaps=None; *N+=2.

Using maximum matching of GENETYX-WIN Ver.4.0, potato type L (SEQ ID NO: 2), sweet potato type L (SEQ ID NO: 4), potato second type L (SEQ ID NO: 6), Fava bean type L (SEQ ID NO: 8), *Arabidopsis thaliana* type L (SEQ ID NO: 10), spinach type L (SEQ ID NO: 12), corn type L (SEQ ID NO: 14), rice type L (SEQ ID NO: 16), rice second type L (SEQ ID NO: 18), wheat type H (SEQ ID NO: 20), Citrus hybrid cultivar type H (SEQ ID NO: 22), rice type H (SEQ ID NO: 24), Fava bean type H (SEQ ID NO: 26), *Arabidopsis thaliana* type H (SEQ ID NO: 28) and potato type H (SEQ ID NO: 30) were aligned with a motif sequence 1L or a motif sequence 1H. Analysis of maximum matching was performed under the condition of Matches=−1; Mismatches=1; Gaps=0; *N+=2.

In maximum matching of GENETYX-WIN Ver.4.0, under the aforementioned condition, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30 were aligned with each motif sequence (motif sequence 1L, 1H, 2, 3L or 3H). As a result, phenylalanine or tyrosine was aligned with a position corresponding to position 4 in the motif sequence 1L or a position corresponding to position 4 in the motif sequence 1H, asparagine was aligned with a position corresponding to position 4 in the motif sequence 2, and threonine, asparagine or aspartic acid was aligned with a position corresponding to position 7 in the motif sequence 3L or a position corresponding to position 7 in the motif sequence 3H. The motif sequences 1L, 2 and 3L are partial sequences of SEQ ID NO: 2, and motif sequences 1H, 2 and 3H are partial sequences of SEQ ID NO: 24.

Regarding each of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30, the results of an alignment using a full length of SEQ ID NO: 2, and results of an alignment using motif sequences 1L, 1H, 2, 3L and 3H were compared. As a result, in each of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30, a position corresponding to position 39 of SEQ ID NO: 2, and a position corresponding to position 4 in the motif sequence 1L or 1H were the same. A position corresponding to position 135 of SEQ ID NO: 2, and a position corresponding to position 4 in the motif 2 were the same. A position corresponding to position 706 of SEQ ID NO: 2, and a position corresponding to position 7 in the motif 3L or 3H were the same. In this manner, it was confirmed that, even when alignment was performed using motif sequences, the same positions are specified as those specified when the amino acid sequence of SEQ ID NO: 2 is used.

A nucleic acid molecule comprising a modified base sequence obtained by modifying a nucleic acid molecule comprising a base sequence encoding the amino acid sequence represented in position 1 to position 916 of SEQ ID NO: 2, position 1 to position 912 of SEQ ID NO: 4, position 1 to position 893 of SEQ ID NO: 6, position 1 to position 939 of SEQ ID NO: 8, position 1 to position 962 of SEQ ID NO: 10, position 1 to position 971 of SEQ ID NO: 12, position 1 to position 983 of SEQ ID NO: 14, position 1 to position 928 of SEQ ID NO: 16, position 1 to position 951 of SEQ ID NO: 18, position 1 to position 832 of SEQ ID NO: 20, position 1 to position 840 of SEQ ID NO: 22, position 1 to position 841 of SEQ ID NO: 24, position 1 to position 842 of SEQ ID NO: 26, position 1 to position 841 of SEQ ID NO: 28, and position 1 to position 838 of SEQ ID NO: 3 set forth in the Sequence Listing is within the scope of the present invention.

A nucleic acid molecule comprising a modified base sequence obtained by modifying a nucleic acid molecule comprising a base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, or SEQ ID NO: 29 set forth in the Sequence Listing is within the scope of the present invention.

A nucleic acid molecule comprising a modified base sequence obtained by modifying a nucleic acid molecule comprising a base sequence encoding an amino acid sequence having at least 50% identity with an amino acid sequence selected from the group consisting of: position 1 to position 916 of SEQ ID NO: 2; position 1 to position 912 of SEQ ID NO: 4; position 1 to position 893 of SEQ ID NO: 6; position 1 to position 939 of SEQ ID NO: 8; position 1 to position 962 of SEQ ID NO: 10; position 1 to position 971 of SEQ ID NO: 12; position 1 to position 983 of SEQ ID NO: 14; position 1 to position 928 of SEQ ID NO: 16; position 1 to position 951 of SEQ ID NO: 18; position 1 to position 832 of SEQ ID NO: 20; position 1 to position 840 of SEQ ID NO: 22; position 1 to position 841 of SEQ ID NO: 24; position 1 to position 842 of SEQ ID NO: 26; position 1 to position 841 of SEQ ID NO: 28; and position 1 to position 838 of SEQ ID NO: 30; as set forth in the Sequence Listing is within the scope of the present invention.

In the present invention, "identity" of a sequence such as an amino acid sequence and a base sequence refers to the degree of occurrence of the same amino acid (base when base sequences are compared) between two sequences. Identity is generally determined by comparing two amino acid sequences or two base sequences, and comparing these two sequences which are aligned in an optimal format, which can contain additions or deletions. Percentage identity is calculated by determining the number of positions where an amino acid (base when base sequences are compared) is the same between these two sequences, dividing the number of the same positions by a total number of compared positions, and multiplying the obtained result by 100 in order to obtain a percentage identity between the two sequences.

As an example, an amino acid sequence of natural α-glucan phosphorylase used for obtaining α-glucan phosphorylase having improved thermostability of the present invention may be the same as, that is, 100% identical with an amino acid sequence (i.e. control amino acid sequence) selected from the group consisting of position 1 to position 916 of SEQ ID NO: 2; position 1 to position 912 of SEQ ID NO: 4; position 1 to position 893 of SEQ ID NO: 6; position 1 to position 939 of SEQ ID NO: 8; position 1 to position 962 of SEQ ID NO: 10; position 1 to position 971 of SEQ ID NO: 12; position 1 to position 983 of SEQ ID NO: 14; position 1 to position 928 of SEQ ID NO: 16; position 1 to position 951 of SEQ ID NO: 18; position 1 to position 832 of SEQ ID NO: 20; position 1 to position 840 of SEQ ID NO: 22; position 1 to position 841 of SEQ ID NO: 24; position 1 to position 842 of SEQ ID NO: 26; position 1 to position 841 of SEQ ID NO: 28; and position 1 to position 838 of SEQ ID NO: 30; or this amino acid sequence may one or more altered amino acid residues as compared with a control amino acid sequence. Such alterations can be selected from the group consisting of a deletion, a substitution including conservative and non-conservative substitution, or an insertion of at least one amino acid. This alteration may occur at a position of an amino terminus or a carboxyl terminus of a control amino acid sequence, or may occur at any position other than these terminuses. Alteration of an amino acid residue may be interspersed with one residue, or a few residues may be contiguous.

In the present specification, the percentage identity of sequences is calculated using maximum matching of GENETYX-WIN Ver.4.0 (Genetics Co., Ltd.). This program aligns sequence data to be analyzed, and sequence data to be compared so that amino acid pairs matched between sequences become greatest while substitution and deletion are considered, and thereupon, gives a score to each of Matches, Mismatches, and Gaps, calculates a sum, outputs alignment at the smallest sum, and calculates identity thereupon (Reference: Takashi, K., and Gotoh, O. 1984. Sequence Relationships among Various 4.5 S RNA Species J. Biochem. 92:1173-1177).

Using maximum matching of GENETYX-WIN Ver.4.0, the percentage identity of sweet potato type L (SEQ ID NO: 4), potato second type L (SEQ ID NO: 6), Fava bean type L (SEQ ID NO: 8), *Arabidopsis thaliana* type L (SEQ ID NO: 10), spinach type L (SEQ ID NO: 12), corn type L (SEQ ID NO: 14), rice type L (SEQ ID NO: 16), rice second type L (SEQ ID NO: 18), and wheat type H (SEQ ID NO: 20), Citrus hybrid cultivar type H (SEQ ID NO: 22), rice type H (SEQ ID NO: 24), Fava bean type H (SEQ ID NO: 26), *Arabidopsis thaliana* type H (SEQ ID NO: 28) and potato type (SEQ ID NO: 30) with potato type L (SEQ ID NO: 2) was calculated, and results are shown in Table 4. Analysis of maximum matching was performed under the condition of Matches=−1; Mismatches=1; Gaps=1; *N+=2.

TABLE 4

| Subject sequence | Identity |
| --- | --- |
| Potato type L | 100 |
| Potato second type L | 70.3 |
| *Arabidopsis thaliana* type L | 72.1 |
| Spinach type L | 72.7 |
| Rice type L | 73.8 |
| Rice second type L | 67.7 |
| Corn type L | 70.2 |
| Sweet potato type L | 78.6 |
| Fava bean type L | 72.5 |
| Potato type H | 57.5 |
| *Arabidopsis thaliana* type H | 57.8 |
| Rice type H | 57.0 |
| Fava bean type H | 58.6 |
| Citrus hybrid cultivar type H | 57.5 |
| Wheat type H | 57.6 |

A nucleic acid molecule comprising a modified base sequence obtained by modifying a nucleic acid molecule which hybridizes under stringent condition with a nucleic acid molecule consisting of a base sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, and SEQ ID NO: 29 as set forth in the Sequence Listing is within the scope of the present invention. Those skilled in the art can easily select a desired α-glucan phosphorylase gene.

As used herein, the term "stringent condition" refers to conditions under which a sequence hybridizes with a specific sequence, but not with a non-specific sequence. Selection of appropriate stringent conditions is well-known to those skilled in the art, and is described, for example, in Molecular Cloning (Sambrook, et al., supra). Specifically, the conditions mean that a polynucleotide which can be identified using the conditions under which hybridization is performed at 65° C. in a solution containing 50% formamide, 5×SSC (750 mM NaCl, 75 mM trisodium citrate), 50 mM sodium phosphate (pH 7.6), 5× Denhart's solution (0.2% BSA, 0.2% Ficoll 400 and 0.2% polyvinylpyrrolidone), 10% dextran sulfate, and 20 μg/ml denatured sheared salmon sperm DNA using a filter on which a DNA derived from a colony or a plaque has been immobilized, and a filter is washed under the condition of 65° C. using a SSC (saline-sodium citrate) solution having a 0.1 to 2-fold concentration (a composition of a SSC solution having a 1-fold concentration is 150 mM sodium chloride, 15 mM sodium citrate).

A modified nucleic acid molecule used in the method of the present invention may be a nucleic acid molecule which was conservatively modified relative to a nucleic acid molecule comprising a base sequence encoding a first α-glucan phosphorylase. The "nucleic acid molecule which was conservatively modified relative to a nucleic acid molecule comprising a base sequence encoding first α-glucan phosphorylase" refers to a nucleic acid molecule comprising a base sequence encoding an amino acid sequence which is the same or essentially the same as an amino acid sequence encoded by a base sequence encoding the first α-glucan phosphorylase. The "amino acid sequence which is essentially the same as an amino acid sequence encoded by a base sequence encoding first α-glucan phosphorylase" refers to an amino acid sequence having essentially the same enzyme activity as that of first α-glucan phosphorylase. Due to degeneracy of a genetic code, many functionally equivalent base sequences encode a prescribed amino acid sequence. For example, codons GCA, GCC, GCG and GCT all encode the amino acid alanine. Therefore, at all positions where alanine is specified by a GCA codon, the codon can be changed to GCC, GCG or GCT without changing the encoded alanine. Similarly, regarding an amino acid encoded by a plurality of codons, at all positions where the amino acid is specified by a codon, the codon can be changed to any another codon encoding the amino acid without changing the particular amino acid coded. Such a variation in a base sequence is a "silent mutation" which is one kind of conservatively altered mutation. All base sequences in the present specification which encode a polypeptide also include all possible silent alterations of the nucleic acid. Silent mutation includes "silent substitution" in which a coding nucleic acid is not changed, and the case where a nucleic acid does not originally encode an amino acid. When a certain nucleic acid encodes an amino acid, silent mutation has the same meaning as that of silent substitution. In the present specification, "silent substitution" refers to substitution of a base sequence encoding a certain amino acid with another base sequence encoding the same amino acid, in a base sequence. Based on the phenomenon of degeneracy in a genetic code, in the case where there are a plurality of base sequences encoding a certain amino acid (e.g. glycine), such a silent substitution is possible. Therefore, a polypeptide having an amino acid sequence encoded by a base sequence produced by silent substitution has the same amino acid sequence as that of the original polypeptide. Therefore, the α-glucan phosphorylase having improved thermostability of the present invention can include silent substitutions at a base sequence level, in addition to modification which is aimed a by the present invention (substitution is performed so that the α-glucan phosphorylase has an amino acid residue which is different from an amino acid residue of the natural α-glucan phosphorylase in at least one position selected from the group consisting of a position corresponding to position 4 in the motif sequence 1L or 1H, a position corresponding to position 4 in a motif sequence 2, or a position corresponding to position 7 in the motif sequence 3L or 3H, or a position corresponding to phenylalanine at position 39 (F39) in an amino acid sequence of SEQ ID NO: 2, a position corresponding to asparagine at position 135 (N135) and a position corresponding to threonine at position 706 (T706). In the art, it is understood that each codon in a nucleic acid (except for ATG which is only one codon usually encoding methionine, and TGG which is only one codon usually encoding tryptophan) can be modified in order to produce the functionally same molecule. Therefore, each silent mutation of a nucleic acid encoding a polypeptide is implicitly included in each described sequence. Preferably, such the alteration can be performed so that substitution of cysteine, which is an amino acid that greatly influences the conformation of a polypeptide, is avoided.

A base sequence encoding α-glucan phosphorylase having improved thermostability of the present invention can be changed in conformity with a codon usage in an organism into which the sequence is introduced for expression. Codon usage reflects the usage in a gene which is highly expressed in the organism. For example, when expression is intended in *Escherichia coli*, the sequence can be made to be optimal for expression in *Escherichia coli* according to the published codon usage table (e.g. Sharp, et al., Nucleic Acids Research 16, No. 17, p. 8207 (1988)).

(2.3 Making Expression Vectors)

An expression vector is made using a nucleic acid molecule comprising the base sequence modified as described above. A method for preparing an expression vector using a particular nucleic acid sequence is well-known to those skilled in the art.

When a nucleic acid molecule is referred in the present specification, a "vector" refers to a nucleic acid molecule which can transfer an objective base sequence into an objective cell. Examples of such vectors include a vector which can autonomously replicate in an objective cell, or can be incorporated into a chromosome of an objective cell, and has a promoter at a position suitable for transcribing a modified base sequence. In the present specification, the vector may be a plasmid.

As used herein, the "expression vector" refers to a vector which can express a modified base sequence (i.e. base sequence encoding modified α-glucan phosphorylase) in an objective cell. An expression vector contains, in addition to a modified base sequence, various regulation elements such as a promoter regulating expression thereof and, if necessary, factors necessary for replication in an objective cell and selection of a recombinant (e.g. origin of replication (ori), and a selectable marker such as a drug resistant gene). In an expression vector, a modified base sequence is operably linked so that it is transcribed and translated. Regulation elements include a promoter, a terminator and an enhancer. In addition, when secretion of an expressed enzyme outside a cell is intended, a base sequence encoding a secretion signal peptide is linked upstream of a modified base sequence in the correct reading frame. It is a matter well-known to those skilled in the art, that both the type of an expression vector used for introduction into a particular organism (e.g. bacterium), and the kind of a regulation element and other factors used in the expression vector, can vary depending on an objective cell.

As used herein, the "terminator" is a sequence which is situated downstream of a protein coding region, and is involved in termination of transcription upon transcription of a base sequence into an mRNA, and in the addition of a poly A sequence. It is known that the terminator influences the expression level of a gene with regard to the stability of an mRNA.

As used herein, the "promoter" refers to a region on a DNA which determines a transcription initiation site of a gene, and directly regulates the transcription frequency, and is abase sequence to which a RNA polymerase binds, thereby, initiating transcription. Since the region of a promoter is usually a region about 2 kbp or less upstream of a first exon of a putative protein coding region in many cases, when a protein coding region in a genome base sequence is predicted using a DNA analyzing software, a promoter region can be putative. A putative promoter region varies with every structural gene, and is usually upstream of a structural gene without limitation, and may be downstream of a structural gene. Preferably, a putative promoter region is present about 2 kbp or less upstream of a first exon translation initiation point.

As used herein, the "enhancer" can be used for enhancing the expression efficiency of an objective gene. Such an enhancer is well-known in the art. A plurality of enhancers can be used, but only one may be used, or may not be used at all.

As used herein, "operably linked" refers to when a desired base sequence is placed under the control of a transcription and translation regulating sequence (e.g. promoter, enhancer and the like) or a translation regulating sequence which effect expression (i.e. operation). In order that a promoter is operably linked to a gene, usually, a promoter is disposed immediately upstream of the gene, but it is not necessary that a promoter is disposed adjacent to the gene.

In order to operably link a modified nucleic acid sequence to the aforementioned regulation element, an objective α-glucan phosphorylase gene should be processed in some cases. Examples include the case where the distance between a promoter and a coding region is too long, and reduction in a transcription efficiency is predicted, the case where the distance between a ribosome binding site and a translation initiation codon is not suitable, and the like. Examples of the procession means include digestion with a restriction enzyme, digestion with an exonuclease such as Bal31 and ExoIII, or introduction of site-directed mutagenesis using a single-stranded DNA such as M13 or PCR.

(2.4 Expression of α-Glucan Phosphorylase Having Improved Thermostability)

Then, the expression vector prepared as described above is introduced into a cell, thereby, α-glucan phosphorylase having improved thermostability is expressed.

In the present specification, "expression" of an enzyme refers to in vivo or in vitro transcription and translation of a base sequence encoding the enzyme, and production of the encoded enzyme.

A cell into which an expression vector is introduced (also referred to as a host) includes prokaryotes and eukaryotes. A cell into which an expression vector is introduced can be easily selected, taking various conditions such as ease of expression of α-glucan phosphorylase, ease of culturing, growth rate, and safety into consideration. For example, when α-glucan phosphorylase is used in synthesizing amylose having a high molecular weight, since it is preferable that α-glucan phosphorylase does not contain amylase as a contaminant, it is preferable to use a cell which does not produce amylase or produce amylase only at a low level. Examples of such a cell include microorganisms such as bacteria and fungi. Examples of more preferable cells include mesophilic microorganisms (e.g. *Escherichia coli, Bacillus subtilis*). In the present specification, the "mesophilic microorganism" is a microorganism having a growth temperature in a normal temperature environment, and particularly refers to a microorganism having an optimal growth temperature of 20° C. to 40° C. A cell may be such as a microorganism cell, or may be a plant or animal cell. Depending on a cell to be used, an enzyme of the present invention can be an enzyme which has undergone post-translational processing. A plant includes, but is not limited to, a dicot, and a monocot such as rice, wheat, barley and corn. A cereal such as rice has a nature of accumulating a storage protein in a seed and, using a storage protein system, the cereal can be expressed so that α-glucan phosphorylase having improved thermostability of the present invention is accumulated in a seed (see Japanese Laid-Open Publication No. 2002-58492 specification).

In the method of the present invention, the technique of introducing an expression vector into a cell may be any technique known in the art. Examples of such the technique include, for example, transformation, transduction, and transfection. Such the technique of introducing a nucleic acid molecule is well-known in the art, and is conventional, and described, for example, in Ausubel F. A., et al. ed. (1988), Current Protocols in Molecular Biology, Wiley, New York, N.Y.; Sambrook J, et al. (1987) Molecular Cloning: A Laboratory Manual, $2^{nd}$ Ed., Cold Spring Harbor Laboratory Press, Cold Spring Harbor, N.Y., and Bessatsu Jikkenkagaku "Idenshidounyu & Hatsugen kaiseki jikkenhou", Yodosha, 1997.

When a plant cell is used as a cell, a method of re-differentiating a transformant into a tissue or a plant is well-known in the art. Examples of such a method are described in following: Rogers, et al., Methods in Enzymology 118:627-640 (1986); Tabata, et al., Plant Cell Physiol., 28:73-82 (1987); Shaw, Plant Molecular Biology: A Practical Approach. IRL press (1988); Shimamoto, et al., Nature 338: 274 (1989); and Maliga, et al., Methods in Plant Molecular Biology: A laboratory course. Cold Spring Harbor Laboratory Press (1995). A method of transforming a woody plant is described in Molecular Biology of Woody Plants (Vol. I, II) (ed. S. Mohan Jain, Subhash C. Minocha), Kluwer Academic Publishers, (2000). In addition, a method of transforming a woody plant is described in detail, for example, in Plant Cell Reports (1999) 19:106-110. Therefore, those skilled in the art can re-differentiate a transformant by appropriately using the aforementioned well-known method depending on an objective transgenic plant. An objective gene is introduced in the thus obtained transgenic plant, and the introduction of a gene can be confirmed using the know method such as Northern blotting, and Western blot analysis or other well-known conventional techniques.

By culturing a cell into which an expression vector has been introduced, and has acquired the ability to express α-glucan phosphorylase having improved thermostability (also referred to as transformed cell), α-glucan phosphorylase having improved thermostability can be expressed in a cell. The condition of culturing a transformed cell is appropriately selected depending on a kind of a host cell to be used, and a kind of an expression regulating factor in an expression vector. For example, a usual shaking culture method can be used.

A medium used for culturing a transformed cell is not particularly limited as long as the cell used is grown, and can express objective α-glucan phosphorylase having improved thermostability. In a medium, in addition to a carbon source and a nitrogen source, inorganic salts such as salts of phosphoric acid, $Mg^{2+}$, $Ca^{2+}$, $Mn^{2+}$, $Fe^{2+}$, $Fe^{2+}$, $Zn^{2+}$, $Co^{2+}$, $Ni^{2+}$, $Na^+$, $K^+$ and the like can be used alone, or by appropriately mixing them, if necessary. In addition, if necessary, various inorganic substances or organic substances necessary for growing a transformed cell, or expressing objective α-glucan phosphorylase having improved thermostability may be added.

A temperature for culturing a transformed cell can be selected so as to be suitable for growing a transformed cell to be used. Usually, the temperature is 15° C. to 60° C. Culturing of a transformed cell is continued for a sufficient time to express α-glucan phosphorylase having improved thermostability.

When an expression vector having an inducible promoter is used, expression can be controlled by addition of an inducer, change of a culturing temperature, and adjustment of medium components. For example, when an expression vector having a lactose inducible promoter is used, expression can be induced by adding isopropyl-β-D-thiogalactopyranoside (IPTG).

(2.5 Recovery of α-Glucan Phosphorylase Having Improved Thermostability)

The thus expressed α-glucan phosphorylase having improved thermostability can be then recovered. For example, when the expressed α-glucan phosphorylase having improved thermostability is produced in a transformed cell, a cell is recovered from a culture of transformed cells by centrifuging or filtering the culture. The recovered cell is suspended in a suitable buffer, and is crushed using a conventional means (ultrasound, French press, lysozyme treatment) to obtain a crude enzyme solution. Further, a crude enzyme solution or a purified enzyme having improved specific activity is obtained by purifying the crude enzyme solution by a method of appropriately combining conventional enzyme purifying means such as centrifugation, chromatography, membrane fractionation, electrophoresis, and salting-out. When an enzyme hydrolyzing a glucan such as α-amylase is not contained, a crude enzyme as it is can be used, for example, in preparation of a glucan having a high-molecular weight.

By producing α-glucan phosphorylase having improved thermostability as described above, it becomes possible to considerably improve thermostability of natural α-glucan phosphorylase. In addition, the expressed α-glucan phosphorylase having improved thermostability can be simply purified utilizing the thermostability thereof. In brief, by heat-treating a cell extract containing α-glucan phosphorylase having improved thermostability at about 60° C., contaminating enzymes are insolubilized. By centrifuging the insolubilized substances to remove them, and performing dialysis treatment, purified α-glucan phosphorylase having improved thermostability is obtained.

(3. α-glucan Phosphorylase Having Improved Thermostability)

The α-glucan phosphorylase having improved thermostability according to the present invention obtained by the aforementioned method has an amino acid residue which is different from an amino acid residue of the natural α-glucan phosphorylase in at least one position selected from the group consisting of a position corresponding to position 4 in the motif sequence 1L: H-A-E-F-T-P-V-F-S (SEQ ID NO 44) or a position corresponding to position 4 in the motif sequence 1 H: H-A-Q-Y-S-P-H-F-S (SEQ ID NO: 45); a position corresponding o position 4 in the motif sequence 2: A-L-G-N-G-G-L-G (SEQ ID NO: 46); and a position corresponding to position 7 in the motif sequence 3L: R-l-V-K-F-I-T-D-V (SEQ ID NO: 47) or a position corresponding to position 7 in the motif sequence 3H: R-l-V-K-L-V-N-D-V (SEQ ID NO: 48).

The α-glucan phosphorylase having improved thermostability according to the present invention has an amino acid residue which is different from an amino acid residue of the natural α-glucan phosphorylase in at least one position selected from the group consisting of a position corresponding to phenylalanine at position 39 (F39) of the amino acid sequence set forth in SEQ ID NO: 2, a position corresponding to asparagine at position 135 (N135) of the amino acid sequence set forth in SEQ ID NO: 2 and a position corresponding to threonine at position 706 (T706) of the amino acid sequence set forth in SEQ ID NO: 2. The α-glucan phosphorylase having improved thermostability of the present invention may contain an amino acid sequence in which, in addition to substitution of an amino acid residue at these positions, one or a several amino acids are deleted, substituted or added relative to an amino acid sequence of natural α-glucan phosphorylase.

In one embodiment, the α-glucan phosphorylase having improved thermostability of the present invention contains an amino acid sequence in which one or a several amino acids are deleted, substituted or added relative to an amino acid sequence of plant-derived α-glucan phosphorylase, and has an amino acid residue which is different from an amino acid residue of the natural α-glucan phosphorylase in at least one position selected from the group consisting of a position corresponding to phenylalanine at position 39 (F39) of the amino acid sequence set forth in SEQ ID NO: 2, a position corresponding to asparagine at position 135 (N135) of the amino acid sequence set forth in SEQ ID NO: 2 and a position corresponding to threonine at position 705 (T706) of the amino acid sequence set forth in SEQ ID NO: 2.

The enzyme of the present invention is α-glucan phosphorylase having improved thermostability, obtained by modifying plant-derived natural α-glucan phosphorylase, contains an amino acid sequence in which one or a several amino acids are deleted, substituted or added relative to an amino acid sequence of the natural α-glucan phosphorylase, and has an amino acid residue which is different from an amino acid residue of the natural α-glucan phosphorylase in at least one position selected from the group consisting of a position: corresponding to phenylalanine at position 39 (F39) of the amino acid sequence set forth in SEQ ID NO: 2; a position corresponding to asparagine at position 135 (N135) of the amino acid sequence set forth in SEQ ID NO: 2; and a position corresponding to threonine at position 706 (T706) of the amino acid sequence set forth in SEQ ID NO: 2.

It is preferable that the enzyme of the present invention has an amino acid residue which is different from that of natural α-glucan phosphorylase in at least two positions selected from the group consisting of: a position corresponding to phenylalanine at position 39 (F39) of the amino acid sequence of SEQ ID NO: 2; a position corresponding to asparagine at position 135 (N135) of the amino acid sequence set forth in SEQ ID NO: 2; and a position corresponding to position 705 threonine (T706) of the amino acid sequence set forth in SEQ ID NO: 2. It is most preferable that the enzyme of the present invention has an amino acid residue which is different from that of natural α-glucan phosphorylase in all positions of a position corresponding to phenylalanine at position 39 (F39) of the amino acid sequence set forth in SEQ ID NO: 2; a position corresponding to asparagine at position 135 (N135) of the amino acid sequence set forth in SEQ ID NO: 2; and a position corresponding to position 706 threonine (T706) of the amino acid sequence offset forth in SEQ ID NO: 2.

It is thought that the aforementioned three positions of natural α-glucan phosphorylase interact with surrounding amino acids in the steric structure of α-glucan phosphorylase to form a steric partial structure which destabilizes the enzyme. By changing a residue at these positions to another amino acid residue, an enzyme is stabilized, and thermostability is improved. In addition, since residues at these positions steric-structurally interact with surrounding amino acid residues, substitution of the amino acid residues has unexpectedly important significant effects. For example, in the case of potato type L α-glucan phosphorylase, substitution of F at a position of F39 with other residues has unexpectedly important significant consequences. In addition, for example, in potato-derived type H α-glucan phosphorylase, an amino acid at a position corresponding to F39 is Y, and substitution of Y with other amino acids has unexpectedly important significant effects.

In the enzyme according to the present invention, an amino acid residue at a position corresponding to position 4 or F39 in the motif sequence 1L or 1 may be an amino acid other than an amino acid residue found in natural o-glucan phosphorylase. An amino acid residue at a position corresponding to position corresponding to position 4 or F39 in the motif sequence 1L or 1H is preferably an aliphatic amino acid, or a heterocyclic amino acid, more preferably an aliphatic amino acid, particularly preferably a branched amino acid (i.e. valine, leucine or isoleucine), specially preferably isoleucine or leucine, most preferably isoleucine.

In the enzyme according to the present invention, an amino acid residue at a position corresponding to position 4 or N135 in a motif sequence 2 can be an amino acid other than an amino acid residue found in natural α-glucan phosphorylase. An amino acid residue at a position corresponding to position 4 or N135 in a motif sequence 2 is preferably an aliphatic amino acid or a heterocyclic amino acid, more preferably alanine, cysteine, aspartic acid, glutamic acid, glycine, histidine, isoleucine, leucine, methionine, phenylalanine, serine, threonine, valine or tyrosine, particularly preferably cysteine, glycine, serine or valine.

In the enzyme according to the present invention, an amino acid residue at a position corresponding to position 7 or T706 in the motif sequence 3L or 3H can be an amino acid other than an amino acid residue found in natural α-glucan phosphorylase. An amino acid residue at a position corresponding to position 7 or T706 in a motif sequence 3L or 3H is preferably an aliphatic amino acid, more preferably a branched amino acid (i.e. valine, leucine or isoleucine) or a sulfur-containing amino acid (i.e. cysteine, cystine, methionine), particularly preferably cysteine, isoleucine, leucine, valine or tryptophan, particularly preferably cysteine, isoleucine, leucine or valine, most preferably isoleucine.

In the method according to the present invention, for preparing α-glucan phosphorylase having improved thermostability, a substitution, addition, deletion or modification of an amino acid can be performed in addition to alteration of the object of the invention (such the substitution that an α-glucan phosphorylase has an amino acid residue which is different from an amino acid residue of the natural α-glucan phosphorylase in at least one position selected from the group consisting of a position corresponding to phenylalanine at position 39 (F39) of the amino acid sequence set forth in SEQ ID NO: 2, a position corresponding to asparagine at position 135 (N135) of the amino acid sequence set forth in SEQ ID NO: 2 and a position corresponding to position 706 threonine (T706) of the amino acid sequence set forth in SEQ ID NO: 2). Substitution of an amino acid refers to substitution of one amino acid with another one amino acid. Addition of an amino acid refers to insertion of one or more, for example, 1 to 10, preferably 1 to 5, more preferably 1 to 3 amino acids into any position of the original amino acid sequence. Deletion of an amino acid refers to removal of one or more, for example, 1 to 10, preferably 1 to 5, more preferably 1 to 3 amino acids from the original amino acid sequence. Examples of amino acid modification include but are not limited to amidation, carboxylation, sulfation, halogenation, alkylation, glycosylation, phosphorylation, hydroxylation, and acylation (e.g. acetylation). The α-glucan phosphorylase having improved thermostability of the present invention may be synthesized by a peptide synthesis method and, in such the case, an amino acid to be substituted or added may be a natural amino acid, a non-natural amino acid or an amino acid analog. A natural amino acid is preferable.

The α-glucan phosphorylase having improved thermostability of the present invention may be an enzyme analog having the same enzyme activity as α-glucan phosphorylase. As used herein, a term "enzyme analog" refers to an entity which is a different compound from a natural enzyme, but has equivalent in at least one chemical function or biological function to that of a natural enzyme. Therefore, the enzyme analog includes an entity in which one or more amino acid analogs are added or substituted relative to the original natural enzyme. The enzyme analog has such an addition or substitution, that its function (e.g. α-phosphorylase activity or thermostability) is substantially the same as, or better than, the function of the original natural enzyme. Such an enzyme analog can be prepared using techniques well-known in the art. Therefore, the enzyme analog can be a polymer containing an amino acid analog. In the present specification, the "enzyme" includes this enzyme analog unless otherwise indicated.

In the present specification, the "amino acid" may be a natural amino acid, a non-natural amino acid, a derivative amino acid, or an amino acid analog. A natural amino acid is preferable.

The term "natural amino acid" means an L-isomer of a natural amino acid. A natural amino acid is glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine, and lysine. Unless otherwise is indicated, all amino acids referred in the present specification are in L form, and an embodiment using an amino acid in D form is also within the scope of the present invention.

The term "non-natural amino acid" means an amino acid which is not usually found in a protein in nature. Examples of the non-natural amino acid include norleucine, para-nitrophenylalanine, homophenylalanine, para-fluorophenylalanine, 3-amino-2-benzylpropionic acid, a D form or an N form of homoarginine, and D-phenylalanine.

The term "derivative amino acid" refers to an amino acid which is obtained by derivatizing an amino acid.

The term "amino acid analog" refers to a molecule which is not an amino acid, but is similar to an amino acid in physical properties and/or function. Examples of the amino acid analog include, for example, ethionine, canavanine, and 2-methylglutamine.

In the present specification, an amino acid can be referred by any of the generally known three letter symbol, and one letter symbol recommended by IUPAC-IUB Biochemical Nomenclature Commission. A nucleotide can be referred by a generally-accepted one letter code, similarly.

α-glucan phosphorylase having improved thermostability including modification due to substitution, addition or deletion of one or a few or more plural amino acids relative to an amino acid sequence of natural α-glucan phosphorylase, in addition to the objective modification is within the scope of the present invention. Such an α-glucan phosphorylase having improved thermostability including substitution, addition or deletion of one or a few or more amino acid can be prepared according to the methods described in, for example, Molecular Cloning, A Laboratory Manual, Second Edition, Cold Spring Harbor Laboratory Press (1989), Current Protocols in Molecular Biology, Supplement 1-38, John Wiley & Sons (1987-1997), Nucleic Acids Research, 10, 6487(1982), Proc. Natl. Acad. Sci., USA, 79, 6409(1982), Gene, 34, 315(1985), Nucleic Acids Research 13, 443 (1985), Proc. Natl. Acad. Sci USA, 82, 488 (1985), Proc. Natl. Acad. Sci., USA, 81, 5662 (1984), Science, 224, 1431(1984), PCT WO 85/00817 (1985), Nature, 316, 601 (1985).

A α-glucan phosphorylase having improved thermostability according to the present invention can be prepared by utilizing methods well-known in the art. For example, deletion, substitution or addition of an amino acid in the α-glucan phosphorylase having improved thermostability of the present invention can be performed by site-directed mutagenesis which is a well-known technique. The procedure of site-directed mutagenesis is well-known in the art. For example, see Nucl. Acid Research, Vol. 10, pp. 6487-6500 (1982).

In the present specification, the "substitution, addition or deletion of one or a few or more plural amino acids" or the "substitution, addition or deletion of at least one amino acid", when used regarding α-glucan phosphorylase having improved thermostability, refers to a number of substitutions, additions or deletions, to such a degree that the enzyme activity of α-glucan phosphorylase is not lost, preferably, the enzyme activity becomes equivalent or superior over a standard (e.g. natural α-glucan phosphorylase). Those skilled in the art can easily select α-glucan phosphorylase having improved thermostability having the desired nature. Alternatively, objective α-glucan phosphorylase having improved thermostability may be directly chemically synthesized. Such chemical synthesis method is well-known in the art.

The thus prepared α-glucan phosphorylase having improved thermostability of the present invention has preferably about 40%, more preferably about 45%, more preferably about 50%, more preferably about 55%, more preferably about 60%, more preferably about 65%, more preferably about 70%, more preferably about 75%, more preferably about 80%, more preferably about 85%, more preferably about 90%, more preferably about 95%, and most preferably about 99% identity to an amino acid sequence of first (natural) α-glucan phosphorylase (preferably, potato type L α-glucan phosphorylase).

Upon design of the aforementioned alteration, the hydrophobicity index of an amino acid can be considered. Significance of a hydrophobic amino acid index upon impartation interacting biological function to a protein is generally recognized in the art (Kyte. J and Doolittle, R. F. J. Mol. Biol. 157 (1): 105-132, 1982). The hydrophobic nature of an amino acid contributes to the secondary structure of a produced protein and, then, defines interaction between the protein and other molecule (e.g. enzyme, substrate, receptor, DNA, antibody, antigen and the like). An amino acid is assigned a hydrophobicity index based on hydrophobicity and a nature of a charge thereof. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5).

It is well-known in the art to substitute a certain amino acid with another amino acid having a similar hydrophobicity index, thereby, a protein still having similar biological functions (e.g. protein equivalent in enzyme activity) can be produced. In such an amino acid substitution, a hydrophobicity index is preferably within ±2, more preferably within ±1, further preferably within ±0.5. It is understood in the art that such the substitution of an amino acid based on hydrophobicity is efficient. As described in U.S. Pat. No. 4,554,101, the following hydrophilicity index is assigned to amino acid residues: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid can be substituted with another amino acid which has a similar hydrophilicity index, and can still impart a biological equivalent. In such the amino acid substitution, the hydrophilicity index is preferably within ±2, more preferably within ±1, and further preferably within ±0.5.

In the present invention, "conservative substitution" refers to substitution in which a hydrophilicity index or/and a hydrophobicity index are similar, as described above, between the original amino acid and an amino acid to be substituted, in amino acid substitution. Examples of conservative substitution are well-known to those skilled in the art, and include, but are not limited to substitution among the following each group, for example: arginine and lysine; glutamic acid and aspartic acid; serine and threonine; glutamine and asparagines; and valine, leucine, and isoleucine.

(3.2 Method of Assessing Thermostability)

The α-glucan phosphorylase having improved thermostability of the present invention has one characteristic, in that enzyme activity of α-glucan phosphorylase having improved thermostability at 37° C., after it is heated in a 20 mM citrate buffer (pH 6.7) at 60° C. for 10 minutes, is 20% or more of enzyme activity of the α-glucan phosphorylase having improved thermostability at 37° C., before heating. Enzyme activity of the α-glucan phosphorylase having improved thermostability at 37° C., after heating in a 20 mM citrate buffer (pH 6.7) at 60° C. for 10 minutes, is preferably about 20% or more, more preferably about 25% or more, more preferably about 30% or more, more preferably about 40% or more, more preferably about 50% or more, more preferably about 55% or more, more preferably about 60% or more, further preferably about 65% or more, further preferably about 70% or more, particularly preferably about 80% or more, most preferably about 90% or more of enzyme activity of α-glucan phosphorylase having improved thermostability at 37° C., before the heating.

Enzyme activity of α-glucan phosphorylase having improved thermostability at 37° C., after heating in a 20 mM citrate buffer (pH 6.7) at 65° C. for 2 minutes is preferably about 40% or more, more preferably about 45% or more, further preferably about 50% or more, further preferably about 55% or more, particularly preferably about 60% or more, most preferably about 65% or more of enzyme activity at 37° C. of α-glucan phosphorylase having improved thermostability, before the heating.

(3.2.1 Method of Measuring α-Glucan Phosphorylase (GP) Activity)

This GP enzyme activity measuring method quantitates free inorganic phosphoric acid (Pi) produced from G-1-P.

(i) 200 µl of a reaction solution (containing 12.5 mM G-1-P, 1% dextrin and an enzyme solution in a 100 mM acetate buffer (pH 6.0)) is incubated at 37° C. for 15 minutes.

(ii) 800 µl of a molybdenum regent (15 mM ammonium molybdate, 100 mM zinc acetate) is added, and this is stirred to stop the reaction.

(iii) 200 µl of 568 mM ascorbic acid (pH 5.8) is added, followed by mixing.

(iv) After incubation at 37° C. for 15 minutes, an absorbance at 850 nm is measured using a spectrophotometer.

(v) An absorbance is measured similarly using inorganic phosphoric acid having the known concentration, and a standard curve is produced.

(vi) An absorbance value obtained for a sample is fitted to this standard curve, and the amount of inorganic phosphoric acid in the sample is determined. Inorganic phosphoric acid is quantitated as a phosphoric acid ion. The amount of glucose-1-phosphate is not quantitated. In the present specification, one unit of α-glucan phosphorylase activity is defined an activity which produces 1 µmol inorganic phosphoric acid (Pi) for one minute as one unit (U) when measured by this measuring method (3.2.2 Method of Measuring Thermostability)

Thermostability is measured according to the following procedure.

(i) 0.2 U/ml of an enzyme solution (in 20 mM citrate buffer (pH 6.7)) is incubated at 55° C., 60° C., or 65° C. for 0 to 60 minutes.

(ii) a sample of enzyme solution is taken a number of time points, and retained on ice.

(iii) The enzyme solution samples of (ii) are diluted 10-fold, and enzyme activity is measured according to a GP activity measuring method. A ratio of enzyme activity $A_{after}$ of α-glucan phosphorylase having improved thermostability at 37° C., after heating in a 20 mM citrate buffer (pH 6.7) at 60° C. for 10 minutes is calculated from enzyme activity $A_{before}$ at 37° C. of the α-glucan phosphorylase having improved thermostability before heating, by $(A_{after})/(A_{before}) \times 100(\%)$. A ratio of enzyme activity $A_{after}$ of α-glucan phosphorylase having improved thermostability after heating relative to enzyme activity $A_{before}$ of the α-glucan phosphorylase having improved thermostability before heating is also referred to as remaining activity.

(3.3 Method of Assessing Ability to Synthesize Amylose)

The α-glucan phosphorylase having improved thermostability of the present invention has one characteristic in that it has the ability to synthesize a glucan (particularly, amylose) having a weight average molecular weight of preferably about 60 kDa or more, more preferably about 100 kDa or more, further preferably about 150 kDa or more, further preferably about 200 kDa or more, further preferably about 250 kDa or more, further preferably about 300 kDa or more, further preferably about 350 kDa or more, further preferably about 400 kDa or more, further preferably about 450 kDa or more, further preferably about 500 kDa or more, further preferably about 550 kDa or more, further preferably about 600 kDa or more, most preferably about 650 kDa or more. A glucan having a weight average molecular weight of about 5 kDa to about 599 kDa is hardly soluble in water, while a glucan having a weight average molecular weight of about 600 kDa or more has the particular advantage that it is water-soluble. A weight average molecular weight of a glucan synthesized by the α-glucan phosphorylase having improved thermostability of the present invention does not have a particular upper limit, but a glucan up to 1000 kDa, up to 10000 kDa, up to 100000 kDa can be synthesized with excellent productivity.

The "has ability to synthesize amylose having a weight average molecular weight of 60 kDa or more" refers to when a weight average molecular weight of amylose synthesized by incubation at 37° C. for 18 hours using 40 µM maltotetraose, 250 mM glucose-1-phosphate, a 200 mM acetate buffer (pH 5.5), and 4 U/ml reaction solution of α-glucan phosphorylase having improved thermostability (purified enzyme), is 60 kDa or more. The ability to synthesize amylose having other weight average molecular weight is similarly defined and, for example, "has ability to synthesize amylose having a weight average molecular weight of 600 kDa or more" refers to when a weight average molecular weight of amylose synthesized under this condition is 600 kDa or more.

A weight average molecular weigh of amylose can be measured, for example, by the following method.

Firstly, synthesized amylose is completely dissolved in 1N sodium hydroxide, this is neutralized with a suitable amount of hydrochloric acid, and about 30 to 300 µg of an aliquot of amylose is subjected to gel filtration chromatography using both a differential refractometer and a multiangular light scatter detector, thereby, obtaining an average molecular weight.

More particularly, as a column, Shodex SB806M-HQ (manufactured by SHOWA DENKO K.K.) is used and, as a detector, a multiangular light scatter detector (DAWN-DSP, manufactured by Wyatt Technology) and a differential refractometer (Shodex RI-71, manufactured by SHOWA DENKO K.K.) are used by connecting them in that order. A column is retained at 40° C., and a 0.1M sodium nitrate solution is used as an eluent at a flow rate of 1 mL/min. The resulting signal is collected using a data analysis software (trade name ASTRA, manufactured by Wyatt Technology), and is analyzed using the same software, thereby, a weight average molecular weight is obtained.

(3.4 Method of Assessing Storage Stability)

The α-glucan phosphorylase having improved thermostability according to the present invention is preferably improved in storage stability as compared with natural α-glucan phosphorylase. In the present specification, the "improved in storage stability" refers to when the enzyme is hardly degraded during storage as compared with natural α-glucan phosphorylase.

In one embodiment, storage stability refers to stability when stored at 4° C. In this case, when the α-glucan phosphorylase having improved thermostability according to the present invention is stored at 4° C. for a certain period of time after purification, the molecular weight of the enzyme protein is almost equivalent to that immediately after purification. Generally, when natural α-glucan phosphorylase is stored at 4° C. for a long term, it is degraded, and the molecular weight of an enzyme protein is reduced as compared with immediately after purification. After the α-glucan phosphorylase having improved thermostability of the present invention is stored preferably at 4° C. for 1 month, stored more preferably at 4° C. for 3 months, stored most preferably at 4° C. for 5 months, it has a molecular weight approximately equivalent to that immediately after purification.

In another aspect, storage stability refers to stability when stored at 37° C. In this case, when the α-glucan phosphorylase having improved thermostability of the present invention is stored at 37° C. for a certain period of time after purification, the molecular weight of the enzyme protein is approximately equivalent to that immediately after purification. Generally, when natural α-glucan phosphorylase is stored at 37° C. for a long term, it is degraded, and the molecular weight of an enzyme protein is reduced as compared with immediately after purification. In another aspect, after the α-glucan phosphorylase having improved thermostability of the present invention is preferably stored at 37° C. for 4 days, more preferably stored at 37° C. for 7 days, most preferably stored at 37° C. for 10 days, it has a molecular weight approximately equivalent to that immediately after purification.

Of course, the α-glucan phosphorylase having improved thermostability of the present invention can be stored at any temperature which is normally used for storage. A temperature used for storage may be any temperature between about 4° C. to about 37° C. (e.g. about 4° C., about 5° C., about 10° C., about 20° C., about 25° C., about 37° C. and the like).

Storage stability can be assessed by any method known in the art. For example, an enzyme protein immediately after purification, and an enzyme protein which has been stored at a predetermined temperature for a certain term are subjected to polyacrylamide gel electrophoresis (Native-PAGE), and storage stability can be assessed by comparing molecular weights of these enzyme proteins.

(4. Method for Producing Glucan Using Enzyme of the Present Invention)

The α-glucan phosphorylase having improved thermostability of the present invention can be advantageously used in a method of synthesizing a glucan. A method of synthesizing a glucan using the α-glucan phosphorylase having improved thermostability of the present invention can be any method of synthesizing a glucan known in the art, but it is preferable to use the present α-glucan phosphorylase in a method (also referred to as SP-GP method) of reacting sucrose phosphorylase and α-glucan phosphorylase on sucrose and a primer at the same time. The SP-GP method has an advantage that a linear glucan can be produced using an inexpensive substrate.

A method of synthesizing a glucan of the preset invention includes reacting a reaction solution containing the α-glucan phosphorylase having improved thermostability according to the present invention, a sucrose phosphorylase, sucrose, a primer, and inorganic phosphoric acid or glucose-1-phosphate, to produce a glucan.

The method of synthesizing a glucan of the present invention may be a method not based on a SP-GP method. In the case of such a method, the method of synthesizing a glucan of the present invention includes reacting a reaction solution containing the α-glucan phosphorylase having improved thermostability of the present invention, a primer, and glucose-1-phosphate, to produce a glucan.

In the present specification, the "glucan" refers to a saccharide containing D-glucose as a constituent unit, and having at least two saccharide units or more of a saccharide unit linked with an α-1,4-glucoside bond. A glucan can be a linear, branched or cyclic molecule. A linear glucan has the same meaning as that of α-1,4-glucan. In a linear glucan, saccharide units are linked only with an α-1,4-glucoside bond. A glucan containing one or more α-1,6-glucoside bonds is a branched glucan. A glucan preferably contains a linear section to some extent. A linear glucan having no branching is more preferable.

It is preferably that a glucan has a small number (i.e. the number of α-1,6-glucoside bonds) of branches in some cases. In such the case, the number of branches is representatively 0 to 10000, preferably 0 to 1000, more preferably 0 to 500, further preferably 0 to 100, further preferably 0 to 50, further preferably 0 to 25, further preferably 0.

In the glucan of the present invention, the ratio of the number of α-1,4-glucoside bonds relative to the number of α-1,6-glucoside bonds letting α-1,6-glucoside bond to be 1, is preferably 1 to 10000, more preferably 2 to 5000, further preferably 5 to 1000, further preferably 10 to 500.

α-1,6-glucoside bond may be distributed in a glucan randomly, or may be distributed uniformly. A distribution to such an extent that a linear part of 5 or more of saccharide units is formed in a glucan is preferable.

A glucan may be constructed only of D-glucose, or may be a derivative modified to such an extent that the nature of such a glucan is not deteriorated. It is preferable that the glucan is not modified.

A glucan has a molecular weight of representatively about $8 \times 10^3$ or more, preferably about $1 \times 10^4$ or more, more preferably about $5 \times 10^4$ or more, further preferably about $1 \times 10^5$ or more, further preferably about $6 \times 10^5$ or more. A glucan has a molecular weight of representatively about $1 \times 10^8$ or less, preferably about $3 \times 10^7$ or less, more preferably about $1 \times 10^7$ or less, further preferably about $5 \times 10^6$ or less, further preferably about $1 \times 10^6$ or less. In the present invention, the molecular weight of a glucan refers to a weight average molecular weight unless otherwise described.

Those skilled in the art easily understands that a glucan having a desired molecular weight is obtained by appropriately selecting an amount of a substrate, an amount of an enzyme, a reaction time and the like used in the production method of the present invention.

The SP-GP method having excellent productivity is described in International Publication WO 02/097107 pamphlet.

In the production method of the present invention, for example, α-glucan phosphorylase having improved thermostability, sucrose phosphorylase, sucrose, a primer, inorganic phosphoric acid or glucose-1-phosphate, a buffer, and a solvent dissolving it are used as main materials. Usually, these materials are all added at reaction initiation, and any material among them may be additionally added during the reaction. In the production method of the present invention, if necessary, an enzyme selected from the group consisting of a debranching enzyme, a branching enzyme, 4-α-glucanotransferase and glycogen debranching enzyme can be used. An enzyme selected from the group consisting of: a debranching enzyme, a branching enzyme, 4-α-glucan transferase and a glycogen debranching enzyme may be added to a reaction solution from beginning of the production method of the present invention, or may be added to a reaction solution midway, depending upon the desired structure of glucan.

In the present specification, the "sucrose phosphorylase" refers to any enzyme which transfers an α-glycosyl group of sucrose to a phosphate group to perform phosphorolysis. A reaction catalyzed by sucrose phosphorylase is represented by the following equation:

Sucrose+inorganic phosphoric acid ⇔ α-D-glucose-1-phosphate+D-fructose

Sucrose phosphorylase is contained in various organisms in a natural world. Examples of an organism producing sucrose phosphorylase include but are not limited to bacteria belonging to genus *Streptococcus* (e.g. *Streptococcus thermophilus, Streptococcus mutans, Streptococcus pneumoniae,* and *Streptococcus mitis*), *Leuconostoc mesenteroides, Pseudomonas* sp., *Clostridium* sp., *Pullularia pullulans, Acetobacter xylinum, Agrobacterium* sp., *Synecococcus* sp., *E. coli, Listeria monocytogenes, Bifidobacterium adolescentis, Aspergillus niger, Monilia sitophila, Sclerotinea escerotiorum,* and *Chlamydomonas* sp.

Sucrose phosphorylase can be derived from any organism producing sucrose phosphorylase. It is preferable that sucrose phosphorylase has thermostability to some extent. It is more preferable that sucrose phosphorylase, when it is present alone, has higher thermostability. For example, it is preferable that, when sucrose phosphorylase is heated at 55° C. for 30 minutes in the presence of 4% of sucrose, activity which is 20% or more of activity of sucrose phosphorylase before heating, is retained. Sucrose phosphorylase can be preferably derived from a bacterium selected from the group consisting of: *Streptococcus mutans, Streptococcus pneumoniae, Leuconostoc mesenteroides, Oenococcus oeni, Bifidobacterium longum, Agrobacterium vitis, Pseudomonas saccharophila, Escherichia coli* and *Listeria innocua*, can be more preferably derived from a bacterium selected from the group consisting of: *Streptococcus mutans, Streptococcus pneumoniae, Leuconostoc mesenteroides* and *Oenococcus oeni*, further preferably can be derived from *Streptococcus mutans* or *Streptococcus pneumoniae*.

Sucrose is a disaccharide having a molecular weight of about 342, represented by $C_{12}H_{22}O_{11}$. Sucrose is present in all plants having photosynthetic ability. Sucrose may be isolated from a plant, or may be chemically synthesized. From the viewpoint of cost, it is preferable that sucrose is isolated from a plant. Examples of a plant containing a large amount of sucrose include sugarcane, and sugar beet. Sugarcane juice contains about 20% sucrose. Sugar beet juice contains about 10 to 15% sucrose. Sucrose may be provided at any purification stage from the sap or juice of a plant containing sucrose, to purified sugar.

α-glucan phosphorylase having improved thermostability and a sucrose phosphorylase used in the production method of the present invention can be used in a reaction, respectively, even when immobilized whether it is a purified enzyme or a crude enzyme, and a reaction format may be a batch format or a continuous format. As a method of immobilization, a carrier binding method (e.g. covalent binding method, ion binding method, or physical adsorbing method), a crosslinking method or an inclusion method (lattice type or microcapsule type) can be used.

Examples of a primer include maltooligosaccharide, amylose, amylopectin, glycogen, dextrin, pullulan, coupling sugar, starch, and a derivative thereof.

In the present specification, inorganic phosphoric acid refers to a substance which can donate a phosphate substrate in the reaction of SP. In the present specification, a phosphate substrate refers to a substance which is a raw material for the phosphate moiety of glucose-1-phosphate. It is thought that, in sucrose phosphorolysis which is catalyzed by sucrose phosphorylase, inorganic phosphoric acid acts as a substrate in a form of a phosphate ion. Since this substrate is conventionally called inorganic phosphoric acid in the art, this substrate is called inorganic phosphoric acid also in the preset specification. Inorganic phosphoric acid includes phosphoric acid and an inorganic salt of phosphoric acid. Usually, inorganic phosphoric acid is used in water containing a cation such as an alkali metal ion. In this case, since phosphoric acid, a phosphate salt and a phosphate ion are in an equilibrium state, it is not possible to discriminate between phosphoric acid and a phosphate salt. Therefore, for convenience, phosphoric acid and a phosphate salt are collectively called inorganic phosphoric acid. In the present invention, inorganic phosphoric acid is preferably any metal salt of phosphoric acid, more preferably an alkali metal salt of phosphoric acid. Preferable specific examples of inorganic phosphoric acid include sodium dihydrogen phosphate, disodium hydrogen phosphate, trisodium phosphate, potassium dihydrogen phosphate, dipotassium hydrogen phosphate, tripotassium phosphate, phosphoric acid ($H_3PO_4$), ammonium dihydrogen phosphate, and diammonium hydrogen phosphate.

Only one kind of, or a plurality of kinds of inorganic phosphoric acids may be contained in a SP-GP reaction system at reaction initiation.

Inorganic phosphoric acid can be provided, for example, by degrading a phosphoric acid condensate such as polyphosphoric acid (e.g. pyrophosphoric acid, triphosphoric acid and tetraphosphoric acid) or a salt thereof, by a physical, chemical or enzymatic reaction, and adding this to a reaction solution.

In the present specification, glucose-1-phosphate refers to glucose-1-phosphate ($C_6H_{13}O_9P$) and a salt thereof. Glucose-1-phosphate is preferably any metal salt of glucose-1-phosphate ($C_6H_{13}O_9P$) in a narrow sense, more preferably any alkali metal salt of glucose-1-phosphate ($C_6H_{13}O_9P$). Preferable specific examples of glucose-1-phosphate include disodium glucose-1-phosphate, dipotassium glucose-1-phosphate, and glucose-1-phosphate ($C_6H_{13}O_9P$). In the present specification, glucose-1-phosphate whose chemical formula is not drawn in a parenthesis indicates glucose-1-phosphate in a wide sense, that is, glucose-1-phosphate ($C_6H_{13}O_9P$) in a narrow sense and a salt thereof.

Only one kind of, or a plurality of kinds of glucose-1-phosphates may be contained in a SP-GP reaction system, at reaction initiation.

In the method for producing a glucan according to the present invention, when a branch is generated in the product, such as when a starting material containing α-1,6-glucoside bond is used, a debranching enzyme can be used, if necessary.

A debranching enzyme which can be used in the present invention is an enzyme which can cut an α-1,6-glucoside bond. A debranching enzyme is classified into two of isoamylase (EC 3.2.1.68) which acts well on both of amylopectin and glycogen, and α-dextrin endo-1,6-α-glucosidase (also referred to as pullulanase) (EC3.2.1.41) which acts on amylopectin, glycogen and pullulan.

A debranching enzyme is present in microorganisms, bacteria, and plants. Examples of a microorganism producing a debranching enzyme include *Saccharomyces cerevisiae*, and *Chlamydomonas* sp. Examples of a bacterium producing a debranching enzyme include *Bacillus brevis, Bacillus acidopullulyticus, Bacillus macerans, Bacillus stearothermophilus, Bacillus circulans, Thermus aquaticus, Klebsiella pneumoniae, Thermoactinomyces thalpophilus, Thermoanaerobacter ethanolicus,* and *Pseudomonas amyloderamosa*. Examples of a plant producing a debranching enzyme include potato, sweet potato, corn, rice, wheat, barley, oat, and sugar beet. An organism producing a debranching enzyme is not limited to the above examples.

In the method according to the invention, when it is desired to generate a branch in the product, a branching enzyme can be used, if necessary.

A branching enzyme which can be used in the present invention is an enzyme which can transfer a part of an α-1,4-glucan chain to position 6 of a certain glucose residue in this α-1,4-glucan chain to make a branch. A branching enzyme is also called a 1,4-α-glucan branching enzyme, a branch making enzyme or a Q enzyme.

A branching enzyme is present in a microorganism, an animal, and a plant. Examples of a microorganism producing a branching enzyme include *Bacillus stearothermophilus, Bacillus subtilis, Bacillus caldolyticus, Bacillus lichecniformis, Bacillus amyloliquefaciens, Bacillus coagulans, Bacillus caldovelox, Bacillus thermocatenulatus, Bacillus smithii, Bacillus megaterium, Bacillus brevis, Alkalophillic Bacillus* sp., *Streptomyces coelicolor, Aquifex aeolicus, Synechosystis* sp., *E. coli, Agrobacterium tumefaciens, Thermus aquaticus, Rhodothermus obamensis, Neurospora crassa*, and yeast. Examples of an animal producing a branching enzyme include mammals such as human, rabbit, rat, and pig. Examples of plants producing a branching enzyme include algae; tuber and root crops such as potatoes, sweet potato, yam, and cassaya; vegetables such as spinach; cereals such as corn, rice, wheat, barley, rye, and foxtail millet; and beans such as peas, soybeans, adzuki beans, and mottled kidney beans. An organism producing a branching enzyme is not limited to the above examples.

In the method according to the invention, when a cyclic structure is generated in the product, 4-α-glucanotransferase can be used, if necessary.

4-α-glucanotransferase which can be used in the present invention is also called a disproportionating enzyme, a D-enzyme, or amylomaltase, and is an enzyme which can catalyze a sugar transferring reaction (disproportionating reaction) of maltooligosaccharide. 4-α-glucanotransferase is an enzyme which transfers a glucosyl group, or a maltosyl or maltooligosyl unit from a non-reducing terminal of a donor molecule to a non-reducing terminal of an acceptor molecule. Therefore, an enzyme reaction leads to disproportion of a polymerization degree of maltooligosaccharide which was first given. When a donor molecule and an acceptor molecule are the same, an intramolecular transfer is caused and, as a result, a product having a cyclic structure is obtained.

4-α-glucanotransferase is present in microorganisms and plants. Examples of a microorganism producing 4-α-glucanotransferase include *Aquifex aeolicus, Streptococcus pneumoniae, Clostridium butylicum, Deinococcus radiodurans, Haemophilus influenzae, Mycobacterium tuberculosis, Thermococcus litralis, Thermotoga maritima, Thermotoga neapolitana, Chlamydia psittaci, Pyrococcus* sp., *Dictyoglomus thermophilum, Borreliaburgdorferi, Synechosystis* sp., *E. coli*, and *Thermus aquaticus*. Examples of plants producing 4-α-glucanotransferase include tuber and root crops such as potatoes, sweet potatoes, yam, and cassaya; cereals such as corn, rice, and wheat; and beans such as peas, and soybeans. An organism producing 4-α-glucanotransferase is not limited to the above examples.

In the method of the present invention, when a cyclic structure is generated in a product, a glycogen debranching enzyme can be used, if necessary.

A glycogen debranching enzyme which can be used in the present invention is an enzyme having two kinds of activities, α-1,6-glucosidase activity and 4-α-glucanotransferase activity. Due to 4-α-glucanotransferase activity possessed by a glycogen debranching enzyme, a product having a cyclic structure is obtained.

A glycogen debranching enzyme is present in microorganisms and animals. Examples of a microorganism producing a glycogen debranching enzyme include yeast. Examples of animals producing a glycogen debranching enzyme include mammals such as human, rabbit, rat, and pig. An organism producing a glycogen debranching enzyme is not limited to the above examples.

A solvent used in the production method of the present invention can be any solvent as far as it is a solvent which does not deteriorate the enzyme activity of sucrose phosphorylase and α-glucan phosphorylase.

As far as a reaction producing a glucan can proceed, it is not necessary that a solvent completely dissolves materials used in the production method according to the present invention. For example, when an enzyme is carried on a solid carrier, it is not necessary that an enzyme is dissolved in a solvent. Further, it is not necessary that all of reaction materials such as sucrose are dissolved, and it is enough that a part of materials, to such an extent that a reaction can proceed, is dissolved.

A representative solvent is water. A solvent may be water in a cell lysate, accompanying sucrose phosphorylase or α-glucan phosphorylase upon the preparation of sucrose phosphorylase or α-glucan phosphorylase.

Any other substance may be contained in a solution containing an α-glucan phosphorylase, a sucrose phosphorylase, sucrose, a primer, and inorganic phosphoric acid or glucose-1-phosphate, as long as interaction between the sucrose phosphorylase and sucrose, and interaction between the α-glucan phosphorylase and the primer are not hampered. Examples of such a substance include a buffer, a component of a microorganism producing α-glucan phosphorylase (e.g. bacterium, fungus), a component of a microorganism producing sucrose phosphorylase (e.g. bacterium, fungus), salts, and a medium component.

Amounts of these materials to be used are the known, and can be appropriately selected by those skilled in the art.

In the production method according to the present invention, firstly, a reaction solution is prepared. A reaction solution can be prepared, for example, by adding an α-glucan phosphorylase, a sucrose phosphorylase, solid sucrose, a primer, and inorganic phosphoric acid or glucose-1-phosphate to a suitable solvent. Alternatively, a reaction solution may be prepared by mixing solutions each containing an α-glucan phosphorylase, a sucrose phosphorylase, sucrose, a primer, or inorganic phosphoric acid or glucose-1-phosphate. Alternatively, a reaction solution may be prepared by mixing other solid components into a solution containing some components amongst an α-glucan phosphorylase, a sucrose phosphorylase, sucrose, a primer, and inorganic phosphoric acid or glucose-1-phosphate. Any buffer may be added to this reaction solution, if necessary, for the purpose of adjusting a pH as long as it does not inhibit an enzyme reaction. To this reaction solution may be added an enzyme selected from the group consisting of: a debranching enzyme, a branching enzyme, 4-α-glucanotransferase and a glycogen debranching enzyme, if necessary.

A reaction solution is then heated, if necessary, by the methods known in the art, to react it. A reaction temperature can be any temperature as long as the effect of the invention is obtained. When a sucrose concentration in a reaction solution at reaction initiation is about 5% to about 100%, a reaction temperature can be representatively a temperature of about 30° C. to about 75° C. It is preferable that the temperature of a solution in this reaction step is such a temperature that activity (activities) which is about 20% or more, preferably about 30% or more of activity of at least one of, preferably activities of both of sucrose phosphorylase and α-glucan phosphorylase contained in this solution before a reaction remain(s) after a predetermined reaction time. This temperature is preferably about 55° C. to about 75° C., more preferably about 60° C. to about 75° C., further preferably about 60° C. to about 70° C., particularly preferably about 60° C. to about 65° C.

A reaction time can be set to be any time, in view of the reaction temperature, the molecular weight of a glucan produced by a reaction and the remaining activity of an enzyme. A reaction time is representatively about 1 hour to about 100 hours, more preferably about 1 hour to about 72 hours, further more preferably about 2 hours to about 36 hours, most preferably about 2 hours to about 24 hours.

In this manner, a solution containing a glucan is produced.

(5. Method of Synthesizing Glucose-1-Phosphate Using an Enzyme According to the Present Invention)

α-glucan phosphorylase having improved thermostability of the present invention can also be advantageously used in a method of synthesizing glucose-1-phosphate. A method of synthesizing glucose-1-phosphate using α-glucan phosphorylase having improved thermostability according to the present invention can be any method of synthesizing glucose-1-phosphate known in the art.

A method of synthesizing glucose-1-phosphate of the present invention includes reacting a reaction solution containing α-glucan phosphorylase having improved thermostability of the present invention, a glucan and inorganic phosphoric acid to produce glucose-1-phosphate.

The definition of a glucan and inorganic phosphoric acid used in a method of synthesizing glucose-1-phosphate according to the present invention is the same as that in the aforementioned 4.

Amounts of materials to be used in a method of synthesizing glucose-1-phosphate are known, and can be appropriately selected by those skilled in the art.

In a method of synthesizing glucose-1-phosphate according to the present invention, firstly, a reaction solution is prepared. A reaction solution can be prepared, for example, by adding α-glucan phosphorylase, a glucan and inorganic phosphoric acid to a suitable solvent. Alternatively, a reaction solution may be prepared by mixing solutions each containing α-glucan phosphorylase, a glucan or inorganic phosphoric acid. Alternatively, a reaction solution may be prepared by mixing solid other components into a solution containing some components among α-glucan phosphorylase, a glucan, and inorganic phosphoric acid. To this reaction solution may be added any buffer, if necessary, for the purpose of adjusting a pH as far as it does not inhibit an enzyme reaction. To this reaction solution may be added a debranching enzyme, if necessary.

Then, the reaction solution is heated, if necessary, by the method known in the art, to react it. A reaction temperature can be any temperature as long as the effect of the invention is obtained. A reaction temperature can be representatively about 30° C. to about 75° C. It is preferable that the temperature of a solution in this reaction step is such a temperature that activity which is about 20% or more, more preferably about 30% or more of activity of α-glucan phosphorylase contained in this solution before a reaction, remains after a predetermined reaction time. This temperature is preferably about 55° C. to about 75° C., more preferably about 60° C. to about 75° C., further preferably about 60° C. to about 70° C., particularly preferably about 60° C. to about 65° C.

A reaction time can be set to be any time, in view of a reaction temperature and the remaining activity of an enzyme. A reaction time is representatively about 1 hour to about 100 hours, more preferably about 1 hour to about 72 hours, further more preferably about 2 hours to about 36 hours, most preferably about 2 hours to about 24 hours.

In this manner, a solution containing glucose-1-phosphate is produced.

(6. Other Production Method Using an Enzyme According to the Present Invention)

α-glucan phosphorylase having improved thermostability according to the present invention can be used in any production methods known in the art using α-glucan phosphorylase, in addition to the aforementioned production methods. Utilization of α-glucan phosphorylase having improved thermostability according to the present invention in these production methods can be easily performed by those skilled in the art.

(7. Use of Glucan Obtained by Production Method According to the Present Invention)

A glucan obtained by the production method according to the present invention can be used in use known in the art regarding a glucan. Among a glucan, particularly, insoluble amylose, the same function as that of dietary fiber is predicted, and utilization in a health food can be expected. Further, since amylose has the characteristic of being capable of including, for example, iodine or fatty acids in a molecule, use in the field of medicaments, cosmetics or sanitary products is expected. Amylose can be utilized as a raw material for producing cyclodextrin and cycloamylose having the same inclusionability as that of amylose. Further, a film containing amylose has a tensile strength comparable to that of a general-use plastic, and is very promising as a material for a biodegradable plastic. In this manner, many uses are expected in amylose.

(8. Use of Glucose-1-Phosphate Obtained by Synthesis Method According to the Present Invention)

Glucose-1-phosphate obtained by the synthesis method according to the present invention can be used in uses known in the art regarding glucose-1-phosphate. Glucose-1-phosphate is utilized as a medical antibacterial agent, an anti-tumor agent (as a platinum complex), a drug to treat heart disease (as an amine salt), or a substrate for synthesizing a glucan.

The present invention will be explained below based on Examples, but the following Examples are provided only for the purpose of exemplification. Therefore, the scope of the present invention is not limited by the aforementioned Detailed Explanation of the Invention and the following Examples, but is limited only by claims.

EXAMPLES (1. Measurement Method and Calculation Method)

Respective substances in the present invention were measured suing the following measurement methods.

(1.1 Quantitation of Glucose)

Glucose was quantitated using a commercially available measuring kit. Glucose is measured using a glucose AR-II color developing reagent (manufactured by Wako Pure Chemical Industries, Ltd.).

(1.2 Quantitation of Fructose)

Fructose was quantitated using a commercially available measuring kit. Fructose is measured using F-kit, D-glucose/D-fructose (manufacture by Roche).

(1.3 Quantitation of Glucose-1-Phosphate)

Glucose-1-phosphate was quantitated by the following method. To 300 µl of a measuring reagent (200 mM Tris-HCl (pH 7.0), 3 mM NADP, 15 mM magnesium chloride, 3 mM EDTA, 15 μM glucose-1,6-diphosphate, 6 μg/ml phosphoglucomutase, 6 μg/ml glucose-6-phosphate dehydrogenase) is added 600μl of a solution containing properly diluted glucose-1-phosphate, this is stirred, and the resulting reaction mixture is reacted at 37° C. for 30 minutes. Thereafter, absorbance at 340 nm is measured using a spectrophotometer. Absorbance is measured similarly using sodium glucose-1-phosphate having a known concentration, to produce a standard curve. An absorbance obtained for a sample is fitted to this standard curve to obtain a glucose-1-phosphate concentration in a sample. Usually, activity of producing one μmol glucose-1-phosphate for 1 minute is defined as one unit. In this quantitation method, only glucose-1-phosphate is quantitated, and an amount of inorganic phosphoric acid is not quantitated.

(1.4 Quantitation of Inorganic Phosphoric Acid)

Inorganic phosphoric acid was obtained as phosphate ions by the following method. Into a solution (200 μl) containing inorganic phosphoric acid is mixed 800 μl of a molybdenum reagent (15 mM ammonium molybdate, 100 mM zinc acetate), subsequently, 200 μl of 568 mM ascorbic acid (pH 5.0) is added, this is stirred, and the resulting reaction mixture is reacted at 37° C. for 30 minutes. Thereafter, absorbance at 850 nm is measured using a spectrophotometer. Absorbance is measured similarly using inorganic phosphoric acid having the known concentration, to produce a standard curve. An absorbance obtained for a sample is fitted to this standard curve, to obtain a measure of the inorganic phosphoric acid in a sample. In this quantitation method, the amount of inorganic phosphoric acid is quantitated, and the amount of a glucose-1-phosphate is not quantitated.

(1.5 Method of Calculating Yield of Glucan Produced from Glucose-1-Phosphate)

A yield of a glucan (e.g. amylose) produced using α-glucan phosphorylase and, as a starting material, glucose-1-phosphate without using sucrose phosphorylase is obtained by the following equation from amounts of inorganic phosphoric acid and glucose in a solution after reaction termination.

(Glucan yield (%)) =(glucose used in glucan synthesis (mM))÷(initial glucose-1-phosphate (mM))×100={(inorganic phosphoric acid produced by reaction (mM))−(glucose after reaction (mM))}÷(initial glucose-1-phosphate (mM))×100

(1.6 Method of Calculating Yield of Glucan Produced from Sucrose)

A yield of a glucan (e.g. amylose) produced using inorganic phosphoric acid as a staring substance in a SP-GP method is obtained by the following equation from amounts of glucose, fructose, and glucose-1-phosphate in a solution after reaction termination.

Glucan (mM glucose equivalent) =fructose (mM)−(glucose-1-phosphate (mM))−(glucose (mM))

This equation is based on the following principle.

In the production method of the present invention, firstly, a reaction (A) according to the following equation can occur.

(A) sucrose+inorganic phosphoric acid→glucose-1-phosphate+fructose

This reaction is catalyzed by sucrose phosphorylase. In this reaction, sucrose and inorganic phosphoric acid are reacted to produce the same molar amounts of glucose-1-phosphate and fructose. Since the resulting fructose reacts with other substance no longer, a molar amount of produced glucose-1-phosphate is known by measuring a molar amount of fructose.

Sucrose phosphorylase can catalyze hydrolysis of sucrose of the following reaction (B) as a side reaction in addition to the aforementioned reaction (A).

(B) Sucrose→glucose+fructose

An amount of glucose incorporated into a glucan is calculated as follows.

Amount of glucose incorporated into a glucan =amount of glucose-1-phosphate produced by reaction (A))−(amount of unreacted glucose-1-phosphate) =amount of fructose produced by reaction (A))−(amount of unreacted glucose-1-phosphate)

In view of the fructose produced by a reaction (B), the amount of fructose produced by a reaction (A) is calculated as follows:

Amount of fructose produced by reaction (A) =amount of fructose after reaction termination)−(amount of glucose after reaction termination)

Therefore, a yield of a glucan is obtained by the following equation.

(Glucan (mM glucose equivalent)) =fructose (mM))−(glucose-1-phosphate (mM))−(glucose (mM))

A yield of a glucan produced using glucose-1-phosphate as a starting material is obtained by the following equation from an amount of initial glucose-1-phosphate, as well as amounts of glucose, fructose and glucose-1-phosphate in a solution after reaction termination.

(Glucan (mM glucose equivalent))

=(initial glucose-1-phosphate (mM)) +( gluctose (mM)−(glucose (nM)) −(glucose-1-phosohate after reation (mM))

This equation is based on the following principle.

In a reaction solution, in addition to initial glucose-1-phosphate, glucose-1-phosphate is produced by a reaction (A). That is, initial glucose-1-phosphate and produced glucose-1-phosphate can be used in glucan synthesis. By subtracting the amount of glucose-1-phosphate remaining in a reaction solution after reaction termination, from the amount of glucose-1-phosphate which can be used in glucan synthesis, the amount of glucose-1-phosphate used in a reaction, that is, an amount of glucose incorporated into a glucan can be calculated. Therefore, an amount of glucose incorporated into a glucan can be obtained by the aforementioned equation. This equation can be also applied when inorganic phosphoric acid and glucose-1-phosphate are used together as a starting material in a SP-GP-reaction system.

(1.7 Method of Calculating Yield of Glucan Produced from Sucrose)

A yield of a glucan when produced using inorganic phosphoric acid as a starting material is obtained by the following equation.

(Glucan yield (%))

=(glucan (mM glucose equivalent))/(initial sucrose (mM)) ×100

A yield of a glucan when produced using glucose-1-phosphate as a starting material is obtained by the following equation.

(Glucan yield (%)) ={(initial glucose-1-phosphate (mM))+(fructose (mM))−(glucose (mM)−(glucose-1-phosphate after reaction (mM))}÷{(initial sucrose (mM))+(initial glucose-1-phosphate (mM))}×100

This equation can be also applied when inorganic phosphoric acid and glucose-1-phosphate are used together as a starting material in a SP-GP reaction system.

Example 1

Preparation, Screening and Sequencing of Potato α-Glucan Phosphorylase Having Improved Thermostability To briefly outline, a random mutation was introduced into a potato-derived type L α-glucan phosphorylase gene, a gene with a random mutation introduced therein was introduced into *Escherichia coli*, α-glucan phosphorylase with a random mutation introduced therein was expressed and, *Escherichia coli* expressing, among expressed α-glucan phosphorylases, α-glucan phosphorylase having improved thermostability having the ability to synthesize a glucan after heating at 60° C. for 10 minutes was selected, a gene of α-glucan phosphorylase having improved thermostability was isolated from this *Escherichia coli*, and the sequence thereof was determined.

Details are as follows.

Firstly, a gene of potato-derived type L α-glucan phosphorylase (GP) was prepared. According to the description of Takaha, et. al. (Journal of Biological Chemistry, vol. 268, pp. 1391-1396, 1993), an mRNA was prepared from a potato tuber using a well-known method, and a cDNA library was prepared using a commercially available kit.

Then, based on the known GP gene sequence (database GenBank accession number D00520), PCR primer 1 and PCR primer 2 were designed. Employing the aforementioned cDNA library as a template, and using, as PCR primers 1 and 2,

```
PCR primer 1:
5'AAATCGATAGGAGGAAAACAT ATG         (SEQ ID NO: 38)
ACC TTG AGT GAG AAA AT 3'
and PCR primer 2:
5'GAAGGTACCTTTTCATTCACTTCCCCCTC3',  (SEQ ID NO: 39)
```

PCR was performed to amplify a gene of potato-derived GP. PCR conditions were a PCR reaction of 30 cycles, one cycle being 94° C. for 30 second, 50° C. for 1 minute, and 72° C. for 3 minutes. The underlined part of PCR primer 1 corresponds to a structural gene sequence at the N-terminal region of a type L GP mature protein, and an underlined part of PCR primer 2 corresponds to a base sequence immediately after a stop codon of a type L GP structural gene.

The amplified GP gene was inserted into a plasmid pMW118 (manufactured by Nippon Gene Co., Ltd.) which had been previously cut with SmaI, and a plasmid having a sequence such as in FIG. 2 was selected. This plasmid was introduced into *Escherichia coli* TG-1 by a calcium phosphate precipitation method, an ampicillin resistant strain was selected, this ampicillin resistant strain was cultured, and a plasmid was recovered from this ampicillin resistant strain, thereby, the gene of a potato-derived type L GP was obtained.

The resulting gene of a potato-derived type L GP, was amplified by an error-prone PCR method known to those skilled in the art (References; Leung, et. al. (Technique 1, 11-15, 1989) and Cadwell and Joyce (PCR Methods Applic. 2, 28-33, 1992), using PCR primer 3 and PCR primer 4,

```
PCR primer 3:
                                    (SEQ ID NO: 40)
5'-TTCGGATCCTCACCTTGAGTGAGAAAATTCAC-3'
and PCR primer 4:
                                    (SEQ ID NO: 41)
5'-TTCGGATCCTTTTCATTCACTTCCCCCTC-3',
``` a PCR reaction of 90° C. for 30 seconds, thereafter, 25 cycles, one cycle being 94° C. for 30 second, and 68° C. for 3 minutes, thereafter, 68° C. for 1 minute was performed. Base substitution was introduced into an average 2 to 3 positions of the amplified DNA fragment. The underlined part of PCR primer 3 corresponds to a structural gene sequence at the N-terminal region of a type L GP mature protein, and the underlined part of PCR primer 4 corresponds to a base sequence immediately after a stop codon of a type L GP structural gene.

A GP gene amplified fragment with a random mutation introduced therein was inserted into a plasmid pET3d (manufactured by STRATAGENE) which had been previously cut with BamHI, and a plasmid library for screening GP having improved thermostability with a random mutation introduced therein was prepared. *Escherichia coli* BL21 (DE3) was transformed with this plasmid, and a transformant was diluted so that an independent colony was obtained, and plated on an ampicillin-containing LB agar medium (50 μg/ml ampicillin, tryptone 1% manufactured by Difco, yeast extract 0.5% manufactured by Difco, NaCl 0.5%, 1.5% agarose, pH 7.3), followed by culturing at 30° C. for 24 hours. Colonies on the resulting plate were transferred onto a nylon membrane filter. The surface of a filter on which colonies were adhered was sufficiently dried, and this filter was incubated at 60° C. for 10 minutes in a 20 mM citrate buffer (pH 6.7). After transfer, the remaining plate was further incubated at 37° C. for a few hours and, thereafter, was stored at 4° C. as a master plate. The heat-treated filter was applied to a gel (containing 0.05% dextrin, 50 mM G-1-P, 100 mM citrate buffer (pH 6.7), 0.7% agarose) containing a substrate for glucan synthesis so that a colony-adhered surface was adhered to a gel surface, and this was incubated at 50° C. for 2 hours. The filter peeled from the gel was immersed in an iodine solution (0.1% potassium iodide, 0.01% iodine), and glucan synthesized on the filter was detected by an iodine starch reaction. Colonies corresponding to spots stained with blue were isolated from a master plate.

From the thus obtained each *Escherichia coli*, a plasmid was recovered according to a method known in the art, and the base sequence of a gene of α-glucan phosphorylase having improved thermostability in this plasmid was determined using a DNA sequencer (manufactured by ABI).

When an amino acid sequence encoded by this gene of α-glucan phosphorylase having improved thermostability was compared with an amino acid sequence of natural potato type L (i.e. before mutation) α-glucan phosphorylase, a mutation was introduced into amino acids at position 39, position 135 or position 706 of natural potato type L α-glucan phosphorylase, and the amino acids were substituted as F39→L, N135→S, or T706→I, respectively. In addition, improvement in thermostability was also seen in a GP in which F39 was mutated into an amino acid other than L, N135 was mutated into an amino acid other than S, or T706 was mutated into an amino acid other than I.

Example 2-1A

Preparation of Potato Type L α-Glucan Phosphorylase Having Improved Thermostability by Site-Directed Mutagenesis In the present Example, GP having improved thermostability having only one substitution at a position which was found to contribute to improve thermostability in Example 1, GP having improved thermostability having a combination of any two, and GP having improved thermostability having all of 3 were prepared. As an example, an amino acid sequence of GP having improved thermostability having three all mutations (F39L+N135S+T706I) is set forth in SEQ ID NO: 34, and a base sequence encoding such is set forth in SEQ ID NO: 33. For comparison, GP in which amino acids at position 39, position 135 and position 706 was not substituted, and an amino acid at a position having no relationship with these amino acid positions was substituted (GP in which only lysine at 467 position was substituted with asparagine, and GP in which only threonine at position 711 was substituted with alanine) was prepared. Many methods of substituting an amino acid are published (Reference: Kinkel, T. A., Proc. Natl. Acad. Sci. USA, 82: 488 (1995), Vandeyar, M., et al., Gene, 65:129-133 (1988), Sugimoto, M., et al., Anal. Biochem., 179:309-311 (1989), Taylor, J. W. and Eckstein, F., Nucl. Acids Res., 13:8764 (1985), Nelson, M. and McClelland, M., Methods Enzymol., 216:279-303(1992)). In the present invention, a Quick change XL Site-Directed Mutagenesis kit (manufactured by STRATAGENE) was used. Employing a plasmid containing a potato-derived type L GP gene inserted in a plasmid pMW-118 shown in Example 1 as a template, and using one set of mutation-introduced primers per mutation, each being about 35 bp complementary relative to a central, mutation-introduced position, and were designed to introduce a mutation of F39L, N135S, T706I, K467D or T711A, PCR was performed to carry out site-directed mutagenesis. A plasmid pMW-PGP containing the thus obtained gene encoding GP having improved thermostability was prepared. *Escherichia coli* TG-1 was transformed with this plasmid, and a transformant was diluted so that an independent colony was obtained, and plated on an ampicillin-containing LB agar medium (50 μg/ml ampicillin, tryptone 1% manufactured by Difco, yeast extract 0.5% manufactured by Difco, NaCl 0.5%, 1.5% agarose, pH 7.3), followed by culturing at 37° C. overnight. *Escherichia coli* grown on this ampicillin-containing LB agar medium harbors an introduced plasmid. In this manner, *Escherichia coli* expressing GP having improved thermostability was prepared. By extracting a plasmid from the resulting *Escherichia coli*, and sequencing a gene encoding GP, it was confirmed that a plasmid contained in *Escherichia coli* obtained in the present Example has a mutant GP gene encoding GP having improved thermostability and having an objective mutation.

It was confirmed as follows that GP expressed by *Escherichia coli* obtained in the present Example is has improved thermostabilty. *Escherichia coli* TG-1 harboring an introduced plasmid was inoculated on an ampicillin-containing LB medium (50 μg/ml ampicillin, tryptone 1% manufactured by Difco, yeast extract 0.5% manufactured by Difco, NaCl 0.5%, pH 7.3), this was grown at 37° C. to a logarithmic middle phase, the temperature was lowered to around 22° C., and ispropyl β-D-thiogalactoside which is a gene expression inducer was added to a final concentration of 0.1 mM, and pyridoxine hydrochloride was added to a final concentration of 1 mM, followed by culturing at 22° C. for about 20 hours. The culture was centrifuged to recover bacterial cells, the bacterial cells were suspended in a buffer, and the suspension was sonicated to obtain a bacterial cell extract. This bacterial extract was treated at 60° C. for 30 minutes to obtain an authentic GP preparation.

When a glucan was produced using the resulting authentic GP preparation by a method of reacting sucrose phosphorylase and α-glucan phosphorylase on sucrose and a primer (method described in International Publication WO 02/097107 pamphlet), a high-molecular glucan could be obtained at a high yield, with respect to all of α-glucan phosphorylase having improved thermostability.

On the other hand, GP in which an amino acid at a position having no relationship with improvement of thermostability had been substituted was inactivated by treatment at 60° C. for 30 minutes, and a glucan could not be produced.

Example 2-1B

Preparation of Modified Potato Type L α-Glucan Phosphorylase Substituted with Various Amino Acids According to the same manner as that of Example 2-1A, except that primers designed so that one place of F39, N135 and T706 was substituted with another amino acid residue were used, a plasmid containing a modified α-glucan phosphorylase gene was prepared, and various modified GP authentic preparations were obtained.

Thermostability of these modified GP authentic preparations were studied in detail in the Example 3-1 (3-1) below.

Example 2-2A

Preparation of Potato Type H α-Glucan Phosphorylase Having Improved Thermostability by Site-Directed Mutagenesis According to the same manner as that of Example 2-1A except that a potato-derived type H α-glucan phosphorylase gene was used in place of a potato-derived type L α-glucan phosphorylase gene, a plasmid containing a gene of α-glucan phosphorylase having improved thermostability was prepared, and a GP authentic preparation was obtained. In the present Example, a GP having improved thermostability having only one substitution at a position corresponding to N135S or T706I of an amino acid sequence of potato type L α-glucan phosphorylase (position 133 and position 628 of an amino acid sequence of potato type H α-glucan phosphorylase, respectively) among substitution positions which were found to contribute to improvement of thermostability in Example 1, was prepared.

When these GP authentic preparations were used to perform a treatment at 60° C. for 30 minutes as in Example 2-1A, and a glucan was prepared, with respect to all of the α-glucan phosphorylase having improved thermostability, a high-molecular weight glucan could be obtained, similar to natural potato type H α-glucan phosphorylase.

Example 2-2B

Preparation of Potato Type H α-Glucan Phosphorylase Having Improved Thermostability by Site-Directed Mutagenesis According to the same manner as that of Example 2-1A, except that a potato-derived type H α-glucan phosphorylase gene was used in place of a potato-derived type L α-glucan phosphorylase gene, and a mutation-introduction primer designed so that amino acid residues of a position corresponding to F39 (Y36), a position corresponding to N135 (N133) and a position corresponding to T706 (T628) were substituted with leucine (L), serine (S) and isoleucine (I), respectively, was used, a plasmid containing a gene of α-glucan phosphorylase having improved thermostability was prepared, and a triple mutant (Y36L+N133S+T628I) GP authentic preparation was obtained. In the present Example, a GP having improved thermostability having substitutions at all three positions which had been found to contribute to improvement of thermostability in Example 1 was prepared.

Heat resistance of these modified GP authentic preparations were studied in detail in Example 3-2 (2) below.

Example 2-2C

Preparation of *Arabidopsis Thaliana* Type H α-Glucan Phosphorylase Having Improved Thermostability by Site Directed Mutagenesis Firstly, a gene of *Arabidopsis thaliana*-derived type H α-glucan phosphorylase (GP) was prepared using a commercially available *Arabidopsis*-derived cDNA (PCR Ready First Strand cDNA, manufactured by Wako Pure Chemical Industries, Ltd.).

More particularly, based on the known *Arabidopsis thaliana* GP gene sequence (database GenBank accession number AL133292; CAB61943.1), PCR primers 5 and 6 were designed. Employing the aforementioned *Arabidopsis*-derived cDNA as a template, and using:

```
PCR primer 5:
                                    (SEQ ID NO: 42)
5'AAATCGATAGGAGGAAAACAT ATG GCA AAC GCC AAT
GGA AAA GCT GCG ACT AGT TTA CCG GAG AAA ATC TC 3'
and PCR primer 6:
                                    (SEQ ID NO: 43)
5'GAAGGTACC TTA GGG AAC AGG ACA AGC CTC AAT
GTT CCA AAT CTC TTT GGC ATA CTG AG 3',
```

PCR was performed to amplify an *Arabidopsis thaliana*-derived type H GP gene. The conditions of the PCR reaction were 30 cycles, one cycle being 94° C. for 30 seconds, 60° C. for 1 minute, and 72° C. for 3 minutes. The underlined part of PCR primer 5 corresponds to a structural gene at the N-terminal region of a mature protein of an *Arabidopsis thaliana*-derived type H GP gene, and the underlined part of PCR primer 6 corresponds to a structural gene at the C-terminal region of a mature protein of an *Arabidopsis thaliana*-derived type H GP gene.

The amplified *Arabidopsis thaliana*-derived type H GP gene was inserted into a plasmid pMW118 (manufactured by Nippon Gene Co., Ltd.) which had been previously cut with SmaI, this plasmid was introduced into *Escherichia coli* TG-1 using a competent cell method, an ampicillin resistant strain was selected, this ampicillin resistant strain was cultured, and a plasmid was recovered from this ampicillin resistant strain, thereby, an *Arabidopsis thaliana*-derived type H GP gene was obtained.

According to the same manner as that of Example 2-1A except that the resulting *Arabidopsis thaliana*-derived type H GP gene was used in place of a potato-derived type L α-glucan phosphorylase gene, and a mutation-introduction promoter designed so that amino acid residues at a position corresponding to F39 (Y40), a position corresponding to N135 (N136) and a position corresponding to T706 (N631) were substituted with leucine (L), serine (S) and isoleucine (I), respectively, was used, a plasmid containing a gene of α-glucan phosphorylase having improved thermostability was prepared, and a triple mutant (Y40L+N136S+N631I) GP authentic preparation was obtained. In the present Example, a GP having improved thermostability having substitutions at all three positions which had been found to contribute to improvement of thermostability in Example 1 was prepared.

Thermostability of these modified GP authentic preparations were studied in detail in Example 3-2 (2) below.

Example 3-1

Preparation of Various α-Glucan Phosphorylases Having Improved Thermostability, on a Large Scale, and Comparison of Thermostability (1) Large Scale Preparation of Enzyme Respective *Escherichia coli*'s expressing a GP having improved thermostability prepared in Example 2-1A or 2-1B were cultured in a TB medium (containing Terrific broth (GIBCO) 47 g/L, glycerol 4 ml/L and 50 µg/ml ampicillin) at 37° C. for 5 hours, IPTG and pyridoxine chloride were added to this culture solution to final concentrations of 0.1 mM IPTG and 1 mM pyridoxine hydrochloride, and this was further cultured at 22° C. for 24 hours. Then, bacterial cells were recovered by centrifuging the culture, medium components were removed by washing with a 20 mM citrate buffer. Bacterial cells after washing were suspended in a 20 mM citrate buffer, bacterial cells were lysed with an sonicator, and centrifuged, and the supernatant was used as a bacterial cell extract. The resulting bacterial cell extract was loaded on a Q-Sepharose FF column which had been previously equilibrated, and a fraction containing a GP having improved thermostability eluting at a concentration gradient of 0.1M to 0.3M NaCl in a 20 mM citrate buffer (pH 6.7) was recovered. The recovered enzyme fraction was loaded on a Phenyl-TOYOPEARL 650M column which had been previously equilibrated, and a fraction containing a GP having improved thermostability-containing fraction eluting at a concentration gradient of 17.5% to 7.5% saturated ammonium sulfate in a 20 mM citrate buffer was recovered. The recovered enzyme fraction was loaded on a HiTrap HQP column which had been previously equilibrated, and an active fraction eluting at a concentration gradient of 0.1M to 0.4M NaCl in a 20 mM citrate buffer was recovered. The resulting active fragment was further loaded on a Resource Q column which had been previously equilibrated, and this was eluted at a concentration gradient of 0.1M to 0.4M NaCl in a 20 mM citrate buffer, to recover a purified enzyme-containing active fragment.

The resulting purified enzyme-containing active fragment was subjected to about 1 µg native PAGE (Native polyacrylamide gel electrophoresis). As a result, for all *Escherichia coli* expressing GP having improved thermostability, a single band was recognized at a molecular weight of about 210 kDa, and no band was seen at any other place. Since GP is predicted to have a molecular weight of about 104 kDa from an amino acid sequence, it is thought that GP takes a dimer structure. In this manner, it was shown that GP having improved thermostability was uniformly purified.

(2) Measurement of Activity of Purified GP Having Improved Thermostability

Activity of GP having improved thermostability purified in the (1) was measured. Measurement was performed as follows. Firstly, a 200 µl reaction solution (containing 12.5 mM G-1-P, 1% dextrin and an enzyme solution in a 100 mM acetate buffer (pH 6.0)) was incubated at 37° C. for 15 minutes. Then, 800 µl of a molybdenum reagent (15 mM ammonium molybdate, 100 mM zinc acetate) was added, and stirred to stop the reaction. Then, 200 µl of 568 mM ascorbic acid (pH 5.8) was added, this was mixed, and incubated at 37° C. for 15 minutes, and an absorbance at 850 nm was measured using a spectrophotometer. In the present Example, GP enzyme activity was measured by quantitating free inorganic phosphoric acid produced from G-1-P. An amount of an enzyme producing 1 µmol inorganic phosphoric acid for one minute was defined as one unit (U).

(3-1) Comparison of Thermostability at 60° C. and 65° C. of GP Having Improved Thermostability Prepared in Example 2-1A Thermostability at 60° C. and 65° C. of respective GPs having improved thermostability which had been prepared in Example 2-1A, and prepared at a large scale and purified in the (1) were compared. As a control, natural (not mutated) potato type L α-glucan phosphorylase purified by the same method was used.

Firstly, 0.2 U/ml of a purified enzyme solution (in a 20 mM citrate buffer (pH 6.7)) was incubated at 60° C. or 65° C. for 0 to 30 minutes. An aliquot of an enzyme solution was taken out at specific time points, such as 0, 2, 10, 20 and 30 minutes, and retained on ice. Samples of enzyme solution retained on ice was 10-fold diluted with a 20 mM citrate buffer (pH 6.7), and enzyme activity was measured according to the activity measuring method described in (2). Thermostability of an enzyme was judged by a ratio of enzyme activity at 37° C. of an enzyme after incubation (i.e. remaining activity), when the enzyme activity at 37° C. of an enzyme before incubation at 60° C. or 65° C. is taken to be 100%. Results of incubation at 60° C. are shown in the following Table 5. Results of incubation at 65° C. are shown in the following Table 6.

TABLE 5

Remaining activity (%) when incubated at 60° C.

| Time (min) | Natural potato type L | F39L | N135S | T706I | F39L + N135S | F39L + T706I | N135S + T706I | F39L + N135S + T706I |
|---|---|---|---|---|---|---|---|---|
| 0 | 100 | 100 | 100 | 100 | 100 | 100 | 100 | 100 |
| 10 | 8.4 | 61.2 | 65.4 | 70.5 | 101 | 100 | 101 | 98.8 |
| 20 | 1.2 | 58.3 | 55.2 | 50.8 | 99.6 | 100 | 100 | 96.3 |
| 30 | 0.7 | 34.7 | 52.1 | 36.6 | 98.3 | 101 | 98.5 | 94.6 |

TABLE 6

Remaining activity (%) when incubated at 65° C.

| Time (min) | Natural potato type L | F39L | N135S | T706I | F39L + N135S | F39L + T706I | N135S + T706I | F39L + N135S + T706I |
|---|---|---|---|---|---|---|---|---|
| 0 | 100 | 100 | 100 | 100 | 100 | 100 | 100 | 100 |
| 2 | 1.3 | 40.2 | 86.5 | 22.9 | 86.8 | 50.8 | 61.9 | 90.3 |
| 10 | 0 | 0.5 | 1.4 | 0.3 | 18.2 | 9.3 | 16.9 | 61.1 |
| 20 | 0 | 0.4 | 0.6 | 0.3 | 2.9 | 0.9 | 2.8 | 47.7 |
| 30 | 0 | 0.4 | 0.2 | 0.3 | 0.2 | 0.2 | 0.7 | 31.4 |

In the above Table 5 and Table 6, natural potato type L indicates natural potato-derived type L α-glucan phosphorylase. F39L indicates natural potato-derived type L α-glucan phosphorylase in which phenylalanine at position 39 is substituted with leucine. T706I indicates natural potato-derived type L α-glucan phosphorylase in which threonine at position 706 is substituted with isoleucine. N135S indicates natural potato-derived type L α-glucan phosphorylase in which asparagine at position 135 is substituted with serine. F39L+T706I indicate natural potato-derived type L α-glucan phosphorylase in which phenylalanine at position 39 is substituted with leucine, and threonine at position 706 is substituted with isoleucine. N135S+T706I indicates natural potato-derived type L α-glucan phosphorylase in which asparagine at position 135 is substituted with serine, and threonine at position 706 is substituted with isoleucine. F39L+N135S indicates natural potato-derived type L α-glucan phosphorylase in which phenylalanine at position 39 is substituted with leucine, and asparagine at position 135 is substituted with serine. F39L+N135S+T706I indicates natural potato-derived type L α-glucan phosphorylase in which phenylalanine at position 39 is substituted with leucine, asparagine at position 135 is substituted with serine, and threonine at position 706 is substituted with isoleucine. Among the results presented in Table 5 and Table 6, the results of heating at 60° C. for 30 minutes and results of heating at 65° C. for 2 minutes are shown in FIG. 3 as a graph.

It was found that GP having improved thermostability of the present invention has very improved thermostability as compared with natural potato type L GP. From GP inferior in thermostability to GP excellent in thermostability is put in order as follows: natural potato type L GP<F39L<T706I<N135S<F39L+T706I<N135S+T706I<F39L+N135S<F39L+N135S+T706I. By substitution at only one place among amino acid residues at three places contributing thermostability improved thermostability. Further, it was seen that, by multiple substitution of these amino acid residues, thermostability is dramatically improved.

(3-2) Comparison of Thermostabilities at 60° C. and 65° C. of Modified GP Prepared in Example 2-1B Heat resistances at 60° C. and 65° C. of respective modified GPs which had been prepared in Example 2-1B, and prepared on a large scale and purified in Example 3-1 (1) were compared. As a control, natural (not mutated) potato-derived type L α-glucan phosphorylase purified by the same method was used.

Figure 8:
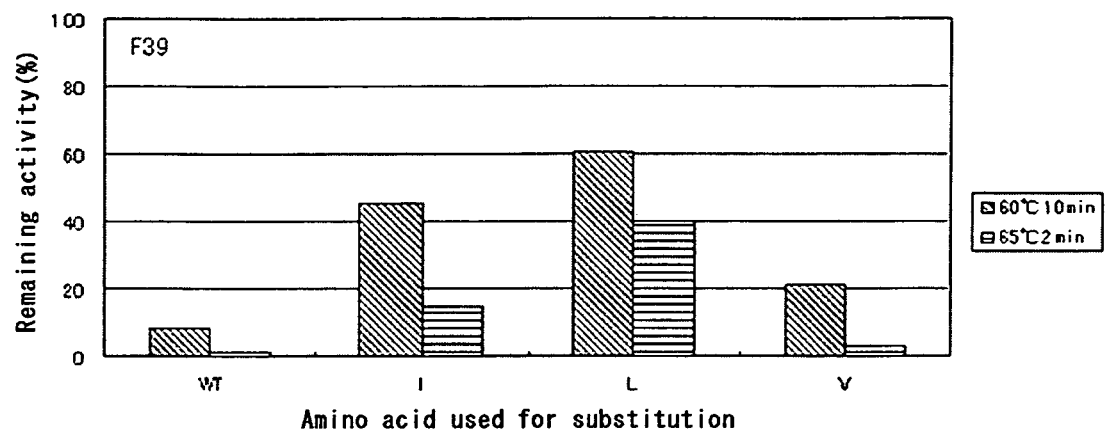
FIG. 8.
Figure 9:
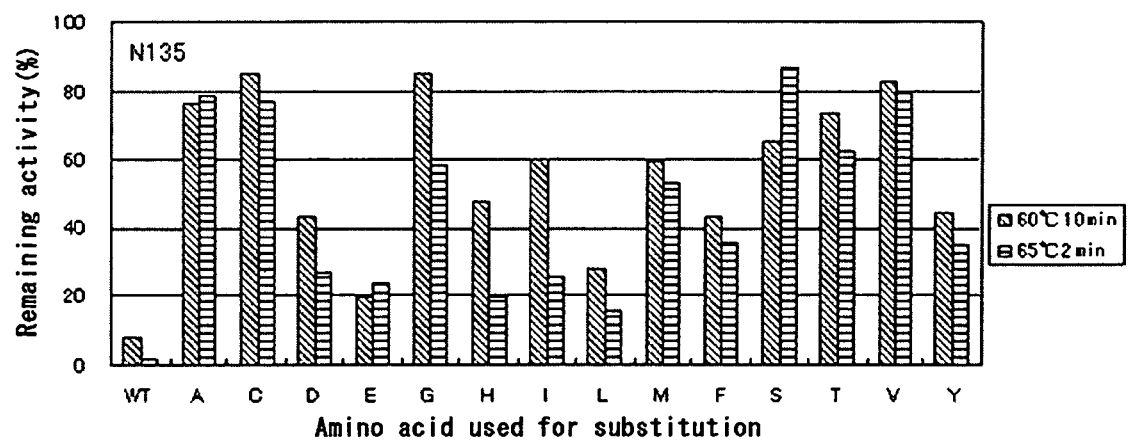
FIG. 9.
Figure 10:
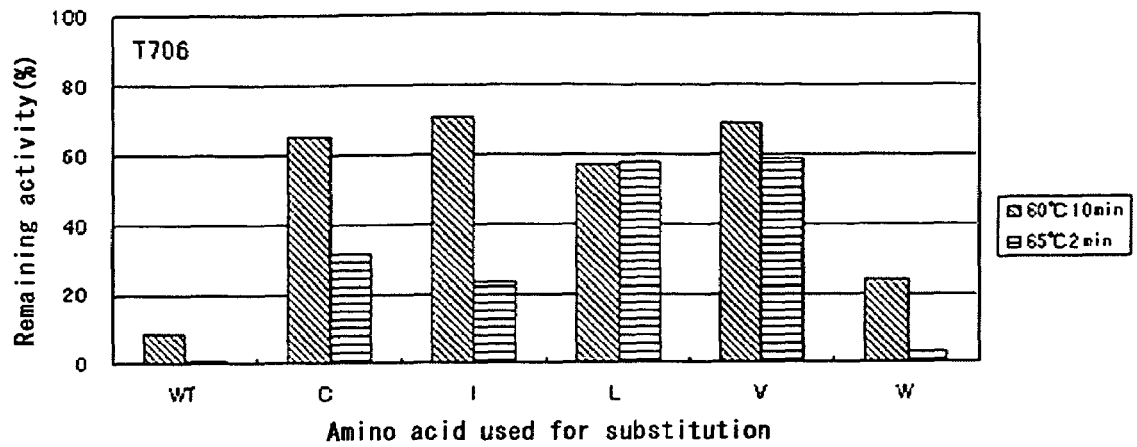
FIG. 10.

Firstly, 0.2 U/ml of a purified enzyme solution (in a 20 mM citrate buffer (pH. 6.7)) was incubated at 60° C. for 10 minutes or 65° C. for 2 minutes. At a predetermined time (10 minutes or 2 minutes), an aliquot of an enzyme solution was taken out, and retained on ice. Samples of enzyme solution retained on ice were 10-fold diluted with a 20 mM citrate buffer (pH 6.7), and enzyme activity was measured according to the activity measuring method described in the (2). Thermostability of an enzyme was judged by a ratio of enzyme activity at 37° C. of an enzyme after incubation (i.e. remaining activity), when enzyme activity at 37° C. of the enzyme before incubation at 60° C. for 10 minutes or 65° C. for 2 minutes is taken to be 100%. Results are shown in the following Table 7 and FIGS. 8 to 10.

TABLE 7

Remaining activity of position 39 substituted mutant

| F39 | Remaining activity (%) | |
|---|---|---|
| | 60° C. 10 min | 65° C. 2 min |
| WT | 8.4 | 1.3 |
| I | 45.2 | 14.5 |
| L | 61.2 | 40.2 |
| V | 21.6 | 3.3 |

Remaining activity of position 706 substituted mutant

| T706 | Remaining activity (%) | |
|---|---|---|
| | 60° C. 10 min | 65° C. 2 min |
| WT | 8.4 | 1.3 |
| C | 65.4 | 31.6 |
| I | 70.5 | 22.9 |
| L | 57.6 | 57.8 |
| V | 68.7 | 59.2 |
| W | 24.4 | 2.9 |

TABLE 7-continued

Remaining activity of position 135 substituted mutant

| N135 | Remaining activity (%) | |
|---|---|---|
| | 60° C. 10 min | 65° C. 2 min |
| WT | 8.4 | 1.3 |
| A | 76.2 | 79.0 |
| C | 85.0 | 76.9 |
| D | 42.8 | 26.7 |
| E | 20.3 | 24.0 |
| G | 85.2 | 58.4 |
| H | 48.4 | 19.6 |
| I | 60.0 | 26.0 |
| L | 27.8 | 15.6 |
| M | 59.4 | 52.6 |
| F | 43.5 | 35.5 |
| S | 65.4 | 86.5 |
| T | 73.4 | 62.4 |
| V | 82.8 | 79.3 |
| Y | 44.8 | 35.4 |

In the above Table 7, WT indicates natural potato-derived type L α-glucan phosphorylase. In each column, an amino acid represented by one letter abbreviation indicates an amino acid substituted in a modified GP. For example, an entity expressed by I in a column labeled with F39 at a left end indicates modified GP in which phenylalanine (F) at position 39 is substituted with isoleucine (I). This is also true for modified GP in other columns.

One letter abbreviation of an amino acid is well-known to those skilled in the art, and is as follows: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; Y, tyrosine.

As a result, it was seen that, when amino acids at position 39, position 135 and position 706 are substituted with amino acids other than particular amino acids substituted in above Example 2-1A, the thermostability of natural potato-derived type L GP is improved.

Seeing remaining activity after incubation at 60° C. for 10 minutes, when phenylalanine at position 39 was substituted with isoleucine, leucine or valine, thermostability of modified GP was superior over that of natural potato-derived type L GP. Regarding substitution at position 39, substitution with leucine (remaining activity after incubation at 60° C. for 10 minutes is 61.2%) was most excellent with respect to thermostability. When asparagine at position 135 was substituted with alanine, cysteine, aspartic acid, glutamic acid, glycine, histidine, isoleucine, leucine, methionine, phenylalanine, serine, threonine, valine or tyrosine, thermostability of modified GP was superior over that of natural potato-derived type L GP. Regarding substitution at position 135, substitution with alanine (remaining activity after incubation at 60° C. for 10 minutes is 76.2%), cysteine (remaining activity after incubation at 60° C. for 10 minutes is 85.0%), glycine (remaining activity after incubation at 60° C. for 10 minutes is 85.2%), isoleucine (remaining activity after incubation at 60° C. for 10 minutes is 60.0%), serine (remaining activity after incubation at 60° C. for 10 minutes is 65.4%), threonine (remaining activity after incubation at 60° C. for 10 minutes is 73.4%) or valine (remaining activity after incubation at 60° C. for 10 minutes is 82.8%) was particularly excellent with respect to thermostability. When threonine at position 706 was substituted with cysteine, isoleucine, leucine, valine or tryptophan, thermostability of modified GP was superior to that of natural potato-derived type L GP. Regarding substitution at a position 706, substitution with cysteine (remaining activity after incubation at 60° C. for 10 minutes is 65.4%), isoleucine (remaining activity after incubation at 60° C. for 10 minutes is 70.5%) or valine (remaining activity after incubation at 60° C. for 10 minutes is 68.7%) was particularly excellent with respect to thermostability.

Seeing remaining activity after incubation at 65° C. for 2 minutes, when phenylalanine at position 39 was substituted with isoleucine, leucine or valine, thermostability of modified GP was superior to that of natural potato-derived type L GP. Regarding substitution at position 39, substitution with leucine (remaining activity after incubation at 65° C. for 2 minutes is 40.2%) was most excellent with respect to thermostability. When asparagine at position 135 was substituted with alanine, cysteine, aspartic acid, glutamic acid, glycine, histidine, isoleucine, leucine, methionine, phenylalanine, serine, threonine, valine or tyrosine, thermostability of modified GP was superior to that of natural potato-derived type L GP. Regarding substitution at position 135, substitution with alanine (remaining activity after incubation at 65° C. for 2 minutes is 79.0%), cysteine (remaining activity after incubation at 65° C. for 2 minutes is 76.9%), glycine (remaining activity after incubation at 65° C. for 2 minutes is 58.4%), methionine (remaining activity after incubation at 65° C. for 2 minutes is 52.6%), serine (remaining activity after incubation at 65° C. for 2 minutes is 86.5), threonine (remaining activity after incubation at 65° C. for 2 minutes is 62.4%) or valine (remaining activity after incubation at 65° C. for 2 minutes is 79.3%) was particularly excellent with respect to thermostability. When threonine at position 706 was substituted with cysteine, isoleucine, leucine, valine or tryptophan, thermostability of modified GP was superior to that of natural potato-derived type L GP. Regarding substitution at a position 706, substitution with leucine (remaining activity after incubation at 65° C. for 2 minutes is 57.8%) or valine (remaining activity after incubation at 65° C. for 2 minutes is 59.2%) was particularly excellent with respect to thermostability.

As a result, it was found that the thermostability of modified GP of the present invention was very improved as compared with natural potato type L GP.

Example 3-2

Preparation of Type H GP Enzyme Having Improved Thermostability (1) Large Scale Preparation of Enzyme Each of *Escherichia coli* expressing potato type H GP having improved thermostability and *Escherichia coli* expressing *Arabidopsis thaliana* type H GP having improved thermostability prepared in Examples 2-2B and 2-2C respectively was cultured in a TB medium (containing Terrific broth (GIBCO) 47 g/L, glycerol 4 ml/L and 50 µg/ml ampicillin) at 37° C. for 5 hours, IPTG and pyridoxine hydrochloride were added to this culture solution to final concentrations of 0.1 mM IPTG and 1 mM pyridoxine hydrochloride, and this was further cultured at 22° C. for 24 hours. Then, bacterial cells were recovered by centrifuging the culture, and culture components were removed by washing with a 20 mM citrate buffer (pH 6.7). Bacterial cells after washing were suspended in a 20 mM citrate buffer (pH 6.7), bacterial cells were lysed with a sonicator, and centrifuged, and the supernatant was used as a bacterial cell extract. The resulting bacterial cell extract was purified using ion exchange chromatography and hydrophobic chromatography to recover a purified enzyme-containing active fraction exhibiting a single band by native PAGE (Native polyacrylamide gel electrophoresis).

(2) Comparison of Thermostabilities of Type H GP Enzymes Having Improved Thermostability Thermostability at 60° C. and 65° C. of respective GPs having improved thermostability purified in (1) were compared. As a control, natural (not mutated) potato type H GP and *Arabidopsis thaliana* type H GP, purified by the same method, were used.

Figure 11:
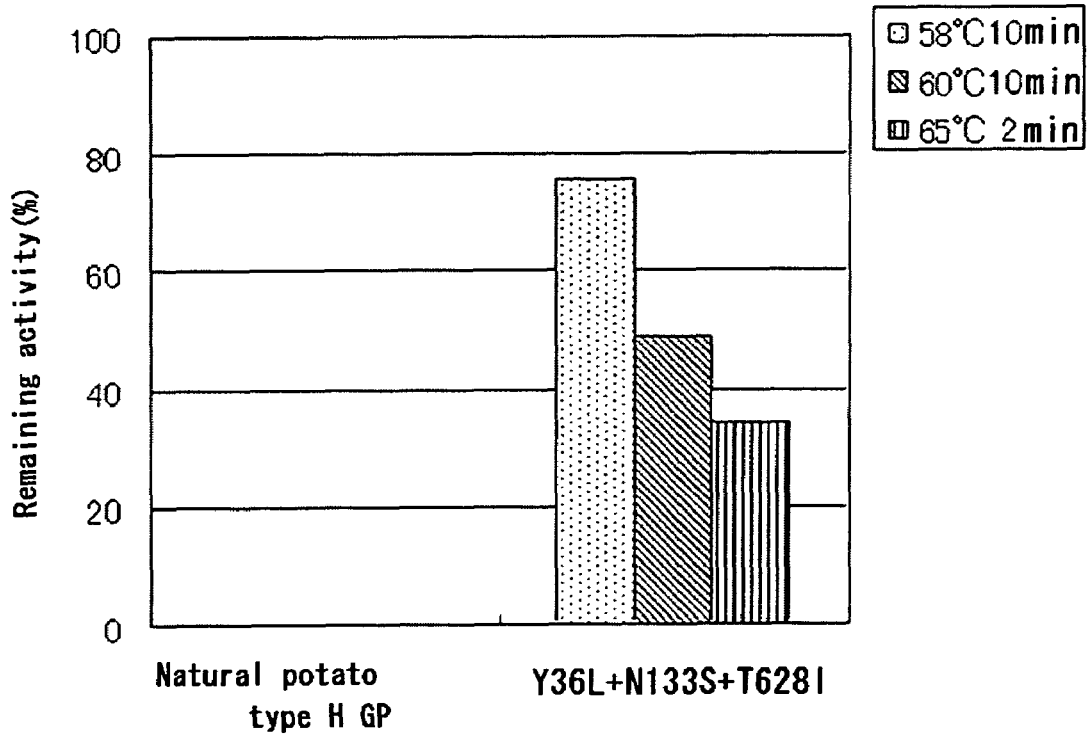
FIG. 11.
Figure 12:
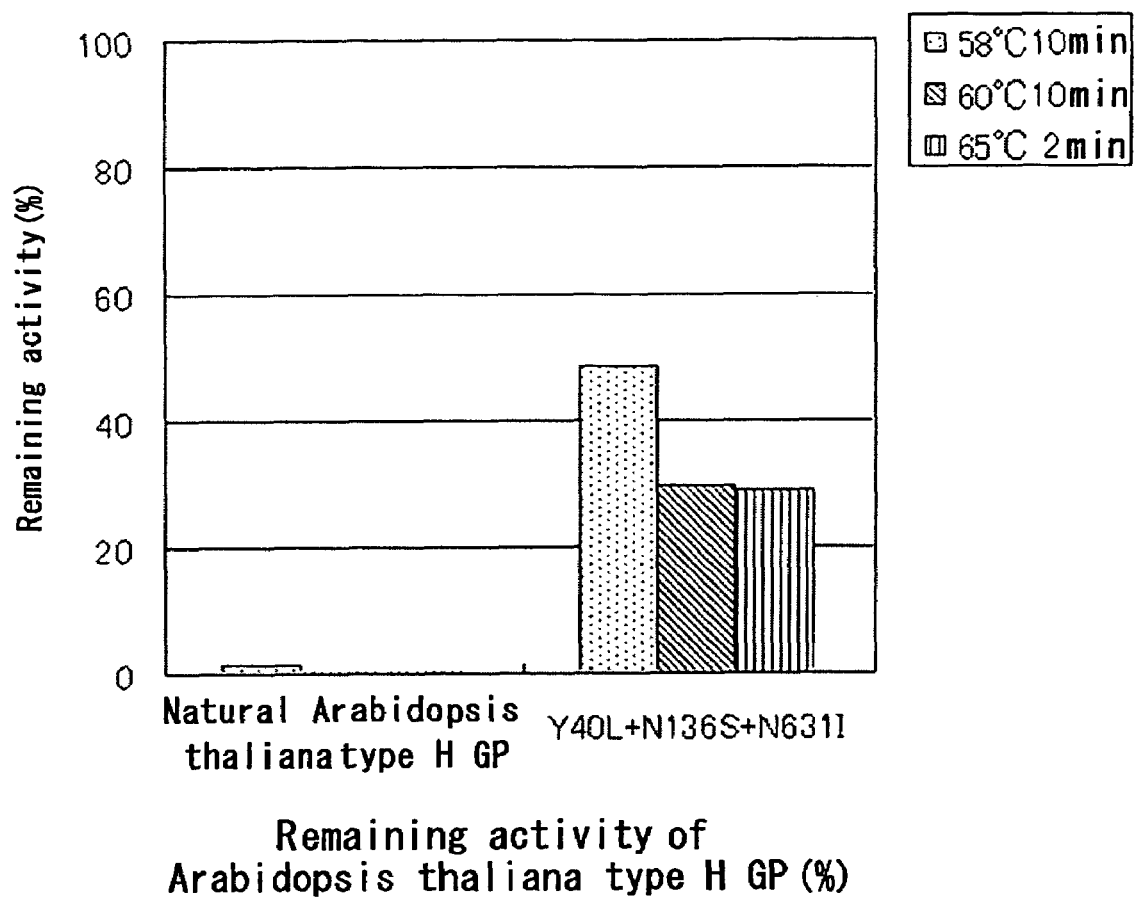
FIG. 12.

0.2 U/ml of a purified enzyme solution (20 mM citrate buffer (pH 6.7)) was incubated at 58° C. for 10 minutes, 60° C. for 10 minutes or 65° C. for 2 minutes, and retained on ice. An enzyme solution retained on ice was 10-fold diluted with a 20 mM citrate buffer (pH 6.7), and enzyme activity was measured according to the activity measuring method described in Example 3-1 (2). Thermostability of an enzyme was judged by a ratio of enzyme activity at 37° C. of the enzyme after incubation (i.e. remaining activity) when enzyme activity at 37° C. of the enzyme before incubation at 58° C. for 10 minutes, 60° C. for 10 minutes or 65° C. for 2 minutes is taken to be 100%. Results regarding potato type H GP having improved thermostability and natural potato type H GP are shown in the following Tables 8 and FIG. 11. Results regarding *Arabidopsis thaliana* type H GP having improved thermostability and natural *Arabidopsis thaliana* type H GP are shown in the following Tables 9 and FIG. 12.

TABLE 8

| Temperature and time of incubation | Remaining activity (%) of natural potato type H GP | Remaining activity (%) of potato type H GP having improved thermostability (Y36L + N133S + T628I) |
| --- | --- | --- |
| 58° C. 10 min | 0 | 75.8 |
| 60° C. 10 min | 0 | 48.8 |
| 65° C. 2 min | 0 | 34.5 |

TABLE 9

| Temperature and time of incubation | Remaining activity (%) of natural *Arabidopsis thaliana* type H GP | Remaining activity (%) of *Arabidopsis thaliana* type H GP having improved thermostability (Y40L + N136S + T631I) |
| --- | --- | --- |
| 58° C. 10 min | 1.5 | 48.8 |
| 60° C. 10 min | 0.5 | 29.3 |
| 65° C. 2 min | 0.5 | 29.2 |

From these results, potato type H GP having improved thermostability of the present invention had remaining an activity of 34.5% even after heating at 65° C. for 2 minutes. On the other hand, natural potato type H GP had remaining activity of 0% after heating at 65° C. for 2 minutes. From this, it was found that potato type H GP having improved thermostability of the present invention has high thermostability compared with natural potato type H GP.

In addition, *Arabidopsis thaliana* type H GP having improved thermostability of the present invention had remaining activity of 29.2% even after heating at 65° C. for 2 minutes. On the other hand, natural *Arabidopsis thaliana* type H GP had remaining activity of 0.5% after heating at 65° C. for 2 minutes. From this, it was found that *Arabidopsis* thaliana type H GP having improved thermostability of the present invention has high thermostability compared with natural *Arabidopsis thaliana* type H GP.

Example 4

Synthesis of Amylose of Weight Average Molecular Weight of 600 kDa or More, Using α-Glucan Phosphorylase Having Improved Thermostability Using α-glucan phosphorylase having improved thermostability according to the present invention, it was investigated whether amylose of a weight average molecular weight of 600 kDa or more can be synthesized. As an α-glucan phosphorylase having improved thermostability, any of the various GPs having improved thermostability (single mutant F39L, single mutant N135S, single mutant T706I, double mutant (F39L+N135S), double mutant (F39L+T706I), double mutant (N135S+T706I) and triple mutant (F39L+N135S+T706I)) prepared in above Example 3-1 (1) was used.

As a control, *Bacillus* stearothermophillus-derived α-glucan phosphorylase (also referred to as *Bacillus* stearothermophillus), and *Thermus aquaticus*-derived α-glucan phosphorylase (also referred to as *Thermus aquaticus*) were used.

An amylose synthesis reaction was performed at 50° C. for 18 hours using a reaction solution having the composition described in the following Table 10.

TABLE 10

| Reaction solution composition | |
|---|---|
| BMaltotetraose(G4) | 40 μM |
| Glucose-1-phosphate | 250 mM |
| Acetate buffer(pH 5.5) | 200 mM |
| α-glucan phosphorylase | 4 U/ml |

A yield of amylose synthesized by this reaction was calculated by a calculation method described in 1.5 of the aforementioned "1. Measuring method and calculating method".

A weight average molecular weight of amylose synthesized by this reaction was measured by the following method. Amylose synthesized by this reaction was completely dissolved in 1N sodium hydroxide, and neutralized with a suitable amount of hydrochloric acid, about 30 to 300 μg of an aliquot of amylose was subjected to gel filtration chromatography using a differential refractometer and a multiangular light scatter detector together to obtain a weight average molecular weight.

More particularly, Shodex SB806M-HQ (manufactured by SHOWA DENKO K.K.) was used as a column and a multiangular light scatter detector (DAWN-DSP, manufactured by Wyatt Technology) was used as a detector, and a differential refractometer (Shodex RI-71, manufactured by SHOWA DENKO K.K.) were used by connecting them in that order. The column was retained at 40° C. and, as an eluent, a 0.1M sodium nitrate solution was used at a flow rate of 1 mL/min. The resulting signal was collected using a data analyzing software (trade name ASTRA, manufactured by Wyatt Technology), and this was analyzed using the same software, and a weight average molecular weight was thereby obtained. This method is also referred to as MALLS analyzing method.

The yields and a molecular weights of synthesized amylose obtained in this manner are shown in the following Table 11.

TABLE 11

Yield and molecular weight of synthesized amylose

| α-glucan phosphorylase | Yield of amylose (%) | Molecular weight of amylose (kDa) |
|---|---|---|
| GP having improved thermostability (F39L) | 51.2 | 668 |
| GP having improved thermostability (N135S) | 47.8 | 735 |
| GP having improved thermostability (T706I) | 45.3 | 675 |
| GP having improved thermostability (F39L + N135S) | 44.7 | 673 |
| GP having improved thermostability (F39L + T706I) | 47.5 | 706 |
| GP having improved thermostability (N135S + T706I) | 42.7 | 655 |
| GP having improved thermostability (F39L + N135S + T706I) | 52.3 | 645 |
| Bacillus stearothrmophillus | 17.3 | 20.0 |
| Thermus aquaticus | 27.8 | 44.3 |

As described above, it was found that the GP having improved thermostability according to the present invention can synthesize high-molecular amylose having a weight average molecular weight of about 600 kDa or more. In addition, it was found that the GP having improved thermostability according to the present invention has a yield of amylose of about 40% or more. *Bacillus* stearothermophillus GP and *Thermus aquaticus* GP used as Comparative Example are enzymes having thermostability, but cannot not synthesize high-molecular amylose.

Example 5

Synthesis of Amylose from Sucrose Using α-Glucan Phosphorylase Having Improved Thermostability Using α-glucan phosphorylase having improved thermostability according to the present invention, and using sucrose as a raw material, amylose was synthesized. As a α-glucan phosphorylase having improved thermostability, any of the various GPs having improved thermostability (single mutant F39L, single mutant N135S, single mutant T706I, double mutant (F39L+N135S), double mutant (F39L+T706I), double mutant (N135S+T706I) and triple mutant (F39L+N135S+T706I)) prepared in Example 3-1 (1) above was used.

An amylose synthesis reaction was performed at 50° C. for 18 hours using a reaction solution of the composition described in the following Table 12.

TABLE 12

| Reaction solution composition | |
|---|---|
| Sucrose | 58.5 mM |
| Maltotetraose (G4) | 10 μM |
| Inorganic phosphoric acid (Pi) | 10 mM |
| Sucrose phosphorylase | 1 U/ml |
| α-glucan phosphorylase | 1 U/ml |

A yield (%) of amylose synthesized by this reaction was calculated by a calculation equation described in 1.7 of the aforementioned "1. Measuring method and calculating method".

A weight average molecular weight of amylose synthesized by this reaction was measured by the same method as that of Example 4 above. The yield sand weight average molecular weights of synthesized amylose obtained like this are shown in the following Table 13.

TABLE 13

Yield and weight average molecular weight of synthesized amylose

| α-glucan phosphorylase | Yield of amylose (%) | Weight average molecular weight of amylose (kDa) |
|---|---|---|
| GP having improved thermostability (F39L) | 50.8 | 672 |
| GP having improved thermostability (N135S) | 47.8 | 740 |
| GP having improved thermostability (T706I) | 44.6 | 675 |
| GP having improved thermostability (F39L + N135S) | 44.9 | 674 |
| GP having improved thermostability (F39L + T706I) | 47.5 | 707 |
| GP having improved thermostability (N135S + T706I) | 42.9 | 657 |
| GP having improved thermostability (F39L + N135S + T706I) | 52.3 | 649 |

As described above, it was found that the GP having improved thermostability according to the present invention can synthesize high-molecular weight amylose of about 600 kDa like natural GP, when amylose is synthesized using sucrose as a raw material. In addition, it was found that an amylose yield is high, such as about 40% or more, similar to natural GP.

Example 6

Synthesis of Glucan from Glucose-1-Phosphate, Using GP Having Improved Thermostability Under High Temperature Condition (50° C., 55° C. and 60° C.)

Using a α-glucan phosphorylase having improved thermostability according to the present invention, and using glucose-1-phosphate as a raw material, amylose was synthesized under high temperature conditions. GP having improved thermostability (triple mutant (F39L+N135S+T706I)) prepared in Example 3-1 (1) was used and, as a control, natural potato type L GP purified by the same method was used.

An amylose synthesizing reaction was performed by retaining a reaction solution containing G-1-P 6.1 g/L, maltotetraose (G4) 0.3 g/L, and GP 20 U/L at 37° C., 50° C., 55° C. or 60° C. for 18 hours. An amount of synthesized amylose in the reaction product was measured over time. The amount of synthesized amylose (g/L) was calculated based on the following equation.

(Amount of synthesized amylose (g/L))

=(Glucose (mM) used in amylose synthesis)×180 (molecular weight of glucose)

=[(inorganic phosphoric acid (mM) produced by reaction)−(glucose (mM) after reaction)]×180 (glucose molecular weight)

Figure 7:
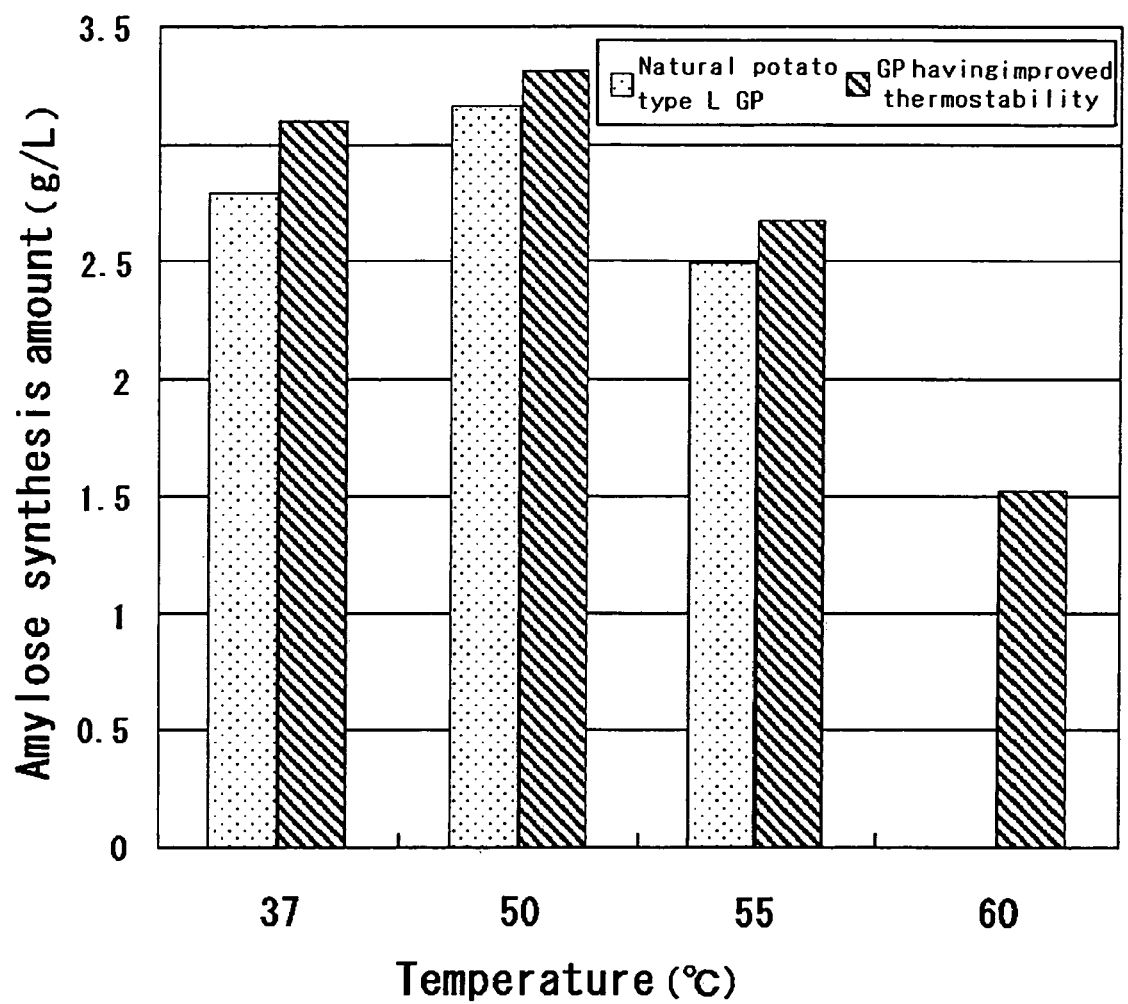
FIG. 7.

The amount of synthesized amylose after reaction for 18 hours is shown in the following Table 14 and FIG. 7.

TABLE 14

| | Amount of synthesized amylose (g/L) | |
|---|---|---|
| Reaction temperature | Natural potato type L GP | GP having improved thermostability |
| 37° C. | 2.8 | 3.1 |
| 50° C. | 3.2 | 3.3 |
| 55° C. | 2.5 | 2.7 |
| 60° C. | 0 | 1.5 |

When GP having improved thermostability was used, about 3 g/L of amylose was synthesized at 37° C., 50° C. and 55° C., and even about 1.5 g/L of amylose was synthesized at 60° C. On the other hand, when natural potato type L GP was used, amylose was synthesized at 37° C., 50° C. and 55° C., but amylose was not synthesized at all at 60° C. It is thought that, in natural potato type L GP, GP was inactivated at an initial stage of the reaction, at 60° C. On the other hand, it is thought that since GP having improved thermostability stably retained enzyme activity also at 60° C., an amylose synthesizing reaction was sufficiently performed. In addition, when GP having improved thermostability was used at each temperature of 37° C., 50° C., 55° C. and 60° C., an amount of synthesized amylose was larger than that when natural potato type L GP was used. It is thought that the amount of synthesized amylose when GP having improved thermostability is used, is further increased as the reaction time is extended. As described above, it was found that GP having improved thermostability according to the present invention can synthesize a glucan at 60° C., at which temperature natural potato type L GP cannot react.

Example 7

Synthesis of Glucan from Glucose-1-Phosphate Using GP Having Improved Thermostability at 65° C. and 70° C.

Using GP having improved thermostability (triple mutant (F39L+N135S+T706I)) prepared in Example 3-1 (1) as in Example 6, a glucan was synthesized from glucose-1-phosphate under further high temperature conditions. As a control, natural potato type L GP was used.

By retaining a reaction solution containing G-1-P15.2 g/L, maltotetraose (G4) 2.7 g/L, and GP 200 U/L at 37° C., 65° C. or 70° C. for 4 hours, an amylose synthesizing reaction was performed. The amount of synthesized amylose was calculated as in Example 6. After reaction time of 4 hours, when natural potato type L GP was used, amylose was not synthesized at all at 65° C. and 70° C., but when GP having improved thermostability was used, about 5.6 g/L of amylose was synthesized from 15.2 g of G-1-P at 65° C., and about 0.3 g/L of amylose was synthesized from 15.2 g of G-1-P at 70° C. As a result, it was found that natural potato type L GP cannot synthesize amylose at 65° C. to 70° C., but GP having improved thermostability retains GP activity at a high temperature such as 70° C., and has amylose synthesizing ability.

Based upon the results of Examples 6 and 7, it was found that the GP having improved thermostability according to the present invention has amylose synthesizing ability at high temperature conditions under which natural potato type L GP cannot react at all.

Example 8

Confirmation of Removal of Contaminating Protein by Heat Treatment

It was confirmed the following method can be used to easily purify α-glucan phosphorylase having improved thermostability, using heat treatment.

*Escherichia coli* (TG-1) expressing GP having an improved thermostability (triple mutant (F39L+N135S+T706I)) gene prepared in Example 2-1A was cultured in a LB medium as in Example 2-1A. As a control, *Escherichia coli* (TG-1) expressing natural potato type L α-glucan phosphorylase was cultured in a LB medium as in Example 2-1A. Bacterial cells were recovered by centrifuging the culture solution, bacterial cells were suspended in a buffer, and this was sonicated to obtain a bacterial cell extract. This bacterial cell extract was heated in a water bath at 60° C. for 0 to 60 minutes, and centrifuged to remove insoluble proteins to obtain the supernatant. GP activity and the protein content of this supernatant were measured, and the specific activity of a GP enzyme was obtained. GP activity was measured using the activity measuring method described in Example 3-1 (2), and the protein content was measured using the Bradford method (Bradford, M., Anal. Biochem., 72, 248-254 (1976). The Bradford method is a calorimetric method in which a chromogenic substrate is bound to all proteins contained in a solution. In the present specification, measurement was performed using a protein assay kit (Nippon Bio-Rad Laboratories, Inc.) and bovine globulin used as a standard.

The specific activity of a GP enzyme was calculated by the following method.

Specific activity (U/ml) =(α-glucan phosphorylase activity)/(mass mg of protein contained in supernatant)

Figure 6:
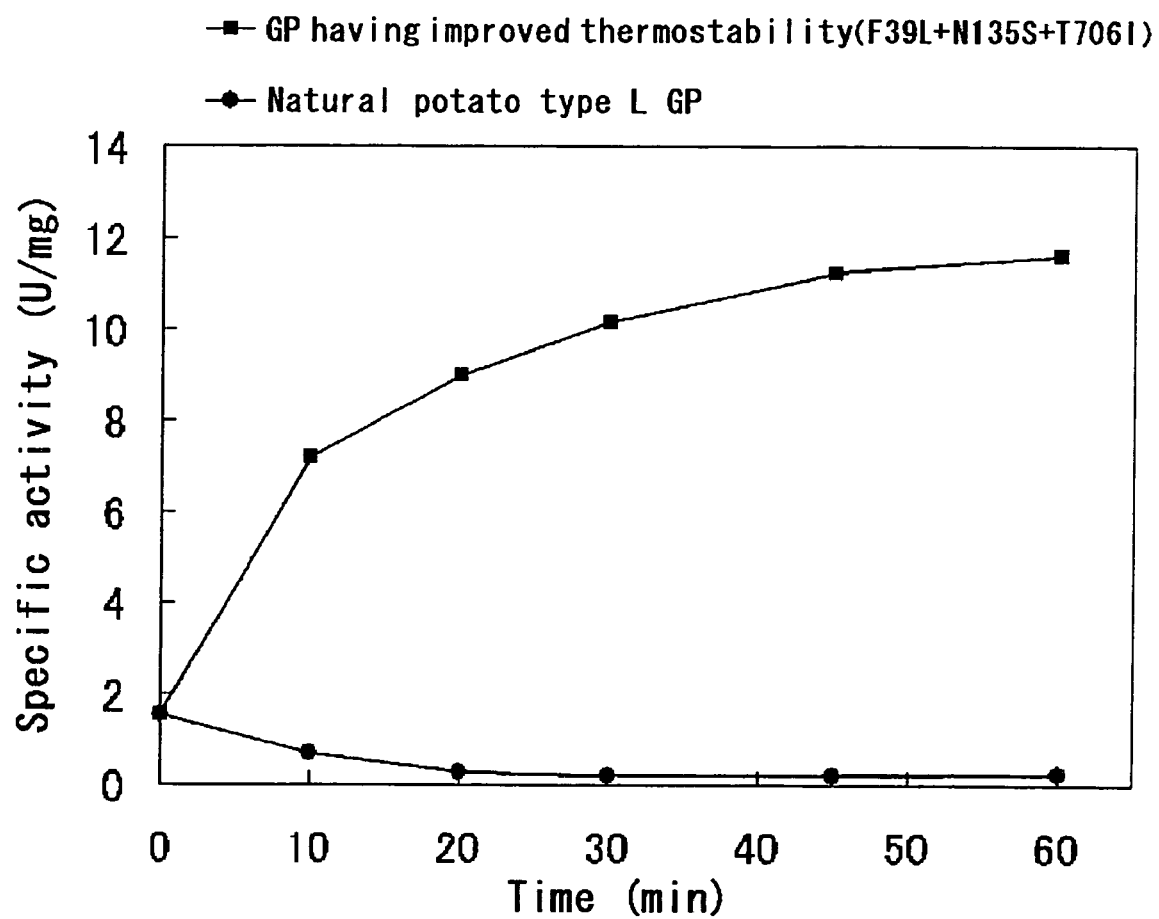
FIG. 6.

FIG. 6 shows the change in specific activity with time of a GP enzyme having improved thermostability (referred to as GP having improved thermostability (F39L+N135S+T706I in FIG. 6)) and natural potato type L GP enzyme.

As shown in FIG. 6, specific activity of GP having improved thermostability increased about 10-fold upon heating at 60° C. Contaminating proteins were almost completely thermally denatured and removed. To the contrary, specific activity of natural potato type L GP reduced with time. It is thought that this is because not only contaminating proteins but also the GP protein were denatured. In this manner, it was found that GP having improved thermostability can be simply purified by heat treatment.

Example 9

Confirmation of Removal of Contaminating Proteins by Heat Treatment

As in Example 8, *Escherichia coli* (TG-1) expressing a gene of GP having improved thermostability (triple mutant (F39L+N135S+T706I)) was cultured, and a bacterial cell extract was prepared. Using this bacterial cell extract, it was confirmed that amylase activity and phosphatase activity can be reduced to a level which can be utilized in industrial production of amylose or G-1-P, by heat treatment at 60° C.

As in Example 8, a bacterial cell extract was heated in a water bath at 60° C. for 30 minutes, and insoluble proteins were removed by centrifugation to obtain the supernatant. Phosphatase activity and amylase activity of this supernatant were measured.

Phosphatase activity was measured by retaining a reaction solution containing 100 μl of this supernatant and 100 μl of 50 mM glucose-1-phosphate at 37° C. for 60 minutes, and quantitating free inorganic phosphoric acid produced from glucose-1-phosphate in a reaction solution by a method described in (1. Measuring method and calculating method). An amount of an enzyme producing 1 μmol of inorganic phosphoric acid for one minute was defined as one unit (U). Amylase activity was obtained by retaining a reaction solution containing 25 μl of the supernatant and 25 μl of 0.5% amylose (weight average molecular weight about 50 kDa) at 37° C. for 60 minutes, adding 1 ml of an iodine solution (0.1% potassium iodide, 0.01%), and measuring the reduction rate of iodine color development accompanied with conversion of amylose in a reaction solution into low-molecular amylose. Activity capable of reducing the absorbance at A660 by 10% for one minute was defined as 1 U.

Amylase activity (U/min) =(absorbance at A660 nm before reaction-absorbance at A660 nm after reaction)+(absorbance at A660 nm before reaction) ×100÷10÷(time (min))

The following Table 15 shows a remaining ratio of phosphatase activity and amylase activity in a bacterial cell extract.

As shown in Table 15, when the activity of a bacterial cell extract before heating is taken to be 100%, phosphatase activity and amylase activity were such that phosphatase activity was about 3%, and amylase activity was about 0.3% after heating at 60° C., and these two contaminating proteins were almost inactivated.

TABLE 15

|  | Phosphatase activity (%) | Amylase activity (%) |
|---|---|---|
| Before heating | 100 | 100 |
| After heating at 60° C. for 30 minutes | 3.1 | 0.3 |

In this manner, α-glucan phosphorylase having improved thermostability according to the present invention is a plant GP enzyme which does not lose activity even after heat treatment at 60° C., and it was found that, by performing heat treatment at 60° C., it is possible to easily produce excellent GP which contains little amylase activity and phosphatase activity.

Example 10

Stability of GP Protein

It has been reported that natural potato-derived type L GP proteins are easily degraded. These GPs, even when refrigerated after purification, are gradually degraded during storage. Generally, when an enzyme is degraded, a change in structure, a change in the nature of an enzyme, reduction in activity and the like occur. If the stability of a GP protein can be enhanced, then influence of the above factors will be reduced, and this is advantageous in terms of storage and use of an enzyme.

A natural potato-derived type L GP protein and seven kinds of GP proteins having improved thermostability (single mutant F39L, single mutant N135S, single mutant T706I, double mutant F39L+N135S, double mutant F39L+T706I, double mutant N135S+T706I, triple mutant F39L+N135S+T706I) prepared in Example 3-1 (1) were stored at 4° C., and the molecular weight of the GP protein was investigated over time for 5 months. In addition, the molecular weight of a GP protein when stored at 37° C. for 10 days was similarly investigated. Immediately after purification, and after storage at 4° C. for 5 months, the molecular weight was investigated by polyacrylamide gel electrophoresis (Native-PAGE), and the results are shown in FIG. 13. The amount of a protein loaded onto a gel was equal for all GP proteins.

As a result, natural potato type L GP and seven kinds of GP having improved thermostability all showed a band at a position of a molecular weight of about 210 kDa (a monomer of GP has a molecular weight of about 104 kDa, and forms a dimer) immediately after purification. On the other hand, natural potato type L GP and a N135S mutant after storage at 4° C. for 5 months had a molecular weight of about 140 kDa, which was smaller than that immediately after purification. This show that natural potato type L GP and a single mutant 135S were degraded during storage. Natural potato type L GP and a N135S mutant, also when stored at 37° C. for 10 days, were degraded during storage. The other six kinds of GPs having improved thermostability (single mutant F39L, single mutant T706I, double mutant F39L+N135S, double mutant F39L+T706I, double mutant N135S+T706I, triple mutant F39L+N135S+T706I) after storage at 4° C. for 5 months had a molecular weight of about 210 kDa, which is the same as that immediately after purification, and degradation of the proteins was not recognized. In addition, these six kinds of GPs having improved thermostability, also after storage at 37° C. for 10 days, had no change in a molecular weight, and degradation of the GP protein was not recognized. This shows that these GPs having improved thermostability are excellent in degradation resistance, and have higher stability than natural potato type L GP, at between 4° C. to 37° C. From this, it was found that substitution at a F39 position and substitution at a T706 position impart not only the effect of improving thermostability effect but also the effect of suppressing degradation to a GP protein.

Example 11

Synthesis of Glucose-1-Phosphate (1) Synthesis of G-1-P Using GP Having Improved Thermostability at 65° C.

Using a α-glucan phosphorylase having improved thermostability according to the present invention, and using a glucan and inorganic phosphoric acid as a raw material, G-1-P was synthesized at 65° C. GP having improved thermostability (triple mutant (F39L+N135S+T706I)) prepared in Example 3-1 (1) was used and, as a control, natural potato type L GP purified by the same method was used. A reaction solution containing 300 mM phosphate buffer (pH 7.0), 10 g/L dextrin, and 1000 U/L of any of the GP was retained at 37° C. or 65° C. for 18 hours, and a G-1-P synthesis reaction was performed. The amount of synthesized G-1-P was calculated by multiplying the G-1-P concentration (mM) obtained by the method of quantitating glucose-1-phosphate described in 1.3 of the "1. Measuring method and calculating method" above, by 260 which is a molecular weight of G-1-P. The amount of synthesized G-1-P after the reaction is shown in the following Table 16.

TABLE 16

| Amount of synthesized glucose-1-phosphate (g/L) | | |
|---|---|---|
| Reaction temperature | Natural potato type L GP | GP having improved thermostability |
| 37° C. | 3.5 | 4.2 |
| 65° C. | 0.0 | 3.7 |

When natural potato type L GP was used, G-1-P was not synthesized at 65° C. However, when GP having improved thermostability was used, it was possible to produce G-1-P even at 65° C.

(2) Synthesis of G-1-P Using GP Having Improved Thermostability, at 70° C.

As in Example 11 (1) above, using GP having improved thermostability according to the present invention and natural potato type L GP, and using a glucan and inorganic phosphoric acid as raw materials, G-1-P was synthesized at 70° C. A reaction solution containing a 300 mM phosphate buffer (pH 7.0), 10 g/L dextrin, and 10,000 U/L of any of the GP was incubated at 70° C. for 4 hours, and G-1-P was synthesized. The amount of synthesized G-1-P was calculated as in the aforementioned Example.

When natural potato type L GP was used, G-1-P was not synthesized at all at 70° C., but when GP having improved thermostability was used, about 1 g of G-1-P was synthesized.

As described above, the present invention was exemplified using preferable embodiments of the present invention, but it should not be construed to limit the present invention to those embodiments. It is understood that the scope of the present invention should be construed only by claims. It is understood that those skilled in the art can practice an equivalent scope based on the description of the present invention and common technical knowledge, from the specific description of preferable embodiments of the present invention. It is understood that the content itself of patents, patent applications and references cited in the present specification should be incorporated by reference, as if the content thereof are specifically described in the present specification.

INDUSTRIAL APPLICABILITY

According to the present invention, a plant-derived GP enzyme having excellent thermostability at a high temperatures (e.g. 60° C. or higher) is obtained. α-glucan phosphorylase having improved thermostability of the present invention is useful in a glucan synthesizing reaction under high temperature conditions (e.g. 60° C. or higher), under which a natural GP enzyme cannot react.

When a gene encoding α-glucan phosphorylase having improved thermostability according to the present invention (e.g. a gene encoding GP having improved thermostability obtained by improving thermostability of potato-derived GP) is highly expressed using a mesophilic bacterium such as Escherichia coli as a host, by heating a bacterial cell extract containing a enzyme having improved thermostability at 60° C., contaminating enzymes derived from a host bacterium can be simply removed. In particular, amylase activity and phosphatase activity, which are a great problem, particularly, during industrial utilization of a GP enzyme, can be considerably reduced by heat treatment. Therefore, the enzyme of the present invention is particularly useful in enzyme purification.

The method of the present invention is effective not only in potato derived GP and *Arabidopsis thaliana* derived GP, but also can be preferably applied to improving the thermostability of other group A GPs exhibiting high homology to an amino acid sequence of potato derived GP or *Arabidopsis thaliana* derived GP. By using the method of the present invention, GP having improved thermostability derived from an organism species other than potato and *Arabidopsis thaliana* can be prepared.

According to the present invention, GP having improved thermostability, in which degradation of an enzyme protein is suppressed, and storage stability is improved, is provided.

(Explanation of Sequence Listing)

SEQ ID NO: 1: base sequence encoding potato type L α-glucan phosphorylase;
SEQ ID NO: 2: amino acid sequence of potato type L α-glucan phosphorylase;
SEQ ID NO: 3: base sequence encoding sweet potato type L α-glucan phosphorylase;
SEQ ID NO: 4: amino acid sequence of sweet potato type L α-glucan phosphorylase;
SEQ ID NO: 5: base sequence encoding potato second type L α-glucan phosphorylase;
SEQ ID NO: 6: amino acid sequence of potato second type L α-glucan phosphorylase;
SEQ ID NO: 7: base sequence encoding Fava bean type L α-glucan phosphorylase;
SEQ ID NO: 8: amino acid sequence of Fava bean type L α-glucan phosphorylase;
SEQ ID NO: 9: base sequence encoding *Arabidopsis thaliana* type L α-glucan phosphorylase;
SEQ ID NO: 10: amino acid sequence of *Arabidopsis thaliana* type L α-glucan phosphorylase;
SEQ ID NO: 11: base sequence encoding spinach type L α-glucan phosphorylase;
SEQ ID NO: 12: amino acid sequence of spinach type L α-glucan phosphorylase;
SEQ ID NO: 13: base sequence encoding corn type L α-glucan phosphorylase;
SEQ ID NO: 14: amino acid sequence of corn type L α-glucan phosphorylase;
SEQ ID NO: 15: base sequence encoding rice type L α-glucan phosphorylase;
SEQ ID NO: 16: amino acid sequence of rice type L α-glucan phosphorylase;
SEQ ID NO: 17: base sequence encoding rice second type L α-glucan phosphorylase;
SEQ ID NO: 18: amino acid sequence of rice second type L α-glucan phosphorylase;
SEQ ID NO: 19: base sequence encoding wheat type H α-glucan phosphorylase;
SEQ ID NO: 20: amino acid sequence of wheat type H α-glucan phosphorylase;
SEQ ID NO: 21: base sequence encoding Citrus hybrid cultivar type H α-glucan phosphorylase;
SEQ ID NO: 22: amino acid sequence of Citrus hybrid cultivar type H α-glucan phosphorylase;
SEQ ID NO: 23: base sequence encoding rice type H α-glucan phosphorylase;
SEQ ID NO: 24: amino acid sequence of rice type H α-glucan phosphorylase;
SEQ ID NO: 25: base sequence encoding Fava bean type H α-glucan phosphorylase;
SEQ ID NO: 26: amino acid sequence of Fava bean type H α-glucan phosphorylase;
SEQ ID NO: 27: base sequence encoding *Arabidopsis thaliana* type H α-glucan phosphorylase;
SEQ ID NO: 28: amino acid sequence of *Arabidopsis thaliana* type H α-glucan phosphorylase;
SEQ ID NO: 29: base sequence encoding potato type H α-glucan phosphorylase;
SEQ ID NO: 30: amino acid sequence of potato type H α-glucan phosphorylase;
SEQ ID NO: 31: a partial sequence of a base sequence encoding sweet potato type H α-glucan phosphorylase;
SEQ ID NO: 32: amino acid sequence of sweet potato type H α-glucan phosphorylase;
SEQ ID NO: 33: base sequence encoding potato type L α-glucan phosphorylase having improved thermostability;
SEQ ID NO: 34: amino acid sequence of potato type L α-glucan phosphorylase having improved thermostability;
SEQ ID NO: 35: amino acid sequence of *Escherichia coli* maltodextrin phosphorylase;
SEQ ID NOS: 36 and 37: base sequence around a linking site with a plasmid pMW118 shown in FIG. 2;
SEQ ID NO: 38: base sequence of PCR primer 1;
SEQ ID NO: 39: base sequence of PCR primer 2;
SEQ ID NO: 40: base sequence of PCR primer 3;
SEQ ID NO: 41: base sequence of PCR primer 4;
SEQ ID NO: 42: base sequence of PCR primer 5;
SEQ ID NO: 43: base sequence of PCR primer 6;
SEQ ID NO: 44: amino acid sequence of motif sequence 1L;
SEQ ID NO: 45: amino acid sequence of motif sequence 1H;
SEQ ID NO: 46: amino acid sequence of motif sequence 2;
SEQ ID NO: 47: amino acid sequence of motif sequence 3L;
SEQ ID NO: 48: amino acid sequence of motif sequence 3H.

The invention claimed is:

1. A modified α-glucan phosphorylase having improved thermostability, which is obtained by modifying a natural α-glucan phosphorylase,
   wherein the natural α-glucan phosphorylase is obtained from a plant;
   wherein the α-glucan phosphorylase having improved thermostability has an amino acid substitution at a position corresponding to position 7 in a motif sequence 3L: R-I-V-K-F-I-T-D-V (SEQ ID NO: 47);
   wherein said substitution is a substitution to C, I, L, V, or W;
   wherein the α-glucan phosphorylase having improved thermostability has an amino acid sequence which is at least 95% identical to the sequence of the natural α-glucan phosphorylase of SEQ ID NO: 2;
   wherein the enzyme activity of the α-glucan phosphorylase having improved thermostability is equivalent or superior to the natural α-glucan phosphorylase; and
   wherein enzyme activity of the α-glucan phosphorylase having improved thermostability at 37° C., after heating in a 20 mM citrate buffer (pH 6.7) at 60° C. for 10 minutes, is 20% or more of enzyme activity of the α-glucan phosphorylase having improved thermostability at 37°C., before heating.

2. The α-glucan phosphorylase having improved thermostability according to claim 1, wherein the amino acid sequence of the natural α-glucan phosphorylase is encoded by a nucleic acid molecule which hybridizes under stringent condition to a nucleic acid molecule consisting of a base sequence encoding the amino acid sequence from position 1 to position 916 of SEQ ID NO: 2,
   wherein the stringent condition is a hybridization at 65° C. in a solution containing 50% formamide, 5 ×SSC (750 mM NaCl, 75 mM trisodium citrate), 50 mM sodium phosphate (pH 7.6), 5×Denhart's solution (0.2% BSA, 0.2% Ficoll 400 and 0.2% polyvinylpyrrolidone), 10% dextran sulfate, and 20 μg/ml denatured sheared salmon sperm DNA, and washing under the condition of 65° C. using a SSC (saline-sodium citrate) solution having a 0.1 to 2-fold concentration, and
   wherein the composition of the SSC solution having a 1-fold concentration is 150 mM sodium chloride and 15 mM sodium citrate.

3. The α-glucan phosphorylase having improved thermostability according to claim 1, wherein the natural α-glucan phosphorylase is a type L α-glucan phosphorylase, and the α-glucan phosphorylase having improved thermostability has an amino acid residue which is different from that of the natural α-glucan phosphorylase in a position corresponding to position 7 in the motif sequence 3L.

4. The α-glucan phosphorylase having improved thermostability according to claim 1, wherein the amino acid sequence of the natural α-glucan phosphorylase is position 1 to position 916 of SEQ ID NO: 2.

5. The α-glucan phosphorylase having improved thermostability according to claim 1, wherein the natural α-glucan phosphorylase is obtained from potato or *Arabidopsis thaliana*.

6. The α-glucan phosphorylase having improved thermostability according to claim 1, wherein an amino acid residue at a position corresponding to position 7 in the motif sequence 3L is selected from the group consisting of C, I, L and V.

7. The α-glucan phosphorylase having improved thermostability according to claim 1, wherein enzyme activity at 37° C. of the α-glucan phosphorylase having improved thermostability after heated in a 20 mM citrate buffer (pH 6.7) at 60° C. for 10 minutes is 30% or more of enzyme activity at 37° C. of the α-glucan phosphorylase having improved thermostability, before the heating.

8. The α-glucan phosphorylase having improved thermostability according to claim 1, wherein enzyme activity of the α-glucan phosphorylase having improved thermostability at 37° C., after heating in a 20 mM citrate buffer (pH 6.7) at 65° C. for 2 minutes, is 10% or more of enzyme activity of the α-glucan phosphorylase having improved thermostability at 37° C., before heating.

9. The α-glucan phosphorylase having improved thermostability according to claim 1, wherein storage stability thereof is improved as compared with the natural α-glucan phosphorylase.

10. A modified α-glucan phosphorylase having improved thermostability, which is obtained by modifying a natural α-glucan phosphorylase obtained from a plant,
    wherein the α-glucan phosphorylase having improved thermostability has an amino acid substitution at a position corresponding to position 7 in a motif sequence 3L: R-l-V-K-F-l-T-D-V (SEQ ID NO: 47);

wherein said substitution is a substitution to C. I, L, V or W:
wherein the α-glucan phosphorylase having improved thermostability has an amino acid sequence which is at least 95% identical to the sequence of the natural α-glucan phosphorylase of SEQ ID NO: 2;
wherein the enzyme activity of the α-glucan phosphorylase having improved thermostability is equivalent or superior to the natural α-glucan phosphorylase,
wherein the enzyme activity of the α-glucan phosphorylase having improved thermostability at 37° C., after heating in a 20 mM citrate buffer (pH 6.7) at 60° C. for 10 minutes, is 20% or more of enzyme activity of the α-glucan phosphorylase having improved thermostability at 37° C., before heating, and
wherein the α-glucan phosphorylase having improved thermostability has ability to synthesize an amylose having a weight average molecular weight of 600 kDa or more.

* * * * *